US008598148B2

(12) United States Patent
Myers et al.

(10) Patent No.: US 8,598,148 B2
(45) Date of Patent: *Dec. 3, 2013

(54) SYNTHESIS OF TETRACYCLINES AND ANALOGUES THEREOF

(75) Inventors: Andrew G. Myers, Boston, MA (US);
Mark G. Charest, Belle Mead, NJ (US);
Christian D. Lerner, Binningen (CH);
Jason D. Brubaker, Cheshire, CT (US);
Dionicio R. Siegel, New York, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 270 days.

This patent is subject to a terminal disclaimer.

(21) Appl. No.: 12/778,797

(22) Filed: May 12, 2010

(65) Prior Publication Data

US 2011/0009371 A1    Jan. 13, 2011

Related U.S. Application Data

(62) Division of application No. 11/133,789, filed on May 20, 2005, now Pat. No. 7,807,842.

(60) Provisional application No. 60/573,623, filed on May 21, 2004, provisional application No. 60/660,947, filed on Mar. 11, 2005.

(51) Int. Cl.
*A61K 31/65* (2006.01)
*C07C 237/26* (2006.01)
*C07D 221/18* (2006.01)
*C07D 235/02* (2006.01)
*C07D 239/70* (2006.01)
*C07D 307/77* (2006.01)

(52) U.S. Cl.
USPC ............ 514/152; 552/203; 544/245; 546/42; 548/301.7; 549/456

(58) Field of Classification Search
USPC .......... 514/152; 544/245; 546/42; 548/301.7; 549/456
See application file for complete search history.

(56) References Cited

U.S. PATENT DOCUMENTS

| | | | |
|---|---|---|---|
| 2,482,055 A | 9/1949 | Duggar et al. |
| 3,019,260 A | 1/1962 | McCormick et al. |
| 3,109,007 A | 10/1963 | Blackwood et al. |
| 3,219,671 A | 11/1965 | Hlavka |
| RE26,253 E | 8/1967 | Petisi et al. |
| 3,338,963 A | 8/1967 | Petisi et al. |
| 3,502,660 A | 3/1970 | Butler et al. |
| 3,509,184 A | 4/1970 | Conover et al. |
| 3,697,552 A | 10/1972 | Conover et al. |
| 3,699,117 A | 10/1972 | Butler et al. |
| 3,772,363 A | 11/1973 | Conover et al. |
| 3,829,453 A | 8/1974 | Conover et al. |
| 3,849,493 A | 11/1974 | Conover et al. |
| 3,862,225 A | 1/1975 | Conover et al. |
| 3,914,299 A | 10/1975 | Muxfeldt |
| 3,947,517 A | 3/1976 | Muxfeldt et al. |
| 3,962,330 A | 6/1976 | Cotti et al. |
| 3,983,173 A | 9/1976 | Hartung et al. |
| 4,052,467 A | 10/1977 | Mills et al. |
| 4,060,605 A | 11/1977 | Corti et al. |
| 4,066,694 A | 1/1978 | Blackwood et al. |
| 4,418,060 A | 11/1983 | Kahan nee Laszlo |
| 4,597,904 A | 7/1986 | Page et al. |
| 5,362,754 A | 11/1994 | Raad et al. |
| 5,529,990 A | 6/1996 | Hlavka et al. |
| 5,538,954 A | 7/1996 | Koch et al. |
| 5,574,026 A | 11/1996 | Backer et al. |
| 5,589,470 A | 12/1996 | Levy et al. |
| 5,688,516 A | 11/1997 | Raad et al. |
| 5,811,412 A | 9/1998 | Levy et al. |
| 5,834,450 A | 11/1998 | Su et al. |
| 6,143,161 A | 11/2000 | Heggie et al. |
| 6,165,999 A | 12/2000 | Vu et al. |
| 6,506,740 B1 | 1/2003 | Ashley et al. |
| 6,509,319 B1 | 1/2003 | Raad et al. |
| 6,617,318 B1 | 9/2003 | Nelson et al. |
| 6,624,168 B2 | 9/2003 | Nelson et al. |
| 6,638,532 B2 | 10/2003 | Rudnic et al. |
| 6,642,270 B2 | 11/2003 | Nelson et al. |
| 6,683,068 B2 | 1/2004 | Nelson et al. |

(Continued)

FOREIGN PATENT DOCUMENTS

CN    101 684 101 A    3/2010
EP      1 241 160 A1    9/2002

(Continued)

OTHER PUBLICATIONS

Extended European Search Report for EP 12156059.3 mailed Jun. 27, 2012.
Extended European Search Report for EP 12156126.0 mailed Jul. 12, 2012.
International Search Report and Written Opinion for PCT/US2011/054791 mailed Jan. 19, 2012.
Notice of Allowance mailed Jun. 14, 2012 for U.S. Appl. No. 13/043,742.
Office Communication mailed May 17, 2012 for U.S. Appl. No. 12/296,223.
Magnus et al., Trimethylsilyl accelerated retro-Diels-Alder reaction: a quantitative measure of the .beta.-effect. J Am Chem Soc. 1987;109(8):2469-2471.
U.S. Appl. No. 61/389,661, Myers et al.

(Continued)

*Primary Examiner* — Barbara P Badio
(74) *Attorney, Agent, or Firm* — Wolf, Greenfield & Sacks, P.C.; C. Hunter Baker; Robin A. Weatherhead

(57) ABSTRACT

The tetracycline class of antibiotics has played a major role in the treatment of infectious diseases for the past 50 years. However, the increased use of the tetracyclines in human and veterinary medicine has led to resistance among many organisms previously susceptible to tetracycline antibiotics. The modular synthesis of tetracyclines and tetracycline analogs described provides an efficient and enantioselective route to a variety of tetracycline analogs and polycyclines previously inaccessible via earlier tetracycline syntheses and semi-synthetic methods. These analogs may be used as anti-microbial agents or anti-proliferative agents in the treatment of diseases of humans or other animals.

25 Claims, 25 Drawing Sheets

(56) References Cited

U.S. PATENT DOCUMENTS

| | | | |
|---|---|---|---|
| 6,818,634 | B2 | 11/2004 | Nelson et al. |
| 6,818,635 | B2 | 11/2004 | Nelson et al. |
| 6,841,546 | B2 | 1/2005 | Draper et al. |
| 6,846,939 | B2 | 1/2005 | Nelson et al. |
| 6,849,615 | B2 | 2/2005 | Nelson et al. |
| 7,001,918 | B2 | 2/2006 | Huss et al. |
| 7,763,735 | B2 | 7/2010 | Myers et al. |
| 7,807,842 | B2 | 10/2010 | Myers et al. |
| 7,960,559 | B2 | 6/2011 | Myers et al. |
| 2002/0045602 | A1 | 4/2002 | Nelson et al. |
| 2002/0103171 | A1 | 8/2002 | Nelson et al. |
| 2002/0111335 | A1 | 8/2002 | Nelson et al. |
| 2002/0128237 | A1 | 9/2002 | Nelson et al. |
| 2002/0128238 | A1 | 9/2002 | Nelson et al. |
| 2002/0132798 | A1 | 9/2002 | Nelson et al. |
| 2002/0136766 | A1 | 9/2002 | Rudnic et al. |
| 2002/0193354 | A1 | 12/2002 | Nelson et al. |
| 2003/0055025 | A1 | 3/2003 | Nelson et al. |
| 2003/0096008 | A1 | 5/2003 | Rudnic et al. |
| 2003/0100017 | A1 | 5/2003 | Draper et al. |
| 2003/0153537 | A1 | 8/2003 | Levy et al. |
| 2003/0166585 | A1 | 9/2003 | Draper et al. |
| 2004/0048835 | A1 | 3/2004 | Nelson et al. |
| 2004/0063674 | A1 | 4/2004 | Levy et al. |
| 2004/0067912 | A1 | 4/2004 | Hlavka et al. |
| 2005/0282782 | A1 | 12/2005 | Martin |
| 2007/0066253 | A1 | 3/2007 | Sorrells et al. |
| 2009/0093640 | A1 | 4/2009 | Myers et al. |
| 2010/0130451 | A1 | 5/2010 | Myers et al. |
| 2012/0029199 | A1 | 2/2012 | Myers et al. |
| 2012/0115818 | A1 | 5/2012 | Myers et al. |

FOREIGN PATENT DOCUMENTS

| | | |
|---|---|---|
| FR | 2 279 720 A1 | 2/1976 |
| GB | 973022 A | 10/1964 |
| GB | 1013576 A | 12/1965 |
| GB | 1013906 A | 12/1965 |
| GB | 1019562 A | 2/1966 |
| GB | 1019563 A | 2/1966 |
| GB | 1100885 A | 1/1968 |
| WO | WO 95/22529 A1 | 8/1995 |
| WO | WO 96/36229 A1 | 11/1996 |
| WO | WO 01/98236 A1 | 12/2001 |
| WO | WO 01/98259 A1 | 12/2001 |
| WO | WO 01/98260 A1 | 12/2001 |
| WO | WO 02/04404 A1 | 1/2002 |
| WO | WO 02/04406 A2 | 1/2002 |
| WO | WO 02/04407 A2 | 1/2002 |
| WO | WO 02/12170 A1 | 2/2002 |
| WO | WO 02/072532 A1 | 9/2002 |
| WO | WO 02/085303 A2 | 10/2002 |
| WO | WO 03/005971 A2 | 1/2003 |
| WO | WO 03/057169 A2 | 7/2003 |
| WO | WO 03/076424 A1 | 9/2003 |
| WO | WO 2004/038001 A2 | 5/2004 |
| WO | WO 2004/064728 A2 | 8/2004 |
| WO | WO 2005/030149 A2 | 4/2005 |
| WO | WO 2005/056538 A1 | 6/2005 |
| WO | WO 2005/112945 A2 | 12/2005 |
| WO | WO 2005/112985 A2 | 12/2005 |
| WO | WO 2007/067807 A1 | 6/2007 |
| WO | WO 2007/112121 A2 | 10/2007 |
| WO | WO 2007/117639 A2 | 10/2007 |
| WO | WO 2007/118237 A2 | 10/2007 |
| WO | WO 2008/127361 A2 | 10/2008 |
| WO | WO 2010/126607 A2 | 11/2010 |
| WO | WO 2012/047907 A1 | 4/2012 |

OTHER PUBLICATIONS

Invitation to Pay Additional Fees for PCT/US2007/081076 mailed Sep. 30, 2008.
Invitation to Pay Additional Fees for PCT/US2010/001284 mailed Feb. 10, 2011.
International Search Report and Written Opinion for PCT/US2010/001284 mailed May 24, 2011.
Notice of Allowance, mailed Nov. 23, 2010 for U.S. Appl. No. 12/833,628.
Curtis et al., A nitrogen-15 nuclear magnetic resonance study of the tetracycline antibiotics. Can J Chem. 1991;69:834-38.
Glatz et al., Tetracyclines. A total synthesis and structural aspects of racemic 8-oxygenated tetracyclines. J Am Chem Soc. 1979;101:2171-81.
Landais et al., Studies on the Mercury-desilylation of Chiral Cyclopropylmethylsilanes. A Stereocontrolled Access to Carba-sugars.. Eur. J. Org. Chem. 2000;2:401-18.
Martin et al., Totalsynthese von d, 1-7-Chlor-6-desoxytetracylinen und d, 1-7-Chlor-6-desmethyl-6-desoxytetracylinen der natürlichen, der 5a-epi- and der 6-epi-Reihe. Tetrahedron Lett. 1973:36:3513-16. German.
Nelson et al., Molecular requirements for the inhibition of the tetracycline antiport protein and the effect of potent inhibitors on the growth of tetracycline-resistant bacteria. J Med Chem. Apr. 29, 1994;37(9):1355-61.
Palenik et al., Structural Studies of Tetracylcines. Crystal and Molecular Structures of Anhydrotetracycline Hydrobromide Monohydrate and 6-Demethyl-7-chlorotetracycline Hydrochloride Trihydrate. J Am Chem Soc. 1978;100(14):4458-64.
Schach Von Wittenau et al., Proton Magnetic Resonance Spectra of Tetracyclines. J Chem Soc. 1966;31:613-15.
Shu et al., BMS-192548, a tetracyclic binding inhibitor of neuropeptide Y receptors, from *Aspergillus niger* WB2346. II. Physico-chemical properties and structural characterization. J Antibiot (Tokyo). Oct. 1995;48(10):1060-5.
Urbach et al., Totalsynthese von d,1 4-Amino-7-chlor-2-N-methylcarbamyl-2-descarbamyl-4-des-dimethylamino-6-desmethyl-6-desoxytetracyclin. Tetrahedron Lett. 1973;49:4907-10. German.
U.S. Appl. No. 60/790,413, filed Apr. 7, 2006, Myers.
U.S. Appl. No. 60/850,859, filed Oct. 11, 2006, Myers, et al.
International Search Report and Written Opinion for PCT/US2007/081076 mailed Dec. 15, 2008.
International Preliminary Report on Patentability for PCT/US2007/081076 mailed Apr. 23, 2009.
Supplementary European Search Report for EP 05779988.4 mailed Jun. 9, 2009.
International Search Report and Written Opinion for PCT/US2005/017831 mailed May 4, 2006.
International Preliminary Report on Patentability for PCT/US2005/017831 mailed Nov. 30, 2006.
International Search Report and Written Opinion for PCT/US2007/008647 mailed Mar. 14, 2008.
International Preliminary Report on Patentability for PCT/US2007/008647 mailed Oct. 16, 2008.
Notice of Allowance mailed Apr. 7, 2010 for U.S. Appl. No. 11/870,772.
Office Communication mailed Oct. 27, 2009 for U.S. Appl. No. 11/133,789.
Notice of Allowance mailed Feb. 22, 2010 for U.S. Appl. No. 11/133,789.
[No Author Listed] March's Advanced Organic Chemistry $4^{th}$ Ed., p. 518-19, 1992.
[No Author Listed] March's Advanced Organic Chemistry $4^{th}$ Ed., p. 1062-75, 1992.
[No Author Listed] Organomagnesium in Organic Synthesis, Academic Press, Inc.: San Diego, p. 51-59. 1995.
Akgun et al., Metalation of 0-Halostyrenes Oxides. Preparation of Benzocyclobutenols. J. Org. Chem. 1981;46:2730-2734.
Allen et al., A Powerful o-Quinone Dimethide Strategy for Intermolecular Diels—Alder Cycloadditions. J. Am. Chem. Soc. 2000;122:571-575.
Allen et al., The Total Synthesis of (±)-Rishirilide B. Am. Chem. Soc. 2001;123:351-352.
Amaro et al., Synthesis of Tetracyclic Hydroxyquinones by Cycloaddition Reactions With Dienols. Tetrahedron Lett. 1979:3983-3986.
Ballard et al., A Biotech Route to Polyphenylene. J. Chem. Soc. Chem. Commun. 1983:954-955.

(56) References Cited

OTHER PUBLICATIONS

Barr et al., Zirconocene(iso-butyl) Chloride: In Situ Generation of a Zirconocene(methyl) Chloride Equivalent for Use in Organic Synthesis. Tetrahedron Lett. 1991;32:5465-5468.
Beard et al., Inhibition of Mammalian Protein Synthesis by Antibiotics. Pharmacol. Revs. 1969;21: 213-245.
Becker et al., Oxidative Formation and Photochemical Isomerization of Spiro-Epoxy-2,4-Cyclohexadienones. Tetrahedron Lett. 1972;13:4205-4208.
Beereboom et al., Further 6-Deoxytetracycline Studies: Effect of Aromatic Substituents on Biological Activity. J. Am. Chem. Soc. 1960;82:1003-1004.
Berge et al., Pharmaceutical Salts. J. Pharmaceutical Sciences 1977;66:1-19.
Berk et al., Preparations and Reactions of Functionalized Benzylic Organometallics of Zinc and Copper. Organometallics. 1990;9:3053-3064.
Boothe et al., Identification of an Antibiotic Polyacetylene From Clitocybe Diatreta as a Suberamic Acid Ene-Diyne. J. Am. Chem. Soc.1953;75:4621.
Boudier et al., New Applications of Polyfunctional Organometallic Compounds in Organic Synthesis Frequently used abbreviations are defined at the end of the article. Angew Chem Int Ed Engl. Dec. 15, 2000;39(24):4414-4435.
Brodersen et al.,The Structural Basis for the Action of the Antibiotics Tetracycline, Pactamycin, and Hygromycin B on the 30S Ribosomal Subunit. Cell. 2000;103:1143-1154.
Brown et al., Activities of the Glycylcyclines N, N-Dimethylglycylamido-Minocycline and N,N-Dimethylglycylamido-6-Deoxytetracycline Against *Nocardia* spp. and Tetracycline-Resistant Isolates of Rapidly Growing Mycobacteria. Antimicrob. Agents Chemother. 1996;40:874-878.
Brubaker et al., A practical, enantioselective synthetic route to a key precursor to the tetracycline antibiotics. Org Lett. Aug. 30, 2007;9(18):3523-5. Epub Aug. 11, 2007.
Burdett, Purification and Characterization of Tet(M), a Protein That Renders Ribosomes Resistant to Tetracycline. J. Biol. Chem. 1991;266:2872-2877.
Burke, Flexible tetracycline synthesis yields promising antibiotics. Nat Chem Biol. Feb. 2009;5(2):77-9.
Bush et al., Taking Inventory: Antibacterial Agents Currently at or Beyond Phase 1. Curr. Opin. Microbiol. 2004;7:466-476.
Cane et al., Harnessing the Biosynthetic Code: Combinations, Permutations, and Mutations. Science 1998;282:63-68.
Carless, The Use of Cyclohexa-3,5-Diene-1,2-Diols in Enantiospecific Synthesis. Tetrahedron Asymmetry. 1992;3:795-826.
Charest et al., A convergent enantioselective route to structurally diverse 6-deoxytetracycline antibiotics. Science. 2005;308:395-398.
Charest et al., Synthesis of (−)-Tetracycline. J. Am. Chem. Soc. 2005;127: 8292-93.
Charette et al., Spectroscopic studies of the electrophilic activation of amides with triflic anhydride and pyridine. CA J Chem. 2001;79:1694-1703.
Col et al., Estimating Worlwide Current Antibiotic Usage: Report of Task Force 1. Reviews of Infectious Diseases. 1987;3: S232-43.
Conover et al., Terramycin. XI. Tetracycline. J. Am. Chem. Soc. 1953;75:4622-23.
Conover et al., The Total Synthesis of 6-Demethyl-6-Deoxytetracycline. J. Am. Chem. Soc. 1962;84:3222-24.
Corey et al., Dimethyloxosulfonium Methylide (($CH_3$)$_2$SOCH$^2$) and Dimethylsulfonium Methylide (($CH_3$)$_2$SOCH$_2$). Formation and Applicaton to Organic Synthesis. J. Am. Chem. Soc. 1965;87:1353-1364.
Corey et al., Highly Enantioselective Borane Reduction of Ketones Catalyzed by Chiral Oxaborolidines. Mechanism and Synthetic Implications. J. Am. Chem. Soc. 1987;109:5551-5553.
Corey et al., Practical Enantioselective Diels-Alder and Aldol Reactions Using a New Chiral Controller System. J. Am. Chem. Soc. 1989;111:5493-5495.
Corey et al., Reduction of Carbonyl Compounds With Chiral Oxaborolidine Catalysts: a New Paradigm for Enantioselective Catalysis and a Powerful New Synthetic Method. Angew. Chem. Int. Ed Engl.1988;37:1986-2012.
Corey et al., Studies With Trialkylsityltrifiates: New Synthesis and Applications. Tetrahedron Lett. 1981;22:3455-3458.
Dale et al., Nuclear Magnetic Resonance Enantiomer Reagents. Configurational Correlations via Nuclear Magnetic Resonance Chemical Shifts of Diastereomeric Mandelate, O-Methylmandelate and α-Methoxy-α-trifluoromethylphenylacetate (MTPA) Esters. J Am Chem Soc. 1973;95:512-19.
Dale et al., α-Methoxy-αTrifluoromethylphenylacetic Acid, a Versatile Reagent for the Determination of Enantiometric Composition of Alcohols and Amines J Org. Chem. 1969;34:2543-2549.
Danishefsky et al., Functionalized Alanes for the Conversion of Epoxides to Trans-Fused γ-Lactones. J Org Chem. 1976;41:1669-71.
Davis et al., Chemistry of Oxaziridines. 18. Synthesis and Enantioselective Oxidations of the [(88-Dihalocamphoryl) Sulfonyl] Oxaziridines. J. Org. Chem. 1992;57:7274-7285.
De Silva et al., Directed Lithiation of N,N-Diethylbenzamides. Tetrahedron Lett. 1978;51:5099-5102.
De Silva et al., General Route to Anthraquinone Natural Products via Directed Metalation of N,N-Diethylbenzamides. J. Org. Chem. 1979;44:4802-4808.
Detty, Electrophilic Conversion of Oxiranes to Allylic Alcohols with tert-Butyldimethylsilyl Iodide. J. Org. Chem. 1980;45:924-926.
Devasthale et al., Dactylocyclines Novel Tetracycline Derivatives Produced by a *Dactylosporangium*. Antibiotics. 1992;45:1907-1913.
Ditrich et al., Synthesis of a Protected C-11/C-17 Segment of Mycinolide-V. Liebigs Ann. Chem. 1990:15-21.
Dodd et al., Synthesis of the Carbon Framework of Olivin. Tetrahedron Lett. 1979;20:3593-3596.
Duggar, Aureomycin: A Product of the Continuing Search for New Antibiotics. Ann. N.Y. Acad. Sci. 1948;51:177-181.
Duhamel et al., A Method for Simple Titration of Organolithium Reagents in Ethers or HydrocarbonsUsing Metalation of N-Benzylidenebenzylamine as Colored Reaction. J. Org. Chem. 1979;44:3404-3405.
Eckert et al., Topology of the Transposon Tn10-Encoded Tetracycline Resistance Protein Within the Inner Membrane of *Escheria coli*. J. Biol. Chem. 1989;264:11663-11670.
Epe et al., Competition Between Tetracycline and tRNA at Both P and a Sites of the Ribosome of *Escheria coil*. FEBS Lett. 1987;213:443-47.
Epe et al., The Binding of 6Demethylchlorotetracyline to 70S, 50S, and 30S Ribosomal Particles—A Quantitative Study by Fluorescence Anisotropy. EMBO J. 1984;3:121-26.
Ettner et al., Proximity Mapping of the Tet Repressor-Tetracycline-$Fe^{2+}$ Complex by Hydrogen Peroxide Mediated Protein Cleavage. Biochemistry. 1995;34:22-31.
Finlay et al., Terramycin, A New Antibiotic. Science 1950;111:85.
Franklin et al., Resistance of *Escherichia coli* to Tetracylines. Biochem J. 1965;94:54-60.
Franklin, The Inhibition of Incorporation of Leucine Into Protein of Cell-Free Systems From Rat Liver and *Escherichia coll* by Chlortetracycline. Biochem. J. 1963;87:449-453.
Frigerio et al., A Mild Oxidizing Reagent for Alcohols and, 1,2-Diols: o-lodoxybenzoic Acid (IBX) in DMSO. Tetrahedron Lett. 1994;35:8019-8022.
Gibson et al., Oxidative Degradation of Aromatic Hydrocarbons by Microorganisms. II. Metabolism of Halogenated Aromatic Hydrocarbons. Biochemistry 1968;7:3795-3802.
Goldman et al., Photoincorporation of Tetracycline Into *Escherichia coil* Ribosomes. Identification of the Major Proteins Photolabeled by Native Tetracycline and Tetracycline Photoproducts and Implications for the Inhibitory Action of Tetracycline on Protein Synthesis. Biochemistry. 1983;22:359-368.
Goldstein et al., N,N-Dimethylglycyl-Amido Derivative of Minocycline and 6-Demethyl-6-Desoxytetracycline, Two New Glycylcyclines Highly Effective Against Tetracycline-Resistant Gram-Positive Cocci. Antimicrob. Agents Chemother. 1994;38:2218-2220.

(56) References Cited

OTHER PUBLICATIONS

Gurevich et al., Synthesis of 12a-Deoxy-5a,6-Anhydrotetracycline. The First Total Synthesis of the Naturally Occurring Tetracycline. Tetrahedron Lett. 1967;8:131-134.

Hauser et al., ortho-Toluate Carbanion Chemistry: Sulfenylation and Selenation. Synthesis. 1980: 72-74.

Hauser et al., New Synthetic Methods for the Regioselective Annelation of Aromatic Rings: 1-Hydroxy-2,3-disubstituted Naphthalenes and 1,4-Dihydrocy-2,3-disubstituted Naphthalenes. J Org Chem. 1978;43:178-180.

He et al., Pyrrocidines A and B, New Antibiotics Produced by a Filamentous Fungus. Tetrahedron Letters. 2002;43:1633-36.

Hiilen et al., Control of the Expression of the Tn10-Encoded Tetracycline Resistance Genes. Equilibrium and Kinetic Investigation of the Regulatory Reactions. J. Mol. Biol. 1983;169:707-721.

Hinrichs et al., Structure of the Tet Repressor-Tetracycline Complex and Regulation of Antibiotic Resistance. Science. 1994;264:418-420.

Hochstein et al., Terramycin. VII. The Structure of Terramycin. J. Am. Chem. Soc. 1952;74:3708-3709.

Hochstein et al., The Structure of Terramycin. J. Am. Chem Soc. 1953;75:5455-75.

Hollinshed et al., Two Practical Syntheses of Sterically Congested Benzophenones. J. Org. Chem. 1994;59:6703-6709.

Holmuland et al., Chemical Hydroxylation of 12a-Dexytetracycline. J. Am. Chem. Soc. 1959;81:4748-4749.

Hong et al., Lewis acid-promoted alpha-hydroxy beta-dicarbonyl to alpha-ketol ester rearrangement. Tetrahedron Lett. Nov. 20, 2006;47(47):8387-8390.

Hudlicky et al., A Short Synthesis of (+)-Lycoricidne. J. Am. Chem. Soc. 1992;114: 9694-9696.

Hudlicky et al., Enantioselective Synthesis Through Microbial Oxidation of Arenes. Efficient Preparation of Terpene and Prostanoid Synthons. J. Am. Chem. Soc. 1988;110:4735-4741.

Hudlicky et al., Enzymatic Dihydroxylation of Aromatics in Enantioselective Synthesis: Expanding Asymmetric Methodology. Aldrichimica Acta. 1999;32:35-62.

Hudlicky et al., Microbial Oxidation of Aromatics in Enantiocontrolled Synthesis. Rational DesignsOf Aza Sugars (endo-Nitrogenous). Total Synthesis of (+)-Kifunensine, Mannorjirimycin, and Other Glycosidase Inhibitors. J. Am. Chem. Soc. 1994;116:5099-5107.

Hudlicky et al., Toluene Dioxygenase-Mediated cis-Dihydroxylation of Aromatics in Enantioselective Synthesis. Asymmetric Total Synthesis of Pancratistatin and 7-Deoxpancratistatin, Promising Antitumor Agents. J. Am. Chem. Soc. 1996;118:10752-10765.

Hyatt et al., Thermal Decomposition of 2,2,6-Trimethyl-4H-1,3-Dioxin-4-One and 1-Ethoxybutyn-3-One. Acetylketene. J. Org. Chem. 1984;49:5105-5108.

Jacouinet et al., Synthesis of Heparin Fragments . A Chemical Synthesis of the Trisaccharide 0-(2-Deoxy-2-Sulfamido-3.6-DI-O-Sulfo-a-D-Glucopyranosyl)-(1→4)-0-(2-0-Sulfo-a-L-Idopyranosyl-Uronic Acid)-(1→4)-2-Deoxy-2-Sulfamido-6-0-Sulfo-D-Gluco- Pyranose Heptasodium Salt. Carbohydr. Res. 1984;130:221-241.

Jenkins et al., Synthetic application of biotransformations: absolute stereochemistry and Diels-Alder reactions of the (1S,2R)-1,2-dihydroxycyclohexa-3,5-diene-1-carboxylic acid from *Pseudomonas putida*. J Chem Soc Perkin Trans. 1995;1:2647-55.

Jensen et al, Unsaturated Four-Membered Ring Compounds. II. 1,2-Diphenylbenzocyclobutene, a Compound Having Unusual Reactivity. J. Am. Chem. Soc.1958; 80:6149.

Johns et al., Synthesis and Biological Evaluation of Aza-C-Disaccharides: (1→6), (1-44), and (1→1) Linked Sugar Mimics. J. Am. Chem. Soc. 1997;119:4856-4865.

Johnson et al., Triply Convergent Synthesis of (−)-Prostaglandin E2 Methyl Ester. J Am Chem Soc. 1988;110:4726-4735.

Johnson, Biotransformations in the Synthesis of Enantiopure Bioactive Molecules. Acc Chem Res. 1998;31:333-341.

Katz, Manipulation of Modular Polyketide Synthases. Chem. Rev. 1997;97:2557-2575.

Kenny et al., Susceptibilities of *Mycoplasma hominis, Mycoplasma pneumoniae*, and *Ureaplasma urealyticum* to New Glycylcyclines in Comparison With Those to Older Tetracyclines. Antimicrob. Agents Chemother. 1994;38:2628-2632.

Khosla et al., Chemistry. A new route to designer antibiotics. Science. Apr. 15, 2005;308(5720):367-8.

Kofron et al., A Convenient Method for Estimation of Alkyllithium Concentrations. J Org Chem. 1976;41:1879-80.

Konno et al., A Practical Preparation of Versatile Cyclohexenoid Chiral Building Blocks. Synthesis. 1999:1135-40.

Korst et al., The Total Synthesis of d/-6-Demethyl-6-Deoxytetracycline. J. Am. Chem. Soc. 1968;90:439-457.

Koza et al., Synthesis and Biological Evaluation of 9-Substituted Tetracycline Derivatives. Bioorgan. & Med. Chem. Letters. 2002;12: 2163-2165.

Koza et al., Synthesis of 7-Substituted Tetracycline Derivatives. Organic Letters. 2000;2:815-817.

Koza, The Synthesis of 8-Substituted Tetracycline Derivatives, The First 8-Position Carbon-Carbon Bond. Tetrahedron Lett. 2000;41:5017-5020.

Laskin et al., Inhibition by Tetracyclines of Polyuridylic Acid Directed Phenylalanine Incorporation in *Escherichia coli* Cell- Free Systems. Biochem Biophys. Res. Commun 1964;14:137-142.

Lederer et al., Thermodynamic Analysis of Tetracycline-Mediated Induction of Tet Repressor by a Quantitative Methylation Protection Assay. Anal. Biochem. 1995;232:190-196.

Leeb, A Shot in the Arm. Nature. 2004;431:892-893.

Leeper et al., Biomimetric Synthesis of Heptaketide Metabolites: Alternariol and a Derivative of Rubrofusarin. J.C.S. Chem. Comm. 1978:406-407.

Levy, Tetracycline Resistance Determinants are Widespread. Amer. Soc. Microbial News. 1988;54: 418-421.

Ley et al., Microbial Oxidation in Synthesis: A Six Step Preparation of (+)-Pinitol From Benzene. Tetrahedron Lett. 1987;28:225-226.

Mao et al., Mode of Action of β-Chelocardin. Biochim. Biophys. Acta. 1971;238: 157-160.

Marchand et al., Facile Stereoselective Reductions of Enediones and Cage Diketones Using $NaBH_4$-$CeCl_3$. J Org Chem. 1986;51:1622-25.

Marger et al., A Major Superfamily of Transmembrane Facilitators That Catalyse Uniport, Symport and Antiport. *Trends Biochem Sci.* 1993;18:13-20.

Martell et al., The 6-Deoxytetracyclines. IX. Imidomethylation. J. Med. Chem. 1967;10:359-363.

Martell et al., The 6-Deoxytetracyclines. VII. Alkylated Aminotetracyclines Possessing Unique Antibacterial Activity. J. Med. Chem. 1967;10: 44-46.

McComsey et al., Improved Synthesis of Pseudo-13-D-Fructopyranose, A Carbocyclic Monosaccharide, From (−)-Quinic Acid. J. Org. Chem. 1994;59:2652-2654.

McCormick et al., The 6-Deoxytetracyclines. Further Studies on the Relationship Between Structure and Antibacterial Activity in the Tetracycline Series. J. Am. Chem. Soc. 1960;82: 3381-3386.

Meister et al., Synthese von 3(2H)-Furanonen and 3-Methoxyfuranen. Synthesis; 1981:737-39.

Mendez et al., Heterogeneity of Tetracycline Resistance Determinants. Plasmid. 1980;3:99-108.

Mercier et al., In Vitro Activities of an Investigational Quinolone, Glycylcycline, Glycopeptide, Streptogramin, and Oxazolidinone Tested Alone and in Combinations Against Vancomycin-Resistant *Enterococcus faecium*. Antimicrob Agents Chemother. 1997;41: 2573-2575.

Movassaghi et al., Direct synthesis of pyridine derivatives. J Am Chem Soc. Aug. 22, 2007;129(33):10096-7. Epub Jul. 31, 2007.

Movassaghi et al., Single-step synthesis of pyrimidine derivatives. J Am Chem Soc. Nov. 8, 2006;128(44):14254-5.

Movassaghi et al., Synthesis of substituted pyridine derivatives via the ruthenium-catalyzed cycloisomerization of 3-azadienynes. J Am Chem Soc. Apr. 12, 2006;128(14):4592-3.

Muxfeldt et al., Tetracyclines. 9. Total Synthesis of dl-Terramycin. J. Am. Chem. Soc. 1979;101:689-701.

(56) References Cited

OTHER PUBLICATIONS

Muxfeldt et al., Tetracyclines. V. A Total Synthesis of (±)-6-Deoxy-6-Demethyltetracycline. J. Am. Chem. Soc. 1965;87:933-934.

Muxfeldt et al., Total Synthesis of Anhydroaureomycin. Angew Chem. Intl. Ed. EngL 1973;12:497-499.

Myers et al., An Efficient Method for the Reductive Transposition of Allylic Alcohols. Tetrahedron Lett. 1996;37:4841-4844.

Myers et al., A Convergent Synthetic Route to (+)-Dynemicin A and Analogs of Wide Structural Variability. J. Am. Chem. Soc. 1997;119:6072-6094.

Myers et al., Synthesis of a Broad Array of Highly Functionalized, Enantiomerically Pure Cyclohexanecarboxylic Acid Derivative by Microbal Dihydroxylation of Benzoic Acid and Subsequent Oxidative and Rearrangement Reactions. Organic Letters. 2001;3(18):2923-26.

Nakashima et al., A Stereocontrolled Route to (−)-Epibatidine Using a Chiral cis-Cyclohexadiene-1,4-diol Equivalent. Synlett. 1999:1405-6.

Nelson et al., Versatile and Facile Synthesis of Diverse Semisynthetic Tetracycline Derivatives Via Pd-Catalyzed Reactions. J. Org. Chem. 2003;68: 5838-5851.

Nicolaou et al., Recent advances in the chemistry and biology of naturally occurring antibiotics. Angew Chem Int Ed Engl. 2009;48(4):660-719.

Oda et al., 2-Cyclohexene-1,4-Dione. Org Syntheses. 1996;73:253.

Oikawa et al., Biosynthesis of Structurally Unique Fungal Metabolite GKK1032A2: Indication of Novel Carbocyclic Formation Mechanism in Polyketide Biosynthesis. J. Org. Chem. 2003;68:3552-3557.

Oikawa et al., Kinetic Acetalization for 1, 2- and 1, 3-Diol Protection by the Reaction of p-Methoxyphenylmethyl Methyl Ether With DDQ. Tetrahedron Lett. 1983;24:4037-4040.

Okamoto et al., Mechanism of Chloramphenicol and Tetracycline Resistance in *Escherichia coli.* J Gen. Microb. 1964;35:125-133.

Oliva et al., Evidence That Tetracycline Analogs Whose Primary Target is not the Bacterial Ribosome Cause Lysis of *Escherichia cox Antimicrob.* Agents Chemother. 1992;36:913-919.

Osman et al., Synthesis and Biological Activity of Certain Nicotinic Acid Derivatives. Revue Roumaine de Chime 1986;31:615-624.

Pangborn et al., Safe and Convenient Procedure for Solvent Purification. Organometallics. 1996;15:1518-1520.

Paradies et al., A New Method for the Preparation of Organomagnesium Compounds of Pyridine. Angew. Chem. Int. Ed. Engl. 1969;8:279.

Parham et al., Selective Halogen-Lithium Exchange in Bromophenylalkyl Halides. J. Org. Chem. 1976; 41: 1184-1186.

Patel et al., A New Tetracycline Antibiotic From a *Dactylosporangium* Species. Antibiotics. 1987;40:1414-1418.

Peláez, The historical delivery of antibiotics from microbial natural products—can history repeat? Biochem Pharmacol. Mar. 30, 2006;71(7):981-90. Epub Nov. 14, 2005.

Pelter et al., Phenolic Oxidation With (Diacetoxyiodo) Benzene. Tetrahedron Lett. 1988;29: 677-680.

Pevarello et al., An Improved Synthesis of Muscimol. Synth. Commun. 1992;22:1939-1948.

Pickens et al., Decoding and engineering tetracycline biosynthesis. Metab Eng. Mar. 2009;11(2):69-75. Epub Oct. 22, 2008.

Pierce et al., Practical Asymmetric Synthesis of Efavirenz (DMP 266), an HIV-1 Reverse Transcriptase Inhibitor. J Org Chem. 1998;63:8536-43.

Pine, The Base-Promoted Rearrangements of Quaternary Ammonium Salts. Organic Reactions. 1970;18:403-433.

Pioletti et al., Crystal Structures of Complexes of the Small Robosomal Subunit With Tetracycline, Edeine, and IF3. EMBO J. 2001;20:1829-1839.

Prilezhaeva, Rearrangements of Sulfoxides and Sulfones in the Total Synthesis of Natural Compounds. Russ. Chem. Rev. 2001;70: 897-920.

Rasmussen et al., Molecular Basis of Tetracycline Action: Identification of Analogs Whose Primary Target is not the Bacterial Ribosome. Antimicrob. Agents Chemother. 1991;35:2306-11.

Rassmussen et al., Inhibition of Protein Synthesis Occurring on Tetracycline-Resistant, TetM-Protected Ribosomes by a Novel Class of Tetracyclines, the Glycylcyclines. Antimicrob. Agents Chemother. 1994;38:1658-1660.

Reineke et al., cis-Dihydrodiols Microbially Produced From Halo- and Methylbenzoic Acids. Tetrahedron. 1978;34:1707-1714.

Reiner et al., Metabolism of Benzoic Acid by Bacteria, Accumulation of (−)-3,5-Cyclohexadiene-1,2—Dio1-1-Carboxylic Acid by a Mutant Strain of *Alcaligenes eutrophus.* Biochemistry. 1971;10:2530-2536.

Rendi et al., Effect of Chloramphenicol on Protein Synthesis in Cell-free Preparations of *Escherichia coli.* J. Biol. Chem. 1962;237:3711-3713.

Riess et al., Evaluation of Protecting Groups for 3-Hydroxyisoxazoles—Short Access to 3-Alkoxyisoxazole-5-Carbaldehydes and 3-Hydroxyisoxazole-5-Carbaldehyde, the Putative Toxic Metabolite of Muscimol. Eur. J. Org. Chem. 1998:473-479.

Rogalski, Chapter 5. Chemical Modification of Tetracyclines. Handbook of Experimental Pharmacology. 1985:179-316.

Rossiter et al., Aromatic Biotransformations 2: Production of Novel Chiral Fluorinated 3,5- Cycloheadiene-CIS-1,2-Dio1-1-Carboxylates. Tetrahedron Lett. 1987;28:5173-5174.

Saenger et al., The Tetracycline Repressor—A Paradigm for a Biological Switch. Angew. Chem. Int. Ed. 2000;39:2042-2052.

Sanchez-Pescador et al., Homology of the TetM With Translational Elongation Factors: Implications for Potential Modes of tetM Conferred Tetracycline Resistance. Nucl. Acids. Res. 1988;16:1218.

Sato et al., Synthesis of 1,3-Dioxin-4-One Deirvatives. Chem. Pharm. Bull. 1983;31:1896-1901.

Schnappinger et al., Tetracyclines: Antibiotic Action, Uptake, and Resistance Mechanisms. Arch. Microbiol. 1996;165:359-369.

Scott et al., Simulation of the Biosynthesis of Tetracyclines . A Partial Syntheis of Tetracycline From Anhydroaureomycin. J Am. Chem. Soc. 1962;84:2271-2272.

Singer et al., Catalytic, Enantioselective Dienolate Additions to Aldehydes: Preparation of Optically Active Acetoacetate Aldol Adducts. J. Am. Chem. Soc. 1995;117:12360-12361.

Stephens et al., 6-Deoxytetracyclines. IV. Preparation, c-6 Stereochemistry, and Reactions. J. Am. Chem. Soc. 1963;85:2643-2652.

Stephens et al., Terramycin. VIII. Structure of Aureomycin and Terramycin. J. Am. Chem. Soc. 1952;74: 4976-77.

Stephens et al., The Structure of Aureomycin. J. Am. Chem. Soc. 1954;76:3568-75.

Stevens et al., Degradation of Quaternary Ammonium Salts. Part I. J. Chem. Soc. 1928: 3193-3197.

Stevens, Degradation of Quaternary Ammonium Salts. Part II. J Chem. Soc. 1930:2107-2125.

Still et al., Rapid Chromatographic Technique for Preparative Separations With Moderate Resolution. J. Org. Chem. 1978;43:2923-2925.

Stork et al., 3-Benzyloxyisoxazole System in Construction of Tetracyclines. J Am Chem Soc. 1978;100(11):3609-11.

Stork et al., Stereocontrolled Synthesis of (±)-12a-Deoxytetracycline. J. Am. Chem. Soc. 1996;118:5304-5305.

Strohl, Biochemical Engineering of Natural Product Biosynthesis Pathways. Metabolic Engineering. 2001;3:4-14.

Sum et al., Glycylcylines. 1. A New Generation of Potent Antibacterial Agents Through Modification of (-Aminotetracyclines. J. Med. Chem. 1994;37:184-188.

Sum et al., Recent developments in tetracycline antibiotics. Curr Pharm Des. Apr. 1998;4(2):119-32.

Sum et al., Synthesis and Structure—Activity Relationship of Novel Glycylcycline Derivatives Leading to the Discovery of Gar-936. Bioorg. Med. Chem. Lett. 1999;9:1459-1462.

Sum et al., Synthesis of Novel Tetracycline Derivatives With Substitution at the C-8 Position. Tetrahedron Lett. 1994;35:1835-1836.

Sum et al., The Design, Synthesis and Structure-Activity Relationships of Novel Glycylcycline Derivatives: a New Generation of Tetracycline Antibacterial Agents. 24th National Medicinal Chemistry Symposium Utah. 1994; 83:119. (Abstract Only).

(56) References Cited

OTHER PUBLICATIONS

Sun et al., A robust platform for the synthesis of new tetracycline antibiotics. J Am Chem Soc. Dec. 31, 2008;130(52):17913-27.
Suzuki et al., Palladium(0) Catalyzed Reaction of 1,3-Diene Epoxides. A Useful Method for the Site Specific Oxygenation of 1,3-Dienes. J. Am. Chem. Soc. 1979;101:1623-1625.
Takano et al., Enantiodivergent Preparation of Chiral 2,5-Cyclohexadienone Synthons. Synthesis. 1993;(7): 948-50.
Tatsuta et al., The First Total Synthesis of Natural (−)- Tetracycline. Chem. Lett. 2000:646-47.
Tatsuta , Total synthesis and development of bioactive natural products. Proc Jpn Acad Ser B Phys Biol Sci. 2008;84(4):87-106.
Tatsuta et al., Total syntheses of bioactive natural products from carbohydrates. Sci Tech Adv Mater. 2006;7:397-410.
Tatsuta et al., Total syntheses of polyketide-derived bioactive natural products. Chem Rec. 2006;6(4):217-33.
Tatsuta et al., Total synthesis of selected bioactive natural products: illustration of strategy and design. Chem Rev. Dec. 2005;105(12):4707-29.
Taylor, Reactions of Epoxides With Ester, Ketone and Amide Enolates. Tetrahedron. 2000;56:1149-1163.
Testa et al., In Vitro and In Vivo Antibacterial Activities of the Glycylcyclines, a New Class of Semisynthetic Tetracyclines. Antimicrob. Agents Chemother. 1993;37:2270-2277.
Tolchin et al., Synthesizing New Antibiotics. Drug Discov & Develop: Reed Life Science News. Apr. 14, 2005.
Tovar et al., Identification and Nucleotide Sequence of the Class E tet Regulatory Elements and Operator and Inducer Binding of the Encoded Purified Tet Repressor. Mol. Gen. Genet. 1988;215:76-80.
Travis, Receiving the Antibiotic Miracle? Science. 1994;264:360-362.
Tymiak et al., Dactylocyclines, Novel Tetracycline Derivatives Produced by a *Dactylosporangium* sp. J. Antibiotics. 1992;45:1899-1906.
Tymiak et al., Dactylocyclines: Novel Tetracyclines Glycosides Active Against Tetracycline-Resistant Bacteria. J. Org. Chem. 1993;58:536-537.
Verma et al., Antibiotic and non-antibiotic tetracycline patents: 2002-2007. Expert Opin Thera Pat. 2008;18(1):69-82.
Vishwakarma et al., (±)-trans-2-(Phenylsulfonyl)-3-Phenyloxaziridine. Org Syntheses. 1988;66:203.
Vu et al., New Functionalized Alkenylmagnesium Reagents Bearing an Oxygen Function in the I3-Position. Preparation and Reaction of 5-Magnesiated-1,3-Dioxin-4-One Derivatives. Tetrehedron Lett. 2001;42:6847-6850.
Vyas et al., A Short, Efficient Total Synthesis of (±) Acivicin and (±) Bromo-Acivicin. Tetrahedron Lett. 1984;25:487-490.
Wasserman et al., On the Total Synthesis of tetracycline. J. Am. Chem. Soc. 1986;108:4237-4238.
Wang et al., Identification of OxyE as an ancillary oxygenase during tetracycline biosynthesis. Chembiochem. Jun. 15, 2009;10(9):1544-50.
Weiss et al., Susceptibility of Enterococci, Methicillin—Resistant *Staphylococcus aureus* and *Steptococcus pneumoniae* to the Glycylcyclines. J Antimicrob. Agents Chemother. 1995;36:225-230.
Wells et al., Dactylocyclines, novel Tetracycline Derivatives Produced by a *Dactylosporangium* sp. Antibiotics. 1992;45:1892-1898.
White et al., Stereochemical Transcription Via the Intramolecular Diels-Alder Reaction. Enantioselective Synthesis of (+)-Pillaromycinone. J. Org. Chem. 1986;51:1150-1152.
Wilson et al., Selective Reduction of 2-Ene-1,4-diones and 2-En-1-ones with Di-ibutylaluminium Hydride. J Chem Soc Chem Commun 1970;(4):213-14.
Wissmann et at., Tetracyclin-Resistenzdeterminanten: Machanismen der Resistenz und Regulation ihrer Epression. Forum Mikrobiol. 1998:292-299.
Woodward, The Total Synthesis of a Tetracycline. Pure Appl Chem. 1963;6:561-573.
Wu et al., [A new era for organic synthesis- Highlights of the recent progress.] Progress in Chemistry. 2007;19(1):6-34. Chinese. Translated copy from Front Chem China, 2007, 2(3): 277-64.
Yarnell et al., Synthetic Route to Tetracyclines: Modular, flexible synthesis yields structurally diverse antibiotics. Chem & Eng News. 2005;83(16):9.
Yersin et al., Polarized Emission of [Ru(bpy)$_3$] (PF$_5$)$_2$Single Crystals. J. Am. Chem. Soc. 1983;48: 4155-4156.
Zakeri et al., Chemical biology of tetracycline antibiotics. Biochem Cell Biol. Apr. 2008;86(2):124-36.
Zhang et al., Engineered biosynthesis of a novel amidated polyketide, using the malonamyl-specific initiation module from the oxytetracycline polyketide synthase. Appl Environ Microbiol. Apr. 2006;72(4):2573-80.
Zhao et al., Nucleotide Sequence Analysis of the Class G Tetracycline Resistance Determinant From *Vibrio anguillarm*. Microbiol Immunol. 1992;36:1051-1060.

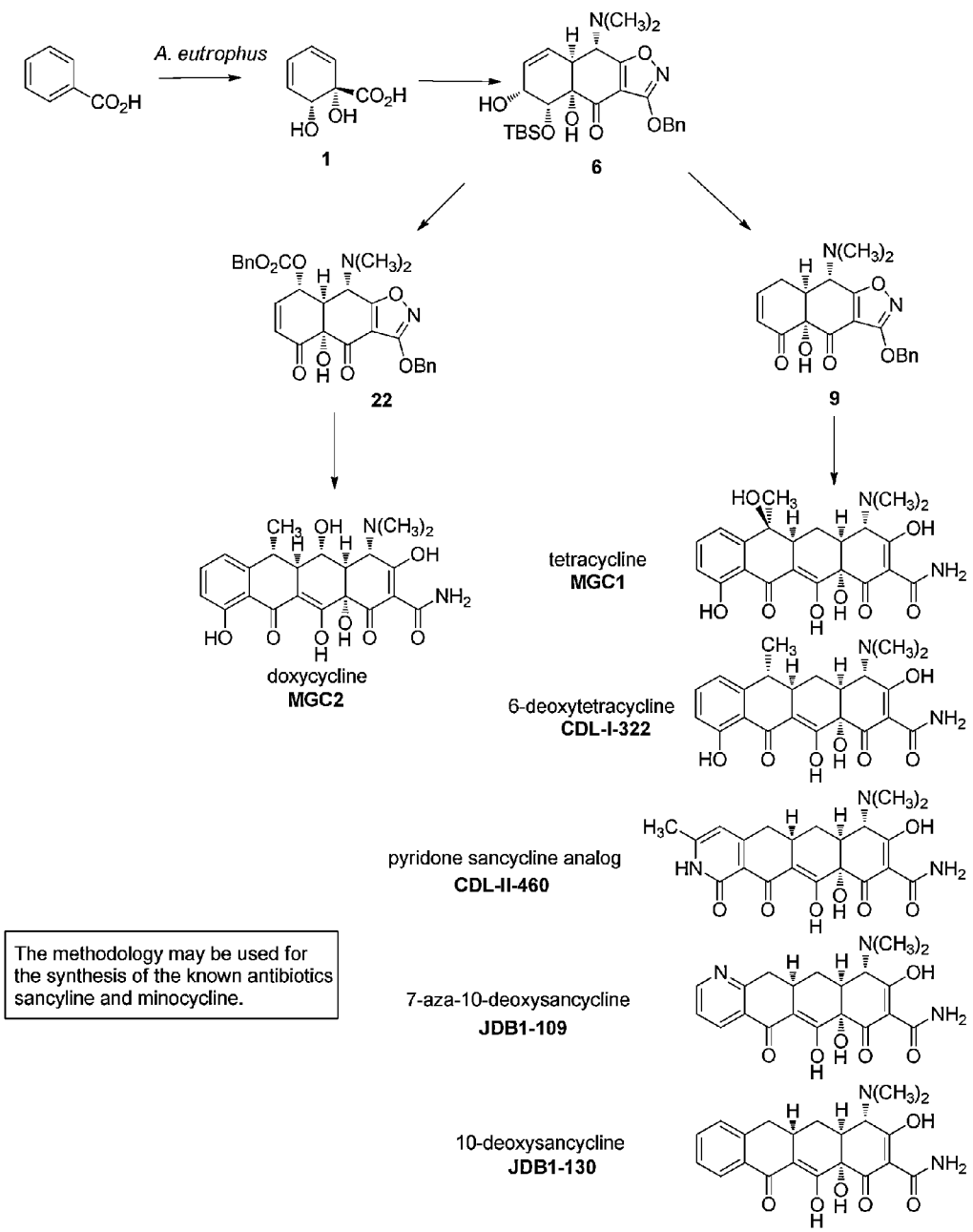

Total Synthesis of Tetracycline

Total Synthesis of Doxycycline

Figure 4
Synthesis of Isoxazole 4

First Generation:

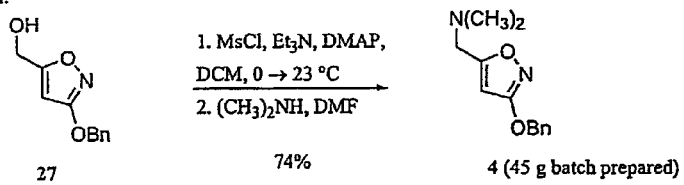

27: prepared in 3 steps from dimethylacetylene dicarboxylate and *N*-hydroxyurea
*Synthesis* 1985, 1100-1104.
*Eur. J. Org. Chem.* 1998, 473-479.

Second Generation:

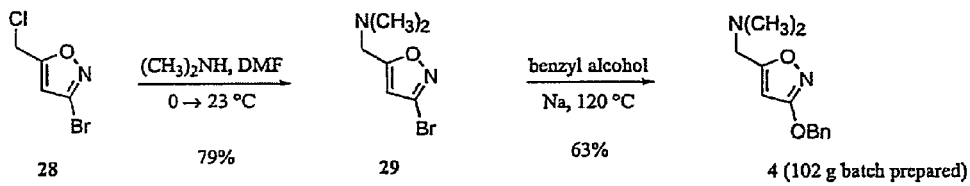

28: prepared in 2 steps from glyoxylic acid and 2,3-dichloro-1-propene
*Synth. Commun.* 1992, *22*, 1939-1948.
*Tetrahedron Lett.* 1984, *25*, 487-490.

Figure 5
Synthesis of Benzocyclobutenol 11:

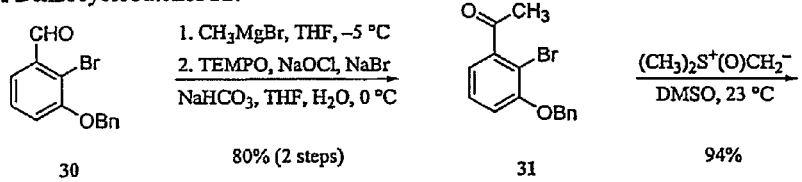

30 prepared in 2 steps from 3-(benzyloxy)benzyl alcohol
*J. Org. Chem.* 1994, *59*, 6703-6709.

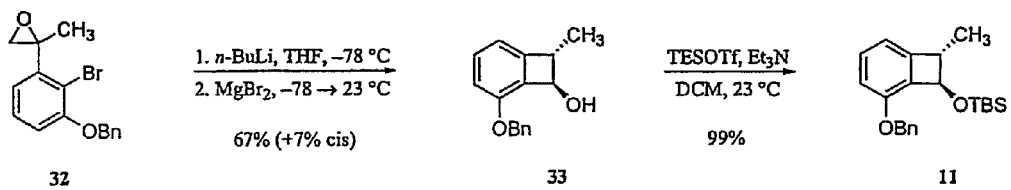

cyclization from 32 to 33 based on: (a) Akgün, E.; Glinski, M. B.; Dhawan, K. L.; Durst, T. *J. Org. Chem.* 1981, *46*, 2730.
(b) Dhawan, K. L.; Gowland, B. D.; Durst, T. *J. Org. Chem.* 1980, *45*, 922.

Figure 6
Selected Analogs Accessible by our Modular Synthesis

Paradigm for Antibiotic Activity of the Tetracyclines

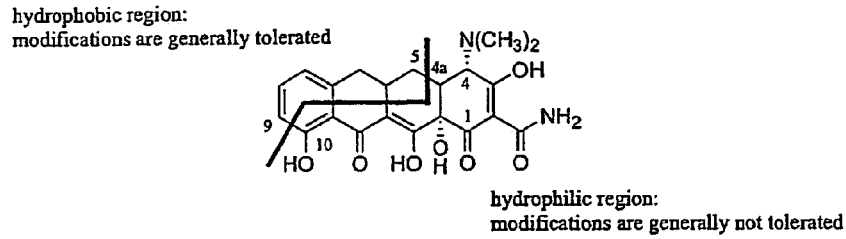

Summary of Targeted "Dicyclines"

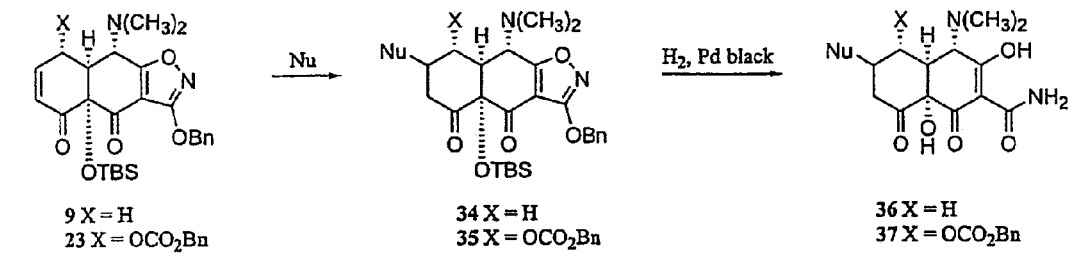

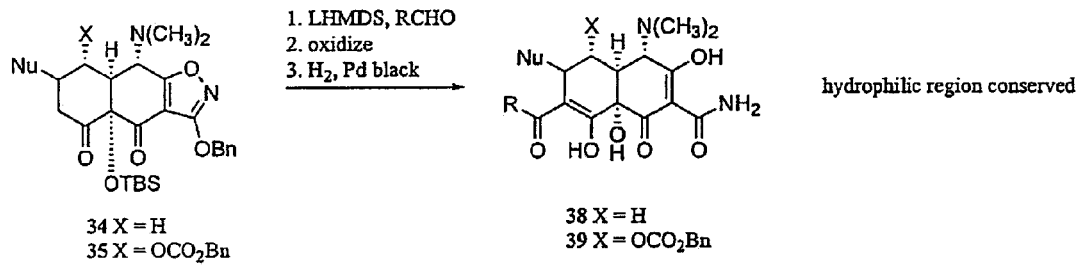

Scope:
Nu = any soft alkyl, aryl, vinyl, or heterocyclic nucleophile. For example alkyl and aryl cuprates and Grignard reagents.
R = any alkyl, aryl, or heterocyclic structure. Basically anything that does not have acidic protons.

Compounds Prepared:

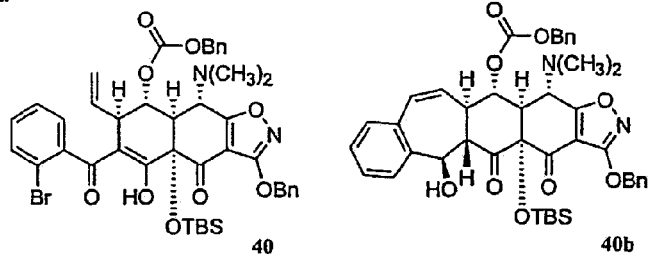

Figure 7
Summary of Targeted "Tricyclines"

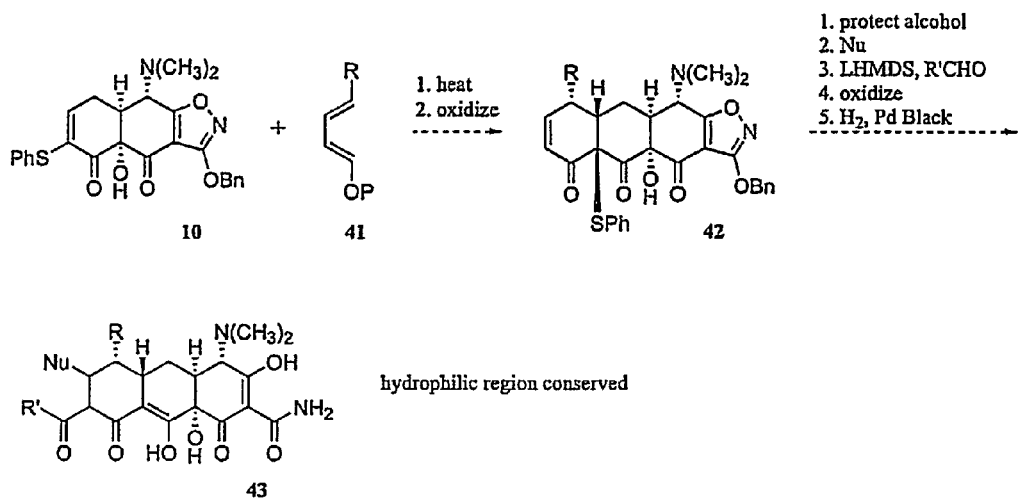

Scope:
Nu = any soft alkyl, aryl, vinyl, or heterocyclic nucleophile. For example alkyl and aryl cuprates and Grignard reagents.
R = sterically non-remanding alkyl or substituted group. Aryl less reasonable.
R' = any alkyl, aryl, or heterocyclic structure. Basically anything that does not have acidic protons.

Figure 8
Summary of Targeted "Pentacyclines"

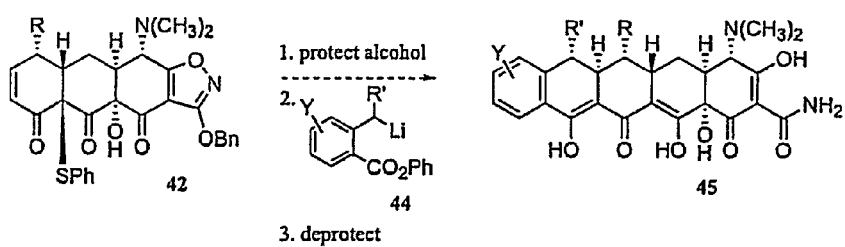

Scope:
Same as other Michael-Dieckmann reactions.

Summary of Targeted "Bridged-Pentacyclines"

Scope:
Same as other Michael-Dieckmann reactions.

Synthesized Compounds as Potential Analog Platforms

Total Synthesis of a Pyridone Sancycline Analog

Total Synthesis of 6-Deoxytetracycline 6-deoxycycline, 8% from benzoic acid in 14 steps (the first 10 steps are identical to the first 10 steps of the tetracycline total synthesis)

Figure 13
A. Synthesis of 7-Aza-10-dexoysancycline
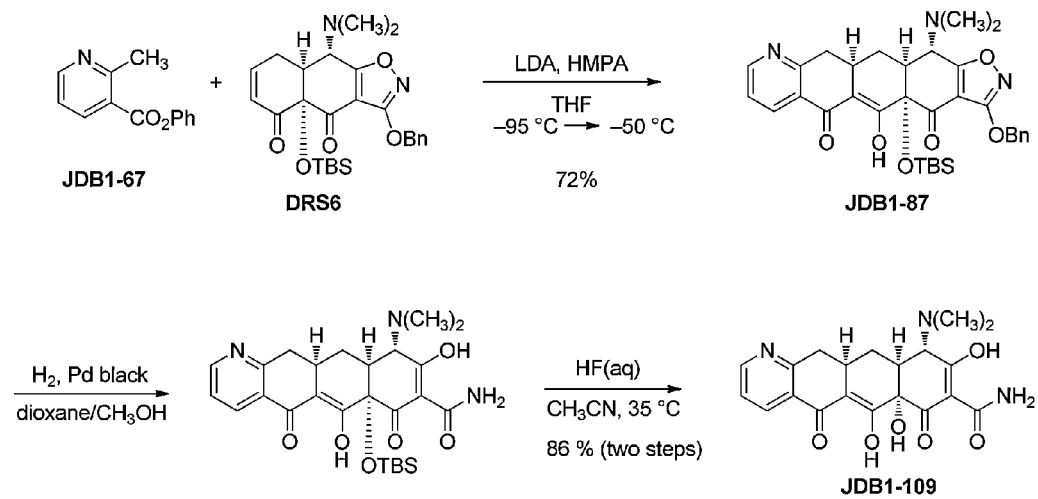
B. Synthesis of 10-Deoxysancycline
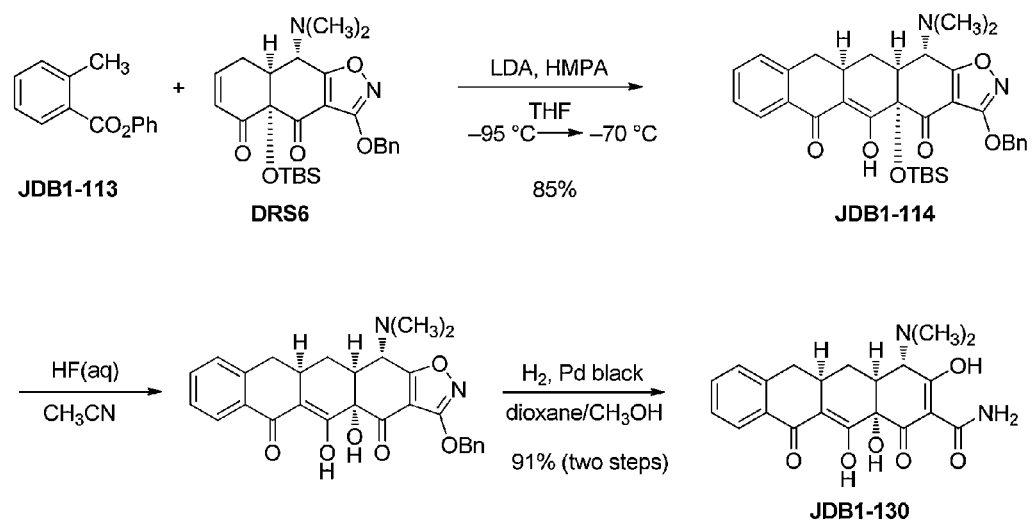

Figure 14A
Representative Structures
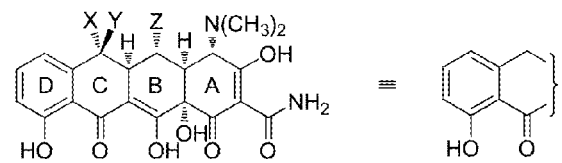
D-ring modifications
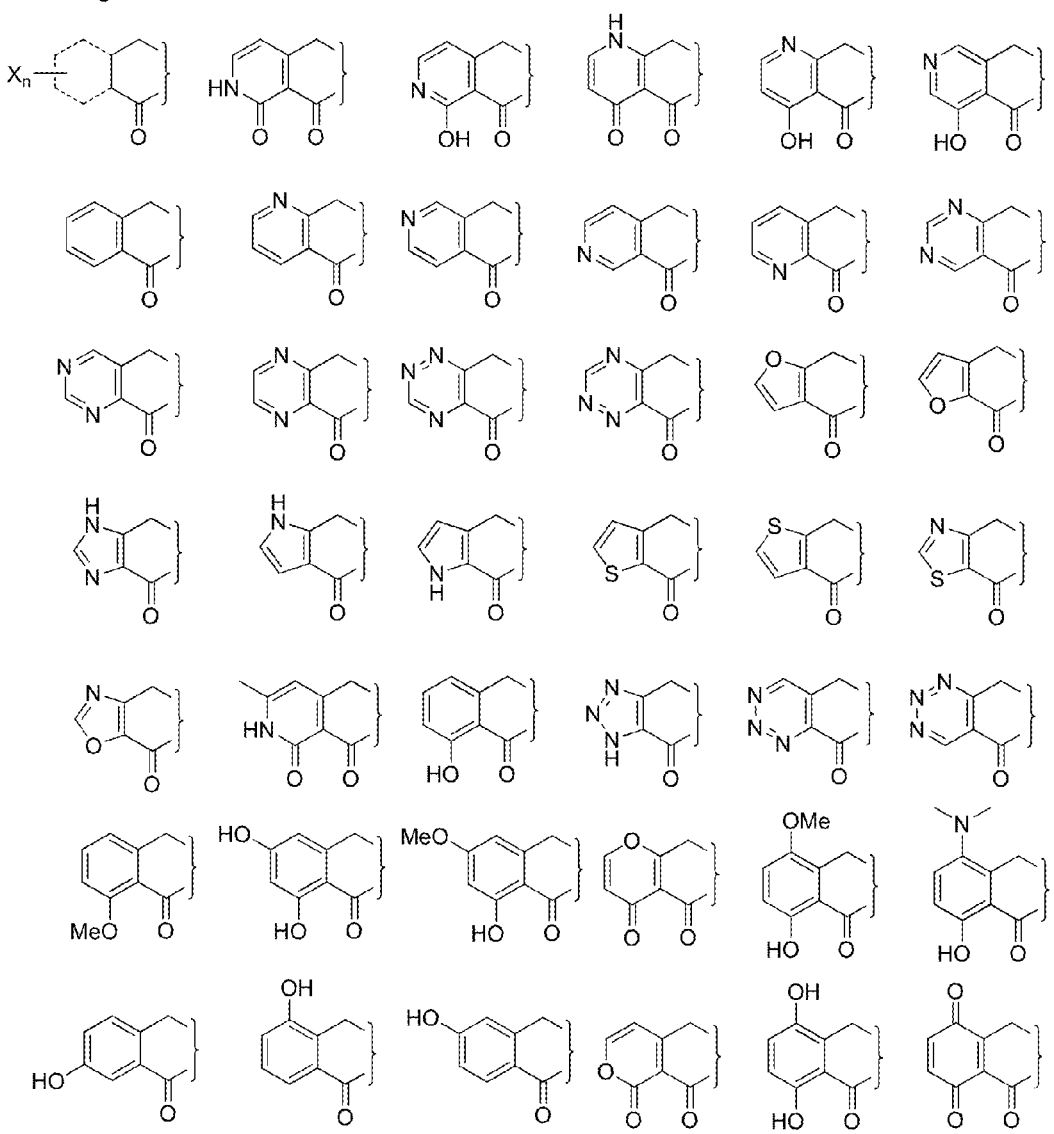

Representative Structures penta- and polycyclines:

R = H, simple alkyl, branched alkyl, aryl, heteroaryl, arylalkyl.

R = H, simple alkyl, branched alkyl, aryl, heteroaryl, arylalkyl.

**Alternative Sequences to AB Enone Precursors from 1*S*,2*R*-*cis*-Dihydroxy Benzoic Acid**
A.
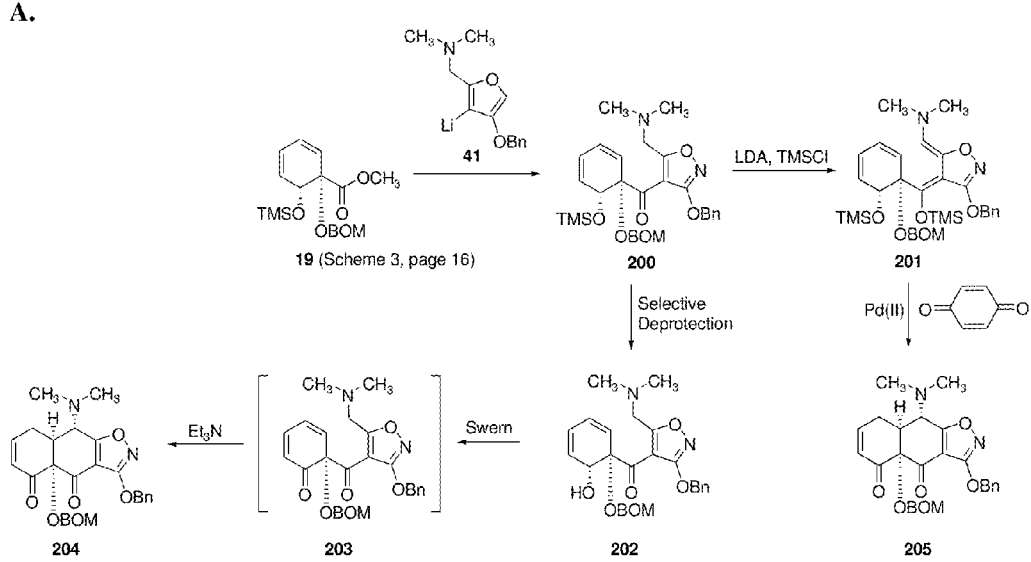
B.
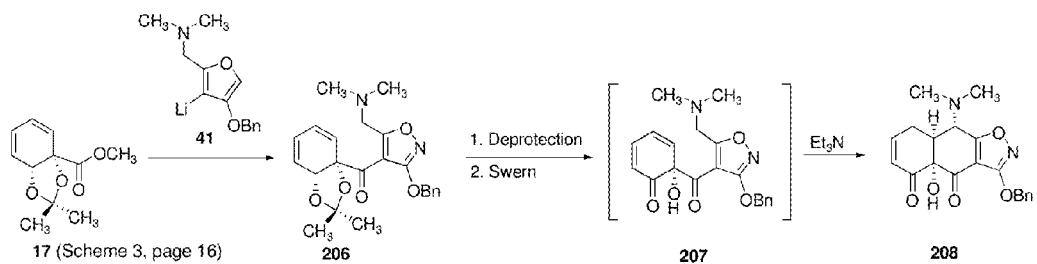
C.
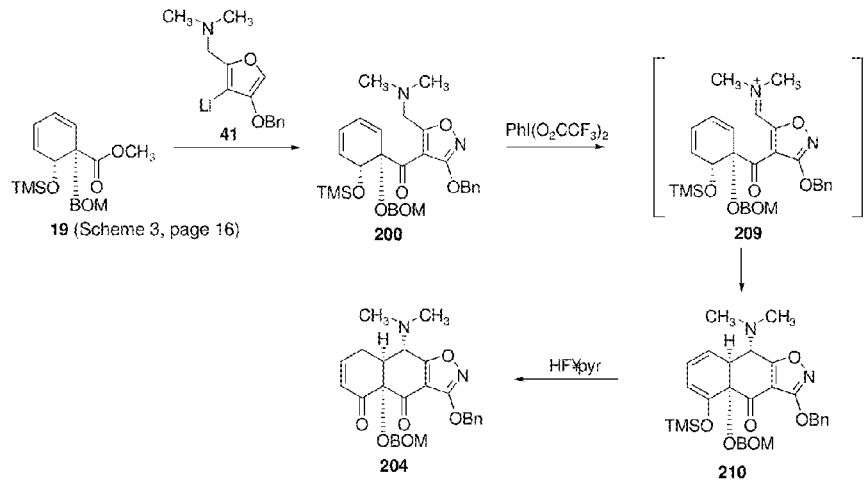
Figure 22

New Routes to AB Precursors That Do Not Involve Microbial Dihydroxylation of Benzoic Acid
A.
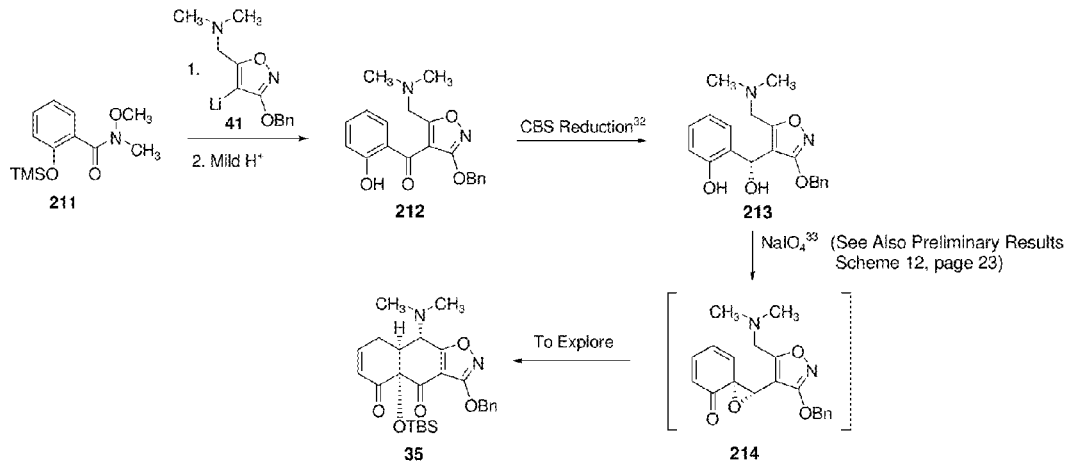
B.
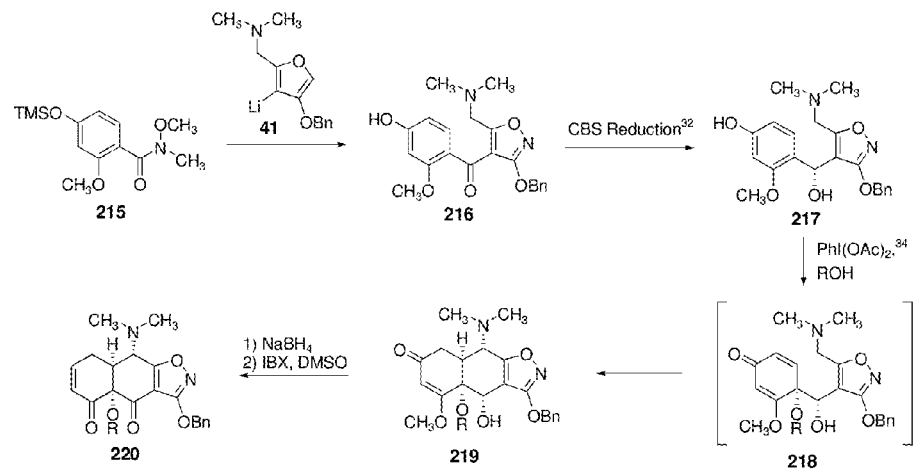
C.
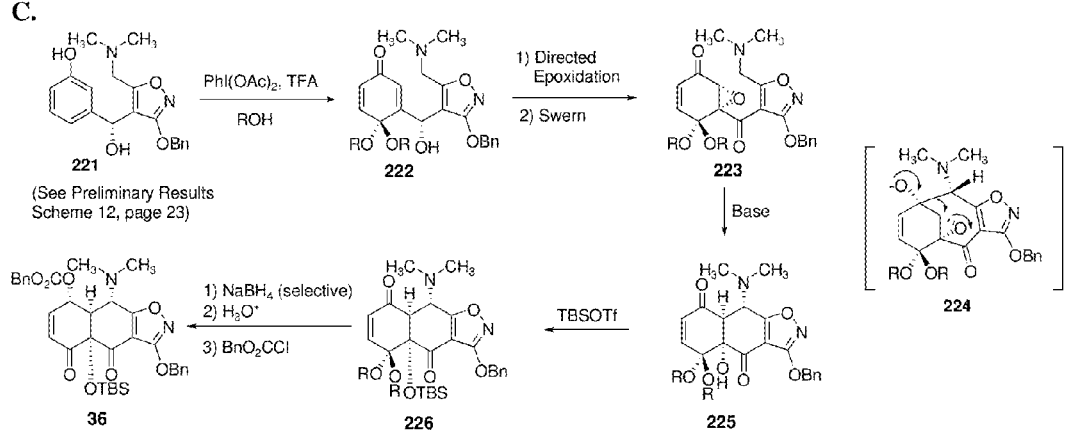
Figure 23

SYNTHESIS OF TETRACYCLINES AND ANALOGUES THEREOF

RELATED APPLICATIONS

The present application is a divisional of U.S. Ser. No. 11/133,789, filed May 20, 2005, which claims priority under 35 U.S.C. §119(e) to U.S. provisional patent applications, U.S. Ser. No. 60/660,947, filed Mar. 11, 2005, and U.S. Ser. No. 60/573,623, filed May 21, 2004, each of which is incorporated herein by reference.

GOVERNMENT SUPPORT

The work described herein was supported, in part, by grants from the National Institutes of Health (R01 AI48825) and the National Science Foundation (predoctoral fellowship R10964). The United States government has certain rights in the invention.

BACKGROUND OF THE INVENTION

The tetracyclines are broad spectrum anti-microbial agents that are widely used in human and veterinary medicine (Schappinger et al., "Tetracyclines: Antibiotic Action, Uptake, and Resistance Mechanisms" *Arch. Microbiol.* 165: 359-69, 1996; Mitscher, *Medicinal Research Series*, Vol. 9, The Chemistry of the Tetracycline Antibiotics, Marcel Dekker Inc. New York, 1978). The total production of tetracyclines by fermentation or semi-synthesis is measured in the thousands of metric tons per year. The first tetracycline, chlorotetracycline (1) (Aureomycin™) was isolated from the soil bacterium *Streptomyces aureofaciens* by Lederle Laboratories (Wyeth-Ayerst Research) in the 1945 (Duggar, *Ann. N.Y. Acad. Sci.* 51:177-181, 1948; Duggar, Aureomycin and Preparation of Some, U.S. Pat. No. 2,482,055, 1949; incorporated herein by reference). Oxytetracycline (2) was isolated soon after from *S. rimosus* by scientists at Pfizer Laboratories (Finlay et al. *Science* 111:85, 1950). The structures of chlorotetracycline and oxytetracycline were elucidated by scientists at Pfizer in collaboration with R. B. Woodward and co-workers at Harvard University (Hochstein et al. *J. Am. Chem. Soc.* 74:3708-3709, 1952; Hochstein et al. *J. Am. Chem. Soc.* 75:5455-75, 1953; Stephens et al. *J. Am. Chem. Soc.* 74:4976-77, 1952; Stephens et al. *J. Am. Chem. Soc.* 76:3568-75, 1954). Tetracycline (3) was later prepared by the hydrogenolysis of chlorotetracycline and was found to retain the anti-microbial activity of chlorotetracycline and oxytetracycline and had increased stability (Boothe et al. *J. Am. Chem. Soc.* 75:4621, 1953; Conover et al. *J. Am. Chem. Soc.* 75:4622-23, 1953). Tetracycline was later found to be a natural product of *S. aureofaciens, S. viridofaciens,* and *S. rimosus*.

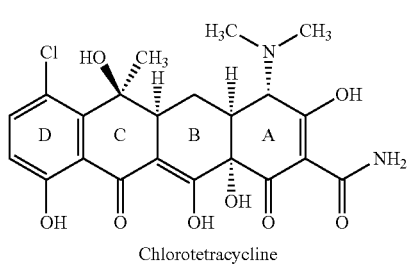

Chlorotetracycline (1)

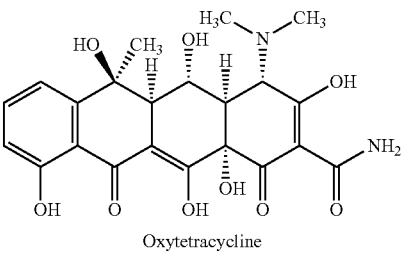

Oxytetracycline (2)

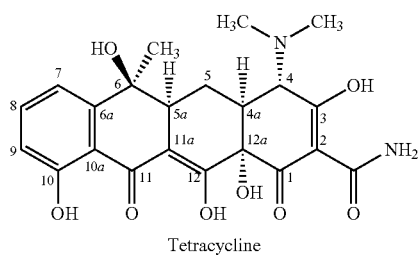

Tetracycline (3)

The primary tetracyclines of clinical importance today include tetracycline (3) (Boothe et al. *J. Am. Chem. Soc.* 75:4621, 1953), oxytetracycline (2, Terramycin™) (Finlay et al. *Science* 111:85, 1950), doxycycline (Stephens et al. *J. Am. Chem. Soc.* 85:2643, 1963), and minocycline (Martell et al. *J. Med. Chem.* 10:44, 1967; Martell et al. *J. Med. Chem.* 10:359, 1967). The tetracyclines exert their anti-microbial activity by inhibition of bacterial protein synthesis (Bentley and O'Hanlon, Eds., *Anti-Infectives: Recent Advances in Chemistry and Structure-Activity Relationships* The Royal Society of Chemistry: Cambridge, UK, 1997). Most tetracyclines are bacteriostatic rather than bactericidal (Rasmussen et al. *Antimicrob. Agents Chemother.* 35:2306-11, 1991; Primrose and Wardlaw, Ed. "The Bacteriostatic and Bacteriocidal Action of Antibiotics" *Sourcebook of Experiments for the Teaching of Microbiology* Society for General Microbiology, Academic Press Ltd., London, 1982). It has been proposed that after tetracycline passes through the cytoplasmic membrane of a bacterium it chelates $Mg^{+2}$, and this tetracycline-$Mg^{+2}$ complex binds the 30S subunit of the bacterial ribosome (Goldman et al. *Biochemistry* 22:359-368, 1983). Binding of the complex to the ribosome inhibits the binding of aminoacyl-tRNAs, resulting in inhibition of protein synthesis (Wissmann et al. *Forum Mikrobiol.* 292-99, 1998; Epe et al. *EMBO J.* 3:121-26, 1984). Tetracyclines have also been found to bind to the 40S subunit of eukaryotic ribosome; however, they do not achieve sufficient concentrations in eukaryotic cells to affect protein synthesis because they are not actively transported in eukaryotic cells (Epe et al. *FEBS Lett.* 213:443-47, 1987).

Structure-activity relationships for the tetracycline antibiotics have been determined empirically from 50 years of semi-synthetic modification of the parent structure (Sum et al. *Curr. Pharm. Design* 4:119-32, 1998). Permutations with the upper left-hand portion of the natural product, also known as the hydrophobic domain, have provided new therapeutically active agents, while modifications of the polar hydrophobic domain result in a loss of activity. However, semi-synthesis by its very nature has limited the number of tetracycline analogs that can be prepared and studied.

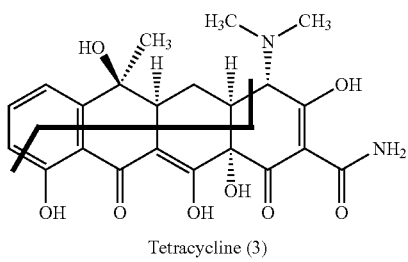 [SMILES: CN(C)[C@@H]1C(O)=C(C(N)=O)C(=O)[C@@]2(O)C(O)=C3C(=O)c4c(O)cccc4[C@@](C)(O)[C@H]3C[C@@H]12]

Tetracycline (3)

The tetracyclines are composed of four linearly fused six-membered rings with a high density of polar functionality and stereochemical complexity. In 1962, Woodward and co-workers reported the first total synthesis of racemic 6-desmethyl-6-deoxytetracycline (sancycline, 4), the simplest biologically active tetracycline (Conover et al. *J. Am. Chem. Soc.* 84:3222-24, 1962). The synthetic route was a remarkable achievement for the time and proceeded by the stepwise construction of the rings in a linear sequence of 22 steps (overall yield ~0.003%). The first enantioselective synthesis of (−)-tetracycline (3) from the A-ring precursor D-glucosamine (34 steps, 0.002% overall yield) was reported by Tatsuda and co-workers in 2000 (Tatsuta et al. *Chem. Lett.* 646-47, 2000). Other approaches to the synthesis of tetracycline antibiotics, which have also proceeded by the stepwise assembly of the ABCD ring system beginning with D or CD precursors, include the Shemyakin synthesis of (±)-12a-deoxy-5a,6-anhydrotetracycline (Gurevich et al. *Tetrahedron Lett.* 8:131, 1967; incorporated herein by reference) and the Muxfeldt synthesis of (±)-5-oxytetracycline (terramycin, 22 steps, 0.06% yield) (Muxfeldt et al. *J. Am. Chem. Soc.* 101:689, 1979; incorporated herein by reference). Due to the length and poor efficiency of the few existing routes to tetracyclines, which were never designed for synthetic variability, synthesis of tetracycline analogs is still limited.

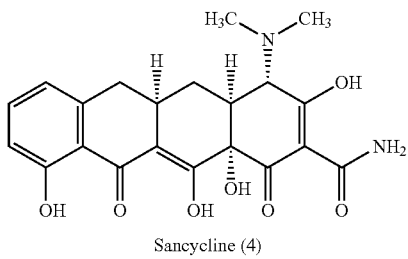 [SMILES: CN(C)[C@@H]1C(O)=C(C(N)=O)C(=O)[C@@]2(O)C(O)=C3C(=O)c4c(O)cccc4C[C@H]3C[C@@H]12]

Sancycline (4)

There remains a need for a practical and efficient synthetic route to tetracycline analogs, which is amenable to the rapid preparation of specific analogs that can be tested for improved antibacterial and potentially antitumor activity. Such a route would allow the preparation of tetracycline analogs which have not been prepared before.

SUMMARY OF THE INVENTION

The present invention centers around novel synthetic approaches for preparing tetracycline analogs. These synthetic approaches are particularly useful in preparing 6-deoxytetracyclines, which are more stable towards acid and base than 6-hydroxytetracyclines. Doxycycline and minocycline, the two most clinically important tetracyclines, as well as tigecycline, an advanced clinical candidate, are members of the 6-deoxytetracycline class.

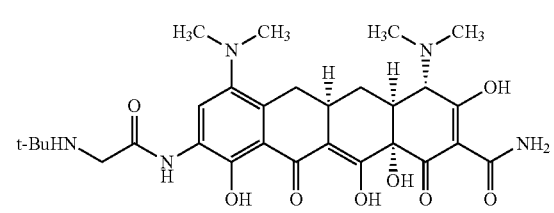

Tigecycline

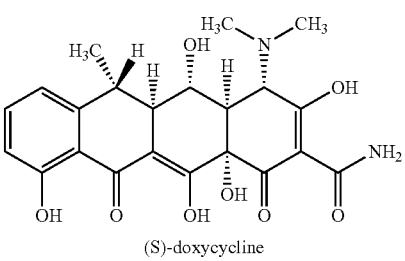

(S)-doxycycline

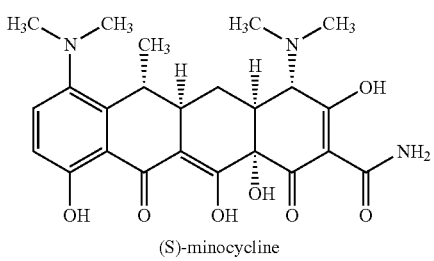

(S)-minocycline

The approaches are also useful in preparing 6-hydroxytetracyclines, pentacyclines, hexacyclines, C5-substituted tetracyclines, C5-unsubstituted tetracyclines, tetracyclines with heterocyclic b-rings, and other tetracycline analogs.

These novel synthetic approaches to tetracycline analogs involve a convergent synthesis of the tetracycline ring system using a highly functionalized chiral enone (5) as a key intermediate. The first approach involves the reaction of the enone with an anion formed by the deprotonation of a toluate (6) or metallation of a benzylic halide as shown below. The deprotonation of a toluate is particularly useful in preparing 6-deoxytetracyclines with or without a C5-substituent. The metallation (e.g., metal-halogen exchange (e.g., lithium-halogen exchange), metal-metalloid exchange (e.g., lithium-metalloid exchange)) is particularly useful in preparing 6-deoxytetracyclines with or without a C5-substituent as well as pentacyclines. Any organometallic reagent may be used in the cyclization process. Particularly useful reagents may include lithium reagents, Grignard reagents, zero-valent metal reagents, and ate complexes. In certain embodiments, milder conditions for the cyclization reaction may be preferred.

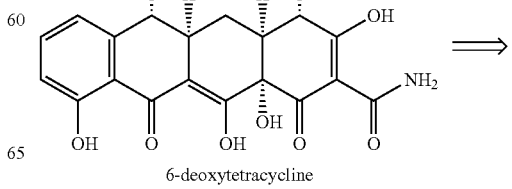

6-deoxytetracycline

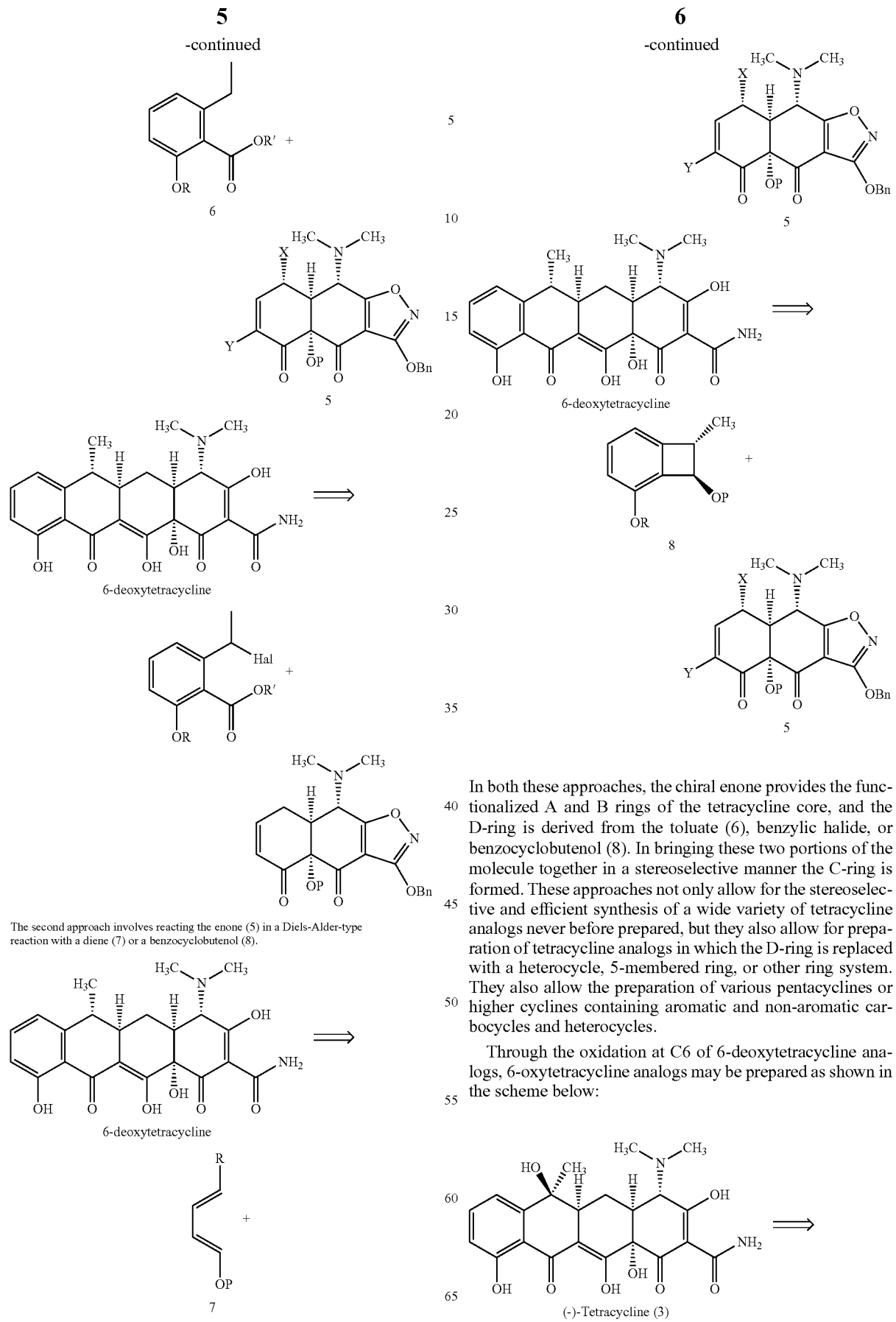

The second approach involves reacting the enone (5) in a Diels-Alder-type reaction with a diene (7) or a benzocyclobutenol (8).

In both these approaches, the chiral enone provides the functionalized A and B rings of the tetracycline core, and the D-ring is derived from the toluate (6), benzylic halide, or benzocyclobutenol (8). In bringing these two portions of the molecule together in a stereoselective manner the C-ring is formed. These approaches not only allow for the stereoselective and efficient synthesis of a wide variety of tetracycline analogs never before prepared, but they also allow for preparation of tetracycline analogs in which the D-ring is replaced with a heterocycle, 5-membered ring, or other ring system. They also allow the preparation of various pentacyclines or higher cyclines containing aromatic and non-aromatic carbocycles and heterocycles.

Through the oxidation at C6 of 6-deoxytetracycline analogs, 6-oxytetracycline analogs may be prepared as shown in the scheme below:

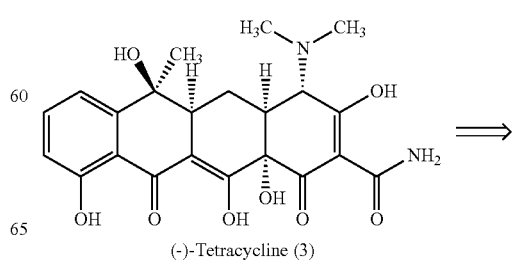

-continued

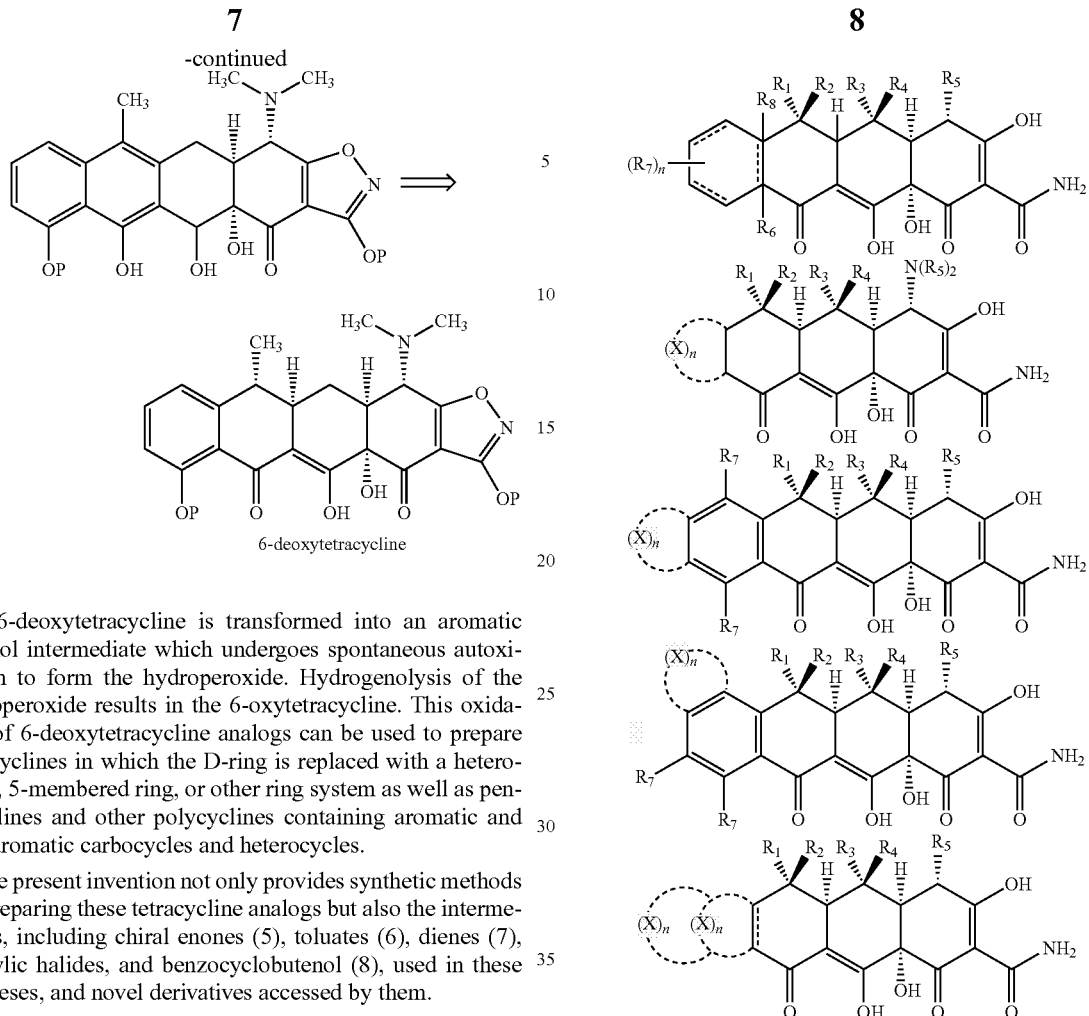

6-deoxytetracycline

The 6-deoxytetracycline is transformed into an aromatic napthol intermediate which undergoes spontaneous autoxidation to form the hydroperoxide. Hydrogenolysis of the hydroperoxide results in the 6-oxytetracycline. This oxidation of 6-deoxytetracycline analogs can be used to prepare tetracyclines in which the D-ring is replaced with a heterocycle, 5-membered ring, or other ring system as well as pentacyclines and other polycyclines containing aromatic and non-aromatic carbocycles and heterocycles.

The present invention not only provides synthetic methods for preparing these tetracycline analogs but also the intermediates, including chiral enones (5), toluates (6), dienes (7), benzylic halides, and benzocyclobutenol (8), used in these syntheses, and novel derivatives accessed by them.

Some of the broad classes of compounds available through these new approaches and considered to be a part of the present invention include tetracyclines and various analogs. Important subclasses of tetracyclines include 6-deoxytetracyclines with or without a C5-hydroxyl group, and 6-hydroxytetracyclines with or without a C5-hydroxyl group. Many of the analogs available through these new approaches have never been synthesized before given the limitations of semi-synthetic approaches and earlier total syntheses. For example, certain substitutions about the D-ring become accessible using the present invention's novel methodologies. In certain classes of compounds of the invention, the D-ring of the tetracyclines analog, which is usually a phenyl ring, is replaced with a heterocyclic moiety, which may be bicyclic or tricyclic. In other classes, the D-ring is replaced with a non-aromatic ring. The size of the D-ring is also not limited to six-membered rings, but instead it may be three-membered, four-membered, five-membered, seven-membered, or larger. In the case of pentacyclines, the five rings may or may not be linear in arrangement. Each of the D- and E-rings may be heterocyclic or carbocyclic, may be aromatic or non-aromatic, and may contain any number of atoms ranging from three to ten atoms. In addition, higher cyclines such as hexacyclines may be prepared. In certain classes, the C-ring may not be fully formed, leading to dicyclines with the A-B fused ring system intact. The compounds of the invention include isomers, stereoisomers, enantiomers, diastereomers, tautomers, protected forms, pro-drugs, salts, and derivatives of any particular compound.

The present invention also includes intermediates useful in the synthesis of compounds of the present invention. These intermediates include chiral enones, toluates, benzylic halides, and benzocyclobutenol. The intermediates includes various substituted forms, isomers, tautomers, stereoisomers, salts, and derivatives thereof.

In another aspect, the present invention provides methods of treatment and pharmaceutical composition including the novel compounds of the present invention. The pharmaceutical compositions may also include a pharmaceutically acceptable excipient. The methods and pharmaceutical compositions may be used to treat any infection including cholera, influenza, bronchitis, acne, malaria, urinary tract infections, sexually transmitted diseases including syphilis and gonorrhea, Legionnaires' disease, Lyme disease, Rocky Mountain spotted fever, Q fever, typhus, bubonic plague, gas gangrene, leptospirosis, whooping cough, and anthrax. In certain embodiments, the infections are caused by tetracycline-resistant organisms. In certain instances, the compounds of the invention exhibit anti-neoplastic or anti-proliferative activity, in which case the compounds may be useful in the treatment of diseases such as cancer, autoimmune diseases, inflammatory diseases, and diabetic retinopathy. The methods and compositions may be used to treat disease in humans and other animals including domesticated animals. Any mode of administration including oral and parenteral administration of the pharmaceutical composition may be used.

Given past work in the synthesis of tetracyclines, the present inventive strategies represent a breakthrough, providing new synthetic routes to tetracyclines and various analogs. The ability to prepare a wide variety of tetracycline analogs and the use of some of these compounds in the treatment of diseases such as cancer and infectious diseases marks an advance not only in synthetic organic chemistry but also in medicine. The tetracycline class of antibiotics has played a major role in the treatment of infectious diseases in human and veterinary medicine for the past 50 years; however, with the high use of these antibiotics over many years resistance has become a major problem. The present invention fortunately allows for the development of tetracycline analogs with activity against tetracycline-resistant organisms. Therefore, the developments described herein will allow the tetracycline class of antibiotics to remain part of a physician's armamentarium against infection diseases.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS),1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of compound in vivo. Due to isotope effects, enzymatic degradation of the deuterated tetracyclines may be slowed thereby increasing the half-life of the compound in vivo. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Tautomers": As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Effective amount": In general, the "effective amount" of an active agent or the microparticles refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a tetracycline analog antibiotic is the amount that results in a sufficient concentration at the site of the infection to kill the microorganism causing the infection (bacteriocidal) or to inhibit the reproduction of such microorganisms (bacteriostatic). In another example, the effective amount of tetracycline analog antibiotic is the amount sufficient to reverse clinicals signs and symptoms of the infection, including fever, redness, warmth, pain, chills, cultures, and pus production.

BRIEF DESCRIPTION OF THE DRAWING

FIG. 4 shows a first and second generation synthesis of isoxazole 4 used in the synthesis of (−)-tetracycline and (−)-doxycycline as shown in FIG. 2.

FIG. 5 shows the synthesis of benzocyclobutenol 11 used in the synthesis of (−)-tetracycline as shown in FIG. 2.

FIG. 6 shows the synthesis of dicyclines. Dicyclines preserve the hydrophilic region thought to be important for the antimicrobial activity of tetracyclines.

FIG. 7 depicts the synthesis of tricyclines via a Diels-Alder reaction with the chiral enone 10 and a diene (41). Tricyclines preserve the hydrophobic region thought to be important for antimicrobial activity.

FIG. 8 shows the synthesis of pentacyclines.

FIG. 13A shows the synthesis of a pyridine analog of sancycline, 7-aza-10-deoxysancycline. FIG. 13B shows the synthesis of 10-deoxysancycline.

FIGS. 14A and 14B show a number of examples of heterocyclines, tetracycline analogs, pentacyclines, and polycyclines potentially accessible via the inventive method.

FIG. 15B depicts a generalized Michael-Dieckmann reaction sequence that forms the C-ring of tetracyclines from the coupling of structurally varied carbanionic D-ring precursors with either of the AB precursors 7 or 8.

FIG. 22 shows alternative sequences to AB enone precursors from 1S,2R-cis-dihydroxybenzoic acid.

FIG. 23 shows novel routes to AB precursors. These routes do not involve the microbial dihydroxylation of benzoic acid.

DETAILED DESCRIPTION OF CERTAIN PREFERRED EMBODIMENTS OF THE INVENTION

Figure 2:
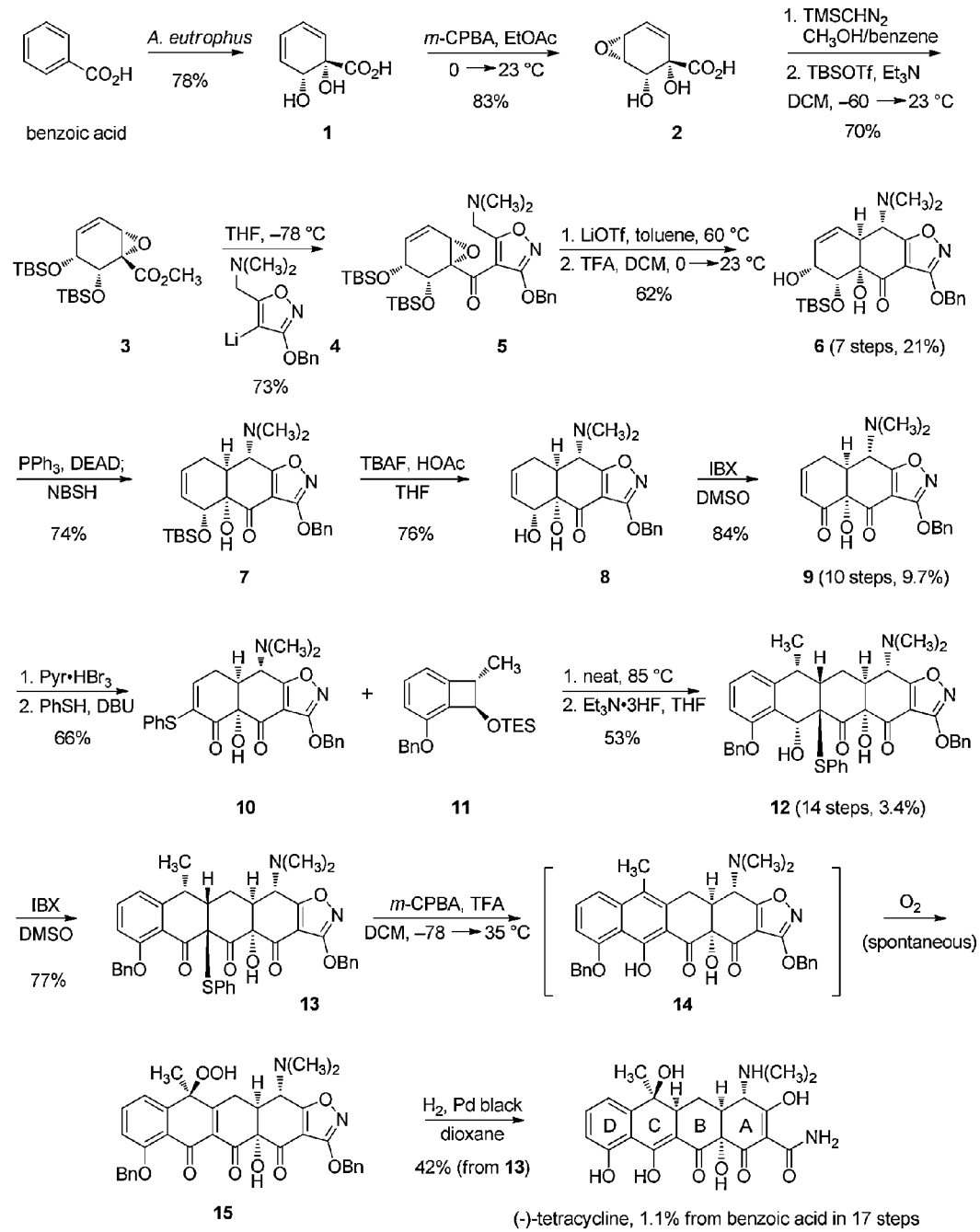
FIG. 2 depicts the total synthesis of (−)-tetracycline starting from benzoic acid and involving an o-quinone dimethide Diels-Alder reaction between the chiral enone 10 and the benzocyclobutenol 11. The overall yield for the 17 step synthesis was 1.1%.
Figure 3:
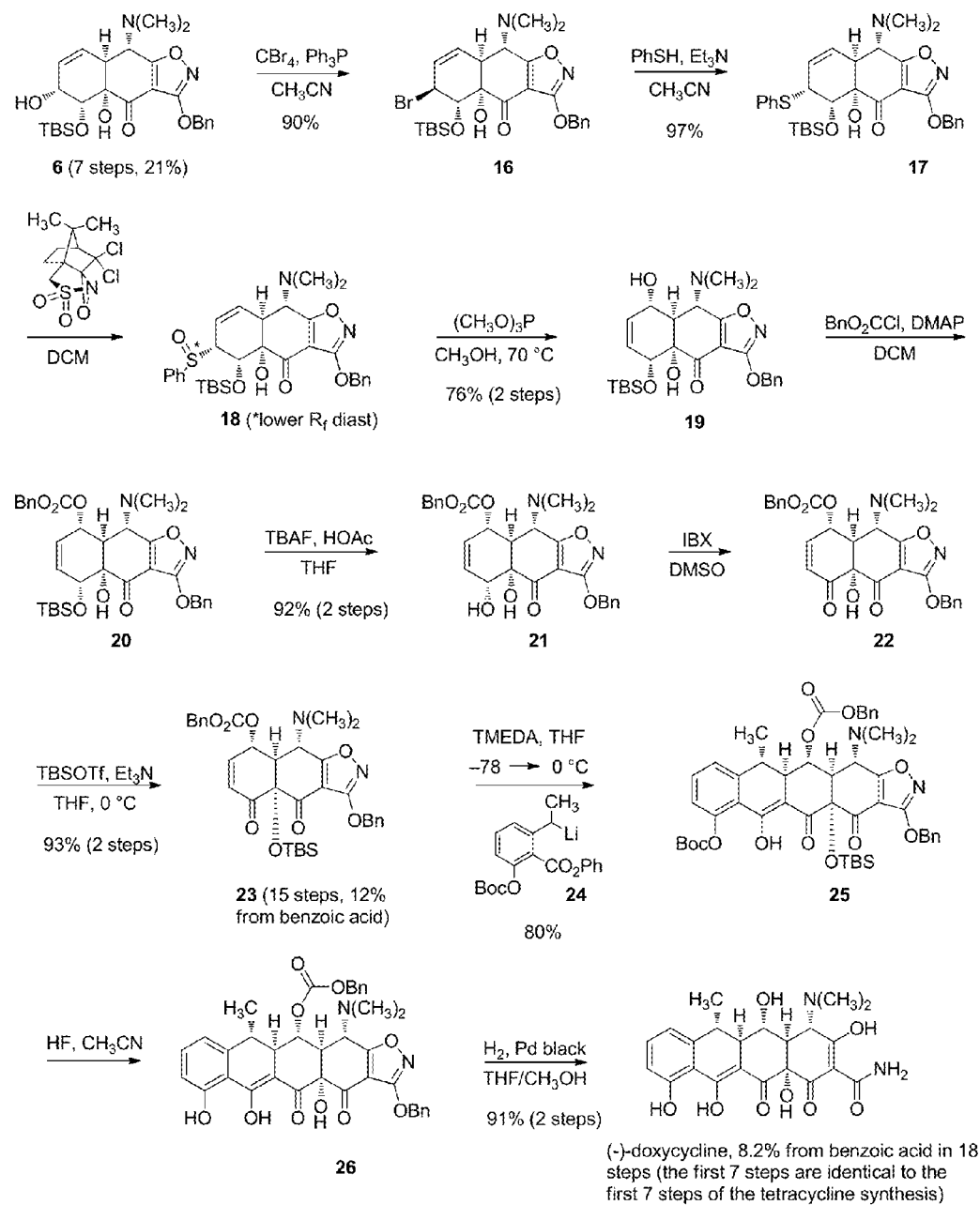
FIG. 3 is the total synthesis of (−)-doxycycline in 18 steps (overall yield 8.2%). The synthesis includes the reaction of the chiral enone 23 with the anion 24 to yield the tetracycline core. The first seven steps are identical to the first seven steps in the synthesis of (−)-tetracycline shown in FIG. 2.
Figure 9:
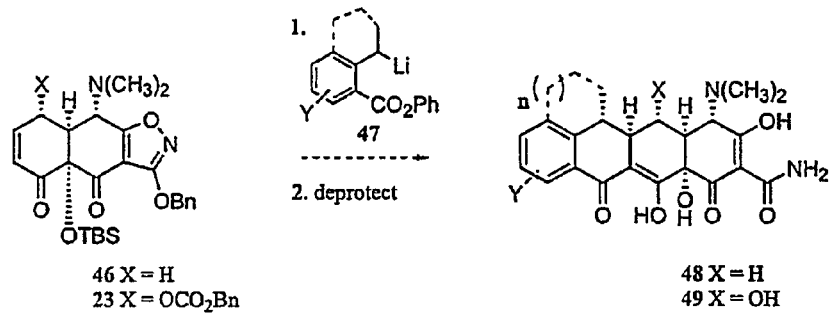
FIG. 9 shows the synthesis of bridge pentacyclines by reacting anion 47 with a chiral enone.
Figure 10:
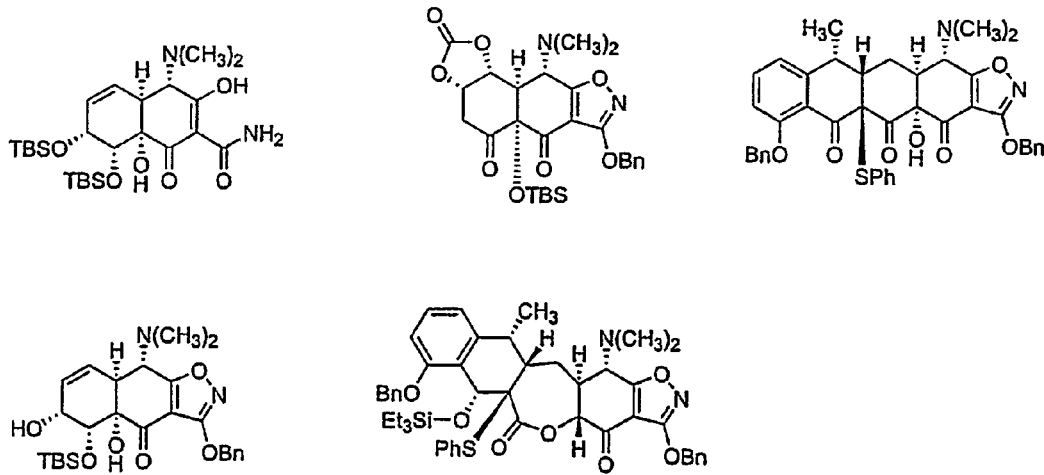
FIG. 10 shows five compounds that may be used as analog platforms for the synthesis of tetracycline analogs.

The present invention provides a strategy for the synthesis of tetracycline analogs via a convergent synthesis using as an intermediate, the highly functionalized chiral enone 9 as shown below:

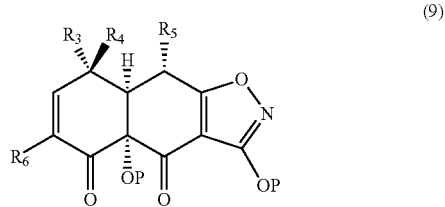

(9)

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; =O; —C(=O)$R_C$; —$CO_2R_C$; —CN; —SCN; —$SR_C$; —$SOR_C$; —$SO_2R_C$; —$NO_2$; —N($R_C$)$_2$; —NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —N($R_D$)$_2$; —NHC(O)$R_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy;

aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_E$; —CN; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, arylthio, —$NO_2$, amino, alkyl amino, and dialkyl amino groups;

P is independently selected from the group consisting of hydrogen or a protecting group. The chiral enone 9 can be reacted with anions of phthalides, anions of toluates, benzocyclobutenole, or dienes to yield tetracycline analogs including heterocyclic tetracyclines, dicyclines, tricyclines, pentacyclines, heterocyclic pentacyclines, polycyclines, and heterocyclic polycyclines. These new compounds are tested for anti-microbial activity against microbes including traditionally tetracycline-sensitive organisms as well as organisms known to be tetracycline-resistant. Compounds found to be bacteriocidal or bacteriostatic are used in formulating pharmaceutical for the treatment of infections in human and veterinary medicine. The compounds are also tested for anti-proliferative activity. Such compounds are useful in the treatment of antiproliferative diseases including cancer, anti-inflammatory diseases, autoimmune diseases, benign neoplasms, and diabetic retinopathy. The inventive approach to the synthesis of tetracycline analogs allows for the efficient synthesis of many compounds never before prepared or available using earlier routes and semi-synthetic techniques.

Compounds

Compounds of the present invention include tetracycline analogs, heterocyclic tetracycline analogs, dicyclines, tricyclines, pentacyclines, heterocylic pentatcyclines, bridged pentacyclines, heterocyclic polycyclines, bridged polycyclines, and other polycyclines. Particularly useful compounds of the present invention include those with biological activity. In certain embodiments, the compounds of the invention exhibit antimicrobial activity. For example, the compound may have a mean inhibitory concentration, with respect to a particular bacteria, of less than 50 µg/mL, preferably less than 25 µg/mL, more preferably less than 5 µg/mL, and most preferably less than 1 µg/mL. For example, infection caused by the following organisms may be treated with antimicrobial compounds of the invention: Gram-positivives—*Staphylococcus aureus, Streptococcus* Group A, *Streptococcus viridans, Streptococcus pneumoniae*; Gram-negatives—*Neisseria meningitidis, Neisseria gonorrhoeae, Haemophilus influenzae, Escherichia coli, Bacteroides fragilis*, other *Bacteroides*; and Others—*Mycoplasma pneumoniae, Treponema pallidum, Rickettsia*, and *Chlamydia*. In other embodiments, the compounds of the invention exhibit anti-proliferative activity.

In certain embodiments, the tetracycline analogs of the present invention are represented by the formula:

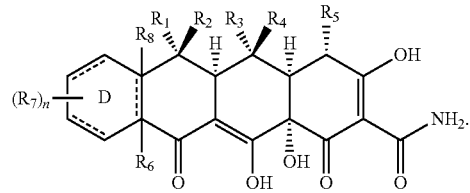

(10)

The D-ring of 10 may include one, two, or three double bonds. In certain embodiments, the D-ring is aromatic. In other embodiments, the D-ring includes only one double bond, and in yet other embodiments, the D-ring includes two double bonds which may or may not be in conjugation. The D-ring may be substituted with various groups $R_7$, $R_6$, and $R_8$ as defined below.

In 10, $R_1$ can be hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —NHC(O)$R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_1$ is hydrogen, In other embodiments, $R_1$ is lower alkyl, alkenyl, or alkynyl. In yet other embodiments, $R_1$ is methyl, ethyl, n-propyl, cyclopropyl, or isopropyl. In still other embodiments $R_1$ is methyl.

$R_2$ may be hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —$N(R_B)_2$; —NHC(O)$R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_2$ is hydrogen. In other embodiments, $R_2$ is hydroxyl or a protected hydroxyl group. In certain embodiments, $R_2$ is alkoxy. In yet other embodiments, $R_2$ is a lower alkyl, alkenyl, or alkynyl group. In certain embodiments, $R_1$ is methyl, and $R_2$ is hydroxyl. In other embodiments, $R_1$ is methyl, and $R_2$ is hydrogen. In certain embodiments, $R_1$ and $R_2$ are taken together to form a carbocyclic or heterocyclic ring system spiro-linked to 10.

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; =O; —C(=O)$R_C$; —$CO_2R_C$; —CN; —SCN; —$SR_C$; —$SOR_C$; —$SO_2R_C$; —$NO_2$; —$N(R_C)_2$; —NHC(O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_3$ is hydrogen. In other embodiments, $R_3$ is a hydroxyl group or a protected hydroxyl group. In yet other embodiments, $R_3$ is alkoxy. In still further embodiments, $R_3$ is lower alkyl, alkenyl, or alkynyl.

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —$C(=O)R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_4$ is hydrogen. In other embodiments, $R_4$ is a hydroxyl group or a protected hydroxyl group. In yet other embodiments, $R_4$ is alkoxy. In still further embodiments, $R_4$ is lower alkyl, alkenyl, or alkynyl. In certain embodiments, both $R_3$ and $R_4$ are hydrogen. In other embodiments, $R_3$ and $R_4$ are taken together to form a carbocyclic or heterocyclic ring system spiro-linked to the B-ring of 10.

$R_5$ may be hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_5$ is amino, alkylamino, or dialkylamino; preferably dimethylamino, diethylamino, methyl(ethyl)amino, dipropylamino, methyl(propyl)amino, or ethyl(propyl)amino. In other embodiments, $R_5$ is hydroxyl, protected hydroxyl, or alkoxy. In yet other embodiments, $R_5$ is sulfhydryl, protected sulhydryl, or alkylthioxy.

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —$C(=O)R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_7$ is hydroxyl, protected hydroxyl, alkoxy, lower alkyl, lower alkenyl, lower alkynyl, or halogen.

$R_6$ and $R_8$ are absent if the dashed line between the carbon atoms which $R_6$ and $R_8$ are attached to represents a bond, or are each selected independently from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, —$NO_2$, amino, alkyl amino, and dialkyl amino groups. In certain embodiments, $R_6$ and $R_8$ are absent. In other embodiments, $R_6$ or $R_8$ is absent.

The variable n is an integer in the range of 0 to 8, inclusive. As will be appreciated by one of skill in the art, when the D-ring is aromatic n is an integer between 0 and 4, preferably between 1 and 3, more preferable between 1 and 2. In certain embodiments, when n is 2, the substituents $R_7$ are in the ortho configuration. In other embodiments, when n is 2, the substituents $R_7$ are in the para configuration. And in yet other embodiments, when n is 2, the substituents $R_7$ are in the meta configuration.

A dashed line in formula 10 may represent a bond or the absence of a bond.

As will be appreciated by one of skill in this art, compounds of formula 10 include derivatives, labeled forms, salts, pro-drugs, isomers, and tautomers thereof. Derivatives include protected forms. Salts include any pharmaceutically acceptable salts including HCl, HBr, HI, acetate, and fatty acid (e.g., lactate, citrate, myristoleate, oleate, valerate) salts. In certain embodiments, the inventive compound exists in zwitterionic form at neutral pH with the $R_5$ being a protonated amino group and the C-3 hydroxyl group deprotonated as shown in formula 10a.

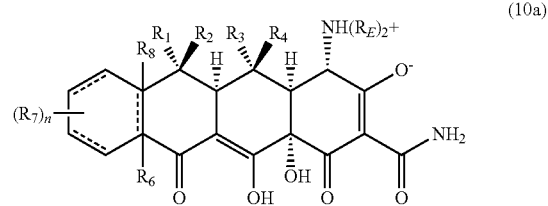
(10a)

Isomers include geometric isomers, diastereomers, and enantiomers. Tautomers include both keto and enol forms of carbonyl moieties as well as various tautomeric forms of substituted and unsubstituted heterocycles. For example, the B-ring as shown in formula 10 includes an enol moiety as drawn, but the enol may exist as the keto form in certain compounds as shown below in formula 10b and 10c:

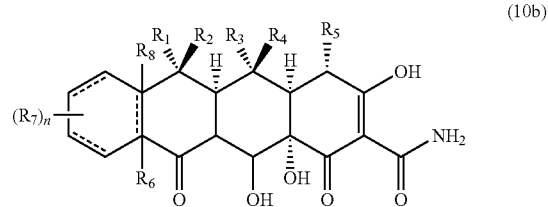
(10b)

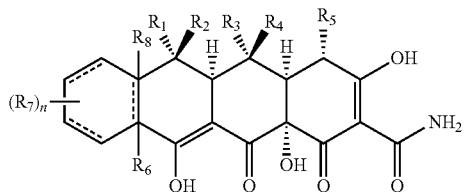

Other tautomeric forms will be appreciated by one of skill in the art and will depend on the substitution pattern of the core ring structure. The formulae drawn are only given as examples and do not in any way represent the full range of tautomers that may exist for a particular compound.

Various subclasses of compounds of the formula 10 which include a substituted or unsubstituted aromatic D-ring are shown below. These subclasses include unsubstituted, monosubstituted, disubstituted, and trisubstituted D-ring.

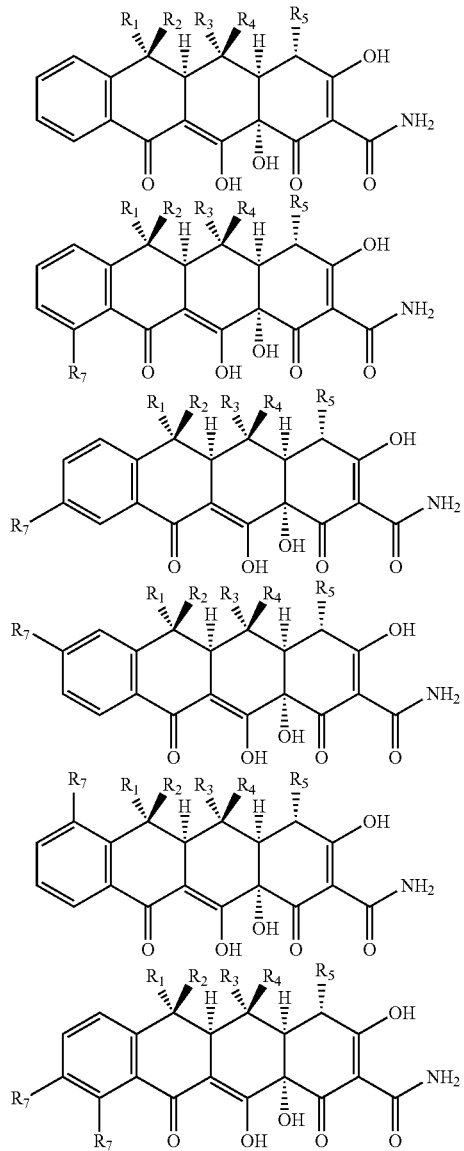

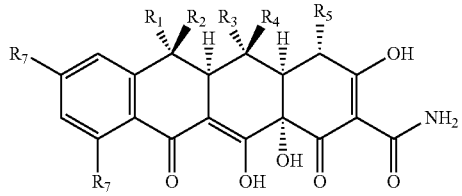

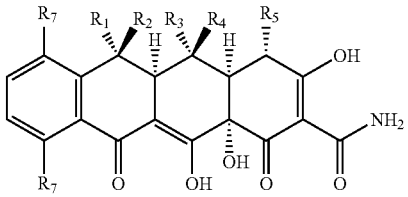

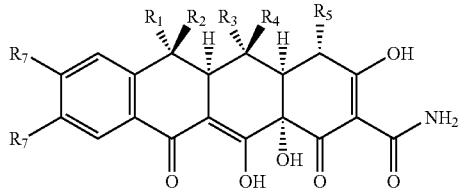

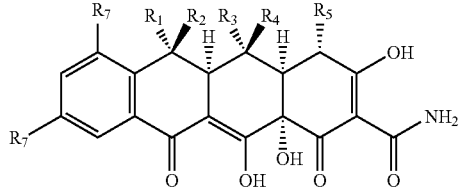

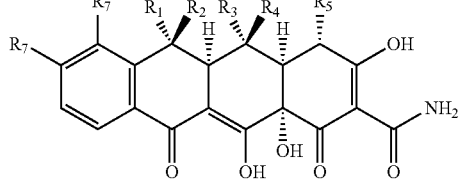

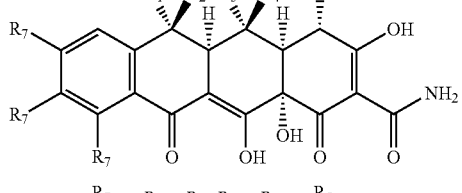

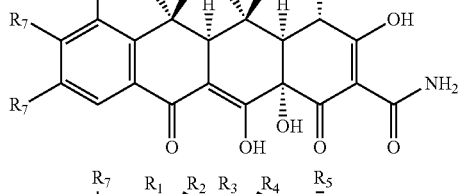

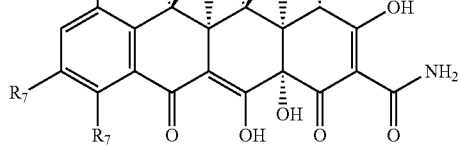

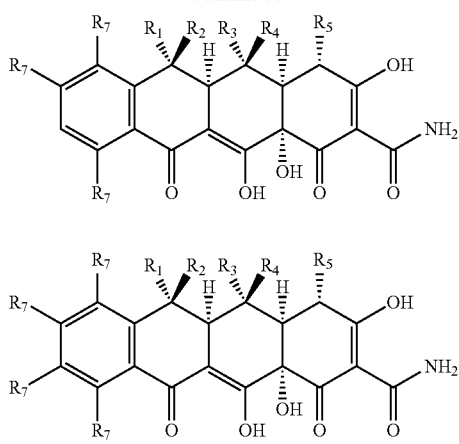

wherein the definitions of $R_1$, $R_2$, $R_3$, $R_4$, and $R_5$ are as described above, and $R_7$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_7$ is hydroxyl, protected hydroxyl, alkoxy, lower alkyl, lower alkenyl, lower alkynyl, or halogen. In other embodiments, $R_7$ is cyclic or acyclic, substituted or unsubstituted, branched or unbranched aliphatic; or cyclic or acyclic, substituted or unsubstituted, branched or unbranched heteroaliphatic. In yet other embodiments, $R_7$ is amino, alkylamino, or dialkylamino. In other embodiments, $R_7$ is substituted or unsubstituted cyclic, heterocyclic, aryl, or heteroaryl. In certain embodiments, $R_7$ is branched or unbranched acyl.

Various subclasses of compounds of the formula 10 which include a hydroxyl group at C10 are shown:

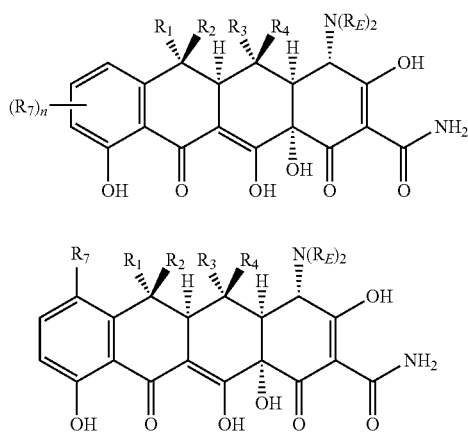

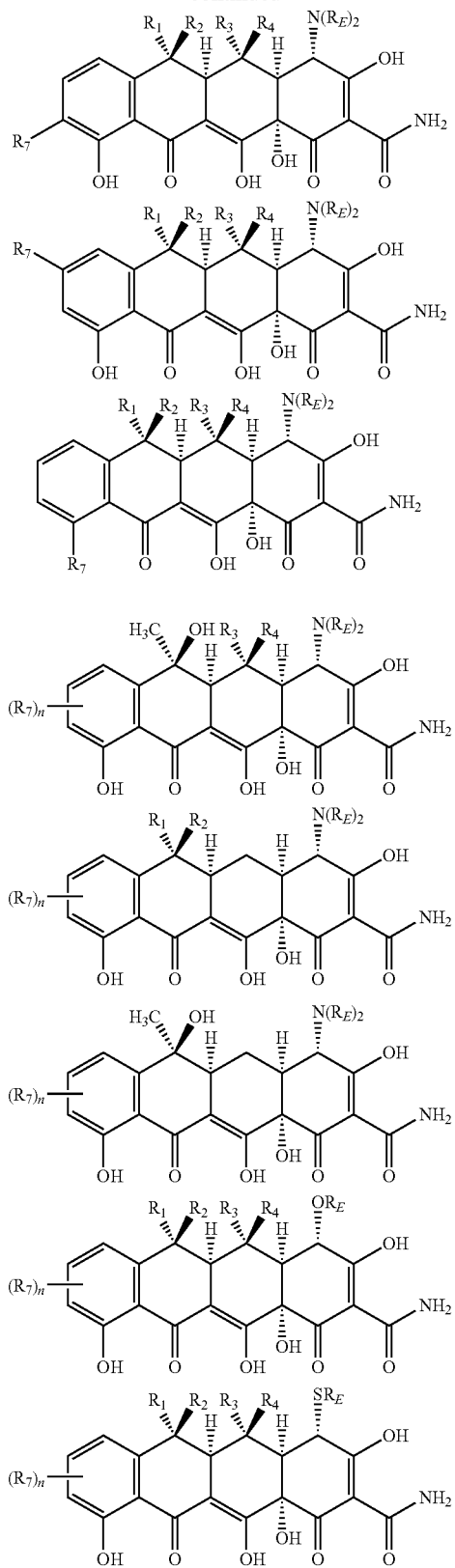

wherein the definitions of $R_1$, $R_2$, $R_3$, $R_4$, $R_5$, $R_E$, and $R_7$ are as described above. In certain embodiments, the compounds are 6-deoxytetracyclines as shown in the formulae below:

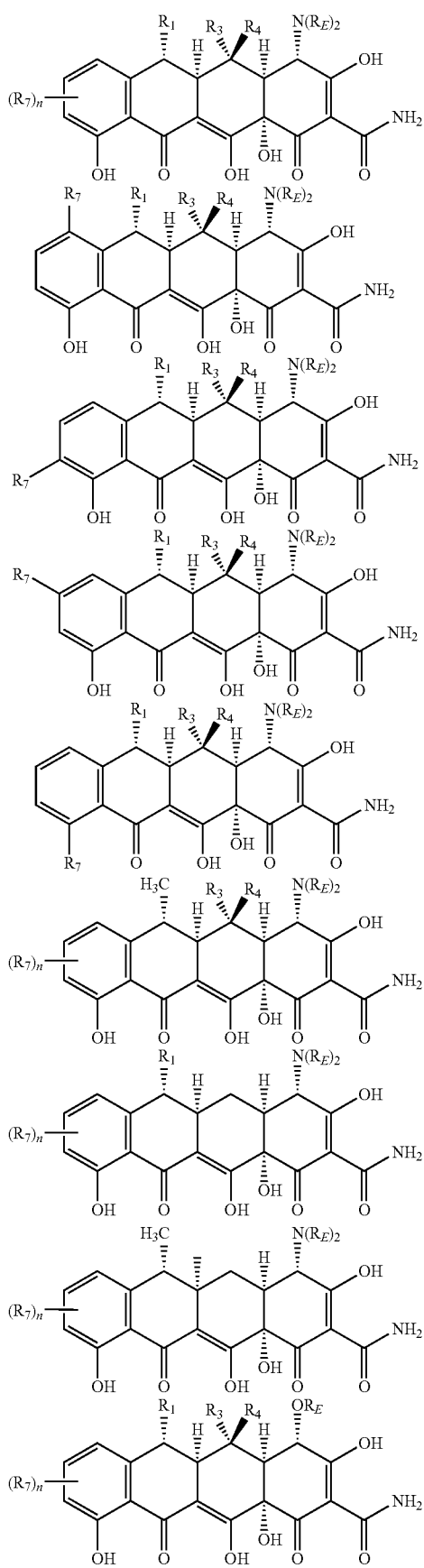

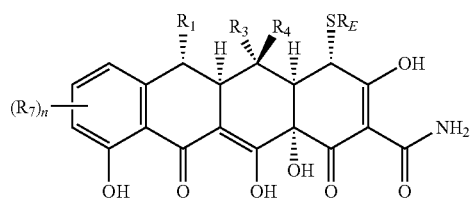

wherein $R_2$ is hydrogen, and the definitions of $R_1$, $R_3$, $R_4$, $R_5$, $R_E$, and $R_7$ are as described above.

In another aspect of the invention, the carbocyclic D-ring of tetracycline is replaced with a heterocyclic or carbocyclic moiety as shown in formula (11):

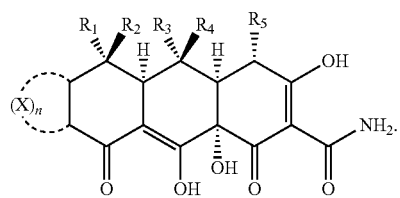

(11)

The definitions of $R_1$, $R_2$, $R_3$, $R_4$, and $R_5$ are as described above for formula 10. The D-ring represented by

can be a substituted or unsubstituted aryl, heteroaryl, carbocyclic, or heterocyclic moiety, in which each occurrence of X is selected from the group consisting of —O—, —S—, —NR$_7$—, —C(R$_7$)$_2$—; n is an integer in the range of 1 to 5, inclusive; and the bonds between adjacent X moieties are either single or double bonds. In certain embodiments,

is a polycyclic ring system such as a bicyclic or tricyclic moiety. In other embodiments,

is a monocyclic moiety. In yet other embodiments,

is a substituted or unsubstituted heterocyclic moiety. In certain embodiments,

is not a substituted or unsubstituted phenyl ring. In other embodiments,

is a pyridinyl moiety as shown:

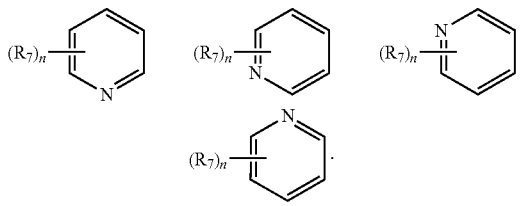

In another embodiment,

is selected from the group consisting of

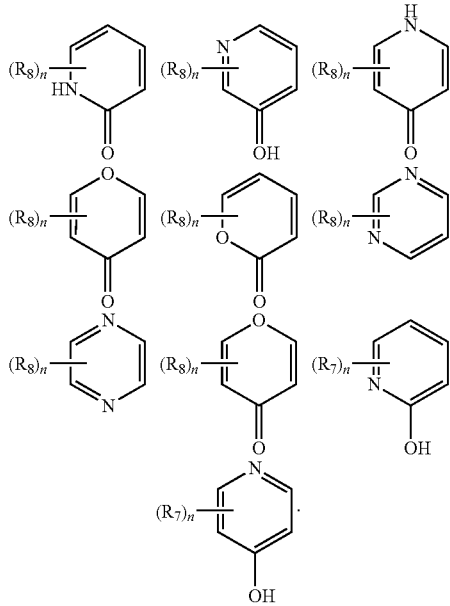

In yet another embodiment,

is a five-membered heterocyclic ring selected from the group consisting of:

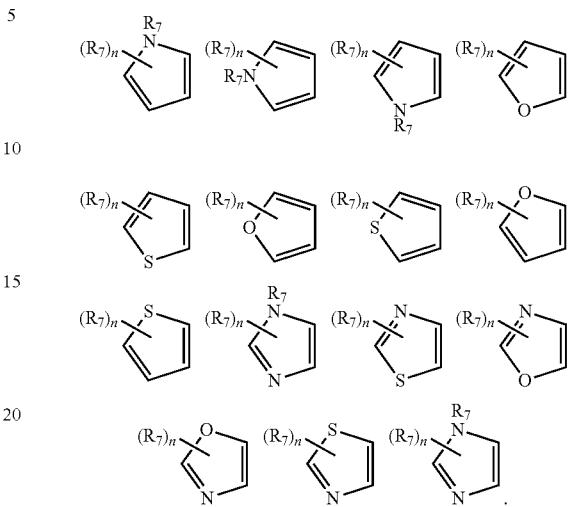

Figure 14B:
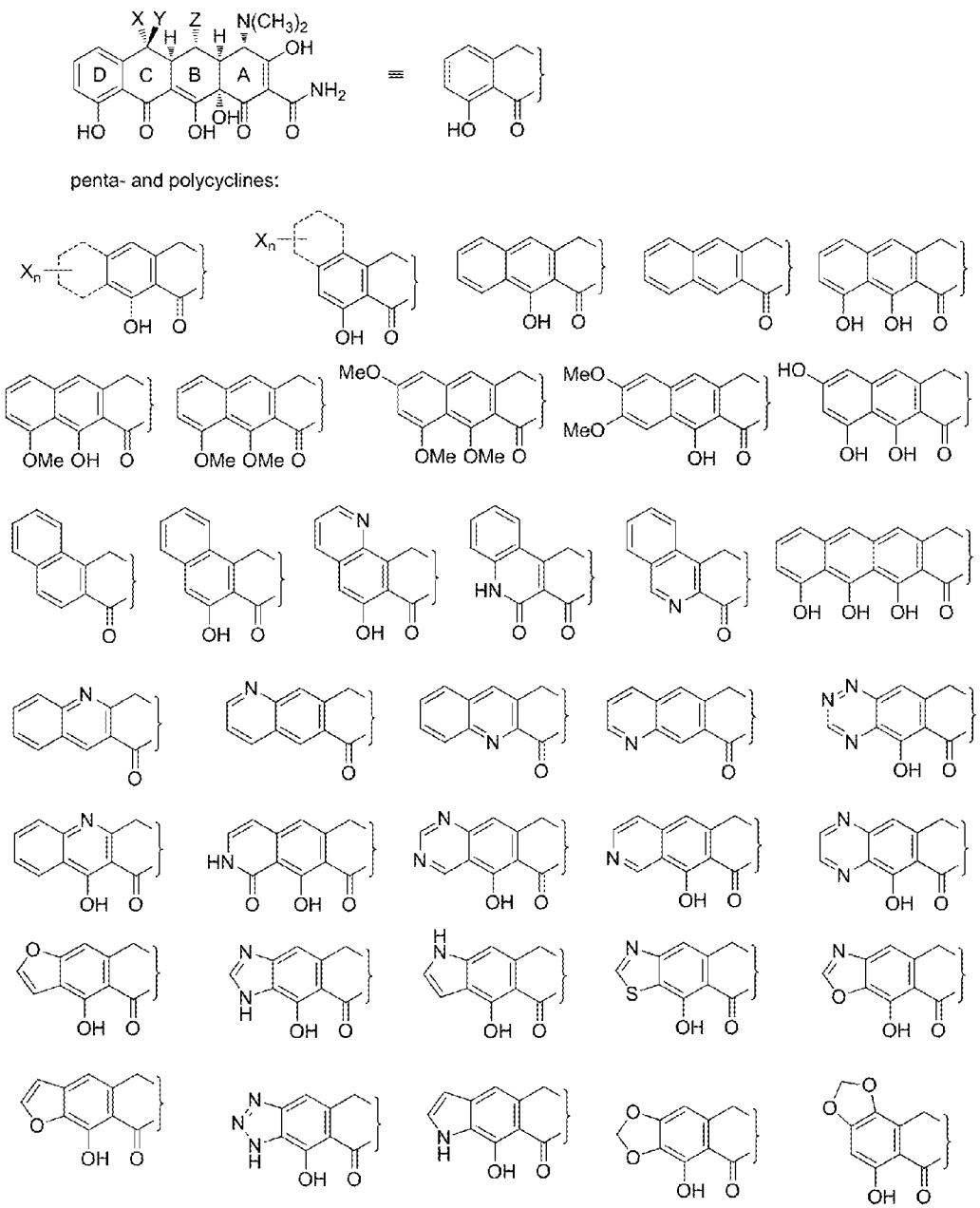

Various tetracyclines (heterocyclines) of the invention are also shown in FIG. 14.

Other compounds of the invention include pentacyclines of the formula:

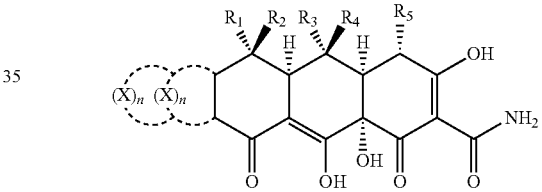

wherein $R_1$, $R_2$, $R_3$, $R_4$, $R_5$, and

are as defined above. In certain embodiments, the rings of the compound are linear. In other embodiments, the ring system is not linear. Each occurrence of the ring

in certain embodiments, is a monocyclic ring system. Each occurrence of

is heterocylic or carbocyclic.

is three-membered, four-membered, five-membered, six-membered, or seven-membered; preferably, five-membered or six-membered. Other classes of pentacyclines include compounds of the formulae (12), (13), and (14):

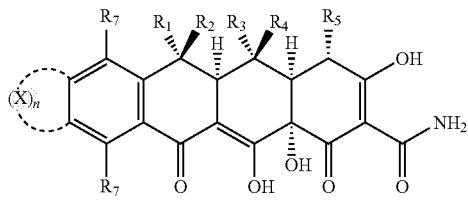
(12)

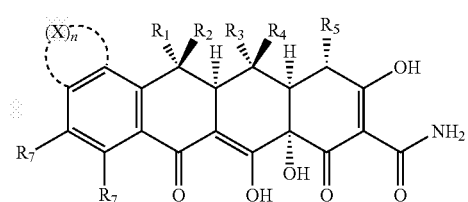
(13)

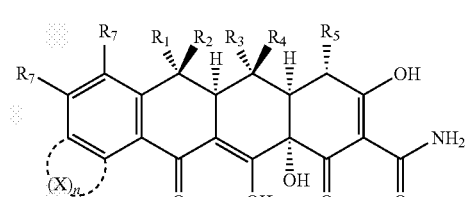
(14)

wherein $R_1$, $R_2$, $R_3$, $R_4$, $R_5$, and $R_7$ are as defined above. In formulae 12, 13, and 14,

represents a substituted or unsubstituted aryl, heteroaryl, carbocyclic, or heterocyclic moiety, in which each occurrence of X is selected from the group consisting of —O—, —S—, —$NR_8$—, —$C(R_8)_2$—; n is an integer in the range of 1 to 5, inclusive; and the bonds between adjacent X moieties are either single or double bonds. In certain embodiments,

is a polycyclic ring system such as a bicyclic or tricyclic moiety. In other embodiments,

is a monocyclic moiety. In other embodiments,

is a substituted or unsubstituted, aromatic or nonaromatic carbocyclic moiety, for example a phenyl ring. In yet other embodiments,

is a substituted or unsubstituted heterocyclic moiety. In certain embodiments,

is not a substituted or unsubstituted phenyl ring. In other embodiments,

is a pyridinyl moiety as shown:

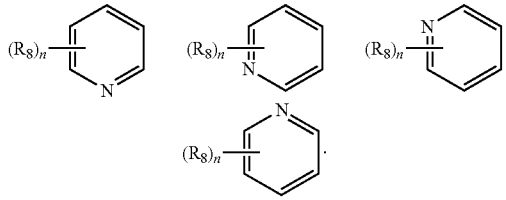

In another embodiment,

is selected from the group consisting of

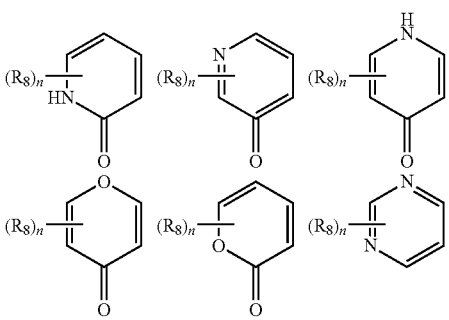

-continued
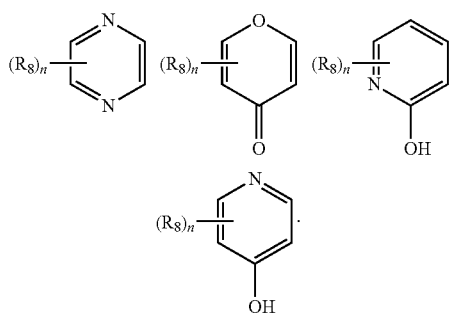
In yet another embodiment,
is a five-membered heterocyclic ring selected from the group consisting of:
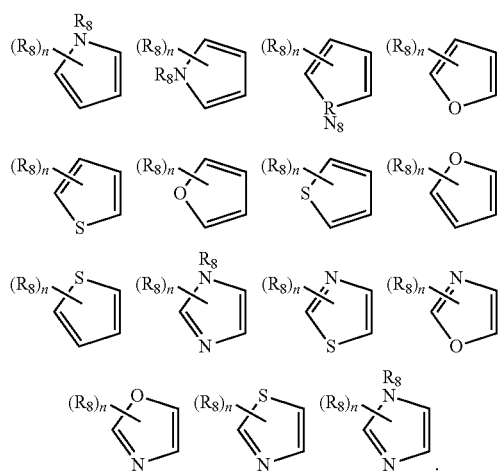
Various subclasses of the formula (12) include:
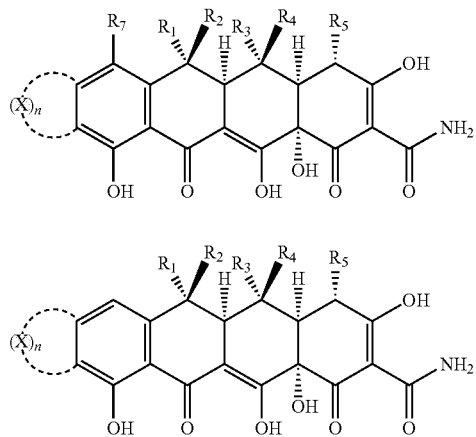
-continued
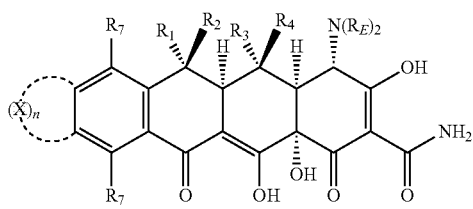
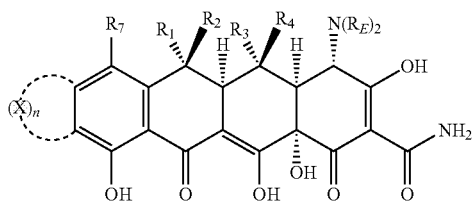
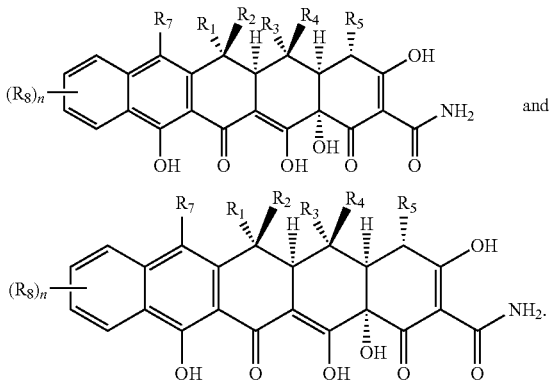
and
Various subclasses of the formula (13) include:
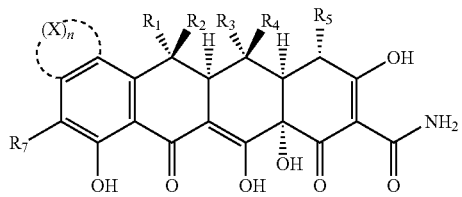
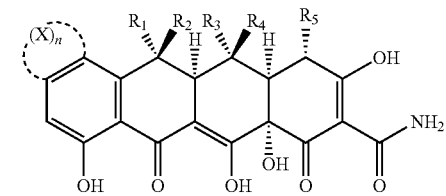
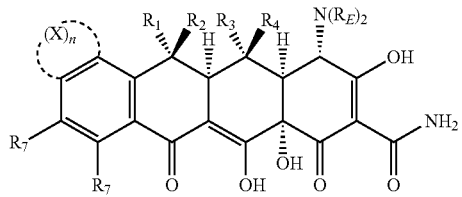
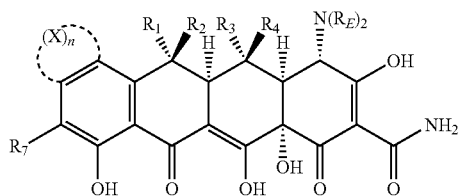

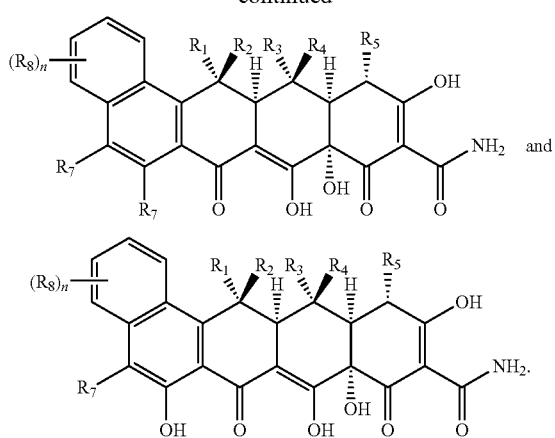

Various subclasses of the formula (14) include:

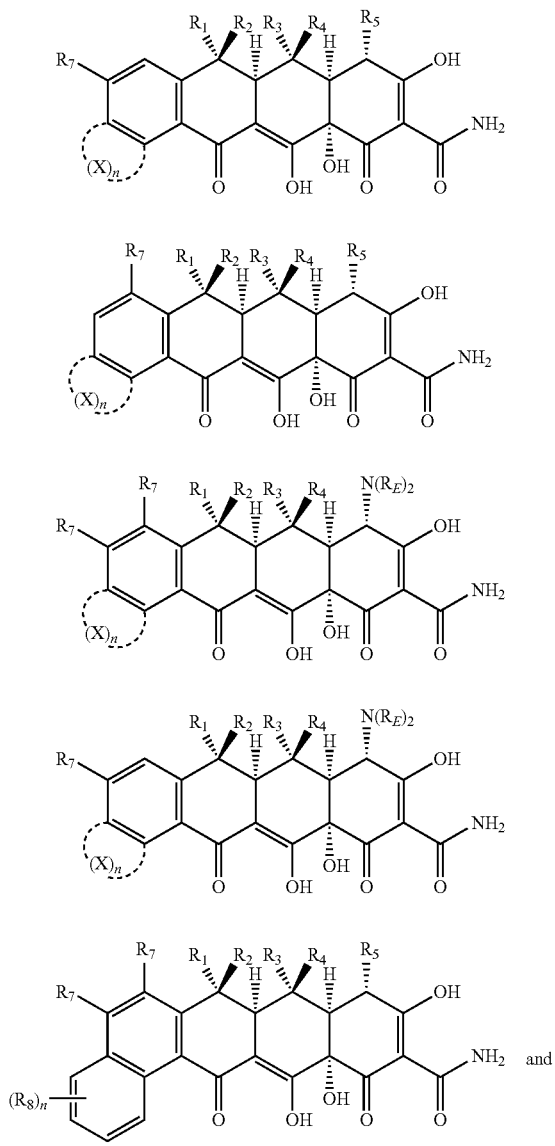

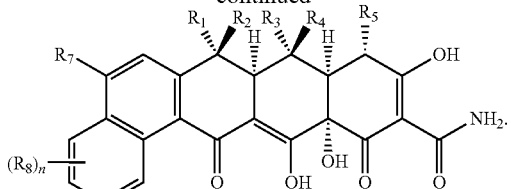

Various pentacyclines of the invention are also shown in FIG. 14.

In certain embodiments, the tetracycline analogs of the present invention are represented by the formula:

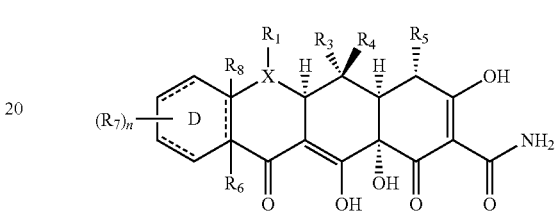

wherein X is nitrogen, sulfur, and oxygen, and $R_1$, $R_3$, $R_4$, $R_5$, $R_6$, $R_7$, $R_8$, and n are defined as above with the caveat that when X is S or O, $R_1$ is absent.

Other classes of compounds of the invention include dicyclines of the formula (15).

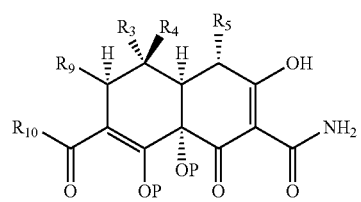

(15)

wherein $R_3$, $R_4$, and $R_5$ are as defined above. P is hydrogen or a protecting group. $R_9$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_I$; —CN; —SCN; —$SR_I$; or —$N(R_I)_2$; wherein each occurrence of $R_I$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_9$ is hydrogen or lower ($C_1$-$C_6$) alkyl, alkenyl, or alkynyl. In other embodiments, $R_9$ is a vinyl group. In yet other embodiments, $R_9$ is a substituted or unsubstituted aryl group. In still other embodiments, $R_9$ is a substituted or unsubstituted heterocyclic group.

$R_{10}$ is cyclic or acyclic, substituted or unsubstituted, branched or unbranched aliphatic; cyclic or acyclic, substituted or unsubstituted, branched or unbranched heteroaliphatic; substituted or unsubstitued, branched or unbranched aryl; or substituted or unsubstituted, branched or unbranched heteroaryl moiety. In certain embodiments, $R_{10}$ is a substituted or unsubstituted phenyl ring. In certain embodiments, $R_{10}$ is a substituted or unsubstituted heterocyclic ring. In certain embodiments, $R_{10}$ is a substituted or unsubstituted aryl ring. In other embodiments, $R_{10}$ is a lower ($C_1$-$C_6$) alkyl, alkenyl, or alkynyl group.

Methods of Synthesis

The present invention also includes all steps and methodologies used in preparing the compounds of the invention as well as intermediates along the synthetic route. The present invention provides for the modular synthesis of tetracyclines and its various analogs by joining a highly functionalized chiral enone, which will become the A- and B-rings of the tetracycline core, with a molecule which will become the D-ring of the tetracycline core. The joining of these two intermediates results in the formation of the C-ring, preferably in an enantioselective manner. This methodology also allows for the synthesis of pentacyclines, hexacyclines, or higher ring systems as well as the incorporation of heterocycles into the ring system. In particular, the joining of these two fragments includes various nucleophilic addition reactions and cycloaddition reactions with enone (9) as described above.

The synthesis begins with the preparation of the enone (9) starting from benzoic acid. As shown in FIG. 2, the first step of the synthesis involves the microbial dihydroxylation of benzoic acid using *Alcaligenes eutrophus*. The diol (1 in FIG. 2), which is preferably optically pure, then undergoes hydroxyl-directed epoxidation to yield the allylic epoxide (2 in FIG. 2). Protection and rearrangement of allylic epoxide 2 yielded the isomeric allylic epoxide (3 in FIG. 2). The metalated isoxazole (4 in FIG. 2) was added to the isomeric allylic epoxide to yield 5 (FIG. 2), which was subsequently metalated to close the six-membered ring by nucleophilic attack of the epoxide. The intermediate 6 (FIG. 2) was then rearranged, deprotected, and oxidized to yield the chiral enone 9 (FIG. 2). As will be appreciated by one of skill in this art, functionalization and rearrangement of intermediates 6, 7, 8, and 9 in FIG. 2 will allow for the preparation of different class of compounds of the invention.

Figure 11:
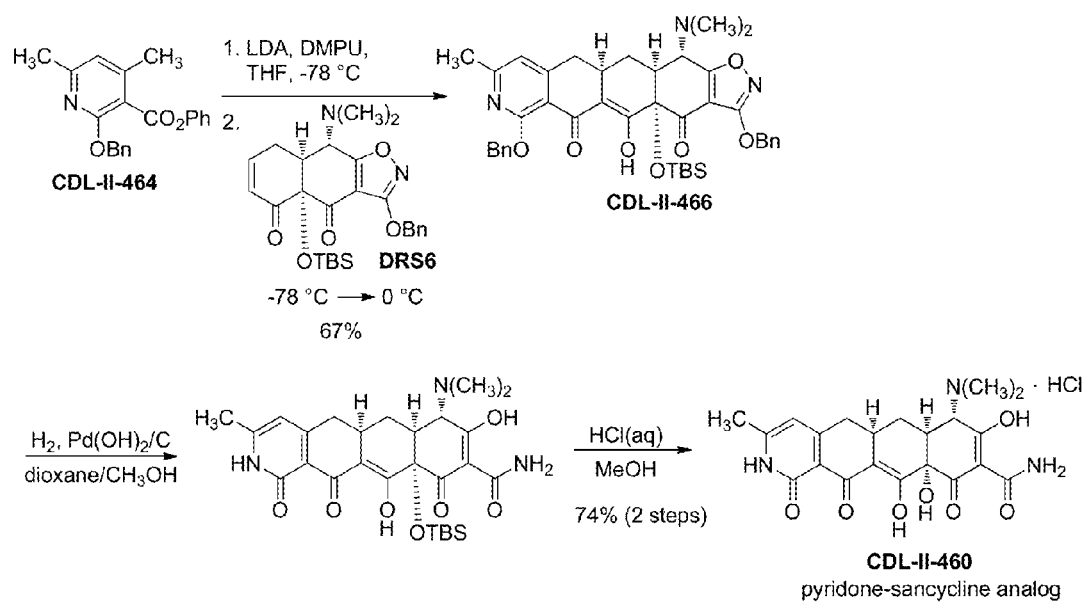
FIG. 11 is a scheme showing the synthesis of a pyridone/hydroxypyridine analog of sancycline.
Figure 12:
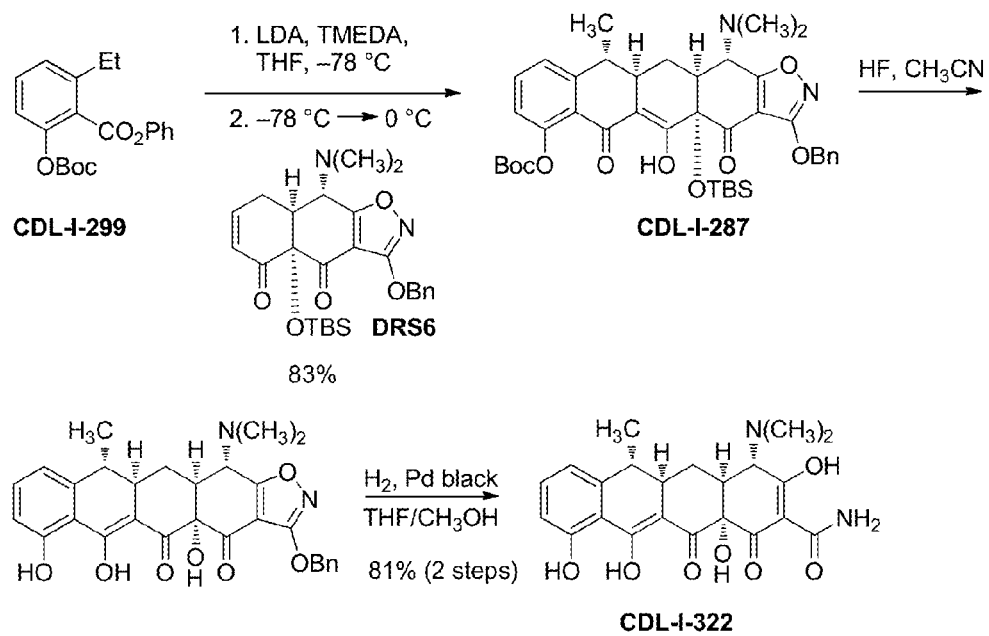
FIG. 12 shows the total synthesis of 6-deoxytetracycline from benzoic acid in 14 steps (overall yield 8%). The first ten steps are identical to the first 10 steps in the synthesis of (−)-tetracycline shown in FIG. 2.

In one embodiment, enone (9) is reacted with an anion resulting from the deprotonation of toluate (6). The toluate of formula:

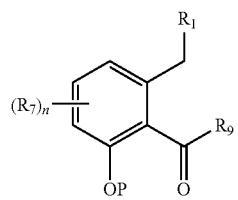

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O) $R_A$; —$CO_2R_A$; —CN; —SCN; —$SR_A$; —$SOR_A$; —$SO_2R_A$; —$NO_2$; —$N(R_A)_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —NHC(O)$R_G$; or —C($R_G$)$_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and n is an integer in the range of 0 to 3, inclusive;

$R_9$ is —$OR_J$; —CN; —SCN; —$SR_J$; or —$N(R_J)_2$; wherein each occurrence of $R_J$ is independently a hydrogen, a protecting group; a cyclic or acyclic, substituted or unsubstituted aliphatic moiety; a cyclic or acyclic, substituted or unsubstituted aliphatic heteroaliphatic moiety; a substituted or unsubstituted aryl moiety; or a substituted or unsubstituted heteroaryl moiety; and P is selected from the group consisting of hydrogen, lower ($C_1$-$C_6$) alkyl group, an acyl group, and a protecting group; is deprotonated under basic conditions (e.g., LDA, HMDS), and the resulting anion is reacted with an enone of formula:

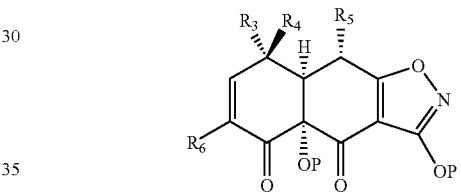

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; =O; —C(=O) $R_C$; —$CO_2R_C$; —CN; —SCN; —$SR_C$; —$SOR_C$; —$SO_2R_C$; —$NO_2$; —$N(R_C)_2$; —NHC(O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_E$; —CN; —SCN; —SR$_E$; or —N(R$_E$)$_2$; wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is selected from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, arylthio, —NO$_2$, amino, alkyl amino, and dialkyl amino groups; and P is independently selected from the group consisting of hydrogen or a protecting group; to form the product:

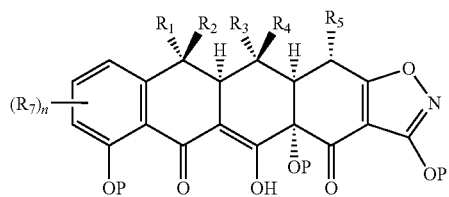

wherein R$_1$, R$_3$, R$_4$, R$_5$, R$_7$, P, and n are as defined above;

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciated by one of skill in this art, the toluate may be further substituted in certain embodiments. In addition, the phenyl ring of the toluate may be substituted for an aromatic heterocyclic ring such as pyridine ring as shown in FIGS. 11 and 13. Other examples of carbocyclic and heterocyclic analogs of toluate (6) include:

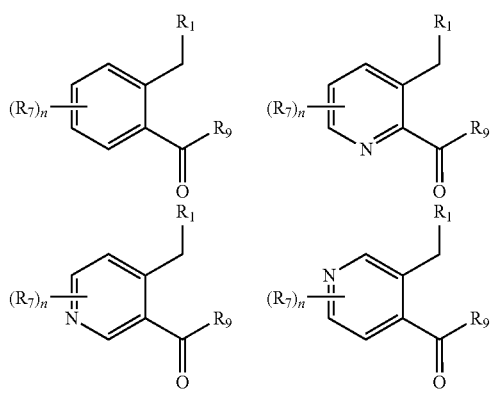

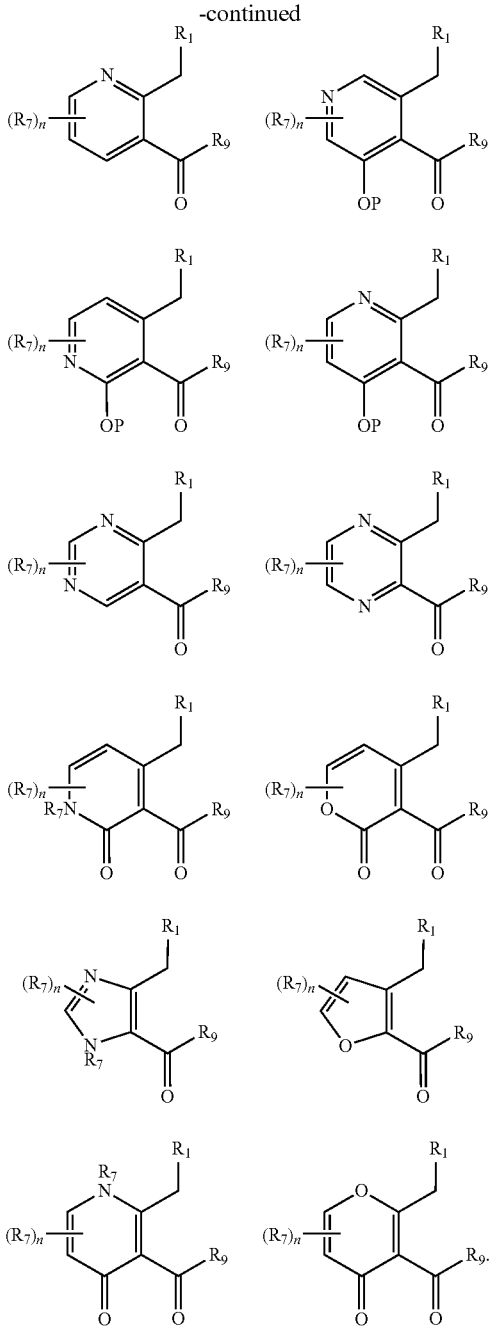

Figure 21A:
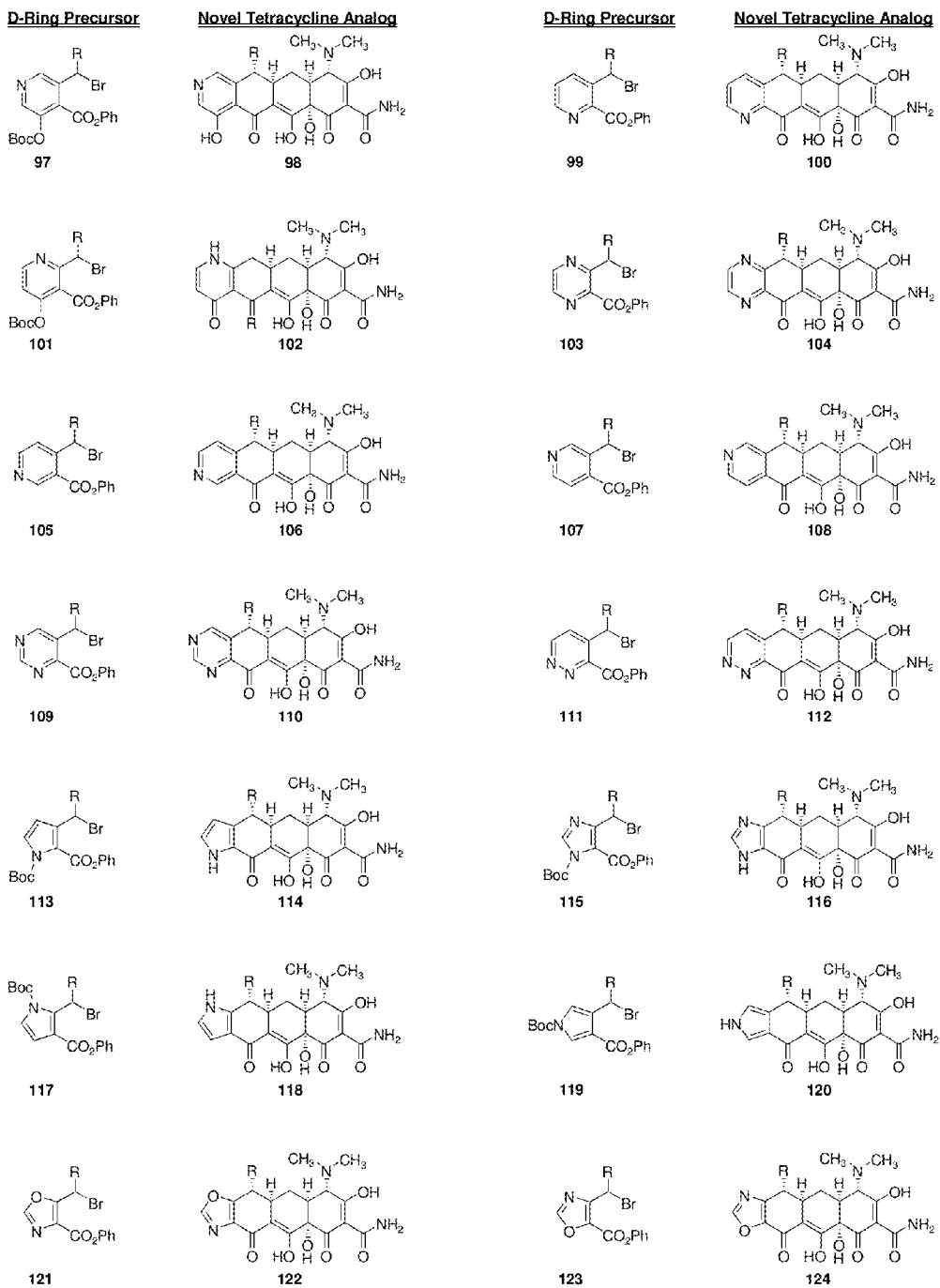
FIG. 21 shows the synthesis of various novel tetracycline analogs and their corresponding D-ring precursor. These compounds represent significant gaps in the tetracycline fields, likely missing from the literature for lack of a viable synthesis.
Figure 21B:
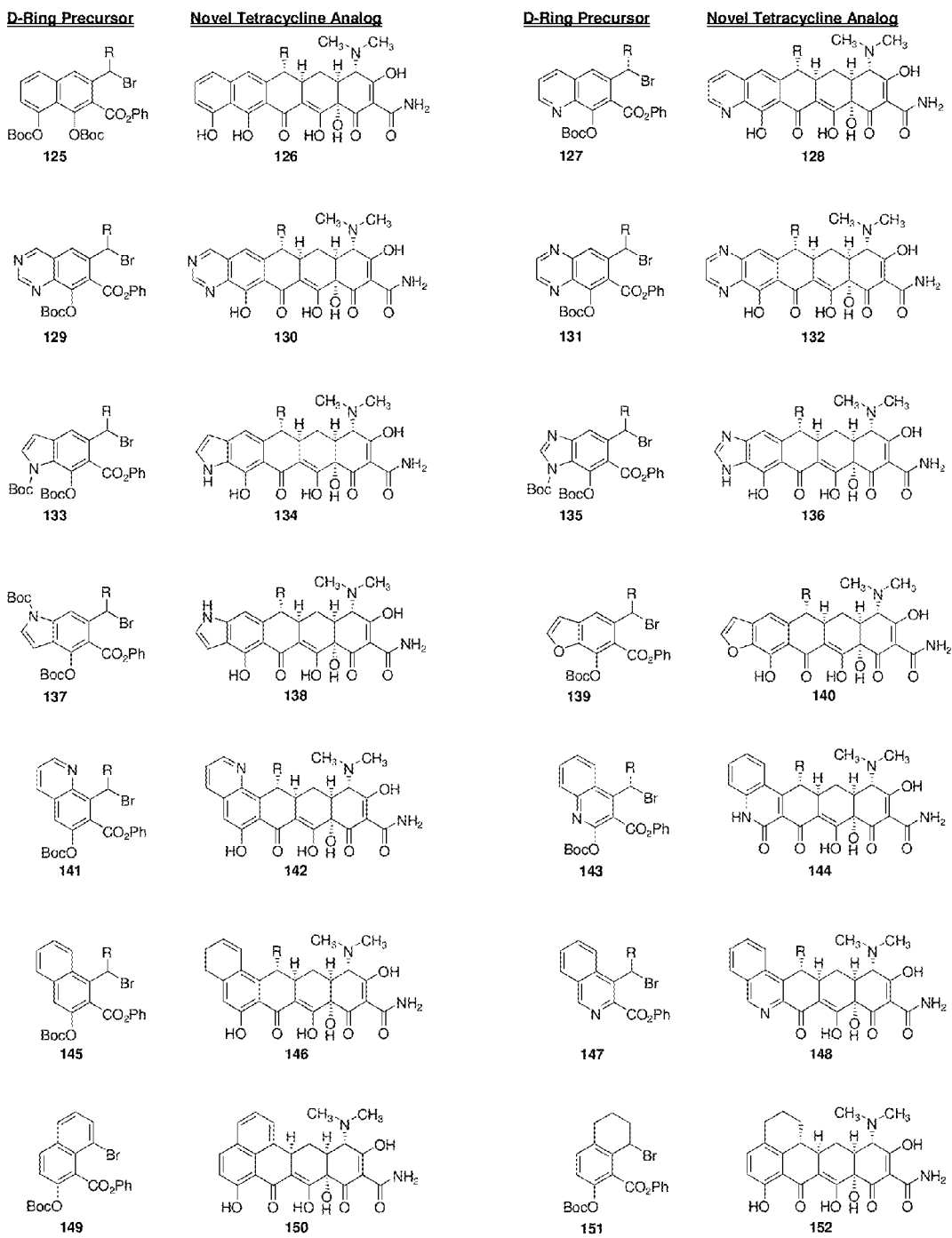
Figure 21C:
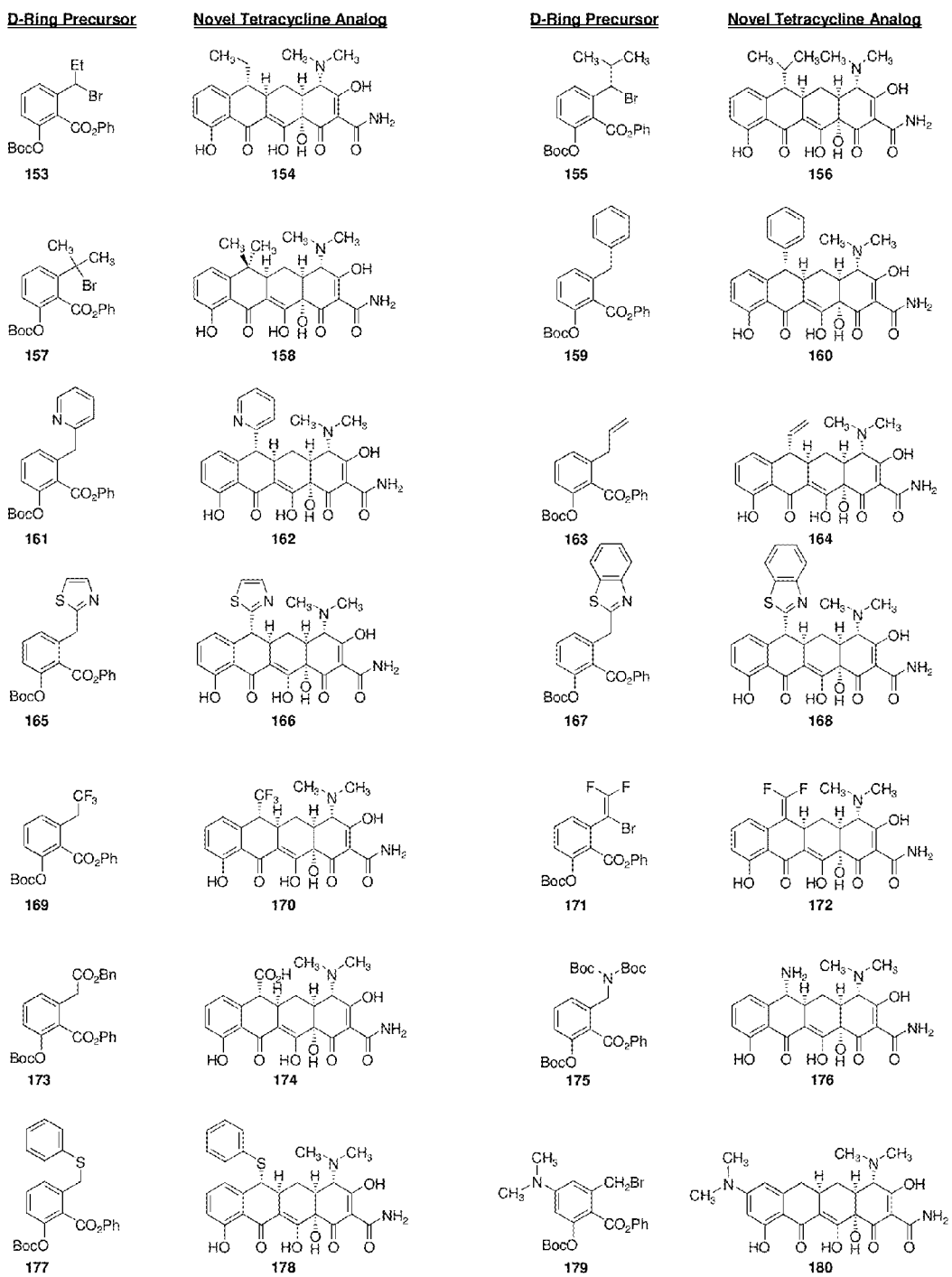

Other toluates are shown in FIG. 21. In certain embodiments, polycyclic toluates are used in the Michael-Dieckmann reaction sequence to form pentacyclines, hexacyclines, or higher cyclines. Toluates useful in preparing pentacyclines are exemplified by the formula:

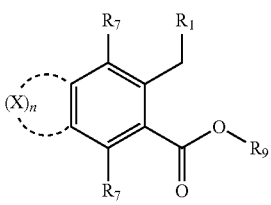

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each $R_7$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

represents a substituted or unsubstituted aryl, heteroaryl, carbocyclic, or heterocyclic moiety, in which each occurrence of X is selected from the group consisting of —O—, —S—, —$NR_8$—, —$C(R_8)_2$—;

$R_8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_H$; =O; —C(=O)$R_H$; —$CO_2R_H$; —CN; —SCN; —$SR_H$; —$SOR_H$; —$SO_2R_H$; —$NO_2$; —$N(R_H)_2$; —$NHC(O)R_H$; or —$C(R_H)_3$; wherein each occurrence of $R_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 1 to 5, inclusive; and the bonds between adjacent X moieties are either single or double bonds; and $R_9$ is selected from the group consisting of substituted or unsubstituted aryl or heteroaryl groups.

In another embodiment, enone (9) is reacted with an anion, which is generated through metallation (e.g., metal-halogen exchange, metal-metalloid exchange, lithium-halogen exchange, lithium-tin exchange, etc. by reacting the toluate with the appropriate metal reagent) of a toluate of the following formula:

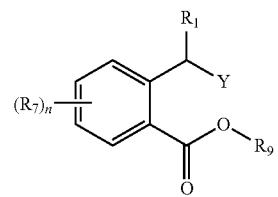

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 0 to 3, inclusive;

$R_9$ is selected from the group consisting of substituted or unsubstituted aryl or heteroaryl groups; and Y is a halogen or $Sn(R_Y)_3$, wherein $R_Y$ is alkyl. The anion generated is reacted with an enone of formula:

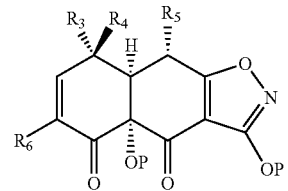

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; =O; —C(=O)$R_C$; —$CO_2R_C$; —CN; —SCN; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —$N(R_D)_2$; —NHC(O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, arylthio, —$NO_2$, amino, alkyl amino, and dialkyl amino groups; and P is independently selected from the group consisting of hydrogen or a protecting group; to generate the product of formula:

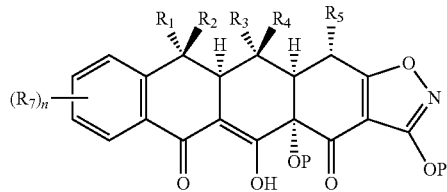

wherein $R_1$, $R_3$, $R_4$, $R_5$, $R_7$, P, and n are as defined above; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_B$; =O; —C(=O)$R_B$; —$CO_2R_B$; —CN; —SCN; —$SR_B$; —$SOR_B$; —$SO_2R_B$; —$NO_2$; —$N(R_B)_2$; —NHC(O)$R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

Any metal may be used in the metallation reaction to generate the metal anionic reagent to be reacted with the enone. In certain embodiments, the metal is a Group I element on the periodic chart. In other embodiments, the metal is a Group II element on the periodic chart. In other embodiments, the metal is a transition metal. Exemplary metals useful in the metallation reaction include sodium, lithium, calcium, aluminium, cadmium, copper, beryllium, arsenic, antimony, tin, magnesium, titanium, zinc, manganese, iron, cobalt, nickel, zinc, platinum, palladium, mercury, and ruthenium. In certain preferred embodiments, the metal is chosen from lithium, magnesium, titanium, zinc, and copper. In yet other embodiments, the metal is magnesium, lithium, sodium, beryllium, zinc, mercury, arsenic, antimony, or tin. In certain particular embodiments, a lithium-halogen exchange is used. The lithium-halogen exchange may be performed in situ in the presence of the enone. The lithium-halogen exchange may be preformed using any lithium reagent including, for example, alkyllithium reagents, n-butyllithium, t-butyllithium, phenyl lithium, mesityl lithium, and methyllithium. In certain embodiments, other organometallics reagents are generated and reacted with the enone. Examples include Grignard reagents, zero-valent metal complexes, ate complexes, etc. In certain embodiments, the metal reagent is a magnesium reagent including, but not limited to, magnesium metal, magnesium anthracene, activated magnesium turnings, etc. In certain embodiments, the reagent is zinc-based. The reagent may be generated in situ in the presence of the enone, or the reagent may be generated separately and later contacted with the enone. In certain embodiments, milder conditions for the cyclization are used (e.g., a zinc reagent).

As will be appreciated by one of skill in this art, the toluate may be further substituted in certain embodiments. In addition, the phenyl ring of the toluate may be substituted for an aromatic heterocyclic ring or ring system such as a pyridine ring. Examples of carbocyclic and heterocyclic analogs of toluate include:

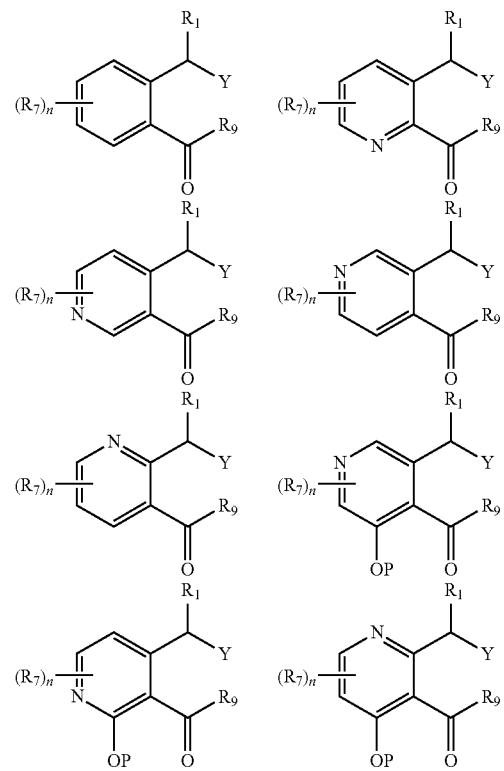

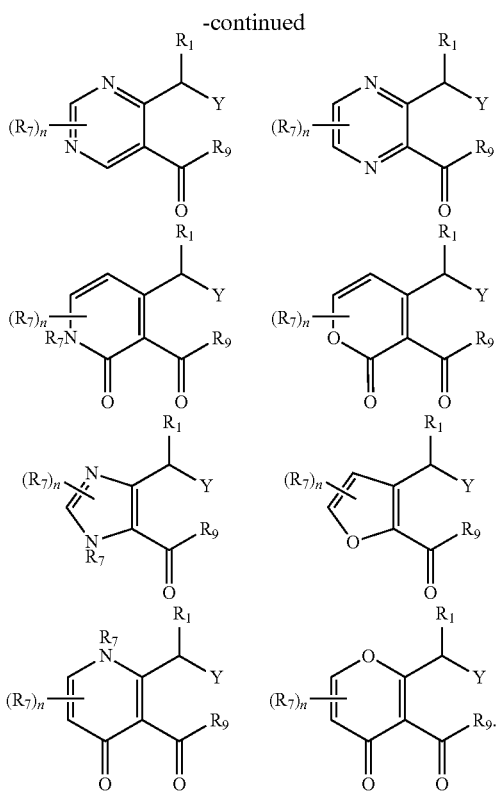

In certain embodiments, the halogen Y is bromine. In other embodiments, Y is iodine. In yet other embodiments, Y is chloride. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metallation reaction, Y is a metal such as lithium, magnesium, zinc, copper, antimony, sodium, etc. In certain embodiments, R$_1$ is hydrogen or lower alkyl (C$_1$-C$_6$). In certain particular embodiments, R$_1$ is hydrogen. Other toluates are shown in FIG. 21.

In other embodiments, polycyclic toluates may be used to prepare pentacyclines, hexacyclines, or higher cyclines. Toluates useful in the preparation of such cyclines are of the formula:

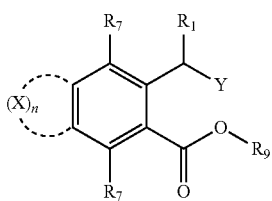

wherein R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each R$_7$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_G$; =O; —C(=O)R$_G$; —CO$_2$R$_G$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

represents a substituted or unsubstituted aryl, heteroaryl, carbocyclic, or heterocyclic moiety, in which each occurrence of X is selected from the group consisting of —O—, —S—, —NR$_8$—, —C(R$_8$)$_2$—;

R$_8$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_H$; =O; —C(=O)R$_H$; —CO$_2$R$_H$; —CN; —SCN; —SR$_H$; —SOR$_H$; —SO$_2$R$_H$; —NO$_2$; —N(R$_H$)$_2$; —NHC(O)R$_H$; or —C(R$_H$)$_3$; wherein each occurrence of R$_H$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

n is an integer in the range of 1 to 5, inclusive; and the bonds between adjacent X moieties are either single or double bonds;

R$_9$ is selected from the group consisting of substituted or unsubstituted aryl or heteroaryl groups; and Y is a halogen or Sn(R$_Y$)3, wherein R$_Y$ is alkyl. In certain embodiments, the halogen Y is bromine. In certain embodiments, the halogen Y is bromine. In other embodiments, Y is iodine. In yet other embodiments, Y is chloride. In certain embodiments, Y is a metalloid (e.g., tin, selenium, tellurium, etc.). In certain embodiments, Y is —SnR$_3$, wherein each occurrence of R is independently alkyl (e.g., —Sn(CH$_3$)$_3$). After the metallation reaction, Y is a metal such as lithium, magnesium, zinc, copper, sodium, mercury, antimony, etc. In certain embodiments, R$_1$ is hydrogen or lower alkyl (C$_1$-C$_6$). In certain particular embodiments, R$_1$ is hydrogen. In certain embodiments, R$_9$ is phenyl or substituted phenyl. In certain embodiments, ortho-R$_7$ is alkoxy such as methoxy. In other embodiments, R$_7$ is hydrogen. Exemplary polycyclic toluates include:

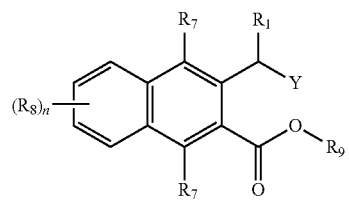
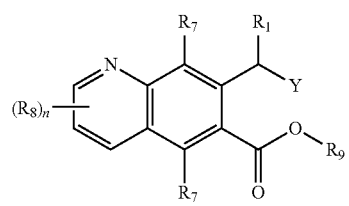
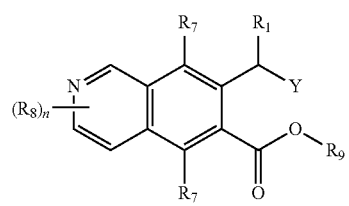
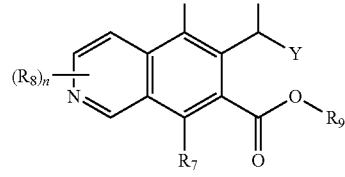
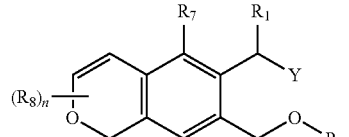
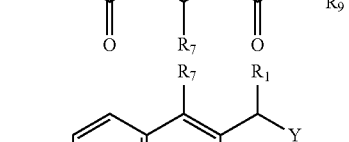
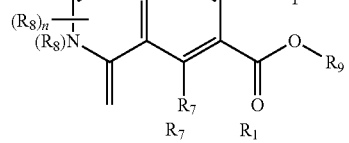
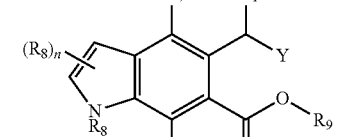
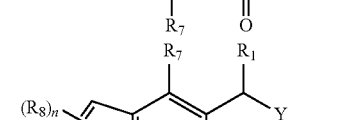
-continued
Compounds of the formula below with a heterocyclic C-ring:
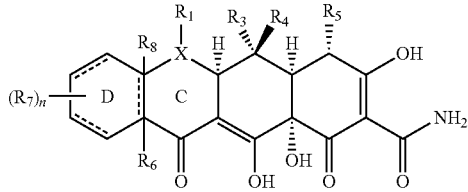
may be prepared by Michael-Dieckmann closure of a D-ring precursor derived from the corresponding anilide, phenol, or thiophenol. A representative example using anthranilic acid (i.e., anilide as the nucleophile in the Michael addition reaction) is shown below:
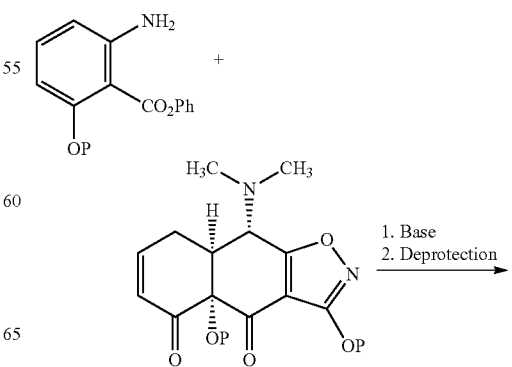

-continued

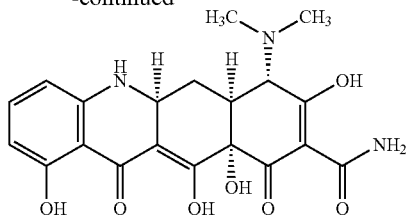

In another embodiment, the enone (9) is reacted with a benzocyclobutenol in an o-quinone dimethide Diels-Alder reaction. The enone of formula:

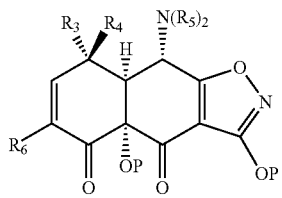

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; =O; —C(=O)$R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, arylthio, —$NO_2$, amino, alkyl amino, and dialkyl amino groups;

P is independently selected from the group consisting of hydrogen or a protecting group; is reacted under suitable conditions (e.g., heat) with a benzocyclobutenol of formula:

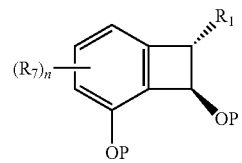

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P are each selected independently from the group consisting of hydrogen or a protecting group; and n is an integer in the range of 0 to 3, inclusive;

to form the product of formula:

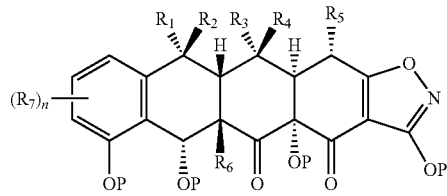

wherein $R_1$, $R_3$, $R_4$, $R_5$, $R_6$, $R_7$, and P are defined as above; and $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciate by one of skill in this art, the reactants may be substituted further and still fall within the claimed invention. For example, the phenyl ring of the benzocyclobutenol ring may be further substituted.

In another embodiment, the enone is reacted with a diene in a Diels-Alder reaction to yield a tricycline. The enone of formula:

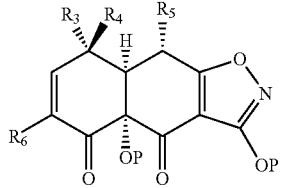

wherein R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_C$; =O; —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_D$; =O; —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstitued, branched or unbranched acyl; substituted or unsubstituted, branched or unbranched aryl; substituted or unsubstituted, branched or unbranched heteroaryl; —OR$_E$; —CN; —SCN; —SR$_E$; or —N(R$_E$)$_2$; wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is selected from the group consisting of hydrogen, halogen, substituted or unsubstitued aliphatic, substituted or unsubstituted heteroaliphatic, substituted or unsubstituted alkoxy, —OH, —CN, —SCN, —SH, alkylthio, arylthioxy, —NO$_2$, amino, alkyl amino, and dialkyl amino groups; are as defined above; and P is independently selected from the group consisting of hydrogen or a protecting group; is reacted under suitable conditions (e.g., heat) with a diene of formula:

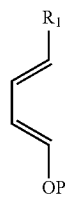

wherein R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_A$; =O; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and P are each selected independently from the group consisting of hydrogen and protecting groups;
to yield a protected tricycline of formula:

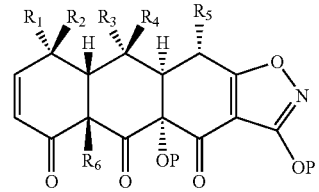

wherein R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —OR$_B$; =O; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. As will be appreciated by one of skill in this art, the enone and diene may be further substituted and still be encompassed within the present invention.

In yet another embodiment, the enone is reacted with an anion of a phthalide or cyano-phthalide. The enone of formula:

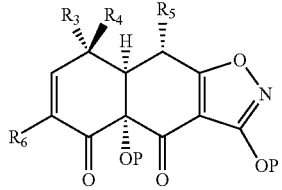

wherein $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_C$; =O; —C(=O) $R_C$; —$CO_2R_C$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_D$; =O; —C(=O)$R_D$; —$CO_2R_D$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_E$; —CN; —SCN; —$SR_E$; or —$N(R_E)_2$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is selected from the group consisting of hydrogen, halogen, substituted or unsubstiued aliphatic, substituted or unsubstituted heteroaliphatic, substituted or unsubstituted alkoxy, —OH, —CN, —SCN, —SH, alkylthio, arylthio, —$NO_2$, amino, alkyl amino, and dialkyl amino groups; and P is independently selected from the group consisting of hydrogen or a protecting group; is reacted under basic conditions (e.g., LDA, $Ph_3CLi$) with the anion of the phthalide of formula:

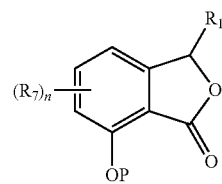

$R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_G$; =O; —C(=O)$R_G$; —$CO_2R_G$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

P are each selected independently from the group consisting of hydrogen, lower alkyl group, acyl group, or a protecting group; and n is an integer in the range of 0 to 3, inclusive;

to yield a product of formula:

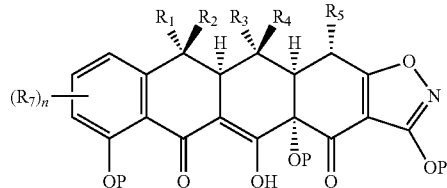

wherein $R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; =O; —C(=O) $R_B$; —$CO_2R_B$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

The products of the above reactions are then further functionalized, reduced, oxidized, rearranged, protected, and deprotected to yield the final desired product. Various exemplary reactions used in the final syntheses of the compounds of the invention are shown in FIGS. 2, 3, 11, 12, and 13. As will be appreciated by one of skill in the art, various isolation and purification techniques including flash chromatography, crystallization, distillation, HPLC, thin layer chromatography, extraction, filtration, etc. may be used in the course of synthesizing compounds of the invention. These techniques may be used in the preparation or purification of intermediates, reagents, products, starting materials, or solvents.

Pharmaceutical Compositions

This invention also provides a pharmaceutical preparation comprising at least one of the compounds as described above and herein, or a pharmaceutically acceptable derivative thereof, which compounds inhibit the growth of or kill microorganisms, and, in certain embodiments of special interest are inhibit the growth of or kill tetracycline-resistant organisms including chlortetracycline-resistant organisms, oxytetracycline-resistant organisms, demeclocycline-resistant organisms, doxycycline-resistant organisms, minocycline-resistant organisms, or any organisms resistant to antibiotics of the tetracycline class used in human or veterinary medicine. In other embodiments, the compounds show cytostatic or cytotoxic activity against neoplastic cells such as cancer cells. In yet other embodiments, the compounds inhibit the growth of or kill rapidly dividing cells such as stimulated inflammatory cells.

As discussed above, the present invention provides novel compounds having antimicrobial and antiproliferative activity, and thus the inventive compounds are useful for the treatment of a variety of medical conditions including infectious diseases, cancer, autoimmune diseases, inflammatory diseases, and diabetic retinopathy. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents, e.g., another anti-microbial agent or another anti-proliferative agent. In other embodiments, these compositions further comprise an anti-inflammatory agent such as aspirin, ibuprofen, acetaminophen, etc., pain reliever, or anti-pyretic.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method of treating infections and inhibiting tumor growth. The method involves the administration of a therapeutically effective amount of the compound or a pharmaceutically acceptable derivative thereof to a subject (including, but not limited to a human or animal) in need of it.

The compounds and pharmaceutical compositions of the present invention may be used in treating or preventing any disease or conditions including infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered orally. In other embodiments, the compound or pharmaceutical composition is administered parenterally.

In yet another aspect, according to the methods of treatment of the present invention, bacteria are killed, or their growth is inhibited by contacting the bacteria with an inventive compound or composition, as described herein. Thus, in still another aspect of the invention, a method for the treatment of infection is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of bacteria. The compounds and compositions, according to the method of the present invention, may be administered using any amount and any route of administration effective for killing or inhibiting the growth of bacteria. The exact amount required will vary from subject to subject, depending on the species, age, and general condition of the subject, the severity of the infection, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis of (−)-Tetracycline

General Procedures.

All reactions were performed in flame-dried round bottomed or modified Schlenk (Kjeldahl shape) flasks fitted with rubber septa under a positive pressure of argon, unless otherwise noted. Air- and moisture-sensitive liquids and solutions were transferred via syringe or stainless steel cannula. Where necessary (so noted), solutions were deoxygenated by alternative freeze (liquid nitrogen)/evacuation/thaw cycles (≥three iterations). Organic solutions were concentrated by rotary evaporation at ~25 Torr (house vacuum). Flash column chromatography was performed on silica gel (60 Å, standard grade) as described by Still et al. (Still, W. C.; Kahn, M.; Mitra, A. *J. Org. Chem.* 1978, 43, 2923-2925; incorporated herein by reference). Analytical thin-layer chromatography was performed using glass plates pre-coated with 0.25 mm 230-400 mesh silica gel impregnated with a fluorescent indicator (254 nm). Thin layer chromatography plates were visualized by exposure to ultraviolet light and/or exposure to ceric ammonium molybdate or an acidic solution of p-anisaldehyde followed by heating on a hot plate.

Materials.

Commercial reagents and solvents were used as received with the following exceptions. Chlorotrimethylsilane, triethylamine, diisopropylamine, 2,2,6,6-tetramethylpiperidine, N,N,N',N'-tetramethylethylenediamine, DMPU, HMPA, and N,N-diisopropylethylamine were distilled from calcium hydride under dinitrogen atmosphere. Benzene, dichloromethane, ethyl ether, methanol, pyridine, tetrahydrofuran, hexane, acetonitrile, N,N-dimethylformamide, and toluene were purified by the method of Pangborn et al. (Pangborn, A. B.; Giardello, M. A.; Grubbs, R. H.; Rosen, R. K.; Timmers, F. J. *Organometallics* 1996, 15, 1518-1520; incorporated herein by reference). The molarity of n-butyllithium, s-butyllithium, and t-butyllithium were determined by titration with a tetrahydrofuran solution of 2-butanol using triphenylmethane as an indicator (Duhamel, L.; Palquevent, J.-C. *J. Org. Chem.* 1979, 44, 3404-3405; incorporated herein by reference).

Instrumentation.

Proton nuclear magnetic resonance ($^1$H NMR) spectra and carbon nuclear magnetic resonance ($^{13}$C NMR) were recorded with Varian Unity/Inova 600 (600 MHz), Varian Unity/Inova 500 (500 MHz/125 MHz), or Varian Mercury 400 (400 MHz/100 MHz) NMR spectrometers. Chemical shifts for protons are reported in parts per million scale (δ scale) downfield from tetramethylsilane and are referenced to residual protium in the NMR solvents (CHCl$_3$: δ 7.26, C$_6$D$_5$H: δ 7.15, D$_2$HCOD: δ 3.31, CDHCl$_2$: δ 5.32, (CD$_2$H)CD$_3$SO: δ 2.49). Chemical shifts for carbon are reported in parts per million (δ scale) downfield from tetramethylsilane and are referenced to the carbon resonances of the solvent (CDCl$_3$: δ 77.0, C$_6$D$_6$: δ 128.0, D$_3$COD: δ 44.9, CD$_2$Cl$_2$: δ 53.8, (CD$_3$)$_2$SO: δ 39.5). Data are represented as follows: chemical shift, multiplicity (s=singlet, d=doublet, t=triplet, q=quartet, m=multiplet, br=broad), integration, coupling constant in Hz, and assignment. Infrared (IR) spectra were obtained using a Perkin-Elmer 1600 FT-IR spectrophotometer referenced to a polystyrene standard. Data are represented as follows: frequency of the absorption (cm$^{-1}$), intensity of absorption (s=strong, sb=strong broad, m=medium, w=weak, br=broad), and assignment (where appropriate). Optical rotations were determined on a JASCO DIP-370 digital polarimeter equipped with a sodium lamp source using a 200-µL or 2-mL solution cell. High resolution mass spectra were obtained at the Harvard University Mass Spectrometry Facilities.

Microbial Dihydroxylation Product DRS1:

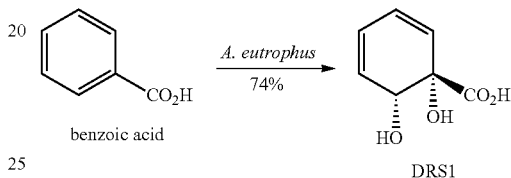

Preparation of Glycerol Stock Solutions

*Alcaligenes eutrophus* B9 cells (lyophilized powder, 20 mg, generously supplied by Prof. George D. Hegeman (Indiana University); Reiner, A. M.; Hegeman, G. D. *Biochemistry* 1971, 10, 2530.) were suspended in nutrient broth (5 mL, prepared by dissolving 8 g of Difco Bacto© Nutrient Broth in 1 L of nanopure water followed by sterilization in an autoclave at 125° C.) in a 20-mL sterile culture tube. Aqueous sodium succinate solution (16.7 µL of a 2.5 M aqueous solution, 5 mM final concentration) was added, and the culture tube was shaken at 250 rpm at 30° C. until cell growth became apparent (3 d). An aliquot (250 µL) of the cellular suspension was then transferred to 5 mL of Hutner's mineral base medium (HMB, see paragraph below) containing sodium succinate (16.7 µL of a 2.5 M aqueous solution, 5 mM final concentration) in a 20-mL sterile culture tube. The culture tube was shaken at 250 rpm for 2 d at 30° C., whereupon an aliquot (250 µL) of the fermentation solution was subcultured in a sterile Erlenmeyer flask containing 50 mL of HMB and aqueous sodium succinate solution (167 µL of a 2.5 M solution, 5 mM final concentration). The flask was shaken at 250 rpm for 24 h at 30° C. The resulting solution was used directly for the preparation of glycerol stock solutions. Thus, a portion of the subcultured cellular suspension (5 mL) was diluted with an equal volume of sterile glycerol, and the resulting solution was divided equally into ten 2-mL sterile Eppendorf tubes. The individual stock solutions were then stored at −80° C.

Hutner's Mineral Base Medium

Hutner's mineral base medium (HMB) was prepared as follows. Solid potassium hydroxide (400 mg) was dissolved in 500 mL of nanopure water in a 2-L Erlenmeyer flask. Nitrilotriacetic acid (200 mg), magnesium sulfate (283 mg), calcium chloride dihydrate (67 mg), ammonium molybdate (0.2 mg), iron (II) sulfate (2.0 mg), Hutner's Metals 44 solution (1 mL, see paragraph below), ammonium sulfate (1.0 g), potassium dihydrogen phosphate (2.72 g) and sodium monohydrogen phosphate heptahydrate (5.36 g) were added sequentially. The solution was diluted to a total volume of 1 L and the pH was adjusted to 6.8 with concentrated hydrochloric acid. The medium was sterilized by filtration or by heating in an autoclave.

Hutner's Metals 44 solution was prepared as follows. Concentrated sulfuric acid (100 μL) was added to nanopure water (50 mL) in a 250-mL Erlenmeyer flask. Solid EDTA (0.50 g), zinc sulfate heptahydrate (2.20 g), iron (II) sulfate heptahydrate (1.0 g), copper (I) sulfate (0.39 g), cobalt (II) nitrate hexahydrate (50 mg) and sodium tetraborate decahydrate (36 mg) were then added in sequence, followed by 50 mL of nanopure water.

Cellular Dihydroxylation of Sodium Benzoate

A sterile pipette tip was streaked across the surface of a frozen glycerol stock solution to produce small shards (ca. 10 mg). The frozen shards were added to a sterile 125 mL Erlenmeyer flask containing HMB (25 mL) and aqueous sodium succinate solution (140 μL of a 1.5 M solution, 5 mM final concentration). The flask was shaken at 250 rpm for 2 days at 30° C. An aliquot (10 mL) of the white, heterogeneous solution was transferred using a sterile pipette to a mammalian cell growth jar containing HMB (6 L) and aqueous sodium succinate solution (20 mL of a 1.5 M solution, 5 mM final concentration). The jar was warmed on a hot plate to an internal temperature of 30° C.; cotton-filtered air was sparged through the medium. After 2 days, the white, heterogeneous solution was treated with aqueous sodium benzoate solution (18 mL of a 1.0 M solution) and aqueous sodium succinate solution (10 mL of a 1.5 M solution), inducing dihydroxylation. The resulting mixture was aerated vigorously for 6 hours at an internal temperature of 30° C. After induction, sufficient aqueous sodium benzoate solution (24 to 48 mL of a 1.0 M solution, depending on the rate of consumption) was added hourly to maintain a concentration of 10-20 mM (determined by UV absorbance at 225 nm). Aqueous sodium succinate solution (10 mL of a 1.5 M solution) was added every fourth hour. These additions proceeded over 18 hours, then the solution was aerated overnight at an internal temperature of 30° C., to ensure complete conversion. The fermentation broth was centrifuged, in portions, at 6000 rpm (Sorvall GS-3 rotor, model SLA-3000) to remove cellular material. The supernatant was concentrated to a volume of 400 mL using a rotary evaporator (bath temperature<45° C.). The concentrate was cooled to 0° C. and then acidified to pH 3.0 using concentrated aqueous hydrochloric acid. The acidified aqueous solution was extracted repeatedly with ethyl acetate (8×500 mL, 4×800 mL, 8×1 L). The ethyl acetate extracts were dried over sodium sulfate before concentration, using a rotary evaporator (bath temperature<45° C.), providing a pale yellow solid residue. Trituration of the residue with dichloromethane (2×200 mL) followed by drying in vacuo afforded pure (1S, 2R)-1,2-dihydroxycyclohexa-3,5-diene-1-carboxylic acid (DRS1) as a white powder mp 95-96° C. dec (38 g, 74%, [α]$_D$–114.8 (c 0.5 in EtOH), lit., [α]$_D$–106 (c 0.5 in EtOH) Jenkins, G. N.; Ribbons, D. W.; Widdowson, D. A.; Slawin, A. M. Z.; Williams, D. J. *J. Chem. Soc. Perkin Trans.* 1 1995, 2647.).

Epoxide DRS2:

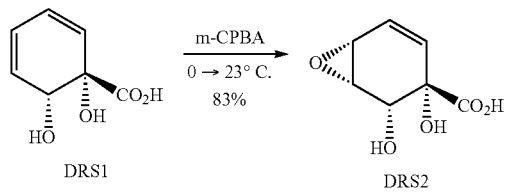 [SMILES: O=C(O)[C@]1(O)C=CC=C[C@H]1O ; O=C(O)[C@]1(O)C=C[C@H]2O[C@H]2[C@H]1O]

m-Chloroperoxybenzoic acid (mCPBA was purified as follows: 50 g of 77% mCPBA (Alrich) was dissolved in benzene (1 L). The benzene solution was then washed with pH 7.4 phosphate buffer (3×1 L) and dried over $Na_2SO_4$ for 3 hours and concentrated (<40° C., thermal detonation hazard) to provide pure mCPBA as a white solid; 10.7 g, 62.3 mmol, 1.2 equiv) was added in three equal portions over 30 min. to a suspension of the microbial dihydroxylation product DRS1 (8.10 g, 51.9 mmol, 1.0 equiv) in ethyl acetate (400 mL) at 23° C. The heterogeneous solution was stirred for 10 h, then was diluted with benzene (80 mL) and stirred for 1 h The supernatant was decanted and the solid residue was triturated with benzene (2×15 mL). The resulting pasty solid was dried in vacuo to provide the epoxide DRS2 as an amorphous white powder (7.36 g, 83%).

mp 87-91° C.; $^1$H NMR (400 MHz, $CD_3OD$) δ 6.23 (dd, 1H, J=9.6, 3.9 Hz, =CHC(OCH)), 5.92 (dd, 1H, J=9.6, 1.9 Hz, =CHC($CO_2H$)), 4.40 (d, 1H, J=1.3 Hz, CHOH), 3.58 (dd, 1H, J=4.4, 1.3 Hz, CHCHOH), 3.49 (m, 1H, =CCHO); $^{13}$C NMR (100 MHz, $CD_3OD$) δ 175.8, 135.1, 128.8, 75.4, 70.9, 57.5, 50.3; FTIR (neat), cm$^{-1}$ 3381 (s, OH), 1738 (s, C=O), 1608 (m), 1255 (m), 1230 (m), 1084 (m, C—O); HRMS (CI) m/z calcd for $(C_7H_8O_5+NH_4)^+$ 190.0715. found 190.0707.

Epoxide DJB1:

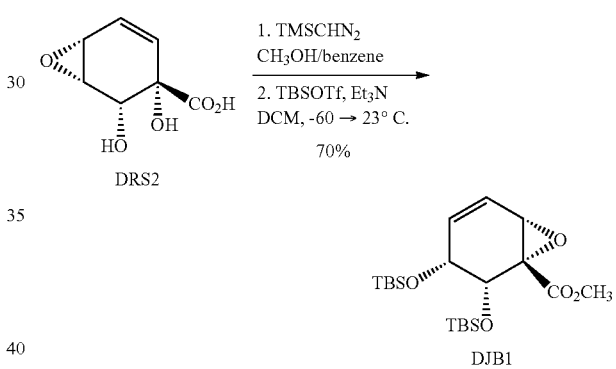

A solution of trimethylsilyldiazomethane in hexanes (2.0 M, 25.5 mL, 51.0 mmol, 1.2 equiv) was added to a solution of the epoxide DRS2 (7.36 g, 42.8 mmol, 1.0 equiv) in methanol-benzene (1:3, 160 mL) at 23° C. Extensive gas evolution was observed upon addition. The yellow solution was stirred for 5 min, then was concentrated, affording a light yellow solid. The solid was dried by azeotropic distillation from benzene (2×25 mL), and the dried solid was suspended in dichloromethane (200 mL). Triethylamine (20.8 ml, 149 mmol, 3.5 equiv) and tert-butyldimethylsilyl trifluoromethanesulfonate (29.4 ml, 128 mmol, 3.0 equiv) were then added in sequence, providing a homogeneous solution. The reaction solution was stirred at 23° C. for 30 min. An aqueous potassium phosphate buffer solution (pH 7.0, 0.2 M, 300 mL) was added followed by dichloromethane (100 ml). The organic phase was separated and dried over anhydrous sodium sulfate. The dried solution was filtered and the filtrate was concentrated, providing a brown oil. The product was purified by flash column chromatography (5:95 ethyl acetate-hexanes), affording the epoxide DJB1 as a light yellow oil (12.4 g, 70% over 2 steps). $R_f$ 0.50 (1:4 ethyl acetate-hexanes); $^1$H NMR (400 MHz, $CDCl_3$) δ 5.95 (dd, 1H, J=9.8, 3.4 Hz, =CHCOTBS), 5.89 (ddd, 1H, J=9.8, 2.9, 1.5 Hz, =CHCHOCCO$_2$), 4.63 (d, 1H, J=3.9 Hz, O$_2$CCCHOTBS), 4.42 (m, 1H, =CCHOTBS), 3.78 (s, 3H, OCH$_3$), 3.31 (d, 1H, J=2.0 Hz, CHOCCO$_2$), 0.90 (s, 9H, C(CH$_3$)$_3$), 0.89 (s, 9H, C(CH$_3$)$_3$), 0.09 (s, 3H, SiCH$_3$), 0.08 (s, 6H, SiCH$_3$), 0.07 (s, 3H, SiCH$_3$); $^{13}$C NMR (100 MHz, CDCl$_3$) δ 170.2, 138.7, 122.6, 69.3, 68.4, 59.7, 52.5, 52.0, 25.9, 25.7, 18.3, 18.2, −4.18, −4.27, −4.45, −5.21; FTIR (neat), cm$^{-1}$ 1759 (m, C=O), 1736 (s, C=O), 1473 (m), 1256 (w), 1253 (s), 1150 (s, C—O), 1111 (m, C—O), 1057 (s, C—O), 940 (m); HRMS (ES) m/z calcd for (C$_{20}$H$_{38}$O$_5$Si$_2$)$^+$414.2258. found 414.2239.

Isoxazole MGC2 (Method A):

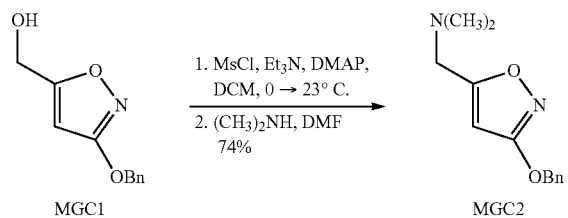 [SMILES: OCc1cc(OCc2ccccc2)no1 ; CN(C)Cc1cc(OCc2ccccc2)no1]

Triethylamine (37.5 mL, 0.269 mol, 1.15 equiv), 4-(dimethylamino)pyridine (289 mg, 2.34 mmol, 0.01 equiv), and methanesulfonyl chloride (20.8 mL, 0.269 mol, 1.15 equiv) were added in sequence to a solution of the alcohol MGC1 (prepared in two steps from commercially available methyl 3-hydroxy-5-isoxazolecarboxylate as previously reported by: Reiss, R.; Schön, M.; Laschat, S.; Jäger, V. Eur. J. Org. Chem. 1998, 473-479.) (48.0 g, 0.234 mol, 1.0 equiv) in dichloromethane (450 mL) at 0° C. The reaction mixture was stirred at 0° C. for 2.5 h, then was concentrated, affording an orange oil. Chilled dimethylamine (condensed using a cold finger with dry ice/acetone, 26.2 mL, 0.480 mol, 2.0 equiv) was added to a mixture of the orange oil prepared above and N,N-dimethylformamide (150 mL) at 0° C., providing a homogenous solution. The solution was stirred at 0° C. for 2 h, then was allowed to warm to 23° C.; stirring was continued at that temperature for 24 h. The solution was partitioned between saturated aqueous sodium bicarbonate solution-brine (2:1, 300 mL) and ethyl acetate-hexanes (1:1, 500 mL). The organic phase was separated and washed with brine (2×200 mL), and dried over anhydrous sodium sulfate The dried solution was filtered and the filtrate was concentrated, furnishing a brown residue. The product was purified by flash column chromatography (1:4 to 1:1 ethyl acetate-hexanes), affording the isoxazole MGC2 as a light yellow oil (40.1 g, 74%). R$_f$ 0.34 (1:1 ethyl acetate-hexanes); $^1$H NMR (500 MHz, CDCl$_3$) δ 7.43-7.31 (m, 5H, ArH), 5.82 (s, 1H, =CH), 5.23 (s, 2H, OCH$_2$Ar), 3.48 (s, 2H, CH$_2$N(CH$_3$)$_2$), 2.27 (s, 6H, N(CH$_3$)$_2$); $^{13}$C NMR (125 MHz, CDCl$_3$) δ 171.9, 171.2, 136.1, 128.8, 128.5, 128.7, 94.8, 71.7, 55.1, 45.3; FTIR (neat), cm$^{-1}$ 2950 (s, CH) 1615 (s), 1494 (s), 1452 (s), 1136 (m); HRMS (ES) m/z calcd for (C$_{13}$H$_{16}$N$_2$O$_2$)$^+$232.1212. found 232.1220.

Isoxazole MGC4:

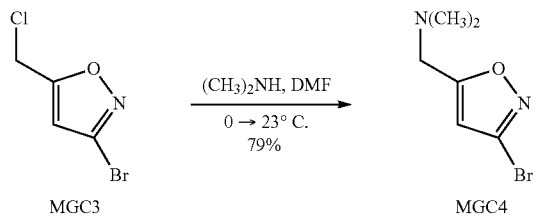 [SMILES: ClCc1cc(Br)no1 ; CN(C)Cc1cc(Br)no1]

Chilled dimethylamine (condensed into a reaction vessel submerged in a 0° C. bath using a cold finger with dry ice/acetone, 106 mL, 1.94 mol, 2.2 equiv) was added dropwise via cannula to a solution of the isoxazole MGC3 (prepared in two steps from glyoxylic acid as reported by: Pevarello, P.; Varasi, M. Synth. Commun. 1992, 22, 1939.) (174 g, 0.884 mol, 1.0 equiv) in acetonitrile (2 L) at 0° C. The reaction mixture was stirred at 0° C. for 2 h, then the cooling bath was removed. The reaction mixture was allowed to warm to 23° C.; stirring was continued at that temperature for 8 h. The mixture was partitioned between brine-saturated aqueous sodium bicarbonate solution (1:1, 1.5 L) and ethyl acetate (1.5 L). The organic phase was separated and the aqueous phase was further extracted with ethyl acetate (3×400 mL). The organic phases were combined and dried over anhydrous sodium sulfate. The dried solution was filtered and the filtrate was concentrated to a volume of 500 mL, resulting in the formation of a white precipitate. The concentrate was filtered and the filtrate was concentrated, providing the isoxazole MGC4 as an orange oil (143 g, 79%). An analytical sample was prepared by flash column chromatography (1:9 to 2:8 ethyl acetate-hexanes), affording the isoxazole MGC4 as a light yellow oil.

R$_f$ 0.30 (1:4 ethyl acetate-hexanes); $^1$H NMR (300 MHz, CDCl$_3$) δ 6.26 (s, 1H, vinyl), 3.63 (s, 2H, CH$_2$N(CH$_3$)$_2$), 2.30 (s, 6H, N(CH$_3$)$_2$); $^{13}$C NMR (100 MHz, CDCl$_3$) δ 172.1, 140.5, 106.8, 54.5, 45.3; FTIR (neat), cm$^{-1}$ 3137 (w), 2945 (m), 2825 (m), 2778 (m), 1590 (s), 1455 (m), 1361 (m), 1338 (s), 1281 (s), 1041 (m); HRMS (ES) m/z calcd for (C$_6$H$_9$BrN$_2$O+H)$^+$204.9976. found 204.9969.

Isoxazole MGC2 (Method B):

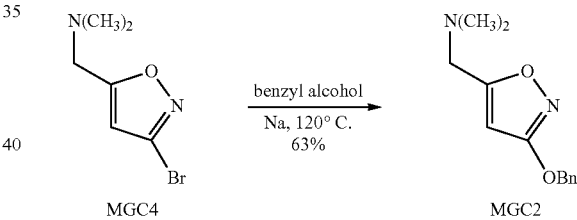

Sodium metal (32.63 g, 1.42 mol, 2.03 equiv) was added portionwise over 8 h to benzyl alcohol (1 L) at 23° C. The resulting mixture was stirred vigorously for 24 h, then was transferred via large bore cannula to the neat isoxazole MGC4 (143 g, 0.700 mol, 1.0 equiv) at 23° C. The resulting light brown mixture was placed in an oil bath preheated to 120° C. and was stirred for 20 h at that temperature. Ethyl acetate (2 L) was added to the cooled reaction mixture and stirring was continued for 15 min. Aqueous hydrochloric acid (1.0 M, 2 L) was added and the aqueous phase was separated. The organic phase was further extracted with two 300-mL portions of 1.0 M aqueous hydrochloric acid. The aqueous phases were combined and the pH adjusted to 9 by slow addition of aqueous sodium hydroxide (6.0 M, approx. 350 mL). The resulting mixture was extracted with dichloromethane (3×500 mL). The organic extracts were combined and dried over anhydrous sodium sulfate. The dried solution was filtered and the filtrate was concentrated, yielding the isoxazole MGC2 as a yellow oil (102 g, 63%). An analytical sample was prepared by flash column chromatography (3:7 ethyl acetate-hexanes, then 5:95 methanol in ethyl acetate), affording the isoxazole MGC2 as a light yellow oil (spectroscopic data was identical to that obtained for material prepared by Method A).

Ketone MGC5:

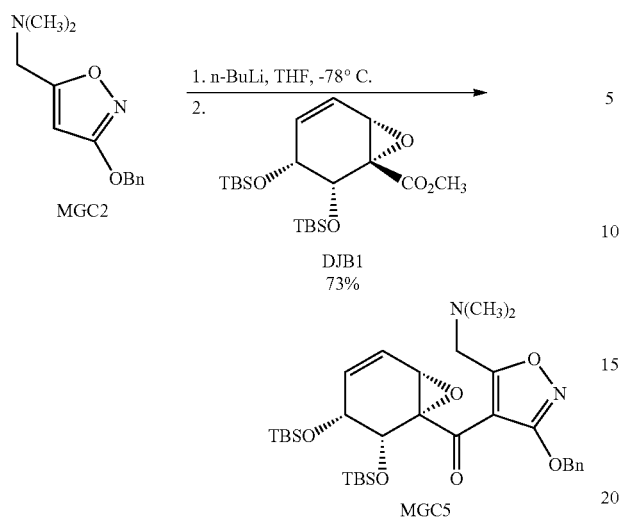

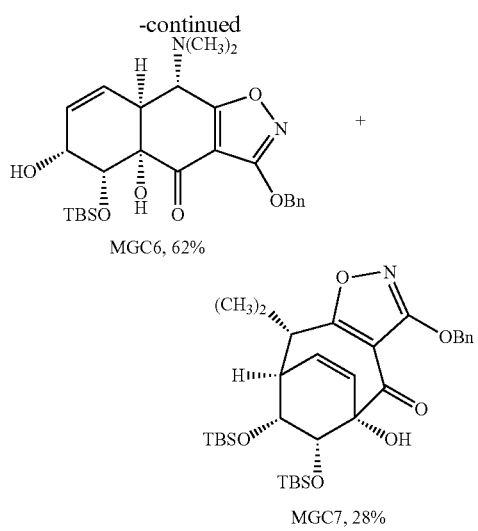

A solution of n-butyllithium in hexanes (2.47 M, 16.0 mL, 39.5 mmol, 1.0 equiv) was added to a solution of the isoxazole MGC2 (9.16 g, 39.5 mmol, 1.0 equiv) in tetrahydrofuran (150 mL) at −78° C. The resulting rust-colored solution was stirred at −78° C. for 1 h whereupon a solution of the methyl ester DJB1 (9.82 g, 23.7 mmol, 0.6 equiv) in tetrahydrofuran (6 mL) was added dropwise via cannula. The transfer was quantitated with two 1-mL portions of tetrahydrofuran. The resulting brown solution was stirred at −78° C. for 1 h, then an aqueous potassium phosphate buffer solution (pH 7.0, 0.2 M, 250 mL) was added. The biphasic mixture was allowed to warm to 23° C., then was extracted with dichloromethane (2×300 mL). The organic extracts were combined and dried over anhydrous sodium sulfate. The dried solution was filtered and the filtrate was concentrated, providing a yellow oil. The product was purified by flash column chromatography (1:9 to 1:3 ethyl acetate-hexanes), affording the ketone MGC5 as a light yellow solid (10.6 g, 73%).

$R_f$ 0.59 (1:3 ethyl acetate-hexanes); $^1$H NMR (500 MHz, CDCl$_3$) δ 7.44-7.35 (m, 5H, ArH), 5.90 (ddd, 1H, J=9.8, 5.9, 2.0 Hz, =CHCHOSi), 5.82 (dd, 1H, J=9.8, 3.4 Hz, =CHCHOCC), 5.31 (m, 2H, OCH$_2$Ar), 4.58 (d, 1H, J=4.2 Hz, (O)CCCHOSi), 4.27 (m, 1H, =CHCHOSi), 3.94 (d, 1H, J=15.6 Hz, CHH'N), 3.77 (d, 1H, J=15.6 Hz, CHH'N), 3.17 (dd, 1H, J=3.4, 1.5 Hz, HCOCC(O)), 2.35 (s, 6H, N(CH$_3$)$_2$), 0.89 (s, 9H, C(CH$_3$)$_3$), 0.83 (s, 9H, C(CH$_3$)$_3$), 0.06 (s, 3H, SiCH$_3$), 0.05 (s, 3H, SiCH$_3$), 0.04 (s, 3H, SiCH$_3$), −0.07 (s, 3H, SiCH$_3$); $^{13}$C NMR (125 MHz, CDCl$_3$) δ 191.8, 176.3, 168.9, 136.5, 135.5, 128.8, 128.7, 125.0, 106.9, 72.4, 69.6, 67.8, 67.4, 55.3, 52.6, 45.9, 26.2, 26.0, 18.5, 18.3, −3.1, −3.8, −3.8, −5.1; FTIR (neat), cm$^{-1}$ 2952 (s, CH), 1682 (s, C=O), 1594 (s), 1502 (s), 1456 (m), 1097 (s, C—O), 774 (s); HRMS (FAB) m/z calcd for (C$_{32}$H$_{50}$N$_2$O$_6$Si$_2$+Na)$^+$ 637.3105. found 637.3097.

Ketones MGC6 and MGC7:

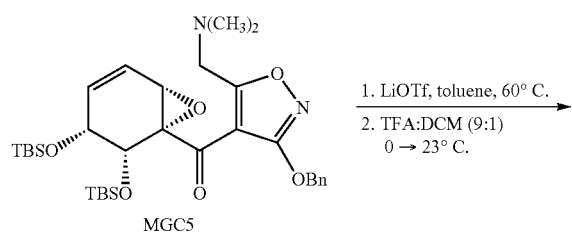

Solid lithium trifluoromethanesulfonate (76.0 mg, 0.490 mmol, 0.05 equiv) was added to a solution of the ketone MGC5 (6.02 g, 9.80 mmol, 1.0 equiv) in toluene (500 mL) at 23° C. The resulting heterogeneous light yellow mixture was placed in an oil bath preheated to 65° C. and was stirred at that temperature for 3 h. The reaction mixture was cooled to 23° C. and was filtered. The solids were washed with toluene (50 mL) and the filtrate was concentrated, providing a yellow oil. The oil was covered with dichloromethane-trifluoroacetic acid (10:1, 165 mL) and the resulting mixture was stirred at 23° C. for 18 h. Aqueous sodium bicarbonate solution (300 mL) was added and extensive gas evolution was observed upon addition. The biphasic mixture was extracted with diethyl ether (4×300 mL) and the organic extracts were combined and dried over anhydrous sodium sulfate. The dried solution was filtered and the filtrate was concentrated, providing a brown oil. The product was purified by flash column chromatography (1:9 to 1:5 ethyl acetate-hexanes), affording the ketone MGC6 as a white foam (3.20 g, 62%) and the ketone MGC7 as a viscous yellow oil (1.68 g, 28%).

Ketone MGC6:

$R_f$ 0.52 (1:3 ethyl acetate-hexanes); $^1$H NMR (500 MHz, CDCl$_3$) δ 7.45 (m, 2H, ArH), 7.36-7.30 (m, 3H, ArH), 5.96 (bs, 1H, =CH), 5.45 (bs, 1H, =CH), 5.32 (m, 2H, OCHH'Ar), 5.33 (bs, 1H, CHOSi), 4.15 (d, 1H, J=8.8 Hz, CHOSi), 3.59 (d, 1H, J=3.9 Hz, CHN(CH$_3$)$_2$), 3.34 (bs, 1H, C$_3$CH), 2.57 (bs, 1H, OH), 2.39 (s, 6H, N(CH$_3$)$_2$), 0.90 (s, 9H, C(CH$_3$)$_3$), 0.16 (s, 3H, SiCH$_3$), 0.11 (s, 3H, SiCH$_3$); $^{13}$C NMR (100 MHz, C$_6$D$_6$) δ 189.2, 178.3, 168.6, 135.3, 128.5, 128.4, 128.3, 125.4, 106.4, 79.8, 72.3, 72.2, 67.1, 63.6, 42.9, 26.1, 18.5, −4.0, −4.8; FTIR (neat), cm$^{-1}$ 3549 (bs, OH), 3455 (bs, OH), 2942 (s, CH), 1698 (s, C=O), 1617 (m), 1508 (s), 1032 (s, C—O), 906 (s); HRMS (ES) m/z calcd for (C$_{26}$H$_{36}$N$_2$O$_6$Si+H)$^+$ 501.2421. found 501.2422.

Ketone MGC7:

$R_f$ 0.64 (1:5 ethyl acetate-hexanes); $^1$H NMR (500 MHz, CDCl$_3$) δ 7.50 (d, 2H, J=1.5 Hz, ArH), 7.40-7.32 (m, 3H, ArH), 5.94 (dd, 1H, J=9.7, 6.4 Hz, =CHCHCHOSi), 5.76 (d, 1H, J=9.7 Hz, =CHCOH), 5.37 (d, 1H, J=12.2 Hz, OCHH'Ph), 5.32 (d, 1H, J=12.2 Hz, OCHH'Ph), 4.09 (d, 1H, J=2.9 Hz, HOCCHOSi), 4.03 (s, 1H, OH), 3.88 (m, 1H, NCHCHCHOSi), 3.74 (d, 1H, J=3.9 Hz, (CH$_3$)$_2$NCH), 2.46 (s, 6H, N(CH$_3$)$_2$), 0.91 (s, 9H, C(CH$_3$)$_3$), 0.87 (s, 9H, C (CH$_3$)$_3$), 0.06 (s, 3H, SiCH$_3$), 0.05 (s, 3H, SiCH$_3$), 0.04 (s, 3H, SiCH$_3$), 0.03 (s, 3H, SiCH$_3$); $^{13}$C NMR (125 MHz, CDCl$_3$) δ 194.9, 173.9, 170.5, 135.8, 132.6, 128.8, 128.5, 128.3, 127.9, 106.2, 81.6, 74.8, 72.0, 71.7, 69.5, 44.6, 43.2, 26.1, 25.9, 18.7, 18.2, −3.6, −4.1, −4.3, −4.3; FTIR (neat), cm$^{-1}$ 3461 (bs, OH), 2940 (s, CH), 1693 (s, C=O), 1663 (s), 1647 (m), 1503 (m), 1080 (s, C—O), 774 (s); HRMS (ES) m/z calcd for (C$_{32}$H$_{50}$N$_2$O$_6$Si$_2$+H)$^+$ 615.3285, found 615.3282.

Alkene DRS3:

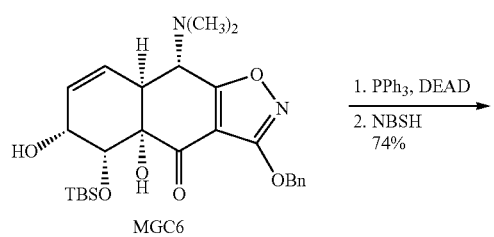

MGC6

1. PPh$_3$, DEAD
2. NBSH
74%

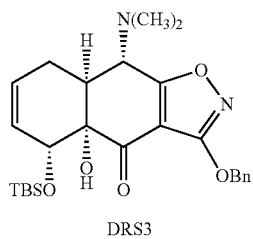

DRS3

Diethyl azodicarboxylate (472 μL, 3.00 mmol, 3.0 equiv) was added to a solution of the ketone MGC6 (500 mg, 1.00 mmol, 1.0 equiv) and triphenylphosphine (789 mg, 3.00 mmol, 3.0 equiv) in toluene (6.0 mL) at 0° C. The mixture was stirred at 0° C. for 90 min whereupon a solution of 2-nitrobenzenesulfonyl hydrazine (651 mg, 3.00 mmol, 3.0 equiv) in tetrahydrofuran (3 mL) was added dropwise via cannula. The resulting mixture was stirred at 0° C. for 10 min, then was allowed to warm to 23° C.; stiffing was continued at that temperature for 23 h. An aqueous potassium phosphate buffer solution (pH 7.0, 0.2 M, 30 mL) was added and the resulting biphasic mixture was extracted with dichloromethane (2×50 mL). The organic extracts were combined and dried over anhydrous sodium sulfate. The dried solution was filtered and the filtrate was concentrated, providing a yellow sludge. The product was purified by flash column chromatography (95:5 to 1:9 ethyl acetate-hexanes), affording the alkene DRS3 as a white solid (356 mg, 74%).

R$_f$ 0.65 (1:3 ethyl acetate-hexanes); $^1$H NMR (500 MHz, CDCl$_3$) δ 7.46 (d, 2H, J=6.8 Hz, ArH), 7.39-7.34 (m, 3H, ArH), 5.81 (m, 1H, =CHCH$_2$), 5.55 (dd, 1H, J=10.3, 2.0 Hz, =CHCOSi), 5.39 (d, 1H, J=12.2 Hz, OCHH'Ph), 5.35 (d, 1H, J=12.2 Hz, OCHH'Ph), 4.15 (s, 1H, CHOSi), 4.04 (bs, 1H, OH), 3.76 (d, 1H, J=10.7 Hz, CHN(CH$_3$)$_2$), 2.58 (dd, 1H, J=10.7, 3.9 Hz, C$_3$CH), 2.47 (m, 8H, N(CH$_3$)$_2$, =CCH$_2$), 0.86 (s, 9H, C(CH$_3$)$_3$), −0.05 (s, 3H, SiCH$_3$), −0.13 (s, 3H, SiCH$_3$); $^{13}$C NMR (125 MHz, CDCl$_3$) δ 191.5, 183.3, 167.9, 135.3, 128.8, 128.7, 128.5, 127.4, 106.8, 78.3, 72.6, 72.0, 67.9, 60.7, 43.0, 42.1, 26.0, 25.8, 23.6, 18.2, −4.6, −5.0; FTIR (neat), cm$^{-1}$ 3528 (w, OH), 2933 (s, CH), 1702 (s, C=O), 1600 (m), 1507 (s), 1092 (s, C—O), 1061 (s, C—O); HRMS (ES) m/z calcd for (C$_{26}$H$_{36}$N$_2$O$_5$Si+H)$^+$ 485.2472. found 485.2457.

Diol DRS4:

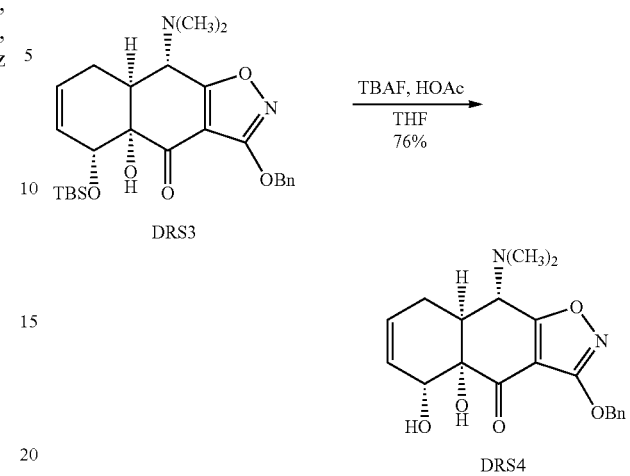

DRS3

TBAF, HOAc
THF
76%

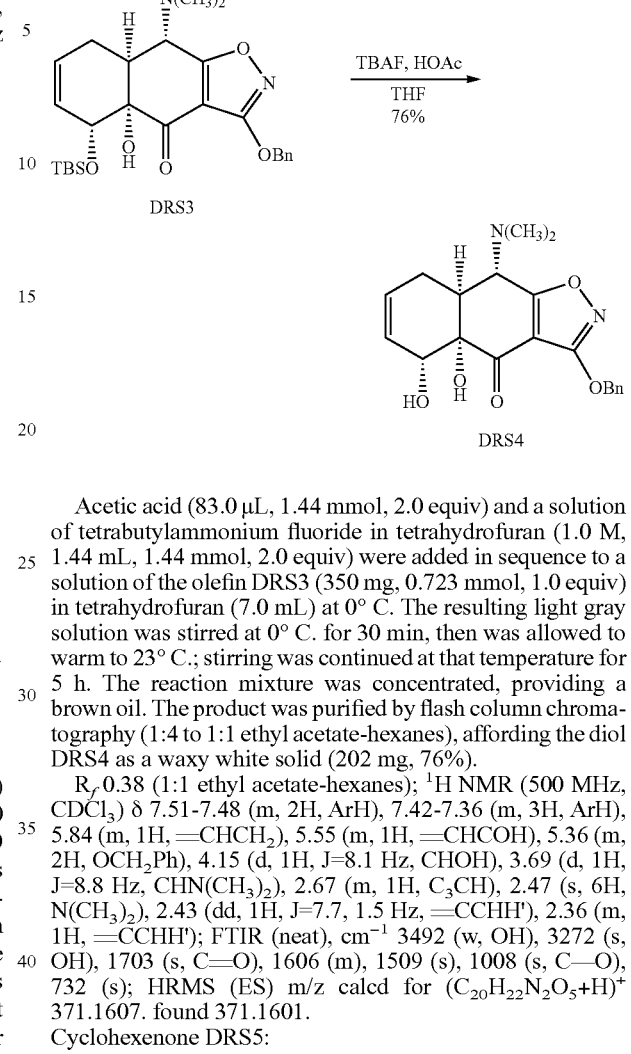

DRS4

Acetic acid (83.0 μL, 1.44 mmol, 2.0 equiv) and a solution of tetrabutylammonium fluoride in tetrahydrofuran (1.0 M, 1.44 mL, 1.44 mmol, 2.0 equiv) were added in sequence to a solution of the olefin DRS3 (350 mg, 0.723 mmol, 1.0 equiv) in tetrahydrofuran (7.0 mL) at 0° C. The resulting light gray solution was stirred at 0° C. for 30 min, then was allowed to warm to 23° C.; stirring was continued at that temperature for 5 h. The reaction mixture was concentrated, providing a brown oil. The product was purified by flash column chromatography (1:4 to 1:1 ethyl acetate-hexanes), affording the diol DRS4 as a waxy white solid (202 mg, 76%).

R$_f$ 0.38 (1:1 ethyl acetate-hexanes); $^1$H NMR (500 MHz, CDCl$_3$) δ 7.51-7.48 (m, 2H, ArH), 7.42-7.36 (m, 3H, ArH), 5.84 (m, 1H, =CHCH$_2$), 5.55 (m, 1H, =CHCOH), 5.36 (m, 2H, OCH$_2$Ph), 4.15 (d, 1H, J=8.1 Hz, CHOH), 3.69 (d, 1H, J=8.8 Hz, CHN(CH$_3$)$_2$), 2.67 (m, 1H, C$_3$CH), 2.47 (s, 6H, N(CH$_3$)$_2$), 2.43 (dd, 1H, J=7.7, 1.5 Hz, =CCHH'), 2.36 (m, 1H, =CCHH'); FTIR (neat), cm$^{-1}$ 3492 (w, OH), 3272 (s, OH), 1703 (s, C=O), 1606 (m), 1509 (s), 1008 (s, C—O), 732 (s); HRMS (ES) m/z calcd for (C$_{20}$H$_{22}$N$_2$O$_5$+H)$^+$ 371.1607. found 371.1601.

Cyclohexenone DRS5:

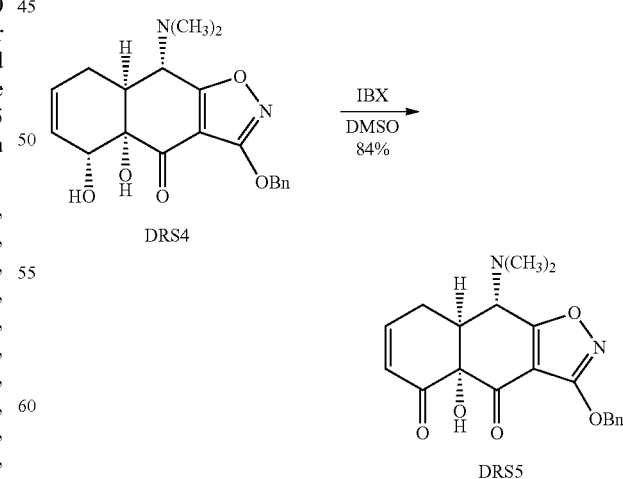

Solid o-iodoxybenzoic acid (558 mg, 1.99 mmol, 3.0 equiv) was added to a solution of the diol DRS4 (246 mg, 0.665 mmol, 1.0 equiv) in dimethylsulfoxide (5.0 mL) at 23°

C. The resulting heterogeneous mixture was stirred for 5 min whereupon it became homogeneous. The brown reaction mixture was stirred at 23° C. for 36 h. Water (10 mL) was added resulting in the precipitation of excess o-iodoxybenzoic acid. The mixture was filtered and the filtrate was partitioned between saturated aqueous sodium bicarbonate solution-brine (1:1, 20 mL) and ethyl acetate-hexanes (2:1, 45 mL). The organic phase was separated and the aqueous phase was further extracted with a 45-mL portion of ethyl acetate-hexanes (2:1). The organic extracts were combined and washed with aqueous sodium sulfite solution (2.0 M, 50 mL), brine (50 mL), and dried over anhydrous sodium sulfate. The dried solution was filtered and the filtrate was concentrated, providing the cyclohexenone DRS5 as a light brown foam (206 mg, 84%).

$R_f$ 0.15 (1:3 ethyl acetate-hexanes); $^1$H NMR (500 MHz, CDCl$_3$) δ 7.48 (d, 2H, J=7.3 Hz, ArH), 7.40-7.34 (m, 3H, ArH), 6.98 (m, 1H, =CHCH$_2$), 6.12 (ddd, 1H, J=12.2, 2.0, 2.0 Hz, =CHC(O)), 5.35 (m, 2H, OCH$_2$Ar), 4.75 (bs, 1H, OH), 3.85 (d, 1H, J=9.8 Hz, CHN(CH$_3$)$_2$), 2.82 (m, 3H, C$_3$CH, =CCH$_2$), 2.48 (s, 6H, N(CH$_3$)$_2$); $^{13}$C NMR (125 MHz, CDCl$_3$) δ 192.8, 188.2, 182.8, 167.6, 149.7, 135.0, 128.9, 128.8, 128.6, 128.3, 107.9, 79.7, 72.8, 60.4, 45.5, 42.4, 25.4; FTIR (neat), cm$^{-1}$ 3447 (w, OH), 1707 (s, C=O), 1673 (s, C=O), 1600 (m), 1512 (s), 1018 (s, C—O), 730 (s); HRMS (ES) m/z calcd for (C$_{20}$H$_{20}$N$_2$O$_5$+H)$^+$369.1450. found 369.1454.

Silyl-Cyclohexenone DRS6:

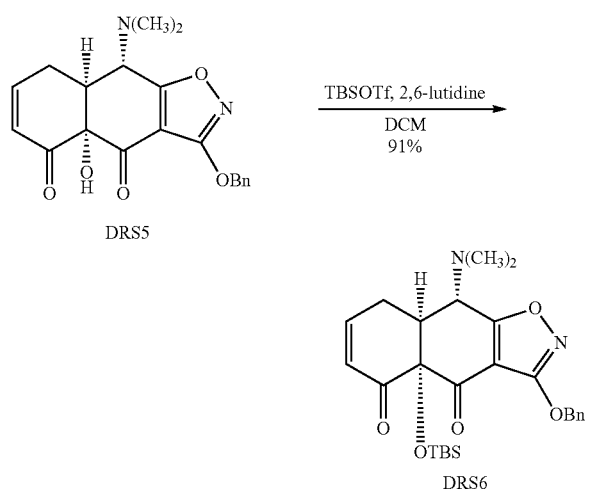

2,6-Lutidine (75.0 μL, 0.640 mmol, 5.0 equiv) and tert-butyldimethylsilyl trifluoromethanesulfonate (88.0 μL, 0.380 mmol, 3.0 equiv) were added in sequence to a solution of the cyclohexenone DRS5 (47.0 mg, 0.130 mmol, 1.0 equiv) in dichloromethane (3 mL) at 23° C. The mixture was stirred at 23° C. for 3 h, then an aqueous potassium phosphate buffer solution (pH 7.0, 0.2 M, 15 mL) was added. The biphasic mixture was extracted with dichloromethane (2×20 mL) and the organic extracts were combined and dried over anhydrous sodium sulfate. The dried solution was filtered and the filtrate was concentrated, affording the silyl-cyclohexenone DRS6 as a white crystalline solid (56.0 mg, 91%).

Mp 157-158° C. (dec); $R_f$ 0.54 (1:3 ethyl acetate-hexanes); $^1$H NMR (500 MHz, CDCl$_3$) δ 7.51 (d, 2H, J=1.5 Hz, ArH), 7.50-7.34 (m, 3H, ArH), 6.94 (m, 1H, =CHCH$_2$), 6.10 (ddd, 1H, J=10.3, 1.5, 1.5 Hz, =CHC(O)), 5.36 (m, 2H, OCH$_2$Ar), 3.79 (d, 1H, J=10.7 Hz, CHN(CH$_3$)$_2$), 2.83 (m, 2H, =CCH$_2$), 2.78 (m, 1H, C$_3$CH), 2.46 (s, 6H, N(CH$_3$)$_2$), 0.84 (s, 9H, C(CH$_3$)$_3$), 0.27 (s, 3H, SiCH$_3$), 0.06 (s, 3H, SiCH$_3$); $^{13}$C NMR (125 MHz, CDCl$_3$) δ 193.4, 187.9, 181.6, 167.7, 149.5, 135.2, 128.8, 128.8, 128.8, 128.6, 108.6, 83.5, 72.8, 59.8, 48.1, 42.2, 26.3, 25.8, 19.3, −2.2, −3.8; FTIR (neat), cm$^{-1}$ 2942 (s), 1719 (s, C=O), 1678 (s, C=O), 1602 (m), 1510 (s), 1053 (s, C—O), 733 (s); HRMS (ES) m/z calcd for (C$_{26}$H$_{34}$N$_2$O$_5$Si+H)$^+$483.2315. found 483.2321.

Ketone MGC9:

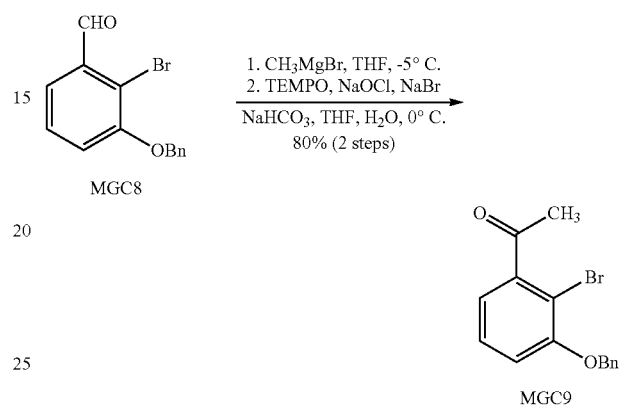

A solution of methylmagnesium bromide in ether (3.15 M, 11.6 mL, 36.7 mmol, 1.07 equiv) was added to a solution of the aldehyde MGC8 (synthesized in 2 steps from commercially available 3-benzyloxy benzyl alcohol as reported by: Hollinshed, S. P.; Nichols, J. B.; Wilson, J. W. *J. Org. Chem.* 1994, 59, 6703.) (10.0 g, 34.3 mmol, 1.0 equiv) in tetrahydrofuran (90 mL) at −5° C. (NaCl/ice bath). The light brown solution was stirred at −5° C. for 60 min, then was partitioned between saturated aqueous ammonium chloride solution (400 mL) and ethyl acetate (400 mL). The organic phase was separated and dried over anhydrous sodium sulfate. The dried solution was filtered and the filtrate was concentrated, providing a light yellow oil (10.1 g, 95% crude). The product was used without further purification.

Sodium bromide (846 mg, 8.22 mmol, 0.25 equiv) and 2,2,6,6-tetramethyl-1-piperidinyloxyl (51.0 mg, 0.329 mmol, 0.01 equiv) were added in sequence to a solution of the light yellow oil prepared above (10.1 g, 32.8 mmol, 1.0 equiv) in tetrahydrofuran (30 mL) at 0° C. A freshly prepared solution of sodium bicarbonate (690 mg, 8.22 mmol, 0.25 equiv) in commercial Clorox bleach (90 mL) was cooled to 0° C. and was added in one portion to the mixture prepared above at 0° C. The resulting bright yellow mixture was stirred vigorously at 0° C. for 1.5 h whereupon sodium sulfite (1.0 g) was added. The resulting mixture was stirred for 15 min at 23° C., then was partitioned between water (400 mL) and ethyl acetate (400 mL). The organic phase was separated and dried over anhydrous sodium sulfate. The dried solution was filtered and the filtrate was concentrated, providing a light brown oil. The product was crystallized from ethanol, furnishing the ketone MGC9 as a white solid (8.08 g, 80% over 2 steps).

$R_f$ 0.80 (3:7 ethyl acetate-hexanes); $^1$H NMR (400 MHz, CDCl$_3$) δ 7.26-7.48 (m, 6H, ArH), 6.98 (m, 2H, ArH), 5.19 (s, 2H, OCH$_2$Ph), 2.62 (s, 3H, C(=O)CH$_3$); $^{13}$C NMR (100 MHz, CDCl$_3$) δ 202.4, 155.5, 144.4, 136.3, 128.9, 128.7, 128.3, 127.2, 120.3, 115.2, 109.1, 71.3, 30.9; FTIR (neat), cm$^{-1}$ 3065 (w), 3032 (w), 2918 (m), 1701 (s, C=O), 1565 (m), 1426 (m), 1300 (s), 1271 (s), 1028 (m); HRMS (ES) m/z calcd for (C$_{15}$H$_{13}$O$_2$Br+H)$^+$304.0099. found 304.0105.

Epoxide MGC10:

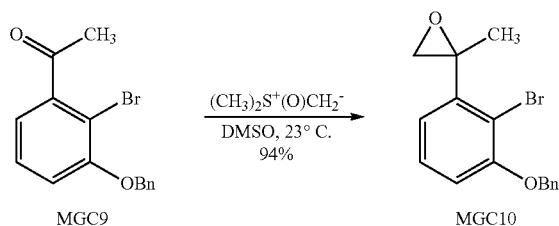

Dimethylsulfoxide (90 mL) was added dropwise via syringe to a mixture of solid trimethylsulfoxonium iodide (694 mg, 3.15 mmol, 1.3 equiv) and solid sodium hydride (60% in oil, 126 mg, 3.15 mmol, 1.3 equiv, washed with three 2-mL portions of n-hexane) at 23° C. Vigorous gas evolution was observed upon addition. The resulting cloudy gray mixture was stirred at 23° C. for 40 min, then a solution of the ketone MGC9 (8.08 g, 26.5 mmol, 1.0 equiv) in dimethylsulfoxide (30 mL) was added dropwise via cannula. The transfer was quantitated with a 2-mL portion of dimethylsulfoxide. The resulting orange mixture was stirred at 23° C. for 35 h, then was partitioned between brine (1 L) and ether (500 mL). The organic phase was separated and the aqueous phase was further extracted with one 500-mL portion of ether. The organic phases were combined and dried over anhydrous sodium sulfate. The dried solution was filtered and the filtrate was concentrated, providing a yellow oil. The product was purified by flash column chromatography (5:95 ethyl acetate-hexanes), affording the epoxide MGC10 as a clear oil (7.94 g, 94%).

$R_f$ 0.90 (3:7 ethyl acetate-hexanes); $^1$H NMR (300 MHz, CDCl$_3$) δ 7.20-7.52 (m, 6H, ArH), 7.10 (dd, 1H, J=7.5, 1.2 Hz, o-ArH), 6.88 (dd, 1H, J=8.1, 1.2 Hz, o-ArH), 5.16 (s, 2H, OCH$_2$Ph), 3.03 (d, 1H, J=4.8 Hz, CHH'OCCH$_3$), 2.87 (d, 1H, J=4.8 Hz, CHH'OCCH$_3$), 1.67 (s, 3H, COCH$_3$); $^{13}$C NMR (100 MHz, CDCl$_3$) δ 155.0, 143.4, 136.7, 128.8, 128.4, 128.2, 127.2, 121.2, 112.8, 112.3, 71.2, 59.7, 55.9, 22.9; FTIR (neat), cm$^{-1}$ 3034 (w), 2981 (w), 2925 (w), 1595 (w), 1567 (s), 1469 (s), 1423 (s), 1354 (s), 1300 (s), 1266 (s), 1028 (s); HRMS (ES) m/z calcd for (C$_{16}$H$_{15}$O$_2$Br+H)$^+$318.0255. found 318.0254.

Benzocyclobutenol MGC11:

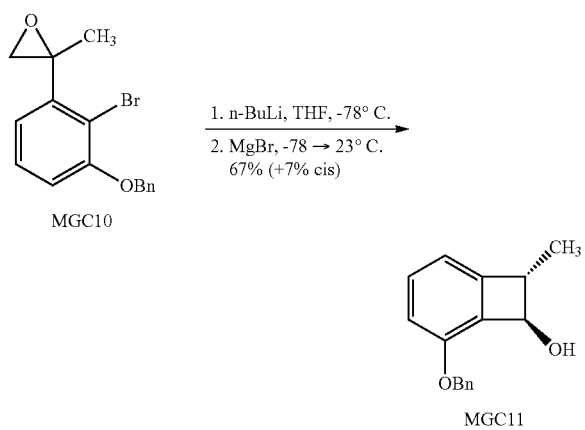

A solution of n-butyllithium in hexanes (1.60 M, 8.25 mL, 13.6 mmol, 1.4 equiv) was added dropwise via syringe down the side of a reaction vessel containing a solution of the epoxide MGC10 (3.11 g, 9.74 mmol, 1.0 equiv) in tetrahydrofuran (90 mL) at −78° C. The resulting yellow solution was stirred at −78° C. for 20 min whereupon a suspension of magnesium bromide (3.95 g, 21.4 mmol, 2.2 equiv) in tetrahydrofuran (25 mL) was added dropwise via cannula. The transfer was quantitated with two 2.5-mL portions of tetrahydrofuran. The resulting cloudy mixture was stirred at −78° C. for 60 min, then the cooling bath was removed and the reaction mixture was allowed to warm to 23° C. The mixture became clear upon warming and was stirred at 23° C. for 1 h. The reaction mixture was poured into aqueous Rochelle's salt solution (10% wt/wt, 1 L) and the resulting mixture was extracted with ethyl acetate (2×400 mL). The organic phases were combined and dried over anhydrous sodium sulfate. The dried solution was filtered and the filtrate was concentrated, providing an off-white solid. The product was purified by flash column chromatography (1:9 to 2:9 ethyl acetate-hexanes), affording the trans-benzocyclobutenol MGC11 as a white solid (1.57 g, 67%).

$R_f$ 0.50 (3:7 ethyl acetate-hexanes); $^1$H NMR (500 MHz, CDCl$_3$) δ 7.44 (br d, 2H, J=7.5 Hz, ArH), 7.38 (br t, 2H, J=7.5 Hz, ArH), 7.22-7.34 (m, 2H, ArH), 6.82 (d, 1H, J=8.5 Hz, o-ArH), 6.75 (d, 1H, J=7.5 Hz, o-ArH), 5.35 (d, 1H, J=12.0 Hz, OCHH'Ph), 5.25 (d, 1H, J=12.0 Hz, OCHH'Ph),), 4.71 (br d, 1H, J=5.5 Hz, CHOH), 3.31 (br q, 1H, J=7.0 Hz, CHCH$_3$), 2.21 (br d, 1H, J=7.0 Hz, OH), 1.38 (d, 3H, J=7.0 Hz, CHCH$_3$); $^{13}$C NMR (100 MHz, CDCl$_3$) δ 154.0, 148.9, 137.4, 131.5, 128.5, 128.4, 127.8, 127.3, 115.2, 114.6, 77.6, 71.2, 50.6, 16.5; FTIR (neat), cm$^{-1}$ 3249 (m, OH), 2958 (w), 1602 (m), 1580 (s), 1453 (s), 1261 (s), 1039 (s); HRMS (ES) m/z calcd for (C$_{16}$H$_{16}$O$_2$+H)$^+$240.1150. found 240.1154.

Benzocyclobutenol MGC12:

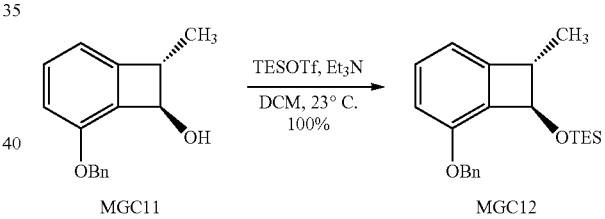

Triethylamine (336 μL, 2.41 mmol, 1.4 equiv) and triethylsilyl trifluoromethanesulfonate (468 μL, 2.07 mmol, 1.2 equiv) were added in sequence to a solution of the benzocyclobutenol MGC11 (500 mg, 1.72 mmol, 1.0 equiv) in dichloromethane (10 mL) at 23° C. The light yellow solution was stirred at 23° C. for 15 min, then was partitioned between water (30 mL) and dichloromethane (30 mL). The organic phase was separated and dried over anhydrous sodium sulfate. The dried solution was filtered and the filtrate was concentrated, providing a yellow oil. The product was purified by flash column chromatography (5:95 ethyl acetate-hexanes), affording the benzocyclobutenol MGC12 (609 mg, 99%) as a clear oil.

$R_f$ 0.85 (1:4 ethyl acetate-hexanes); $^1$H NMR (400 MHz, CDCl$_3$) δ 7.48-7.32 (m, 5H, ArH), 7.24 (m, 2H, ArH), 6.82 (d, 1H, J=8.4 Hz, o-ArH), 6.74 (d, 1H, J=7.2 Hz, o-ArH), 5.37 (d, 1H, J=11.2 Hz, CHH'Ph),), 5.20 (d, 1H, J=11.2 Hz, CHH'Ph),), 4.87 (d, 1H, J=1.6 Hz, CHOTES), 3.45 (dq, 1H, J=7.2, 1.6 Hz, CHCH$_3$), 1.42 (d, 3H, J=7.2 Hz, CHCH$_3$), 0.98 (t, 9H, J=7.6 Hz, TES), 0.56 (q, 6H, J=7.6 Hz, TES); $^{13}$C NMR (100 MHz, CDCl$_3$) δ 154.2, 148.8, 137.6, 131.3, 129.0, 128.7, 128.1, 127.8, 115.1, 114.7, 71.7, 49.9, 16.9, 7.1, 5.2, 5.1; FTIR (neat), cm$^{-1}$ 2952 (w), 2923 (w), 2854 (w), 1606

(w), 1469 (w), 1371 (m), 1265 (s), 1086 (s), 1057 (s), 1048 (s); HRMS (ES) m/z calcd for $(C_{22}H_{30}O_2Si+H)^+$ 354.2015. found 354.2006.
Vinyl Sulfide MGC13:

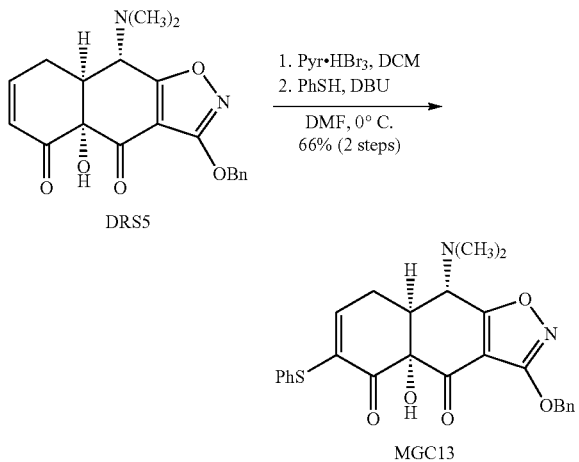

Solid pyridinium hydrobromide perbromide (293 mg, 0.917 mmol, 2.5 equiv) was added to a solution of the cyclohexenone DRS5 (135 mg, 0.367 mmol, 1.0 equiv) in dichloromethane (4 mL) at 23° C. The brown solution was stirred vigorously at 23° C. for 17 h whereupon sodium sulfite (150 mg, 1.19 mmol, 3.25 equiv) was added. The resulting mixture was partitioned between an aqueous potassium phosphate buffer solution (pH 7.0, 0.2 M, 30 mL) and dichloromethane (30 mL). The organic phase was separated and dried over anhydrous sodium sulfate. The dried solution was filtered and the filtrate was concentrated, providing a light brown foamy solid. The product was used immediately without further purification. $R_f$ 0.45 (2:3 ethyl acetate-hexanes); $^1$H NMR (500 MHz, $C_6D_6$) δ 7.24 (d, 2H, J=7.0 Hz, o-ArH), 7.02 (t, 2H, J=7.0 Hz, m-ArH), 6.99 (d, 1H, J=7.0 Hz, p-ArH), 6.42 (ddd, 1H, J=6.0, 3.5, 2.0 Hz, CH=CBr), 5.12 (d, 1H, J=12.5 Hz, CHH'Ph),), 5.03 (d, 1H, J=12.5 Hz, CHH'Ph),), 4.00 (br s, 1H, OH), 3.25 (d, 1H, J=11.0 Hz, CHN(CH$_3$)$_2$), 2.28-2.22 (m, 2H, CH$_2$CH, CH$_2$CH), 2.16 (dd, 1H, J=18.0, 6.0 Hz, CH$_2$CH), 1.83 (s, 6H, N(CH$_3$)$_2$); FTIR (neat), cm$^{-1}$ 3397 (m, OH), 3063 (m), 2943 (m), 1714 (s, C=O), 1606 (s), 1514 (s), 1477 (s), 1371 (m), 1022 (m); HRMS (ES) m/z calcd for $(C_{20}H_{19}O_5BrN_2)^+$ 447.0555. found 447.0545.

Benzenethiol (39.0 µL, 0.378 mmol, 1.03 equiv) and 1,8-diazabicyclo[5,4,0]undec-7-ene (56.0 µL, 0.378 mmol, 1.03 equiv) were added in sequence to a solution of the product prepared above (164 mg, 0.367 mmol, 1.0 equiv) in N,N-dimethylformamide (4 mL) at 0° C. The resulting dark brown mixture was stirred vigorously at 0° C. for 25 min, then was partitioned between ethyl acetate-hexanes (1:1, 30 mL) and an aqueous potassium phosphate buffer solution (pH 7.0, 0.2 M, 30 mL). The organic phase was separated and the aqueous phase was further extracted with two 15-mL portions of ethyl acetate-hexanes (1:1). The organic phases were combined and dried over anhydrous sodium sulfate. The dried solution was filtered and the filtrate was concentrated, providing a brown oil. The product was purified by flash column chromatography (15:85 to 1:4 ethyl acetate-hexanes), furnishing the vinyl sulfide MGC13 as a white foam (116 mg, 66% over two steps).

$R_f$ 0.47 (2:3 ethyl acetate-hexanes); $^1$H NMR (500 MHz, $C_6D_6$) δ 7.34 (dd, 2H, J=7.0, 1.0 Hz, o-ArH), 7.23 (d, 2H, J=6.5 Hz, o-ArH), 6.85-7.04 (m, 6H, ArH), 6.27 (ddd, 1H, J=6.0, 3.0, 1.0 Hz, CH=CSPh), 5.11 (d, 1H, J=12.0 Hz, OCHH'Ph), 5.02 (d, 1H, J=12.0 Hz, OCHH'Ph), 4.62 (br s, 1H, OH), 3.42 (d, 1H, J=10.5 Hz, CHN(CH$_3$)$_2$), 2.44 (ddd, 1H, J=20.0, 5.5, 3.0 Hz, CH$_2$CH), 2.27-2.34 (m, 2H, CH$_2$CH, CH$_2$CH), 1.87 (s, 6H, N(CH$_3$)$_2$); $^{13}$C NMR (100 MHz, CDCl$_3$) δ 188.9, 187.4, 182.5, 167.6, 145.4, 135.3, 135.2, 132.8, 132.6, 129.5, 128.6, 128.4, 128.3, 128.0, 127.8, 108.1, 80.3, 72.5, 59.8, 45.7, 41.4, 25.9; FTIR (neat), cm$^{-1}$ 3445 (w, OH), 3056 (w), 2943 (m), 2800 (w), 1711 (s, C=O), 1682 (s), 1600 (m), 1507 (s), 1471 (s), 1451 (m), 1333 (m), 1020 (m); HRMS (ES) m/z calcd for $(C_{26}H_{24}O_5N_2S+H)^+$ 477.1484. found 447.1465.

Diel-Alder Addition Product MGC14 and Lactone MGC15:

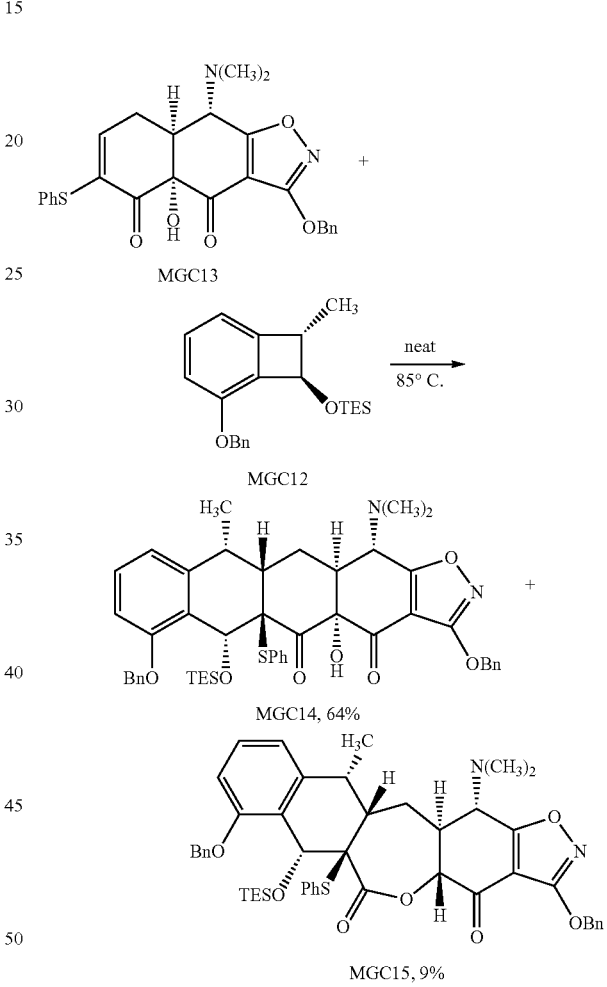

A reaction vessel containing a mixture of the vinylsulfide MGC13 (131 mg, 0.275 mmol, 1.0 equiv) and the benzocyclobutenol MGC12 (750 mg, 2.11 mmol, 7.7 equiv) was placed in an oil bath preheated to 85° C. The light yellow solution was stirred at 85° C. for 48 h, then was allowed to cool to 23° C. The cooled mixture was purified by flash column chromatography (1:19 to 1:4 ethyl acetate-hexanes), affording the Diels-Alder addition product MGC14 as an off-white foamy solid (145 mg, 64%), the lactone MGC15 as a clear oil (20.0 mg, 9%), and the recovered benzocyclobutenol MGC12 as a clear oil (650 mg).

Diels-Alder Addition Product MGC14:

mp 178-179° C.; $R_f$ 0.55 (2:3 ethyl acetate-hexanes); $^1$H NMR (600 MHz, $C_6D_6$) δ 7.27 (d, 2H, J=7.2 Hz, o-ArH), 7.06-7.22 (m, 8H, ArH), 6.92-6.96 (m, 3H, ArH), 6.85 (d, 1H, J=7.2 Hz, ArH), 6.70-6.75 (m, 3H, ArH), 6.55 (d, 1H, J=8.4 Hz, o-ArH), 5.75 (s, 1H, CHOTES), 5.29 (br s, 1H, OH), 5.16 (d, 1H, J=12.0 Hz, OCHH'Ph), 5.10 (d, 1H, J=12.0 Hz, OCHH'Ph), 4.66 (d, 1H, J=10.8 Hz, OCHH'Ph'), 4.63 (d, 1H, J=10.8 Hz, OCHH'Ph'), 4.36 (d, 1H, J=6.6 Hz, CHN(CH$_3$)$_2$), 3.02 (dq, 1H, J=7.8, 6.0 Hz, CH$_3$CH), 2.77 (ddd, 1H, J=6.6, 6.0, 4.2 Hz, CHCHN(CH$_3$)$_2$), 2.41-2.52 (m, 2H, CHCHH'CH, CH$_3$CHCHCH$_2$), 2.08 (s, 6H, N(CH$_3$)$_2$), 1.83 (ddd, 1H, J=13.2, 4.2, 4.2 Hz, CHCHH'CH), 1.34 (d, 3H, J=7.8 Hz, CH$_3$CH), 0.70 (t, 9H, J=7.8 Hz, Si(CH$_2$CH$_3$)$_3$), 0.48 (d, 6H, J=7.8 Hz, Si(CH$_2$CH$_3$)$_3$); $^{13}$C NMR (100 MHz, CDCl$_3$) δ 196.3, 186.1, 181.4, 168.3, 156.3, 143.9, 137.6, 136.6, 135.4, 130.6, 129.8, 129.3, 128.6, 128.5, 128.4, 128.2, 128.0, 127.8, 125.4, 121.1, 109.3, 108.4, 80.6, 72.4, 70.2, 66.0, 62.5, 61.7, 43.2, 42.0, 38.1, 37.2, 27.4, 20.5, 6.9, 4.9; FTIR (neat), cm$^{-1}$ 3490 (w, OH), 3063 (w), 3023 (w), 2951 (m), 2871 (m), 1715 (s, C=O), 1602 (m), 1589 (m), 1513 (s), 1457 (s), 1366 (m), 1260 (s), 1065 (s), 1012 (s); HRMS (FAB) m/z calcd for (C$_{48}$H$_{54}$O$_7$N$_2$SSi+Na)$^+$ 853.3318. found 853.3314.

Lactone MGC15:

R$_f$ 0.55 (3:7 ethyl acetate-hexanes); $^1$H NMR (600 MHz, C$_6$D$_6$) δ 7.34 (d, 2H, J=7.2 Hz, o-ArH), 7.02-7.18 (m, 4H, ArH), 6.72-6.84 (m, 4H, ArH), 6.54 (d, 1H, J=7.8 Hz, o-ArH), 5.73 (s, 1H, CHOTES), 5.49 (d, 1H, J=6.6 Hz, (C=O) OCHC=O), 5.20 (s, 2H, OCH$_2$Ph), 4.60 (d, 1H, J=11.4 Hz, OCHH'Ph'), 4.57 (d, 1H, J=11.4 Hz, OCHH'Ph'), 3.49 (d, 1H, J=11.4 Hz, CHN(CH$_3$)$_2$), 3.23 (dq, 1H, J=9.0, 7.2 Hz, CH$_3$CH), 2.49 (m, 1H, CH$_3$CHCHCHH'), 2.30-2.40 (m, 2H, CHCHN(CH$_3$)$_2$, CH$_3$CHCHCH$_2$), 2.16 (dd, 1H, J=12.0, 0.6 Hz, CH$_3$CHCHCHH'), 1.96 (s, 6H, N(CH$_3$)$_2$), 1.33 (d, 3H, J=7.2 Hz, CH$_3$CH), 0.73 (t, 9H, J=7.8 Hz, Si(CH$_2$CH$_3$)$_3$), 0.46-0.62 (m, 6H, Si(CH$_2$CH$_3$)$_3$); $^{13}$C NMR (100 MHz, CDCl$_3$) δ 196.4, 176.0, 170.0, 157.9, 156.0, 144.0, 136.6, 136.5, 135.6, 129.8, 129.7, 129.4, 128.9, 128.6, 128.4, 128.3, 128.2, 128.1, 127.8, 125.1, 121.2, 108.8, 101.9, 75.9, 72.1, 70.1, 64.7, 64.6, 62.9, 41.4, 36.7, 35.6, 27.7, 21.7, 6.9, 4.9; FTIR (neat), cm$^{-1}$ 3062 (w), 3033 (w), 2950 (m), 2874 (m), 1731 (s, C=O), 1599 (m), 1590 (m), 1514 (s), 1453 (s), 1365 (m), 1259 (s), 1120 (s), 1059 (s), 1010 (s); HRMS (ES) m/z calcd for (C$_{48}$H$_{34}$O$_7$N$_2$SSi+H)$^+$ 831.3499. found 831.3509.

Alcohol MGC16:

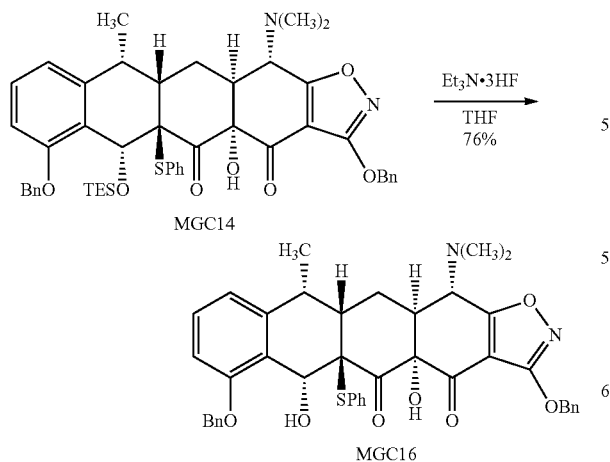

MGC14

MGC16

Triethylamine trihydrofluoride (200 μL, 1.23 mmol, 8.5 equiv) was added to a solution of the Diels-Alder addition product MGC14 (120 mg, 0.144 mmol, 1.0 equiv) in tetrahydrofuran (6 mL) at 23° C. The mixture was stirred vigorously at 23° C. for 12 h, then was partitioned between an aqueous potassium phosphate buffer solution (pH 7.0, 0.2 M, 30 mL) and ethyl acetate (30 mL). The organic phase was separated and dried over anhydrous sodium sulfate. The dried solution was filtered and the filtrate was concentrated, providing a light brown solid. The product was purified by flash column chromatography (1:4 to 1:1 ethyl acetate-hexanes), affording the alcohol MGC16 as a colorless oil (78.3 mg, 76%).

R$_f$ 0.20 (2:3 ethyl acetate-hexanes); $^1$H NMR (600 MHz, C$_6$D$_6$) δ 7.69 (dd, 2H, J=7.2, 0.6 Hz, o-ArH), 7.24 (d, 2H, J=7.2 Hz, ArH), 6.92-7.06 (m, 12H, ArH), 6.76 (d, 1H, J=7.8 Hz, ArH), 6.47 (d, 1H, J=8.4 Hz, o-ArH), 5.44 (br s, 1H, CHOH), 5.18 (d, 1H, J=12.0 Hz, OCHH'Ph), 5.16 (d, 1H, J=12.0 Hz, OCHH'Ph), 4.57 (d, 1H, J=12.6 Hz, OCHH'Ph'), 4.52 (d, 1H, J=12.6 Hz, OCHH'Ph'), 3.44 (dq, 1H, J=6.6, 5.4 Hz, CH$_3$CH), 2.98 (d, 1H, J=3.0 Hz, CHN(CH$_3$)$_2$), 2.90 (m, 1H, CHCHN(CH$_3$)$_2$), 2.76 (br s, 1H, OH), 2.32 (m, 1H, CH$_3$CHCHCH$_2$), 1.94 (m, 1H, CH$_3$CHCHCH$_2$), 1.79 (s, 6H, N(CH$_3$)$_2$), 1.07 (m, 1H, CH$_3$CHCHCH$_2$), 0.84 (d, 3H, J=6.6 Hz, CH$_3$CH); $^{13}$C NMR (100 MHz, CDCl$_3$) δ 202.5, 185.6, 179.2, 168.9, 156.9, 139.4, 139.1, 137.1, 136.5, 135.3, 130.5, 129.6, 128.8, 128.7, 128.6, 128.5, 128.4, 128.3, 127.8, 126.9, 124.7, 119.3, 110.0, 106.8, 82.3, 72.5, 69.9, 66.4, 64.2, 59.3, 43.0, 39.1, 37.8, 32.6, 25.3, 16.8; FTIR (neat), cm$^{-1}$ 3435 (w, OH), 3066 (w), 2964 (w), 2933 (w), 2871 (w), 1738 (s, C=O), 1698 (s, C=O), 1614 (m), 1583 (m), 1513 (s), 1471 (s), 1453 (s), 1369 (m), 1263 (m), 1035 (m), 1014 (m); HRMS (ES) m/z calcd for (C$_{42}$H$_{40}$O$_7$N$_2$S+H)$^+$ 717.2634. found 717.2631.

Triketone MGC17:

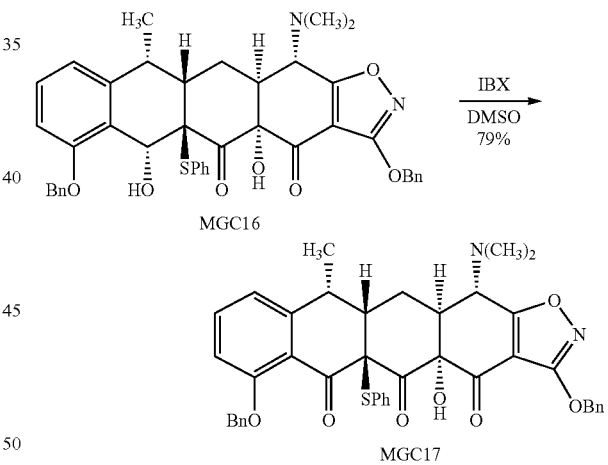

MGC16

MGC17

Solid o-iodoxybenzoic acid (459 mg, 1.64 mmol, 15.0 equiv) was added in one portion to a solution of the alcohol MGC16 (78.3 mg, 0.109 mmol, 1.0 equiv) in dimethylsulfoxide (3.0 mL) at 23° C. The resulting heterogeneous mixture was stirred for 5 min whereupon it became homogeneous. The reaction vessel was protected from light and was placed in an oil bath preheated to 35° C. The brown solution was stirred vigorously at 35° C. for 18 h, then was partitioned between saturated aqueous sodium bicarbonate solution-brine-water (2:1:1, 75 mL) and ethyl acetate-ether (1:2, 35 mL). The organic phase was separated and the aqueous phase was further extracted with two 25-mL portions ethyl acetate-ether (1:2). The organic phases were combined and dried over anhydrous sodium sulfate. The dried solution was filtered and the filtrate was concentrated, providing a yellow oil. The product was purified by flash column chromatography (1:2 ethyl acetate-hexanes), affording the ketone MGC17 as a yellow oil (61.7 mg, 79%).

$R_f$ 0.45 (2:3 ethyl acetate-hexanes); $^1$H NMR (600 MHz, $C_6D_6$) δ 7.57 (d, 2H, J=7.2 Hz, o-ArH), 7.40 (d, 2H, J=7.2 Hz, ArH), 7.18-7.23 (m, 3H, ArH), 6.94-7.06 (m, 6H, ArH), 6.76-6.84 (m, 3H, ArH), 6.59 (d, 1H, J=7.8 Hz, ArH), 6.53 (d, 1H, J=8.4 Hz, o-ArH), 5.09 (d, 1H, J=12.6 Hz, OCHH'Ph), 4.96 (d, 1H, J=12.6 Hz, OCHH'Ph), 4.77 (d, 1H, J=12.0 Hz, OCHH'Ph'), 4.72 (d, 1H, J=12.0 Hz, OCHH'Ph'), 4.48 (br s, 1H, OH), 4.06 (dq, 1H, J=7.2, 3.0 Hz, $CH_3CH$), 3.15 (d, 1H, J=12.0 Hz, $CHN(CH_3)_2$), 2.20 (ddd, 1H, J=12.6, 5.4, 3.0 Hz, $CH_3CHCHCH_2$), 2.13 (ddd, 1H, J=12.0, 3.0, 0.6 Hz, $CHCHN(CH_3)_2$), 1.81-1.88 (m, 7H, $N(CH_3)_2$, $CH_3CHCHCHH'$), 1.78 (ddd, 1H, J=13.8, 5.4, 0.6 Hz, $CH_3CHCHCHH'$), 1.01 (d, 3H, J=7.2 Hz, $CH_3CH$); $^{13}$C NMR (100 MHz, $CDCl_3$) δ 200.3, 187.5, 183.1, 167.8, 160.6, 146.4, 138.2, 137.1, 135.3, 134.3, 131.7, 129.6, 128.9, 128.6, 128.5, 128.4, 128.3, 127.7, 126.7, 121.3, 118.0, 112.8, 108.3, 82.9, 77.5, 72.4, 70.3, 58.1, 47.0, 44.1, 32.4, 18.7, 18.0, 16.3; FTIR (neat), cm$^{-1}$ 3457 (w, OH), 3063 (w), 2939 (w), 2878 (w), 2795 (w), 1727 (s, C=O), 1704 (s, C=O), 1667 (m, C=O), 1593 (s), 1513 (s), 1471 (s), 1453 (s), 1371 (m), 1276 (m), 1044 (m); HRMS (ES) m/z calcd for $(C_{42}H_{38}O_7N_2S+H)^+$ 715.2478. found 715.2483.

Peroxide MGC18:

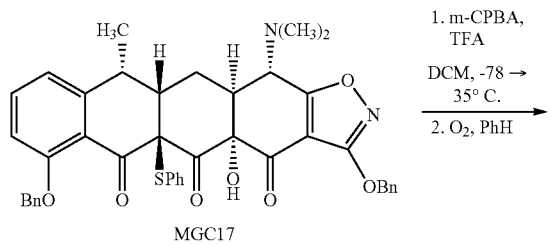

A solution of trifluoroacetic acid in dichloromethane (1.0 M, 0.189 mL, 0.189 mmol, 2.5 equiv) and a solution of m-chloroperoxybenzoic acid in dichloromethane (0.5 M, 0.228 mL, 0.114 mmol, 1.5 equiv) were added in sequence to a solution of the sulfide MGC17 (54.2 mg, 0.0758 mmol, 1.0 equiv) in dichloromethane (4.0 mL) at −78° C. The resulting cloudy mixture was stirred at −78° C. for 10 min, then the −78° C. bath was replaced with a 0° C. bath. The mixture became homogeneous upon warming. The solution was stirred at 0° C. for 30 min, then was partitioned between an aqueous potassium phosphate buffer solution (pH 7.0, 0.2 M, 10 mL) and dichloromethane (10 mL). The organic phase was separated and dried over anhydrous sodium sulfate. The dried solution was filtered and the filtrate was concentrated, providing a bright yellow oil. The oil was taken up in toluene (1 mL) and dried by azeotropic distillation at 40° C. under high vacuum. The resulting yellow oil was dissolved in chloroform (2 mL) and the reaction vessel was exposed to atmospheric oxygen. The mixture was allowed to stand until oxidation was complete as evidenced by $^1$H NMR spectroscopy. The mixture was filtered and the filtrate was concentrated, providing the peroxide MGC18 as a brown oil. The product was reduced immediately to tetracycline.

The peroxide MGC18 can also be prepared by following the procedure reported by Wasserman (J. Am. Chem. Soc. 1986, 108, 4237-4238.):

A solution of trifluoroacetic acid in dichloromethane (1.0 M, 24.5 μL, 0.0245 mmol, 2.5 equiv) and a solution of m-chloroperoxybenzoic acid in dichloromethane (0.5 M, 29.4 μL, 0.0147 mmol, 1.5 equiv) were added in sequence to a solution of the sulfide MGC17 (7.00 mg, 0.00979 mmol, 1.0 equiv) in dichloromethane (0.5 mL) at −78° C. The resulting cloudy mixture was stirred at −78° C. for 10 min, then the −78° C. bath was replaced with a 0° C. bath. The mixture became homogeneous upon warming. The solution was stirred at 0° C. for 30 min, then was partitioned between an aqueous potassium phosphate buffer solution (pH 7.0, 0.2 M, 8 mL) and dichloromethane (8 mL). The organic phase was separated and dried over anhydrous sodium sulfate. The dried solution was filtered and the filtrate was concentrated, providing a bright yellow oil. The oil was taken up in toluene (1 mL) and dried by azeotropic distillation at 40° C. under high vacuum. The resulting yellow oil was dissolved in chloroform (2 mL) and meso-tetraphenylporphine (0.6 mg, 0.979 μmmol, 0.10 equiv) was added in one portion. Oxygen gas was bubbled through the resulting mixture under UV irradiation (200 W Hg lamp) for 10 min. The mixture was concentrated to 0.5 mL and was diluted with methanol (5 mL) resulting in precipitation of meso-tetraphenylporphine. The resulting mixture was filtered and the filtrate was concentrated, providing the peroxide MGC18a light yellow solid.

$R_f$ 0.10 (2:3 ethyl acetate-hexanes); $^1$H NMR (500 MHz, $C_6D_6$, keto tautomer reported) δ 8.95 (br s, 1H, OOH), 7.48 (d, 2H, J=7.0 Hz, o-ArH), 7.28 (d, 2H, J=7.0 Hz, ArH), 6.96-7.16 (m, 8H, ArH), 6.53 (d, 1H, J=8.0 Hz, ArH), 5.14 (d, 1H, J=12.0 Hz, OCHH'Ph), 5.03 (d, 1H, J=12.0 Hz, OCHH'Ph), 4.83 (d, 1H, J=12.5 Hz, OCHH'Ph'), 4.74 (d, 1H, J=12.5 Hz, OCHH'Ph'), 4.60 (br s, 1H, OH), 3.54 (d, 1H, J=11.0 Hz, $CHCHN(CH_3)_2$), 3.12 (dd, 1H, J=18.0, 0.5 Hz, $CHCHH'CH$), 2.82 (dd, 1H, J=18.0, 4.5 Hz, $CHCHH'CH$), 2.44 (ddd, 1H, J=11.0, 4.5, 0.5 Hz, $CHCHN(CH_3)_2$), 1.86 (s, 6H, $N(CH_3)_2$), 1.01 (s, 3H, $CH_3$); $^{13}$C NMR (100 MHz, $C_6D_6$, enol and keto tautomers reported) δ 194.4, 188.6, 187.8, 187.2, 182.3, 178.4, 171.9, 167.7, 165.6, 159.5, 158.4, 147.9, 145.9, 137.0, 136.8, 136.6, 135.4, 135.3, 134.5, 134.3, 133.5, 133.4, 133.1, 132.9, 131.0, 130.8, 130.2, 129.9, 129.7, 129.2, 128.9, 126.8, 126.7, 124.5, 124.3, 122.2, 118.6, 116.9, 116.5, 113.4, 113.3, 113.2, 108.2, 107.9, 103.3, 83.7, 81.7, 80.1, 79.1, 72.4, 70.7, 70.4, 63.9, 59.1, 46.1, 44.9, 41.4, 40.8, 31.5, 30.0, 26.8, 22.9, 21.4; FTIR (neat film), cm$^{-1}$ 3035 (w), 2946 (w), 1907 (w), 1731 (s, C=O), 1410 (s), 1379 (m), 1235 (m), 1170 (m), 1136 (m); HRMS (ES) m/z calcd for $(C_{36}H_{32}O_9N_2+H)^+$ 637.2186. found 637.2190.

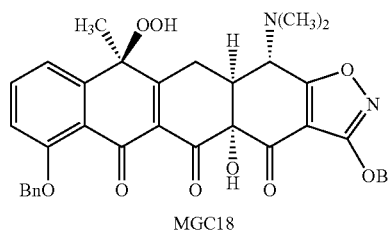

(−)-Tetracycline (MGC29):

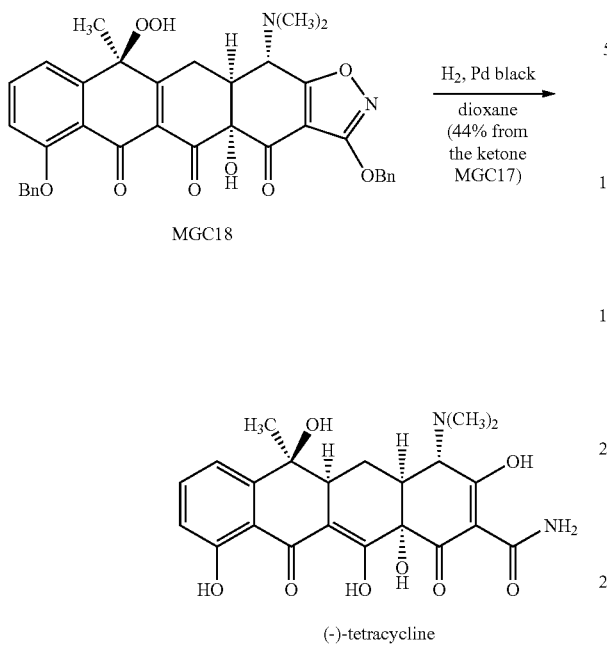

Pd black (14.1 mg, 0.133 mmol, 1.75 equiv) was added in one portion to a solution of the peroxide MGC18 (48.2 mg, 0.0758 mmol, 1.0 equiv) in dioxane (3 mL) at 23° C. An atmosphere of hydrogen was introduced by briefly evacuating the flask, then flushing with pure hydrogen (1 atm). The Pd catalyst was initially present as a fine dispersion, but aggregated into clumps within 5 min. The yellow heterogeneous mixture was stirred at 23° C. for 2 h, then was filtered through a plug of cotton. The filtrate was concentrated, affording a yellow solid. The product was purified by preparatory HPLC on a Phenomenex Polymerx DVB column (10 μM, 250×10 mm, flow rate 4.0 mL/min, Solvent A: methanol-0.005 N aq. HCl (1:4), Solvent B: acetonitrile) using an injection volume of solvent A (500 μL) containing oxalic acid (10 mg) and an isochratic elution of 5% B for 2 min, then a gradient elution of 5-50% B for 20 min. The peak eluting at 11-16 min was collected and concentrated, affording (−)-tetracycline hydrochloride as a yellow powder (16.0 mg, 44% from triketone MGC17), which was identical with natural (−)-tetracycline hydrochloride in all respects.

$^1$H NMR (600 MHz, CD$_3$OD, hydrochloride) δ 7.50 (dd, 1H, J=8.4, 7.8 Hz, ArH), 7.13 (d, 1H, J, 7.8 Hz, ArH), 6.91 (d, 1H, J=8.4 Hz, ArH), 4.03 (s, 1H, CHN(CH$_3$)$_2$), 2.96-3.04 (m, 7H, HOC(CH$_3$)CH, N(CH$_3$)$_2$), 2.91 (br dd, 1H, J=12.6, 2.4 Hz, (CH$_3$)$_2$NCHCH), 2.18 (ddd, 1H, J=12.6, 6.0, 2.4 Hz, CHCHH'CH), 1.90 (ddd, 1H, J=12.6, 12.6, 12.0 Hz, CHCHH'CH), 1.60 (s, 3H, CH$_3$); $^{13}$C NMR (100 MHz, CD$_3$OD) δ 195.4, 174.5, 163.8, 148.3, 137.8, 118.7, 116.4, 116.0, 107.5, 96.5, 74.7, 71.2, 70.1, 43.5, 43.0, 35.9, 27.8, 22.9; UV max (0.1 N HCl), nm 217, 269, 356; [α]$_D$=−251° (c=0.12 in 0.1 M HCl); lit. (*The Merck Index: An Encyclopedia of Chemicals, Drugs, and Biologicals*, 12$^{th}$ ed. Budavari, S.; O'Neal, M. J.; Smith, A.; Heckelman, P. E.; Kinneary, J. F., Eds.; Merck & Co.: Whitehouse Station, N.J., 1996; entry 9337.) UV max (0.1 N HCl), nm 220, 268, 355; [α]$_D$=−257.9° (c=0.5 in 0.1 M HCl); HRMS (ES) m/z calcd for (C$_{22}$H$_{24}$O$_8$N$_2$+H)$^+$445.1611. found 445.1608.

Example 2

Synthesis of (−)-Doxycycline

Allylic Bromide MGC19:

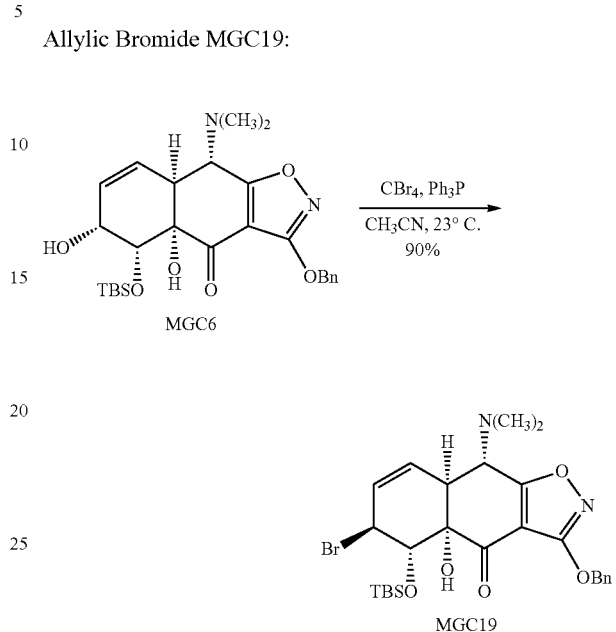

Triphenylphosphine (297 mg, 1.13 mmol, 3.5 equiv) and carbon tetrabromide (376 mg, 1.13 mmol, 3.5 equiv) were added in sequence to a solution of the allylic alcohol MGC6 (162 mg, 0.324 mmol, 1.0 equiv) in acetonitrile (2.5 mL) at 0° C. The resulting brown suspension was stirred at 0° C. for 10 min, then the cooling bath was removed. The mixture was allowed to warm to 23° C. and stirring was continued at that temperature for 10 min. The mixture was partitioned between ethyl acetate (50 mL) and saturated aqueous sodium bicarbonate solution (40 mL). The organic phase was separated and the aqueous phase was further extracted with an additional 50 mL-portion of ethyl acetate. The organic phases were combined and dried over anhydrous sodium sulfate. The dried solution was filtered and the filtrate was concentrated, providing a brown oily solid. The product was purified by flash column chromatography (1:9 to 2:8 ethyl acetate-hexanes), yielding the allylic bromide MGC19 (164 mg, 90%) as a white solid.

R$_f$ 0.30 (3:7 ethyl acetate-hexanes); $^1$H NMR (500 MHz, C$_6$D$_6$) δ 7.30 (d, 2H, J=7.0, o-ArH), 7.06 (dd, 2H, J=7.0, 6.0 Hz, m-ArH), 7.01 (d, 1H, J=6.0, p-ArH), 5.75 (dd, 1H, J=10.5, 2.5 Hz, =CHCHBr), 5.71 (m, 1H, CH=CHCHBr), 5.17 (d, 1H, J=11.5 Hz, OCHH'Ph), 5.07 (d, 1H, J=11.5 Hz, OCHH'Ph), 4.69 (m, 1H, =CHCHBr), 4.43 (br s, 1H, OH), 4.24 (d, 1H, J=7.0 Hz, CHOTBS), 3.57 (d, 1H, J=10.0 Hz, CHN(CH$_3$)$_2$), 2.69 (ddd, 1H, J=10.0, 4.5, 0.5 Hz, CHCHN (CH$_3$)$_2$), 1.92 (s, 6H, N(CH$_3$)$_2$), 0.99 (s, 9H, SiC(CH$_3$)$_3$), 0.22 (s, 3H, SiCH$_3$), −0.02 (s, 3H, SiCH$_3$); $^{13}$C NMR (125 MHz, C$_6$D$_6$) δ 189.3, 181.3, 167.8, 135.2, 129.5, 128.6, 128.6, 128.5, 128.2, 127.6, 107.3, 80.8, 76.9, 72.4, 64.8, 54.6, 46.3, 41.5, 26.2, 18.4, −2.9, −4.2; FTIR (neat), cm$^{-1}$ 3499 (m, OH), 2930 (m), 2856 (m), 2799 (w), 1704 (s, C=O), 1605 (s), 1514 (s), 1471 (s), 1362 (s), 1255 (s), 1144 (s), 1053 (s); HRMS (ES) m/z calcd for (C$_{26}$H$_{35}$BrN$_2$O$_5$Si+H)$^+$563.1577. found 563.1575.

Allylic Sulfide MGC20:

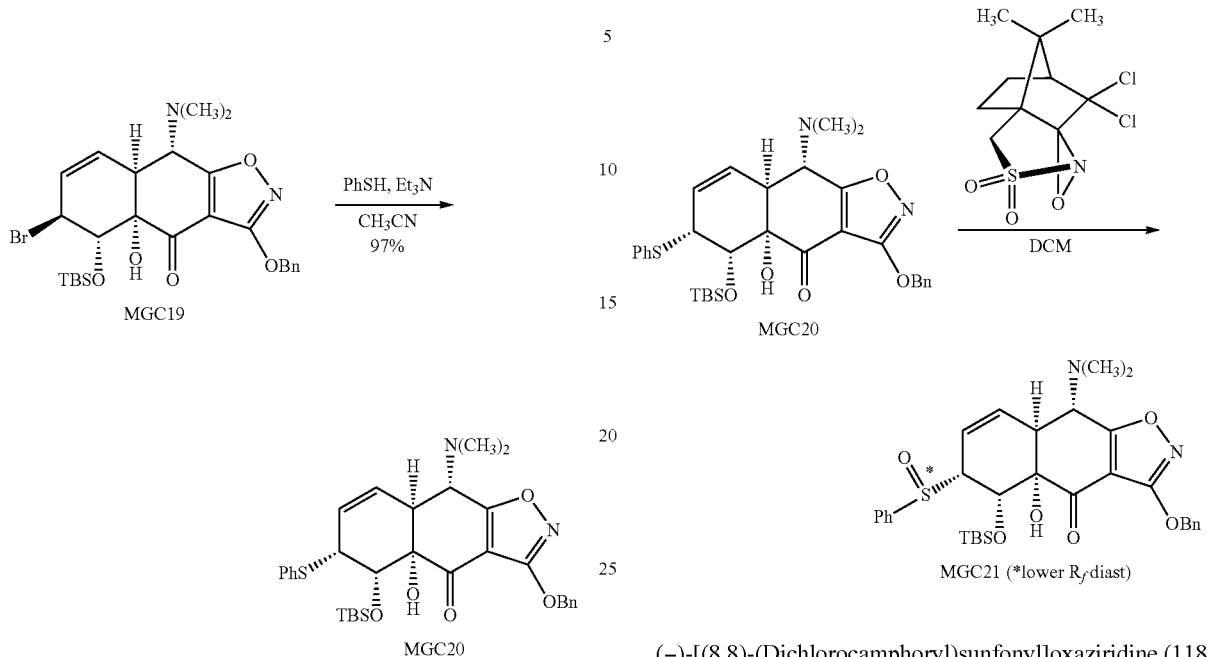

Triethylamine (0.229 mL, 1.64 mmol, 1.3 equiv) and benzenethiol (0.150 mL, 1.45 mmol, 1.15 equiv) were added in sequence to a solution of the allylic bromide MGC19 (712 mg, 1.26 mmol, 1.0 equiv) in acetonitrile (17 mL) at 0° C. The mixture was stirred at 0° C. for 20 min, then the cooling bath was removed. The reaction mixture was allowed to warm to 23° C. and stirring was continued at that temperature for 10 min. The reaction mixture was partitioned between ethyl acetate (100 mL) and an aqueous potassium phosphate buffer solution (pH 7.0, 0.2 M, 100 mL). The organic phase was separated and the aqueous phase was further extracted with an additional 30-mL portion of ethyl acetate. The organic phases were combined and dried over anhydrous sodium sulfate. The dried solution was filtered and the filtrate was concentrated, furnishing a clear oil. The product was purified by flash column chromatography (0.01:2:8 to 0.013:7 triethylamine-ethyl acetate-hexanes), affording the allylic sulfide MGC20 as a white foamy solid (728 mg, 97%).

$R_f$ 0.65 (3:7 ethyl acetate-hexanes); $^1$H NMR (400 MHz, $C_6D_6$) δ 7.35 (d, 2H, J=7.2 Hz, o-ArH), 7.19 (m, 2H, o-ArH), 6.95 (m, 3H, p, m-ArH), 6.89 (m, 2H, p, m-ArH), 6.83 (d, 1H, J=7.2 Hz, p-ArH), 5.51 (m, 1H, CH=CHCHSPh), 5.12 (m, 2H, CHOTBS, OCHH'Ph), 5.05 (d, 1H, J=12.4 Hz, OCHH'Ph), 4.73 (dt, 1H, J=10.0, 2.0 Hz, CH=CHCHSPh), 4.38 (m, 1H, CH=CHCHSPh), 3.47 (m, 1H, CHCHN(CH$_3$)$_2$), 2.92 (d, 1H, J=2.0 Hz, CHCHN(CH$_3$)$_2$), 1.75 (s, 6H, N(CH$_3$)$_2$), 1.14 (s, 9H, SiC(CH$_3$)$_3$), 0.35 (s, 3H, SiCH$_3$), 0.31 (s, 3H, SiCH$_3$); $^{13}$C NMR (125 MHz, $C_6D_6$) δ 189.9, 177.0, 168.9, 136.7, 135.2, 131.3, 130.3, 129.2, 128.5, 128.4, 128.3, 126.2, 124.0, 106.2, 79.2, 72.4, 71.7, 63.2, 49.8, 43.4, 39.0, 26.6, 19.1, −2.9, −4.5; FTIR (neat), cm$^{-1}$ 3310 (m, OH), 2927 (m), 2854 (m), 2792 (w), 1697 (s, C=O), 1621 (s), 1505 (s), 1470 (s), 1365 (s), 1254 (s), 1145 (s), 1089 (s); HRMS (ES) m/z calcd for (C$_{32}$H$_{40}$N$_2$O$_5$SSi+H)$^+$593.2505. found 593.2509.

Lower $R_f$ Sulfoxide MGC21:

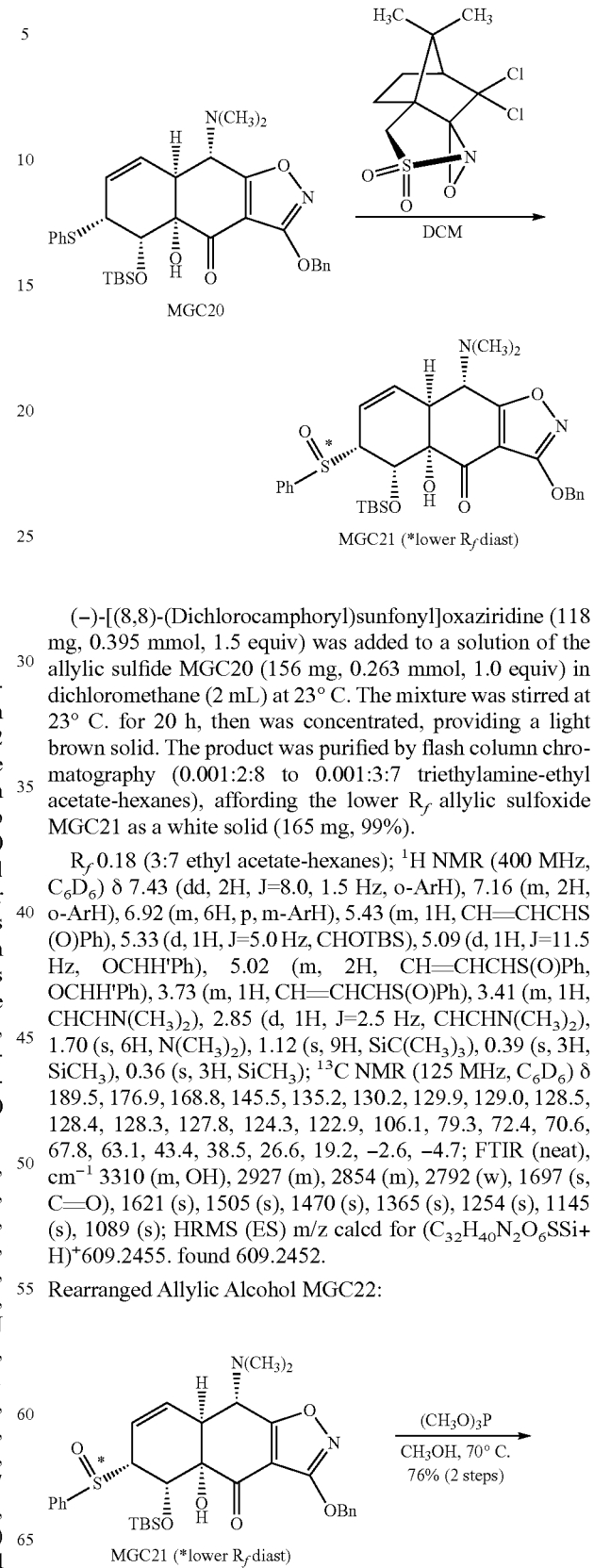

(−)-[(8,8)-(Dichlorocamphoryl)sunfonyl]oxaziridine (118 mg, 0.395 mmol, 1.5 equiv) was added to a solution of the allylic sulfide MGC20 (156 mg, 0.263 mmol, 1.0 equiv) in dichloromethane (2 mL) at 23° C. The mixture was stirred at 23° C. for 20 h, then was concentrated, providing a light brown solid. The product was purified by flash column chromatography (0.001:2:8 to 0.001:3:7 triethylamine-ethyl acetate-hexanes), affording the lower $R_f$ allylic sulfoxide MGC21 as a white solid (165 mg, 99%).

$R_f$ 0.18 (3:7 ethyl acetate-hexanes); $^1$H NMR (400 MHz, $C_6D_6$) δ 7.43 (dd, 2H, J=8.0, 1.5 Hz, o-ArH), 7.16 (m, 2H, o-ArH), 6.92 (m, 6H, p, m-ArH), 5.43 (m, 1H, CH=CHCHS(O)Ph), 5.33 (d, 1H, J=5.0 Hz, CHOTBS), 5.09 (d, 1H, J=11.5 Hz, OCHH'Ph), 5.02 (m, 2H, CH=CHCHS(O)Ph, OCHH'Ph), 3.73 (m, 1H, CH=CHCHS(O)Ph), 3.41 (m, 1H, CHCHN(CH$_3$)$_2$), 2.85 (d, 1H, J=2.5 Hz, CHCHN(CH$_3$)$_2$), 1.70 (s, 6H, N(CH$_3$)$_2$), 1.12 (s, 9H, SiC(CH$_3$)$_3$), 0.39 (s, 3H, SiCH$_3$), 0.36 (s, 3H, SiCH$_3$); $^{13}$C NMR (125 MHz, $C_6D_6$) δ 189.5, 176.9, 168.8, 145.5, 135.2, 130.2, 129.9, 129.0, 128.5, 128.4, 128.3, 127.8, 124.3, 122.9, 106.1, 79.3, 72.4, 70.6, 67.8, 63.1, 43.4, 38.5, 26.6, 19.2, −2.6, −4.7; FTIR (neat), cm$^{-1}$ 3310 (m, OH), 2927 (m), 2854 (m), 2792 (w), 1697 (s, C=O), 1621 (s), 1505 (s), 1470 (s), 1365 (s), 1254 (s), 1145 (s), 1089 (s); HRMS (ES) m/z calcd for (C$_{32}$H$_{40}$N$_2$O$_6$SSi+H)$^+$609.2455. found 609.2452.

Rearranged Allylic Alcohol MGC22:

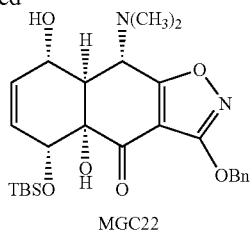

MGC22

Trimethylphosphite (0.620 mL, 5.26 mmol, 20.0 equiv) was added to a solution of the lower $R_f$ allylic sulfoxide MGC21 (160 mg, 0.263 mmol, 1.0 equiv) in methanol (5 mL) at 23° C. The solution was placed in an oil bath preheated to 65° C. and was stirred at that temperature for 36 h. The solution was concentrated, providing a light yellow oil. The product was purified by flash column chromatography (0.001:1:9 to 0.001:2:8 triethylamine-ethyl acetate-hexanes), affording the allylic alcohol MGC22 as a white solid (100 mg, 76%).

$R_f$ 0.40 (3:7 ethyl acetate-hexanes); $^1$H NMR (500 MHz, $C_6D_6$) δ 7.30 (d, 2H, J=7.0 Hz, o-ArH), 7.06 (dd, 2H, J=7.5, 7.0 Hz, m-ArH), 7.00 (d, 1H, J=7.5 Hz, p-ArH), 5.85 (m, 1H, =CHCHOH), 5.42 (br d, 1H, J=10.5 Hz, =CHCHOTBS), 5.16 (d, 1H, J=12.5 Hz, OCHH'Ph), 5.06 (d, 1H, J=12.5 Hz, OCHH'Ph), 4.44 (m, 1H, =CHCHOH), 4.31 (br s, 1H, OH), 4.07 (br s, 1H, =CHCHOTBS), 3.34 (br s, 1H, OH), 3.33 (d, 1H, J=11.5 Hz, CHCHN(CH$_3$)$_2$), 2.75 (br d, 1H, J=11.5 Hz, CHCHN(CH$_3$)$_2$), 2.03 (s, 6H, N(CH$_3$)$_2$), 0.89 (s, 9H, SiC(CH$_3$)$_3$), −0.11 (s, 3H, SiCH$_3$), −0.13 (s, 3H, SiCH$_3$); $^{13}$C NMR (100 MHz, $C_6D_6$) δ 189.7, 182.2, 167.7, 135.2, 129.2, 128.8, 128.3, 128.2, 106.6, 78.6, 71.9, 68.1, 64.1, 59.6, 48.8, 41.2, 25.5, 17.8, −5.2, −5.6; FTIR (neat), cm$^{-1}$ 3515 (m, OH), 2917 (m), 2852 (m), 1708 (s, C=O), 1601 (s), 1511 (s), 1471 (m), 1369 (m), 1254 (m), 1100 (m), 1022 (m); HRMS (ES) m/z calcd for $(C_{26}H_{36}N_2O_6Si+H)^+$ 501.2421. found 501.2424.

Benzyl Carbonate MGC23:

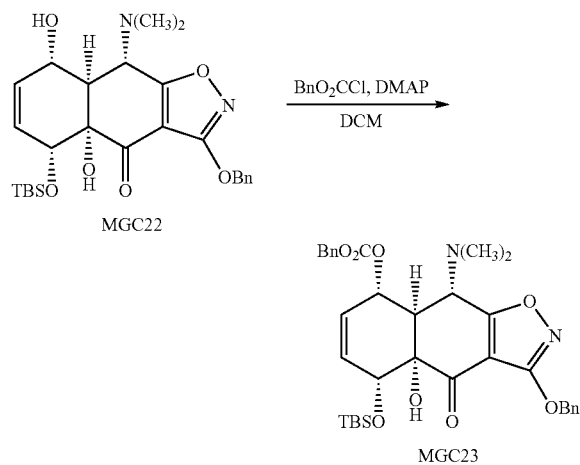

Benzyl chloroformate (120 μL, 0.841 mmol, 2.95 equiv) and 4-(dimethylamino)pyridine (104 mg, 0.852 mmol, 3.0 equiv) were added in sequence to a solution of the allylic alcohol MGC22 (142 mg, 0.284 mmol, 1.0 equiv) in dichloromethane (3 mL) at 23° C. The reaction mixture was stirred at 23° C. for 2 h, then was partitioned between ethyl acetate (50 mL) and saturated aqueous sodium bicarbonate solution (50 mL). The organic phase was separated and the aqueous phase was further extracted with an additional 30-mL portion of ethyl acetate. The organic phases were combined and dried over anhydrous sodium sulfate. The dried solution was filtered and the filtrate was concentrated, providing a clear oil (180 mg, 99%). The product was used in the next step without further purification. An analytical sample was prepared by purification of the crude reaction mixture by flash column chromatography (0.001:2:8 to 0.001:3:7 triethylamine-ethyl acetate-hexanes), affording the benzyl carbonate MGC23 as a white solid.

$R_f$ 0.60 (3:7 ethyl acetate-hexanes); $^1$H NMR (500 MHz, $C_6D_6$) δ 7.26 (d, 2H, J=7.0 Hz, o-ArH), 7.02 (m, 8H, ArH), 5.75 (br dd, 1H, J=10.5, 3.0 Hz, =CHCHOCO$_2$Bn), 5.70 (br dd, 1H, J=10.5, 2.5 Hz, =CHCHOTBS), 5.37 (m, 1H, =CHCHOCO$_2$Bn), 5.10 (d, 1H, J=12.5 Hz, OCHH'Ph), 5.06 (d, 1H, J=12.5 Hz, OCHH'Ph), 4.91 (d, 1H, J=12.0 Hz, OCHH'Ph'), 4.88 (d, 1H, J=12.0 Hz, OCHH'Ph'), 4.41 (m, 1H, =CHCHOTBS), 3.38 (d, 1H, J=7.5 Hz, CHCHN(CH$_3$)$_2$), 3.11 (m, 1H, CHCHN(CH$_3$)$_2$), 1.92 (s, 6H, N(CH$_3$)$_2$), 0.92 (s, 9H, SiC(CH$_3$)$_3$), 0.02 (s, 3H, SiCH$_3$), −0.02 (s, 3H, SiCH$_3$); $^{13}$C NMR (100 MHz, $C_6D_6$) δ 188.9, 179.9, 168.3, 155.2, 135.6, 135.4, 133.2, 128.6, 128.5, 128.4, 128.3, 127.7, 124.9, 107.0, 77.3, 72.2, 71.6, 69.6, 66.6, 60.3, 44.4, 42.2, 25.9, 18.2, −4.8, −4.8; FTIR (neat), cm$^{-1}$ 3532 (w, OH), 2948 (m), 2842 (m), 1738 (s, C=O), 1708 (s, C=O), 1608 (s), 1512 (s), 1471 (m), 1383 (m), 1258 (s), 1101 (m); HRMS (ES) m/z calcd for $(C_{34}H_{42}N_2O_8Si+H)^+$ 635.2789. found 635.2786.

Diol MGC24:

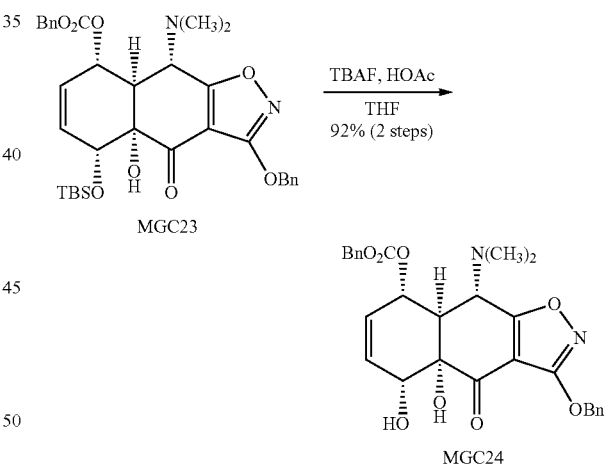

Acetic acid (40.0 μL, 0.709 mmol, 2.5 equiv) and a solution of tetrabutylammonium fluoride in tetrahydrofuran (1.0 M, 0.709 mL, 0.709 mmol, 2.5 equiv) were added in sequence to a solution of the benzyl carbonate MGC23 (180 mg, 0.284 mmol, 1.0 equiv) in tetrahydrofuran (3 mL) at 23° C. The resulting yellow solution was stirred at 23° C. for 4 h, then was partitioned between ethyl acetate (50 mL) and an aqueous potassium phosphate buffer solution (pH 7.0, 0.2 M, 50 mL). The organic phase was separated and the aqueous phase was further extracted with two 20-mL portions of ethyl acetate. The organic phases were combined and dried over anhydrous sodium sulfate. The dried solution was filtered and the filtrate was concentrated, providing a brown oil. The product was purified by flash column chromatography (2:8 to 1:1 ethyl acetate-hexanes), affording the diol MGC24 as a white solid (135 mg, 92% over 2 steps).

$R_f$ 0.15 (3:7 ethyl acetate-hexanes); $^1$H NMR (500 MHz, $C_6D_6$) δ 7.24 (d, 2H, J=7.0 Hz, o-ArH), 7.02 (m, 8H, ArH), 5.68 (br dd, 1H, J=10.5, 2.5 Hz, =CHCHOCO$_2$Bn), 5.63 (br dd, 1H, J=10.5, 3.0 Hz, =CHCHOH), 5.26 (m, 1H, =CHCHOCO$_2$Bn), 5.09 (d, 1H, J=12.0 Hz, OCHH'Ph), 5.05 (d, 1H, J=12.0 Hz, OCHH'Ph), 4.89 (d, 1H, J=12.0 Hz, OCHH'Ph'), 4.86 (d, 1H, J=12.0 Hz, OCHH'Ph'), 4.16 (m, 1H, =CHCHOH), 3.24 (d, 1H, J=6.5 Hz, CHCHN(CH$_3$)$_2$), 2.94 (m, 1H, CHCHN(CH$_3$)$_2$), 2.25 (br s, 1H, OH), 1.82 (s, 6H, N(CH$_3$)$_2$); $^{13}$C NMR (100 MHz, CDCl$_3$) δ 168.1, 154.8, 135.1, 134.9, 132.2, 128.9, 128.9, 128.8, 128.7, 128.6, 126.4, 106.7, 76.6, 72.9, 71.3, 70.3, 64.9, 60.3, 44.4, 43.3; FTIR (neat), cm$^{-1}$ 3468 (m, OH), 3034 (w), 2949 (m), 2798 (m), 1738 (s, C=O), 1705 (s, C=O), 1606 (s), 1513 (m), 1475 (m), 1379 (m), 1261 (s), 1022 (m); HRMS (ES) m/z calcd for $(C_{28}H_{28}N_2O_8+H)^+$ 521.1929. found 521.1926.

Cyclohexenone MGC25:

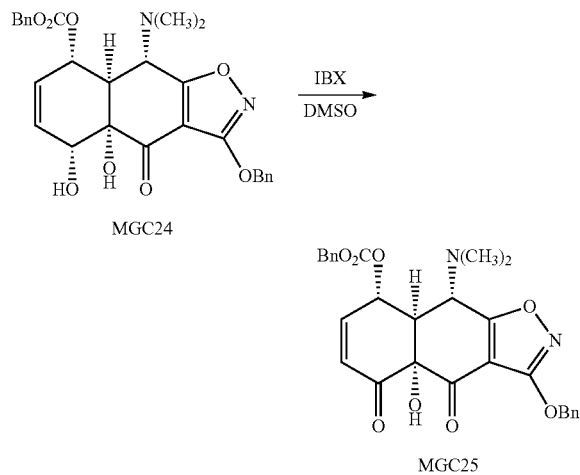

Solid o-iodoxybenzoic acid (79.0 mg, 0.281 mmol, 6.5 equiv) was added in one portion to a solution of the diol MGC24 (22.5 mg, 0.0433 mmol, 1.0 equiv) in dimethylsulfoxide (0.7 mL) at 23° C. The reaction mixture was initially heterogeneous, but became homogeneous within 5 min. The brown reaction mixture was protected from light and was stirred vigorously at 23° C. for 12 h. The resulting orange reaction mixture was partitioned between ether (20 mL) and water (20 mL). The organic phase was separated and the aqueous phase was further extracted with two 10 mL-portions ether. The organic phases were combined and washed with saturated aqueous sodium bicarbonate solution (8 mL, containing 30 mg of sodium bisulfite) and brine (10 mL). The washed solution was dried over anhydrous sodium sulfate and filtered. The filtrate was concentrated, yielding the cyclohexenone MGC25 as a white oily solid (22.2 mg, 99%).

$R_f$ 0.33 (2:3 ethyl acetate-hexanes); $^1$H NMR (400 MHz, $C_6D_6$) δ 7.22 (d, 2H, J=6.8 Hz, o-ArH), 6.99 (m, 8H, ArH), 6.12 (ddd, 1H, J=10.4, 4.0, 1.2 Hz, CH=CHCHOCO$_2$Bn), 5.74 (dd, 1H, J=10.4, 1.2 Hz, CH=CHCHOCO$_2$Bn), 5.41 (ddd, 1H, J=4.0, 1.2, 1.2 Hz, CH=CHCHOCO$_2$Bn), 5.18 (br s, 1H, OH), 5.08 (d, 1H, J=12.0 Hz, OCHH'Ph), 5.01 (d, 1H, J=12.0 Hz, OCHH'Ph), 4.89 (d, 1H, J=12.4 Hz, OCHH'Ph'), 4.83 (d, 1H, J=12.4 Hz, OCHH'Ph'), 3.28 (d, 1H, J=8.4 Hz, CHCHN(CH$_3$)$_2$), 2.85 (ddd, 1H, J=8.4, 4.0, 1.2 Hz, CHCHN(CH$_3$)$_2$), 1.92 (s, 6H, N(CH$_3$)$_2$); $^{13}$C NMR (100 MHz, $C_6D_6$) δ 192.3, 186.2, 180.5, 167.8, 154.8, 141.8, 135.3, 135.2, 129.9, 128.6, 128.6, 128.5, 128.4, 127.8, 107.7, 78.9, 72.5, 69.9, 59.9, 48.4, 41.9; FTIR (neat), cm$^{-1}$ 3442 (m, OH), 3030 (w), 2948 (m), 2793 (m), 1742 (s, C=O), 1711 (s, C=O), 1608 (s), 1510 (s), 1448 (m), 1376 (m), 1258 (s), 1056 (m); HRMS (ES) m/z calcd for $(C_{28}H_{26}N_2O_8+H)^+$ 519.1767. found 519.1773.

Silyl-Cyclohexenone MGC26:

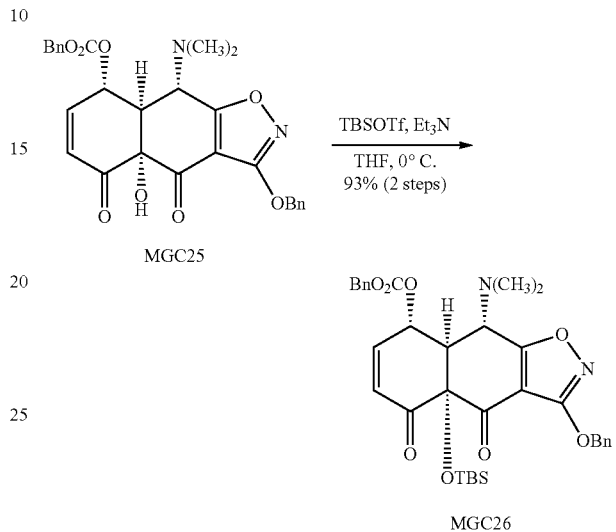

Triethylamine (172 μL, 1.24 mmol, 3.5 equiv) and tert-butyldimethylsilyl trifluoromethanesulfonate (243 μL, 1.06 mmol, 3.0 equiv) were added in sequence to a solution of the cyclohexenone MGC25 (183 mg, 0.353 mmol, 1.0 equiv) in tetrahydrofuran (8 mL) at 0° C. The reaction mixture was stirred at 0° C. for 40 min, then was partitioned between ethyl acetate (50 mL) and an aqueous potassium phosphate buffer solution (pH 7.0, 0.2 M, 50 mL). The organic phase was separated and the aqueous phase was further extracted with a 25-mL portion of ethyl acetate. The organic phases were combined and dried over anhydrous sodium sulfate. The dried solution was filtered and the filtrate was concentrated, providing a yellow oily solid. The product was purified by flash column chromatography (1:9 to 2:8 ethyl acetate-hexanes), affording the silyl-cyclohexenone MGC26 as a clear oil (207 mg, 93%).

$R_f$ 0.50 (3:7 ethyl acetate-hexanes); $^1$H NMR (400 MHz, $C_6D_6$) δ 7.21 (dd, 2H, J=7.5, 1.0 Hz, o-ArH), 7.15 (d, 2H, J=8.0 Hz, o-ArH), 7.05 (t, 2H, J=8.0 Hz, m-ArH), 6.98 (m, 4H, m, p-ArH), 6.30 (ddd, 1H, J=10.5, 5.0, 2.0 Hz, CH=CHCHOCO$_2$Bn), 5.68 (dd, 1H, J=10.5, 1.0 Hz, CH=CHCHOCO$_2$Bn), 5.65 (br d, 1H, J=5.0 Hz, CH=CHCHOCO$_2$Bn), 5.10 (d, 1H, J=12.5 Hz, OCHH'Ph), 5.01 (d, 1H, J=12.5 Hz, OCHH'Ph), 4.95 (d, 1H, J=12.5 Hz, OCHH'Ph'), 4.82 (d, 1H, J=12.5 Hz, OCHH'Ph'), 3.11 (d, 1H, J=11.0 Hz, CHCHN(CH$_3$)$_2$), 2.94 (br d, 1H, J=11.0 Hz, CHCHN(CH$_3$)$_2$), 1.96 (s, 6H, N(CH$_3$)$_2$), 1.08 (s, 9H, SiC (CH$_3$)$_3$), 0.59 (s, 3H, SiCH$_3$), 0.29 (s, 3H, SiCH$_3$); $^{13}$C NMR (100 MHz, $C_6D_6$) δ 193.3, 186.7, 180.3, 167.8, 154.9, 140.9, 135.6, 135.3, 129.9, 128.6, 128.5, 128.5, 128.4, 128.0, 127.8, 108.6, 82.4, 72.4, 69.6, 69.3, 59.7, 50.2, 41.4, 26.5, 19.6, −1.9, −3.4; FTIR (neat), cm$^{-1}$ 2930 (m), 2855 (m), 1745 (s, C=O), 1722 (s, C=O), 1691 (m), 1613 (m), 1513 (s), 1473 (m), 1455 (m), 1378 (m), 1264 (s), 1231 (s), 1046 (m); HRMS (ES) m/z calcd for $(C_{34}H_{40}N_2O_8+H)^+$ 633.2632. found 633.2620.

Michael-Dieckmann Addition Product MGC27:

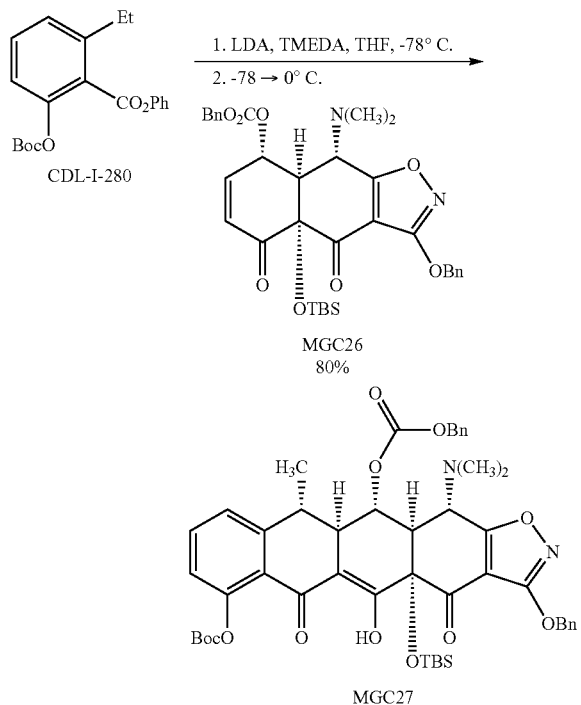

A solution of n-butyllithium in hexanes (1.55 M, 155 µL, 0.241 mmol, 5.1 equiv) was added to a solution of N,N,N',N'-tetramethylethylenediamine (39.0 µL, 0.261 mmol, 5.5 equiv) and diisopropyl amine (34.0 µL, 0.249 mmol, 5.25 equiv) in tetrahydrofuran (1 mL) at −78° C. The resulting mixture was stirred vigorously at −78° C. for 30 min whereupon a solution of the ester CDL-I-280 (73.0 mg, 0.213 mmol, 4.5 equiv) in tetrahydrofuran (1 mL) was added dropwise via cannula. The resulting deep red mixture was stirred vigorously at −78° C. for 75 min, then a solution of the silyl-cyclohexenone MGC26 (30.0 mg, 0.0474 mmol, 1.0 equiv) in tetrahydrofuran (1 mL) was added dropwise via cannula. The resulting light red mixture was allowed to warm slowly to 0° C. over 2 h, then was partitioned between an aqueous potassium phosphate buffer solution (pH 7.0, 0.2 M, 10 mL) and dichloromethane (10 mL). The organic phase was separated and the aqueous phase was further extracted with two 10-mL portions of dichloromethane. The organic phases were combined and dried over anhydrous sodium sulfate. The dried solution was filtered and the filtrate was concentrated, providing a yellow oil. The product was purified by preparatory HPLC on a Coulter Ultrasphere ODS column (10 µM, 250×10 mm, flow rate 3.5 mL/min, Solvent A: methanol, Solvent B: water) using an injection volume of 400 µL (methanol) and an isochratic elution of 10% B for 75 min. The peak eluting at 36-42 min was collected and concentrated, affording the Michael-Dieckmann addition product MGC27 (33.0 mg, 80%) as a light yellow solid.

$R_f$ 0.35 (1:4 ethyl acetate-hexanes); $^1$H NMR (500 MHz, $C_6D_6$) δ 16.55 (br s, 1H, enol), 7.26 (d, 2H, J=7.0 Hz, o-ArH), 7.14 (d, 2H, J=7.5 Hz, ArH), 6.85-7.05 (m, 6H, ArH), 6.66-6.74 (m, 2H, ArH), 6.51 (dd, 1H, J=9.0, 1.5 Hz, ArH), 5.73 (br d, 1H, J=4.0 Hz, BnOCO$_2$CH), 5.17 (d, 1H, J=12.5 Hz, OCHH'Ph), 5.03 (d, 1H, J=12.5 Hz, OCHH'Ph), 4.99 (d, 1H, J=12.5 Hz, OCHH'Ph), 4.93 (d, 1H, J=12.5 Hz, OCHH'Ph'), 3.58 (d, 1H, J=11.5 Hz, CHCHN(CH$_3$)$_2$), 3.35 (dd, 1H, J=12.5, 4.0 Hz, CH$_3$CHCH), 2.99 (d, 1H, J=11.5 Hz, CHCHN(CH$_3$)$_2$), 2.56 (dq, 1H, J=12.5, 7.0 Hz, CH$_3$CH), 2.18 (s, 6H, N(CH$_3$)$_2$), 1.33 (s, 9H, C(CH$_3$)$_3$), 1.16 (d, 3H, J=7.0 Hz, CH$_3$CH), 1.11 (s, 9H, C(CH$_3$)$_3$), 0.61 (s, 3H, CH$_3$), 0.36 (s, 3H, CH$_3$); $^{13}$C NMR (100 MHz, CDCl$_3$) δ 189.7, 186.3, 180.9, 178.4, 167.9, 154.7, 152.1, 150.8, 145.9, 136.1, 135.5, 133.9, 128.7, 128.6, 128.5, 127.3, 123.8, 122.7, 122.6, 108.9, 105.5, 83.0, 82.9, 74.8, 72.4, 69.2, 60.8, 52.7, 43.2, 38.4, 27.5, 26.6, 19.5, 16.3, −1.8, −2.7; FTIR (neat film), cm$^{−1}$ 2974 (w), 2933 (w), 2851 (w), 1760 (s, C=O), 1748 (s, C=O), 1723 (s, C=O), 1606 (m), 1513 (m), 1471 (m), 1370 (m). 1260 (s), 1232 (s), 1148 (s); HRMS (ES) m/z calcd for (C$_{48}$H$_{56}$O$_{12}$N$_2$Si)$^+$ 881.3681. found 881.3684.

Initial Deprotection of Michael-Dieckmann Addition Product MGC28:

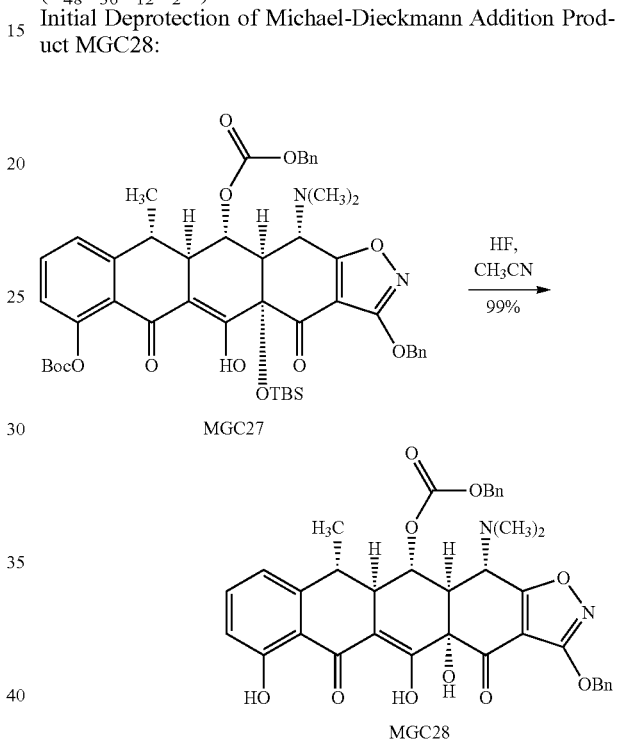

Hydrofluoric acid (1.2 mL, 48% aqueous) was added to a polypropylene reaction vessel containing a solution of the Michael-Dieckmann addition product MGC27 (33.0 mg, 0.0375 mmol, 1.0 equiv) in acetonitrile (7.0 mL) at 23° C. The resulting mixture was stirred vigorously at 23° C. for 60 h, then was poured into water (50 mL) containing K$_2$HPO$_4$ (7.0 g). The resulting mixture was extracted with ethyl acetate (3×20 mL). The organic phases were combined and dried over anhydrous sodium sulfate. The dried solution was filtered and the filtrate was concentrated, furnishing the pentacyclic phenol MGC28 as a yellow oil (25.0 mg, 99%). The product was used in the next step without further purification.

$R_f$ 0.05 (1:4 ethyl acetate-hexanes); $^1$H NMR (600 MHz, $C_6D_6$, crude) δ 14.86 (br s, 1H, enol), 11.95 (s, 1H, phenol), 7.23 (d, 2H, J=7.8 Hz, o-ArH), 7.14 (d, 2H, J=7.2 Hz, o-ArH), 6.94-7.02 (m, 6H, ArH), 6.86 (t, 1H, J=8.4 Hz, ArH), 6.76 (d, 1H, J=8.4 Hz, ArH), 6.28 (d, 1H, J=7.8 Hz, ArH), 5.46 (dd, 1H, J=3.6, 3.0 Hz, BnOCO$_2$CH), 5.12 (d, 1H, J=12.0 Hz, OCHH'Ph), 5.04 (d, 1H, J=12.0 Hz, OCHH'Ph), 4.92 (s, 2H, OCH$_2$Ph), 3.41 (d, 1H, J=9.6 Hz, CHCHN(CH$_3$)$_2$), 2.82 (dd, 1H, J=9.6, 3.0 Hz, CHCHN(CH$_3$)$_2$), 2.65 (dd, 1H, J=13.2, 3.6 Hz, CH$_3$CHCH), 2.78 (dq, 1H, J=13.2, 7.2 Hz, CH$_3$CH), 2.05 (s, 6H, N(CH$_3$)$_2$), 1.04 (d, 3H, J=7.2 Hz, CH$_3$CH); $^{13}$C NMR (100 MHz, $C_6D_6$, crude) δ 193.4, 186.2, 181.3, 172.3, 167.9, 163.3, 154.6, 145.8, 136.6, 135.8, 128.6, 128.4, 127.2, 116.8, 116.0, 115.6, 107.6, 104.7, 76.8, 73.9, 72.5, 69.5, 60.3, 48.7, 43.0, 41.8, 37.5, 15.3; FTIR (neat film), cm$^{-1}$ 3424 (m, OH), 3059, 3030, 2925, 2857, 1744 (s, C=O), 1713 (s, C=O), 1614 (s), 1582 (s), 1455 (s), 1252 (s); HRMS (ES) m/z calcd for $(C_{37}H_{34}O_{10}N_2+H)^+$ 667.2292. found 667.2300.

(−)-Doxycycline (MGC30):

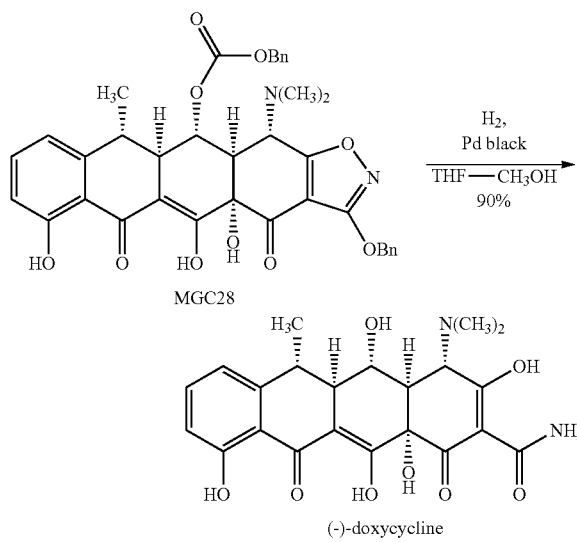

Pd black (7.00 mg, 0.0657 mmol, 1.75 equiv) was added in one portion to a solution of the pentacyclic phenol MGC28 (25.0 mg, 0.0375 mmol, 1.0 equiv) in tetrahydrofuran-methanol (1:1, 2.0 mL) at 23° C. An atmosphere of hydrogen was introduced by briefly evacuating the flask, then flushing with pure hydrogen (1 atm). The Pd catalyst was initially present as a fine dispersion, but aggregated into clumps within 5 min. The yellow heterogeneous mixture was stirred at 23° C. for 2 h, then was filtered through a plug of cotton. The filtrate was concentrated, affording a yellow oil (>95% doxycycline based on $^1$H NMR analysis). The product was purified by preparatory HPLC on a Phenomenex Polymerx DVB column (10 250×10 mm, flow rate 4.0 mL/min, Solvent A: methanol-0.005 N aq. HCl (1:4), Solvent B: acetonitrile) using an injection volume of solvent A (400 µL) containing oxalic acid (10 mg) and an isochratic elution of 5% B for 2 min, then a gradient elution of 5-50% B for 20 min. The peak eluting at 12-17 min was collected and concentrated, affording (−)-doxycycline hydrochloride as a yellow powder (16.2 mg, 90%), which was identical with natural (−)-doxycycline hydrochloride in all respects.

$^1$H NMR (600 MHz, CD$_3$OD, hydrochloride) δ 7.47 (t, 1H, J=8.4 Hz, ArH), 6.93 (d, 1H, J=8.4 Hz, ArH), 6.83 (d, 1H, J=8.4 Hz, ArH), 4.40 (s, 1H, (CH$_3$)$_2$NCH), 3.53 (dd, 1H, J=12.0, 8.4 Hz, CHOH), 2.95 (s, 3H, N(CH$_3$)CH$_3$'), 2.88 (s, 3H, N(CH$_3$)CH$_3$'), 2.80 (d, 1H, J=12.0 Hz, CHCHN(CH$_3$)$_2$), 2.74 (dq, 1H, J=12.6, 6.6 Hz, CH$_3$CH), 2.58 (dd, 1H, J=12.6, 8.4 Hz, CH$_3$CHCH), 1.55 (d, 3H, J=6.6 Hz, CH$_3$CHCH); $^{13}$C NMR (100 MHz, CD$_3$OD) δ 195.3, 188.2, 173.8, 172.1, 163.2, 149.0, 137.7, 117.1, 116.9, 116.6, 108.4, 96.0, 74.5, 69.8, 66.9, 47.5, 43.4, 43.0, 41.9, 40.0, 16.3; UV max (0.01 N methanolic HCl), nm 218, 267, 350; [α]$_D$=−109° (c=0.16 in 0.01 M methanolic HCl); lit. (*The Merck Index: An Encyclopedia of Chemicals, Drugs, and Biologicals*, 12$^{th}$ ed. Budavari, S.; O'Neal, M. J.; Smith, A.; Heckelman, P. E.; Kinneary, J. F., Eds.; Merck & Co.: Whitehouse Station, N.J., 1996; entry 3496.) UV max (0.01 N methanolic HCl), nm 267, 351; [α]$_D$=−110° (c=1 in 0.01 M methanolic HCl); HRMS (ES) m/z calcd for $(C_{22}H_{24}O_8N_2+H)^+$ 445.1611. found 445.1603.

Example 3

Synthesis of 6-Deoxytetracycline

Ester CDL-I-280:

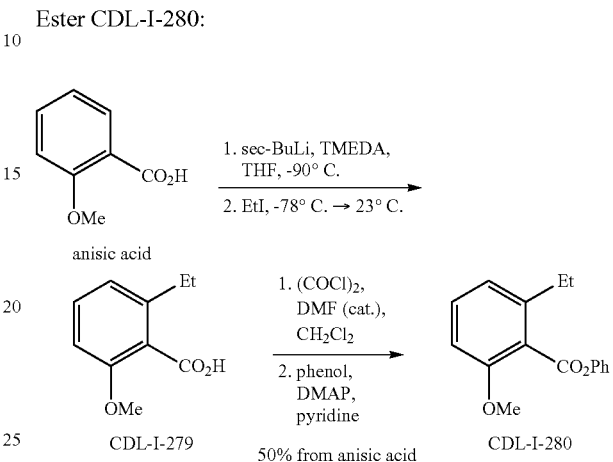

A solution of sec-butyllithium in cyclohexane (1.40 M, 24.0 mL, 33.6 mmol, 2.6 equiv) was added to a solution of N,N,N',N'-tetramethylethylenediamine (4.9 mL, 33 mmol, 2.5 equiv) in tetrahydrofuran (25 mL) at −78° C. The resulting yellow solution was cooled to −90° C. (internal temperature) in a liquid nitrogen-ethanol bath. A solution of o-anisic acid (2.00 g, 13.1 mmol, 1.0 equiv) in tetrahydrofuran (10 mL) was added dropwise via cannula over a period of 30 min to the yellow solution. The resulting orange suspension was stirred for an additional 30 min at −90° C., then was allowed to warm to −78° C. over 15 min, whereupon iodoethane (4.2 mL, 52 mmol, 4.0 equiv) was added. The mixture was allowed to warm to 23° C. over 15 min, then was partitioned between water (50 mL) and ether (50 mL). The aqueous layer was separated and diluted with aqueous hydrochloric acid (1.0 M, 100 mL). The resulting mixture was extracted with ethyl acetate (4×80 mL). The organic layers were combined and then dried over anhydrous sodium sulfate. The dried solution was filtered and the filtrate was concentrated, providing a brown oil (1.8 g). $^1$H NMR (500 MHz, CDCl$_3$) analysis of the crude product showed an 8:2 ratio of the carboxylic acid CDL-I-279 (δ 3.89, OCH$_3$) and unreacted anisic acid (δ 4.07, OCH$_3$). Oxalyl chloride (1.0 mL, 11 mmol, 0.8 equiv) and N,N-dimethylformamide (100 µL) were added in sequence to a solution of the residue in dichloromethane (20 mL) at 23° C. Vigorous gas evolution was observed upon addition of N,N-dimethylformamide. The reaction mixture was stirred for 2 h at 23° C., whereupon phenol (1.4 g, 15 mmol, 1.1 equiv), pyridine (2.4 mL, 30 mmol, 2.3 equiv), and 4-(dimethylamino)pyridine (10 mg, 0.081 mmol, 0.006 equiv) were added in sequence at 23° C. The resulting brown reaction mixture was then stirred for 2 h at 23° C. Aqueous hydrochloric acid (1 M, 50 mL) was added and the resulting mixture was extracted with ethyl acetate (2×50 mL). The organic layers were combined, then washed with an aqueous sodium hydroxide solution (0.1 M, 50 mL), followed by brine (50 mL), and were then dried over anhydrous sodium sulfate. The dried solution was filtered and the filtrate was concentrated, providing a clear oil. The product was purified by flash column chromatography (5:95 ethyl acetate-hexanes), affording the ester CDL-I-280 as a colorless oil (1.7 g, 50%).

$R_f$ 0.28 (5:95 ethyl acetate-hexanes); $^1$H NMR (500 MHz, CDCl$_3$) δ 7.56 (t, 2H, J=7.8 Hz, ArH), 7.37 (t, 1H, J=7.8 Hz, ArH), 7.31-7.26 (m, 3H, ArH), 6.93 (d, 1H, J=7.8 Hz, ArH), 6.85 (d, 1H, J=8.3 Hz, ArH), 3.91 (s, 3H, OCH$_3$), 2.79 (q, 2H, J=7.8 Hz, CH$_2$CH$_3$), 1.33 (t, 3H, J=7.8 Hz, CH$_2$CH$_3$); $^{13}$C NMR (125 MHz, CDCl$_3$) δ 166.9, 156.5, 150.8, 142.8, 130.9, 129.5, 125.9, 122.5, 121.6, 120.9, 108.5, 55.9, 26.6, 15.6; FTIR (neat film), cm$^{-1}$ 2970 (m), 1740 (s, C=O), 1583 (s), 1488 (s), 1471 (s), 1438 (m), 1298 (w), 1270 (s), 1236 (s), 1186 (s), 1158 (m), 1091 (m), 1046 (s), 1001 (w); HRMS (ES) m/z calcd for (C$_{16}$H$_{16}$O$_3$+H)$^+$ 257.1178. found 257.1183.

Phenol CDL-I-298:

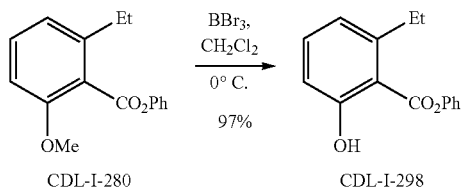

A solution of boron tribromide in dichloromethane (1.0 M, 5.2 mL, 5.2 mmol, 2.0 equiv) was added to a solution of the ester CDL-I-280 (662 mg, 2.58 mmol, 1.0 equiv) in dichloromethane (10 mL) at 0° C. The resulting yellow solution was stirred for 70 min at 0° C., whereupon saturated aqueous sodium bicarbonate solution (50 mL) was added. The resulting biphasic mixture was stirred for 20 min at 0° C., dichloromethane (50 mL) was added, the layers were separated, and the aqueous phase was further extracted with dichloromethane (50 mL). The organic layers were combined and then dried over anhydrous sodium sulfate. The dried solution was filtered and the filtrate was concentrated, providing the phenol CDL-I-298 as a colorless oil (605 mg, 97%).

$R_f$ 0.47 (5:95 ethyl acetate-hexanes); $^1$H NMR (500 MHz, CDCl$_3$) δ 10.94 (s, 1H, OH), 7.49 (t, 2H, J=7.8 Hz, ArH), 7.41 (t, 1H, J=7.8 Hz, ArH), 7.35 (t, 1H, J=7.3 Hz, ArH), 7.24 (d, 2H, J=7.8 Hz, ArH), 6.93 (d, 1H, J=8.3 Hz, ArH), 6.85 (d, 1H, J=8.3 Hz, ArH), 3.13 (q, 2H, J=7.8 Hz, CH$_2$CH$_3$), 1.34 (t, 3H, J=7.8 Hz, CH$_2$CH$_3$); $^{13}$C NMR (125 MHz, CDCl$_3$) δ 170.3, 163.2, 149.8, 147.8, 135.1, 129.7, 126.4, 122.0, 121.6, 115.9, 111.1, 29.8, 16.4; FTIR (neat film), cm$^{-1}$ 2973 (w), 1670 (s, C=O), 1609 (m), 1588 (m), 1490 (w), 1444 (m), 1311 (m), 1295 (m), 1234 (m), 1187 (s), 1162 (s), 1105 (m); HRMS (ES) m/z calcd for (C$_{15}$H$_{14}$O$_3$+H)$^+$ 243.1021. found 243.1014.

Ester CDL-I-299:

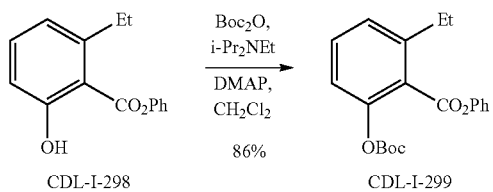

N,N-diisopropylethylamine (520 μL, 2.99 mmol, 1.2 equiv), di-t-butyl dicarbonate (645 mg, 2.96 mmol, 1.2 equiv), and 4-(dimethylamino)pyridine (31 mg, 0.25 mmol, 1.5 equiv) were added in sequence to a solution of the phenol CDL-I-298 (605 mg, 2.50 mmol, 0.1 equiv) in dichloromethane (10 mL) at 23° C. The reaction mixture was stirred for 1 h at 23° C., whereupon saturated aqueous ammonium chloride solution (50 mL) was added. Dichloromethane (50 mL) was added, the layers were separated, and the aqueous phase was extracted with dichloromethane (50 mL). The organic layers were combined and then dried over sodium sulfate. The dried solution was filtered and the filtrate was concentrated, providing a brown oil. The product was purified by flash column chromatography (1:9 ether-hexanes), affording the ester CDL-I-299 as a colorless oil, which crystallized upon standing overnight at −14° C. (733 mg, 86%), mp 58° C.

$R_f$ 0.23 (1:9 ether-hexanes); $^1$H NMR (500 MHz, CDCl$_3$) δ 7.46-7.42 (m, 3H, ArH), 7.31-7.26 (m, 3H, ArH), 7.22 (d, 1H, J=7.3 Hz, ArH), 7.15 (d, 1H, J=7.3 Hz, ArH), 2.86 (q, 2H, J=7.3 Hz, CH$_2$CH$_3$), 1.46 (s, 9H, Boc), 1.31 (t, 3H, J=7.3 Hz, CH$_2$CH$_3$); $^{13}$C NMR (125 MHz, CDCl$_3$) δ 165.1, 151.6, 150.6, 148.7, 144.5, 131.3, 129.4, 126.8, 126.1, 125.4, 121.7, 120.5, 83.8, 27.5, 26.8, 15.6; FTIR (neat film), cm$^{-1}$ 2964 (w), 1754 (s, C=O), 1586 (w), 1491 (w), 1467 (w), 1457 (w), 1368 (w), 1278 (s), 1234 (s), 1190 (s), 1145 (s), 1051 (m); HRMS (ES) m/z calcd for (C$_{20}$H$_{22}$O$_5$+NH$_4$)$^+$ 360.1811. found 360.1808.

Michael-Dieckmann Addition Product CDL-I-287:

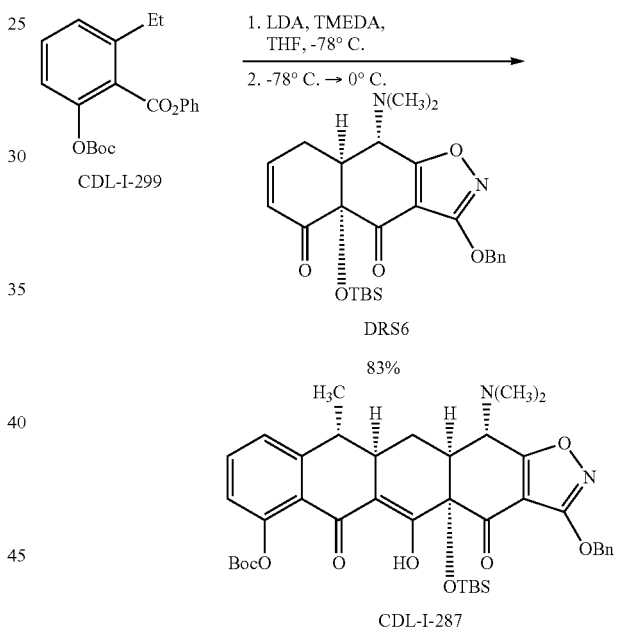

A solution of n-butyllithium in hexanes (1.45 M, 47 μL, 0.068 mmol, 6.8 equiv) was added to a solution of diisopropylamine (10 μL, 0.071 mmol, 7.1 equiv) and N,N,N',N'-tetramethylethylenediamine (10 μL, 0.066 mmol, 6.6 equiv) in tetrahydrofuran (300 μL) at −78° C. The resulting solution was stirred at −78° C. for 30 min whereupon a solution of the ester CDL-I-299 (17 mg, 0.050 mmol, 5.0 equiv) in tetrahydrofuran (200 μL) was added, forming a deep red solution. The solution was stirred at −78° C. for 75 min, then a solution of the enone DRS6 (5.0 mg, 0.010 mmol, 1.0 equiv) in tetrahydrofuran (100 μL) was added at −78° C. The color of the reaction mixture remained deep red following the addition. The mixture was allowed to warm to 0° C. over 150 min. Upon reaching 0° C., an aqueous potassium phosphate buffer solution (pH 7.0, 0.2 M, 15 mL) was added. The resulting yellow mixture was extracted with dichloromethane (3×15 mL). The organic layers were combined and then dried over anhydrous sodium sulfate. The dried solution was filtered and the filtrate was concentrated, providing a yellow oil. The product was purified by preparatory HPLC on a Coulter Ultrasphere ODS column (5 250×10 mm, flow rate 3.5 mL/min, Solvent A: water, Solvent B: methanol, UV detection at 350 nm) using an injection volume of 500 μL methanol with an isochratic elution of 89.5% B. The peak eluting at 31-40 min was collected and concentrated affording the Michael-Dieckmann product CDL-I-287 as a light yellow solid (6.1 mg, 83%), mp 114° C.

$R_f$ 0.37 (2:8 tetrahydrofuran-hexanes); $^1$H NMR (500 MHz, CDCl$_3$) δ (s, 1H, 16.24, enol-OH), 7.55-7.50 (m, 3H, ArH), 7.40-7.35 (m, 4H, ArH), 7.10 (d, 1H, J=7.8 Hz, ArH), 5.39-5.34 (m, 2H, OCH$_2$Ph), 3.92 (d, 1H, J=10.7 Hz, CHN(CH$_3$)$_2$), 2.81-2.71 (m, 2H, CH$_3$CH, CH$_3$CHCH), 2.55 (dd, 1H, J=10.7, 5.7 Hz, CHCHN(CH$_3$)$_2$), 2.48 (s, 6H, N(CH$_3$)$_2$), 2.40 (d, 1H, J=14.7 Hz, CHH'CHCHN(CH$_3$)$_2$), 2.31 (ddd, 1H, J=14.7, 9.3, 5.7, CHH'CHCHN(CH$_3$)$_2$), 1.56 (s, 3H, CH$_3$), 1.55 (s, 9H, Boc), 0.84 (s, 9H, TBS), 0.27 (s, 3H, TBS), 0.13 (s, 3H, TBS); $^{13}$C NMR (125 MHz, CDCl$_3$) δ 187.4, 183.1, 182.8, 181.6, 167.6, 151.7, 150.2, 147.4, 135.0, 134.0, 128.5, 128.5, 123.4, 123.0, 122.4, 108.3, 107.4, 94.8, 83.9, 81.5, 72.5, 61.5, 46.4, 41.9, 39.5, 34.9, 27.7, 26.0, 20.7, 19.0, 16.0, −2.6, −3.7; FTIR (neat film), cm$^{-1}$ 2923 (m), 2841 (m), 1759 (s, C=O), 1718 (s, C=O), 1605 (s), 1508 (s), 1467 (m), 1456 (m), 1369 (m), 1277 (s), 1262 (m), 1231 (s), 1144 (s), 1005 (w); HRMS (ES) m/z calcd for (C$_{40}$H$_{50}$N$_2$O$_9$Si+H)$^+$ 731.3364. found 731.3370.

6-Deoxytetracycline CDL-I-322

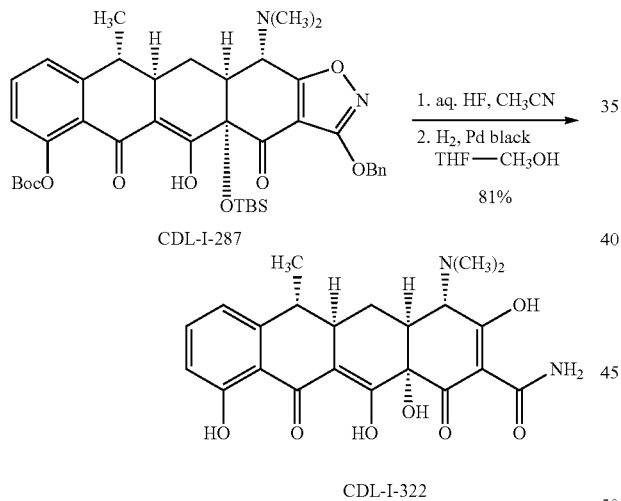

Hydrofluoric acid (0.6 mL, 48% aqueous) was added to a polypropylene reaction vessel containing a solution of the Michael-Dieckmann addition product CDL-I-287 (15 mg, 0.021 mmol, 1.0 equiv) in acetonitrile (3.5 mL) at 23° C. The reaction mixture was stirred at 23° C. for 55 h, then was poured into water (20 mL) containing K$_2$HPO$_4$ (4.0 g). The resulting mixture was extracted with ethyl acetate (4×20 mL). The organic phases were combined and then dried over anhydrous sodium sulfate. The dried solution was filtered and the filtrate was concentrated, providing a light yellow oil. Pd black (7.6 mg, 0.071 mmol, 3.4 equiv) was added in one portion to a solution of the residue in methanol-tetrahydrofuran (1:1, 2 mL). An atmosphere of hydrogen gas was introduced by briefly evacuating the flask, then flushing with pure hydrogen (1 atm). The mixture was stirred at 23° C. for 2 h. Within 5 min, the color changed from light yellow to dark yellow. The reaction mixture was filtered through a plug of cotton. The filtrate was concentrated, affording a yellow oil (10 mg). The product was purified by preparatory HPLC on a Phenomenex Polymerx DVB column (10 μm, 250×10 mm, flow rate 5 mL/min, Solvent A: methanol-0.02 N HCl (1:4), Solvent B: acetonitrile, UV detection at 365 nm) using an injection volume of 400 μL methanol containing oxalic acid monohydrate (10 mg) and an isochratic elution of 18% B for 15 min, then a linear gradient elution of 18-60% B in 15 min. The peak eluting at 17.5-22.5 min was collected and concentrated to give 6-deoxytetracycline hydrochloride (CDL-I-322.HCl) as a yellow powder (8.1 mg, 81%).

$^1$H NMR (500 MHz, CD$_3$OD, hydrochloride) δ 7.49 (t, 1H, J=7.8 Hz, ArH), 6.95 (d, 1H, J=7.8 Hz, ArH), 6.84 (d, 1H, J=7.8 Hz, ArH), 4.09 (s, 1H, CHN(CH$_3$)$_2$), 3.03 (br s, 3H, N(CH$_3$)), 2.97 (br s, 3H, N(CH$_3$)), 2.90 (br d, 1H, J=12.7 Hz, CHCHN(CH$_3$)$_2$), 2.67 (ddd, 1H, J=12.7, 12.7, 5.2 Hz, CH$_3$CHCH), 2.61-2.56 (m, 1H, CH$_3$CH), 2.30 (ddd, J=13.7, 5.2, 2.9 Hz, CHH'CHCHN(CH$_3$)$_2$), 1.54 (ddd, J=13.7, 12.7, 12.7 Hz, CHH'CHCHN(CH$_3$)$_2$), 1.38 (d, 3H, J=6.8 Hz, CH$_3$CH). HRMS (ES) m/z calcd for (C$_{22}$H$_{24}$N$_2$O$_7$+H)$^+$ 429.1662. found 429.1660.

Example 4

Synthesis of a Pyridone Sancycline Analog

Phenyl Ester CDL-II-464:

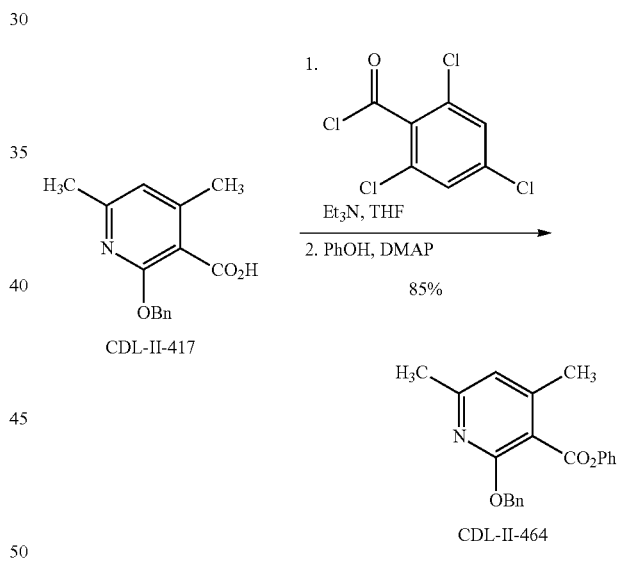

2,4,6-Trichlorobenzoyl chloride (356 μL, 2.28 mmol, 1.1 equiv) was added to a solution of the carboxylic acid CDL-II-417 (reported by A. N. Osman, M. M Ismail, M. A. Barakat, *Revue Roumaine de Chime* 1986, 31, 615-624) (534 mg, 2.08 mmol. 1.0 equiv) and triethylamine (320 μL, 2.28 mmol, 1.1 equiv) in tetrahydrofuran (25 mL) at 23° C. A white precipitate was formed upon addition. The reaction mixture was stirred for 30 min at 23° C. A solution of phenol (489 mg, 5.20 mmol, 2.5 equiv) and 4-(dimethylamino)pyridine (583 mg, 5.20 mmol, 2.5 equiv) in tetrahydrofuran (10 mL) was added via cannula to the reaction mixture prepared above at 0° C. The resulting mixture was allowed to warm to 23° C. over 10 min, and was stirred for 90 min at that temperature. An aqueous potassium phosphate buffer solution (pH 7.0, 0.2 M, 30 mL) was then added and the resulting mixture was extracted with dichloromethane (3×30 mL). The organic extracts were combined and then dried over anhydrous sodium sulfate. The dried solution was filtered and the filtrate concentrated, providing a colorless oil. The product was purified by flash column chromatography (6:94 ethyl acetate-hexanes), affording the phenyl ester CDL-II-464 as a white solid (590 mg, 85%), mp 65° C.

$R_f$ 0.33 (1:9 ethyl acetate-hexanes); $^1$H NMR (500 MHz, CDCl$_3$) δ 7.49 (d, 2H, J=7.3 Hz, ArH), 7.40-7.24 (m, 6H, ArH), 7.14 (d, 2H, J=7.3 Hz, ArH), 6.69 (s, 1H, pyr-H), 5.49 (s, 2H, CH$_2$Ph), 2.47 (s, 3H, CH$_3$), 2.43 (s, 3H, CH$_3$); $^{13}$C NMR (125 MHz, CDCl$_3$) δ 165.9, 160.1, 157.8, 150.7, 148.5, 137.3, 129.4, 128.3, 127.7, 127.6, 125.9, 121.7, 118.1, 113.4, 67.8, 24.1, 19.2; FTIR (neat film), cm$^{-1}$ 1738 (s, C=O), 1600 (s), 1569 (s), 1492 (m), 1441 (m), 1400 (m), 1333 (s), 1272 (s), 1185 (s), 1159 (m), 1097 (m), 1051 (s); HRMS (ES) m/z calcd for $(C_{21}H_{19}NO_3+H)^+$ 334.1443. found 334.1442.

Michael-Dieckmann Addition Product CDL-II-466:

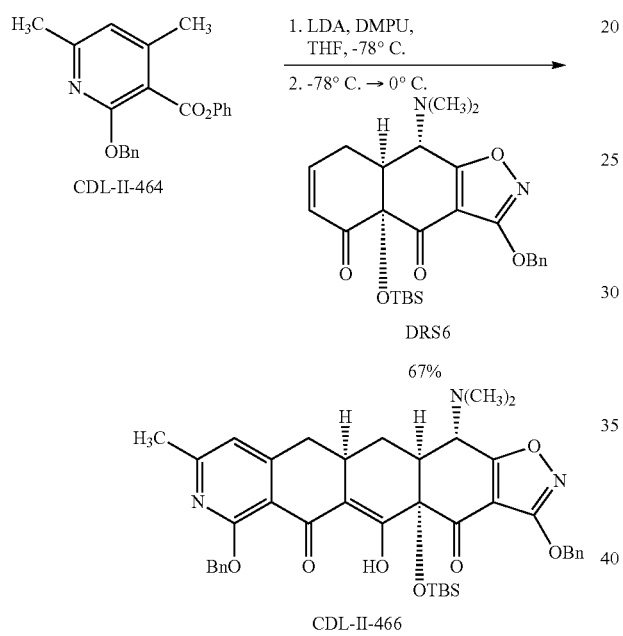

A solution of n-butyllithium in hexanes (1.67 M, 80 μL, 0.13 mmol, 4.2 equiv) was added to a solution of diisopropylamine (20 μL, 0.14 mmol, 4.5 equiv) in tetrahydrofuran (2.5 mL) at −78° C. The resulting solution was allowed to warm to 0° C. over 15 min. N,N'-dimethylpropyleneurea (17 μL, 0.14 mmol, 4.5 equiv) was added to the mixture prepared above at 0° C., whereupon the mixture was cooled to −78° C. A solution of the ester CDL-II-464 (31 mg, 0.093 mmol, 3.0 equiv) in tetrahydrofuran (250 μL) was then added at −78° C. The resulting yellow solution was stirred for 5 min at −78° C., then a solution of the enone DRS6 (15 mg, 0.031 mmol, 1.0 equiv) in tetrahydrofuran (250 μL) was added at −78° C. The resulting deep red mixture was allowed to warm to 0° C. over 4 h. Acetic acid (40 μL) was added at to the deep red mixture at 0° C., followed by an aqueous potassium phosphate buffer solution (pH 7.0, 0.2 M, 15 mL). The resulting yellow mixture was extracted with dichloromethane (3×15 mL). The organic extracts were combined and then dried over anhydrous sodium sulfate. The dried solution was filtered and the filtrate was concentrated, providing a yellow oil. The product was purified by preparatory HPLC on a Coulter Ultrasphere ODS column (5 250×10 mm, flow rate 3.5 mL/min, Solvent A: water, Solvent B: methanol, UV detection at 350 nm) using an injection volume of 500 μL DMSO and a gradient elution of 92-100% B over 30 min. The peak eluting at 21-29 min was collected and concentrated to give enol CDL-II-466 as a light yellow solid (15.0 mg, 67%).

$R_f$ 0.55 (3:7 ethyl acetate-hexanes); $^1$H NMR (600 MHz, CD$_2$Cl$_2$) δ 16.05 (s, 1H, enol-OH), 7.52-7.26 (m, 10H, ArH), 6.66 (s, 1H, pyr-H), 5.57 (d, 1H, J=12.7 Hz, OCHH'Ph), 5.43 (d, J=12.7 Hz, 1H, OCHH'Ph), 5.33-5.28 (m, 2H, OCH$_2$Ph), 3.99 (d, 2H, J=10.5 Hz, CHN(CH$_3$)$_2$), 3.04-3.00 (m, 1H, CHCH$_2$CHCHN(CH$_3$)$_2$), 2.84 (dd, 1H, J=16.1, 4.9 Hz, CHH'CHCH$_2$CHCHN(CH$_3$)$_2$), 2.74 (dd, 1H, J=16.1, 16.1 Hz, CHH'CHCH$_2$CHCHN(CH$_3$)$_2$), 2.53 (dd, 1H, J=10.5, 3.9 Hz, CHCHN(CH$_3$)$_2$), 2.51-2.43 (m, 10H, N(CH$_3$)$_2$, Ar—CH$_3$, CHH'CHCHN(CH$_3$)$_2$), 2.07 (d, 1H, J=14.2 Hz, CHH'CHCHN(CH$_3$)$_2$), 0.82 (s, 9H, TBS), 0.22 (s, 3H, TBS), 0.10 (s, 3H, TBS); $^{13}$C NMR (100 MHz, CD$_2$Cl$_2$) δ 187.9, 185.2, 182.5, 178.8, 167.9, 161.9, 161.8, 154.8, 137.9, 135.6, 129.1, 129.0, 129.0, 128.7, 127.9, 127.9, 116.4, 111.6, 108.6, 107.5, 82.0, 73.0, 68.1, 61.7, 46.9, 42.0, 39.2, 28.6, 26.1, 24.6, 23.0, 19.3, −2.4, −3.5; FTIR (neat film), cm$^{-1}$ 2939 (m), 2857 (w), 1720 (s, C=O), 1593 (s), 1510 (s), 1469 (m), 1449 (m), 1326 (s), 1254 (m), 1187 (w), 1157 (m), 1090 (m), 1064 (m), 1007 (m); HRMS (ES) m/z calcd for $(C_{41}H_{47}N_3O_7Si+H)^+$ 722.3262. found 722.3261.

Pyridone Sancycline Analog CDL-II-460:

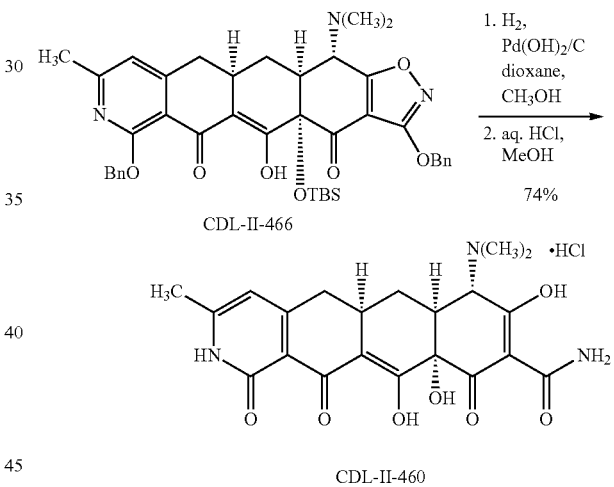

Palladium hydroxide on carbon (20 wt. % Pd, wet, water max. 50%, 10 mg, 0.0094 mmol, 0.7 equiv) was added to a solution of the Michael-Dieckmann addition product CDL-II-466 (10 mg, 0.014 mmol, 1.0 equiv) in dioxane-methanol (1:1, 10 mL) at 23° C. An atmosphere of hydrogen gas was introduced by briefly evacuating the flask, then flushing with pure hydrogen (1 atm). The resulting mixture was stirred at 23° C. for 2 h. The color turned green after 5 min and then gradually to yellow within the reaction time. The mixture was filtered through a plug of cotton and then concentrated to a yellow oil. Aqueous hydrochloric acid (37%, 100 μL) was added to a solution of the residue in methanol (10 mL) at 23° C. The reaction was monitored by analytical HPLC on a Coulter Ultrasphere ODS column (5 μm, 250×4.6 mm, flow rate 1 ml/min, Solvent A: 0.1% TFA in water, Solvent B: 0.1% TFA in acetonitrile, UV detection at 395 nm) with a gradient elution of 10-100% B over 15 min. The peak at 7.0 min indicated the desired product. After stirring for 3 h at 23° C. the deprotection was complete and the mixture was concentrated to a yellow oil. The crude mixture was purified by preparatory HPLC on a Phenomenex Polymerx DVB column (10 μm, 250×10 mm, flow rate 4 ml/min, Solvent A: 0.01 N aqueous hydrochloric acid, Solvent B: acetonitrile, UV detection at 365 nm) using an injection volume of 500 μL methanol containing oxalic acid monohydrate (30 mg) and a linear gradient of 0-20% B over 40 min. The peak eluting at 20-29 min was collected and concentrated to give the hydrochloride of CDL-II-460 as a yellow powder (4.8 mg, 74%).

$^1$H NMR (500 MHz, CD$_3$OD, hydrochloride) δ 6.37 (s, 1H, ArH), 4.06 (s, 1H, CHN(CH$_3$)$_2$), 3.05-2.95 (m, 8H, N(CH$_3$)$_2$, CHCHN(CH$_3$)$_2$, CHCH$_2$CHCHN(CH$_3$)$_2$), 2.79 (dd, 1H, J=16.1, 3.9 Hz, CHH'CHCH$_2$CHCHN(CH$_3$)$_2$), 2.55 (dd, 1H, J=16.1, 16.1 Hz, CHH'CHCH$_2$CHCHN(CH$_3$)$_2$)), 2.40 (s, 3H, Ar—CH$_3$), 2.18 (br. d, 1H, J=12.7 Hz, CHH'CHCHN(CH$_3$)$_2$), 1.59 (ddd, 1H, J=12.7, 12.7, 12.7 Hz, CHH'CHCHN(CH$_3$)$_2$); $^{13}$C NMR (100 MHz, (CD$_3$)$_2$SO) δ 187.3, 183.5, 177.8, 172.1, 160.6, 159.8, 153.3, 115.3, 107.2, 106.9, 95.6, 74.2, 68.4, 41.5, 35.7, 34.5, 33.9, 31.0, 19.2; HRMS (ES) m/z calcd for (C$_{21}$H$_{23}$N$_3$O$_7$+H)$^+$430.1614. found 430.1607.

Example 5

Synthesis of Pyridine Sancycline Analog
(7-Aza-10-Deoxysancycline)

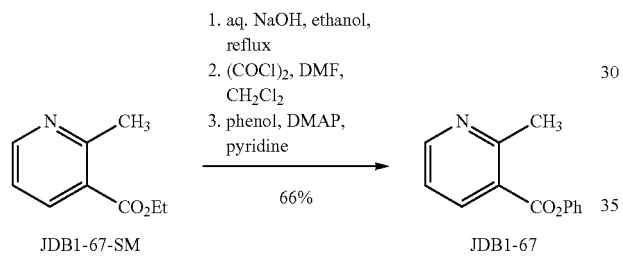

A solution of 2-methyl-nicotinic acid ethyl ester JDB1-67-SM (0.589 g, 3.56 mmol, 1.0 equiv), aqueous sodium hydroxide (1.0 M, 3.9 mL, 3.9 mmol, 1.1 equiv), and ethanol (5 mL) was heated at reflux for 18 h. The reaction mixture was allowed to cool to 23° C., and was concentrated, affording the carboxylate salt (710 mg) as a white solid. Oxalyl chloride (357 μL, 4.09 mmol, 1.15 equiv) was added to a mixture of the carboxylate salt in dichloromethane (20 mL) at 23° C. Vigorous gas evolution was observed upon addition. The reaction mixture was stirred at 23° C. for 30 min, then N,N-dimethylformamide (20 μL) was added. After stirring for an additional 30 min at 23° C., phenol (837 mg, 8.90 mmol, 2.5 equiv), pyridine (864 μL, 10.7 mmol, 3.0 equiv), and dimethylaminopyridine (3 mg) were added in sequence. The resulting solution was stirred for 90 min at 23° C., whereupon an aqueous potassium phosphate buffer solution (pH 7.05, 0.2 M, 5.0 mL) was added. The resulting mixture was partitioned between water (30 mL) and ethyl acetate (50 mL). The aqueous phase was extracted with an additional 50-mL portion of ethyl acetate. The organic layers were combined and washed with an aqueous sodium hydroxide solution (50 mL, 1M), brine (50 mL), and then dried over anhydrous sodium sulfate. The dried solution was decanted and concentrated, affording a colorless oil (900 mg). The product was purified by flash column chromatography (25:75 ethyl acetate-hexanes), providing the ester JDB1-67 as a colorless oil (500 mg, 66%).

R$_f$ 0.15 (3:7 ethyl acetate-hexanes); $^1$H NMR (300 MHz, CDCl$_3$) δ 8.70 (dd, 1H, J=1.7, 4.95 Hz, pyr-H), 8.44 (dd, 1H, J=1.7, 7.8 Hz, pyr-H), 7.48-7.43 (m, 2H, ArH), 7.33-7.20 (m, 4H, ArH, pyr-H), 2.93 (s, 1H, CH$_3$); $^{13}$C NMR (100 MHz, CDCl$_3$) δ 164.8, 160.8, 152.4, 150.5, 138.9, 129.5, 126.1, 124.5, 121.6, 121.0, 25.0; FTIR (neat film), cm$^{-1}$ 3406 (m), 1948 (w), 1747 (s), 1578 (s), 1487 (s), 1435 (s), 1273 (s), 1237 (s), 1191 (s), 1046 (s), 915 (m), 822 (m), 749 (s), 689 (s); HRMS (ES) m/z calcd for (C$_{13}$H$_{11}$NO$_2$+H)$^+$214.0868. found 214.0866.

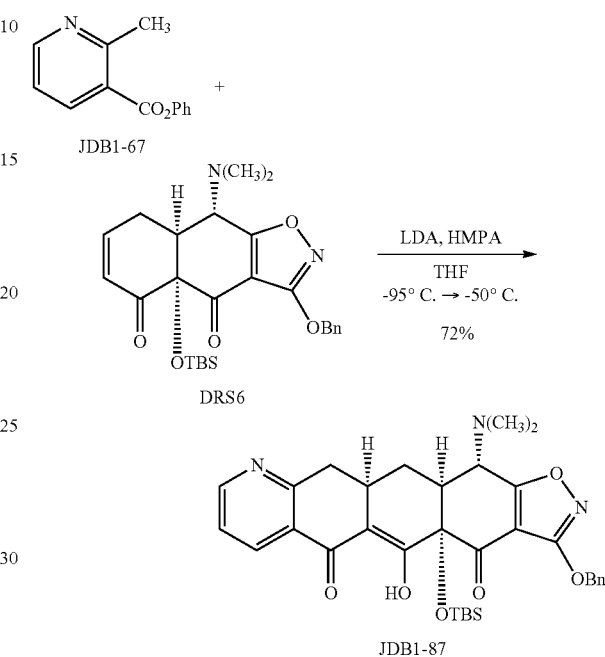

A solution of n-butyllithium in hexanes (1.47 M, 136 μL, 0.200 mmol, 8.03 equiv) was added to a solution of diisopropylamine (26.5 μL, 0.202 mmol, 8.05 equiv) in tetrahydrofuran (0.750 mL) at −78° C. The reaction mixture was briefly (10 min) transferred to an ice bath, with stirring, then was cooled to −78° C. Hexamethylphosphoramide (49.0 μL, 0.399 mmol, 16.0 equiv) was added to the mixture prepared above at −78° C. The resulting mixture was stirred for 5 minutes whereupon a colorless solution was formed. The resulting solution was added dropwise via cannula to a solution of the ester JDB1-67 (36.0 mg, 0.169 mmol, 6.79 equiv), and the enone DRS6 (12.2 mg, 0.0249 mmol, 1.00 equiv) in tetrahydrofuran (1 mL) at −95° C. dropwise via cannula. The light red mixture was allowed to warm to −50° C. over 50 min and was then partitioned between an aqueous potassium phosphate buffer solution (pH 7.0, 0.2 M, 5.0 mL) and dichloromethane (25 mL). The organic phase was separated and the aqueous phase was further extracted with dichloromethane (3×15 mL). The organic phases were combined and dried over anhydrous sodium sulfate. The dried solution was decanted and concentrated, affording a yellow solid. The product was purified by preparatory HPLC on a Coulter Ultrasphere ODS column (10 μm, 250×10 mm, 3.5 mL/min, Solvent A: water, Solvent B: methanol, UV detection at 350 nm) using an injection volume of 500 μL methanol and a linear gradient elution of 85-100% B over 30 min. The peak at 21-27 min was collected and concentrated to give enol JDB1-87 as a white solid (11.0 mg, 72%).

R$_f$ 0.07 (3:7 ethyl acetate-hexanes); $^1$H NMR (500 MHz, CD$_2$Cl$_2$) δ 15.21 (s, 1H, enol), 8.63 (d, 1H, J=4.5 Hz, pyr-H), 8.19 (d, 1H, J=7.5 Hz, pyr-H), 7.54-7.43 (m, 5H, ArH), 7.34 (d, 1H, J=4.5, 7.5 Hz, pyr-H), 5.36 (d, 1H, J=12.0 Hz, OCHH'Ph), 5.33 (d, 1H, J=12.0 Hz, OCHH'Ph), 4.03 (d, 1H, J=10.7 Hz, CHN(CH$_3$)$_2$), 3.36-3.31 (m, 1H, CHCH$_2$CHCHN (CH$_3$)$_2$), 3.23 (dd, 1H, J=16.3, 5.6 Hz, CHH'CHCH$_2$CHCHN (CH$_3$)$_2$), 2.99 (dd, 1H, J=16.3, 16.3 Hz, CHH'CHCH$_2$CHCHN(CH$_3$)$_2$), 2.63 (ddd, 1H, J=1.6, 4.4, 10.7 Hz, CHCHN(CH$_3$)$_2$), 2.54-2.48 (m, 7H, N(CH$_3$)$_2$, CHH'CHCHN(CH$_3$)$_2$), 2.19 (dd, 1H, J=1.6, 14.5 Hz, CHH'CHCHN(CH$_3$)$_2$), 0.87 (s, 9H, TBS), 0.26 (s, 3H, TBS), 0.13 (s, 3H, TBS); $^{13}$C NMR (100 MHz, CD$_2$Cl$_2$) δ 187.7, 183.5, 182.6, 182.2, 167.9, 161.2, 153.4, 137.6, 134.1, 129.2, 129.1, 129.1, 126.8, 123.0, 108.7, 106.9, 82.2, 73.0, 61.8, 47.0, 42.1, 41.4, 30.1, 28.4, 26.1, 23.2, 19.3, −2.4, −3.5; HRMS (ES) m/z calcd for (C$_{33}$H$_{39}$N$_3$O$_6$Si+H)$^+$602.2686. found 602.2686.

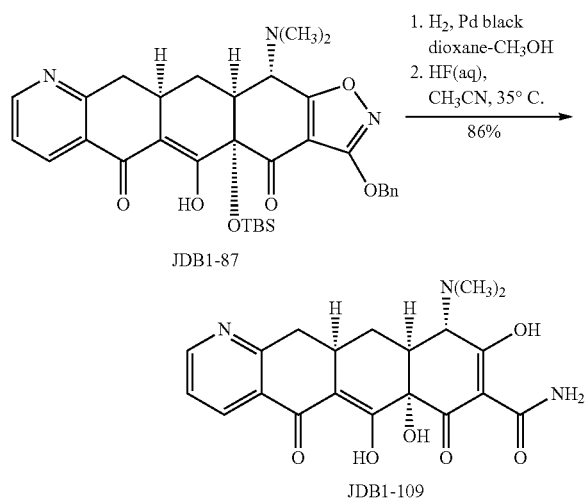

Pd black (3.0 mg, 0.028 mmol, 2.6 equiv) was added in one portion to a solution of the enol JDB1-87 (6.5 mg, 0.011 mmol, 1.0 equiv) in dioxane-methanol (7:2, 9.0 mL) at 23° C. An atmosphere of hydrogen was introduced by briefly evacuating the flask, then flushing with pure hydrogen (1 atm). The green mixture was stirred for 7 hr, and then filtered through a plug of cotton. The filtrate was concentrated, providing the carboxamide as a yellow oil (7.0 mg). Aqueous hydrofluoric acid (48%, 0.5 mL) was added to a polypropylene reaction vessel containing a solution of the carboxamide in acetonitrile (4.5 mL) at 23° C. The reaction mixture was heated to 35° C. and was stirred at that temperature for 27 hr. The excess hydrofluoric acid was quenched with methoxytrimethylsilane (3.5 mL, 25 mmol). The reaction mixture was concentrated, affording a yellow solid. The product was purified by preparatory HPLC on a Phenomenex Polymerx DVB column (10 µm, 250×10 mm, 4 mL/min, Solvent A: 0.5% trifluoroacetic acid in water, Solvent B: 0.5% trifluoroacetic acid in methanol-acetonitrile (1:1), UV detection at 350 nm) using an injection volume of 500 µL methanol and a linear gradient of 0-20% B over 40 min. The peak at 35-45 min was collected and concentrated to give a yellow oil. The oil was dissolved in 1 mL methanol, treated with concentrated hydrochloric acid (20 µL), and then concentrated to give the hydrochloride of JDB1-109 as a yellow powder (3.7 mg, 86%).

$^1$H NMR (500 MHz, CD$_3$OD, hydrochloride) δ 8.79-8.77 (m, 2H, pyr-H) 7.91 (dd, 1H, J=6.8, 6.8 Hz, pyr-H), 4.12 (s, 1H, CHN(CH$_3$)$_2$), 3.41-3.22 (m, 2H, CHH'CHCH$_2$CHCHN (CH$_3$)$_2$, CHCH$_2$CHCHN(CH$_3$)$_2$), 3.11-3.00 (m, 8H, CHH'CHCH$_2$CHCHN(CH$_3$)$_2$, CHCHN(CH$_3$)$_2$, N(CH$_3$)$_2$), 2.34 (ddd, 1H, J=12.9, 4.4, 2.4 Hz, CHH'CHCHN(CH$_3$)$_2$), 1.77 (ddd, 1H, J=12.9, 12.9, 12.9 Hz, CHH'CHCHN(CH$_3$)$_2$); HRMS (ES) m/z calcd for (C$_{20}$H$_{21}$N$_3$O$_6$+H)$^+$400.1508. found 400.1504.

Example 6

Synthesis of 10-Deoxysancycline

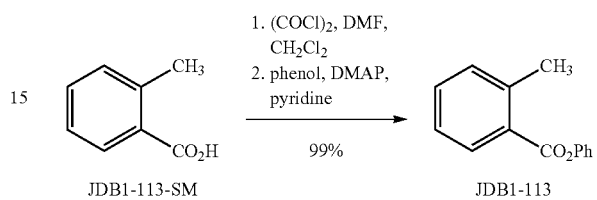

N,N-dimethylformamide (20 µL) was added was added to a solution of the carboxylic acid JDB1-113-SM (500 mg, 3.67 mmol, 1.0 equiv) and oxalyl chloride (367 µA 4.22 mmol, 1.15 equiv) in dichloromethane (20 mL) at 23° C. Vigorous gas evolution was observed. After stirring for 80 min at 23° C., phenol (863 mg, 9.18 mmol, 2.5 equiv), pyridine (890 µL, 11.0 mmol, 3.0 equiv), and dimethylaminopyridine (3 mg) were added in sequence. The resulting solution was stirred for 90 min at 23° C., whereupon an aqueous potassium phosphate buffer solution (pH 7.05, 0.2 M, 5.0 mL) was added. The resulting mixture was partitioned between water (30 mL) and ethyl acetate (50 mL). The aqueous phase was extracted with an additional 50-mL portion of ethyl acetate. The organic layers were combined and washed with an aqueous sodium hydroxide solution (50 mL, 1M), brine (50 mL), and then dried over anhydrous sodium sulfate. The dried solution was decanted and concentrated, affording a colorless oil (850 mg). The product was purified by flash column chromatography (25:75 ethyl acetate-hexanes), providing the ester JDB1-113 as a colorless oil (774 mg, 99%).

R$_f$ 0.43 (3:7 ethyl acetate-hexanes); $^1$H NMR (300 MHz, CDCl$_3$) δ 8.18 (d, 1H, J=8.1 Hz, ArH), 7.49-7.20 (m, 8H, ArH, OArH), 2.69 (s, 3H, ArCH$_3$); $^{13}$C NMR (100 MHz, CDCl$_3$) δ 165.8, 150.9, 141.3, 132.7, 132.0, 131.2, 129.5, 128.5, 125.9, 125.8, 121.8, 22.0; FTIR (neat film), cm$^{-1}$ 3046 (w), 2923 (w), 1739 (s), 1594 (m), 1487 (m), 1287 (m), 1241 (s), 1189 (s), 1159 (m), 1041 (s), 733 (s); HRMS (ES) m/z calcd for (C$_{14}$H$_{12}$O$_2$+NH$_4$)$^+$230.1181. found 230.1187.

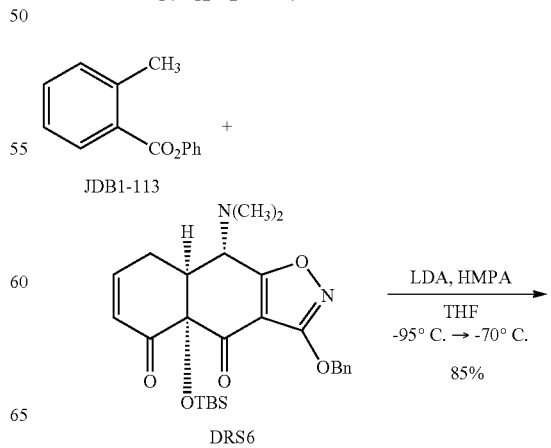

-continued

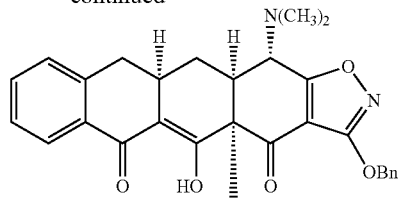

JDB1-114

A solution of n-butyllithium in hexanes (1.47 M, 38.0 µL, 0.0565 mmol, 8.26 equiv) was added to a solution of diisopropylamine (7.4 µL, 0.057 mmol, 8.3 equiv) in tetrahydrofuran (0.50 mL) at −78° C. The reaction mixture was briefly (10 min) transferred to an ice bath, with stiffing, then was cooled to −78° C. Hexamethylphosphoramide (13.9 µL, 0.113 mmol, 16.5 equiv) was added to the mixture prepared above at −78° C. The resulting mixture was stirred for 5 minutes whereupon a colorless solution was formed. The resulting solution was added dropwise via cannula to a solution of the ester JDB1-113 (10.0 mg, 0.0471 mmol, 6.88 equiv), and the enone DRS6 (3.3 mg, 0.00684 mmol, 1.00 equiv) in tetrahydrofuran (0.50 mL) at −95° C. dropwise via cannula. The light red mixture was allowed to warm to −70° C. over 30 min and was then partitioned between an aqueous potassium phosphate buffer solution (pH 7.0, 0.2 M, 5.0 mL) and dichloromethane (20 mL). The organic phase was separated and the aqueous phase was further extracted with an additional 20-mL portion of dichloromethane. The organic phases were combined and dried over anhydrous sodium sulfate. The dried solution was decanted and concentrated, affording a yellow solid. The product was purified by preparatory HPLC on a Coulter Ultrasphere ODS column (10 µm, 250×10 mm, 3.5 mL/min, Solvent A: water, Solvent B: methanol, UV detection at 350 nm) using an injection volume of 500 µL methanol and a linear gradient elution of 85-100% B over 30 min. The peak at 25-30 min was collected and concentrated to give enol JDB1-87 as a white solid (3.5 mg, 85%).

$R_f$ 0.46 (3:7 ethyl acetate-hexanes); $^1$H NMR (500 MHz, $CD_2Cl_2$) δ 15.53 (s, 1H, enol), 7.94 (d, 1H, J=7.9 Hz, ArH), 7.54-7.28 (m, 8H, ArH, OCH$_2$ArH), 5.37-5.34 (m, 2H, OCH$_2$Ph), 4.05 (d, 1H, J=10.7 Hz, CHN(CH$_3$)$_2$), 3.24-3.18 (m, 1H, CHCH$_2$CHCHN(CH$_3$)$_2$), 2.99 (dd, 1H, J=15.5, 5.6 Hz, CHH'CHCH$_2$CHCHN(CH$_3$)$_2$), 2.88 (dd, 1H, J=15.5, 15.5 Hz, CHH'CHCH$_2$CHCHN(CH$_3$)$_2$), 2.61 (dd, 1H, J=4.4, 10.7 Hz, CHCHN(CH$_3$)$_2$), 2.54-2.44 (m, 7H, N(CH$_3$)$_2$, CHH'CHCHN(CH$_3$)$_2$), 2.14 (d, 1H, J=14.3 Hz, CHH'CHCHN(CH$_3$)$_2$), 0.86 (s, 9H, TBS), 0.25 (s, 3H, TBS), 0.12 (s, 3H, TBS); $^{13}$C NMR (100 MHz, $CD_2Cl_2$) δ 187.8, 183.0, 182.8, 182.4, 167.7, 141.7, 135.4, 133.4, 130.9, 129.0, 128.9, 128.9, 128.1, 127.5, 126.5, 108.5, 106.8, 82.1, 72.8, 61.5, 58.5, 46.9, 41.9, 38.6, 29.0, 25.9, 23.1, 19.1, −2.6, −3.7; HRMS (ES) m/z calcd for $(C_{34}H_{40}N_3O_6Si+H)^+$ 601.2734. found 601.2730.

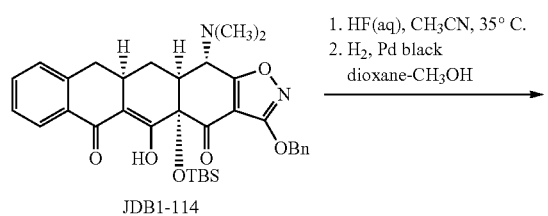

1. HF(aq), CH$_3$CN, 35° C.
2. H$_2$, Pd black
dioxane-CH$_3$OH

JDB1-114

-continued

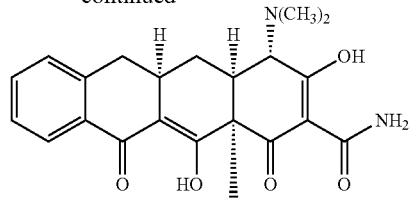

JDB1-130

Hydrofluoric acid (1.1 mL, 48% aqueous) was added to a polypropylene reaction vessel containing a solution of the enol JDB1-114 (15.1 mg, 0.0251 mmol, 1.0 equiv) in acetonitrile (10 mL) at 23° C. The resulting mixture was stirred vigorously at 23° C. for 12 hr, then was poured into water (50 mL) containing K$_2$HPO$_4$ (4.7 g). The resulting mixture was extracted with ethyl acetate (3×25 mL). The organic phases were combined and dried over anhydrous sodium sulfate. The dried solution was filtered and the filtrate was concentrated, furnishing the intermediate alcohol as a yellow solid (12.2 mg, 99%). Pd black was added in one portion to a solution of the residue in methanol-dioxane (1:1, 3.0 mL). An atmosphere of hydrogen was introduced by briefly evacuating the flask, then flushing with pure hydrogen (1 atm). The mixture was stirred at 23° C. for 20 min. Within 5 min, the color changed from light yellow to green. The reaction mixture was filtered through a plug of cotton. The filtrate was concentrated to a yellow solid (13 mg). The product was purified by preparatory HPLC on a Phenomenex Polymerx DVB column (10 µm, 250×10 mm, flow rate 5 mL/min, Solvent A: 0.01 N HCl, Solvent B: acetonitrile, UV detection at 350 nm) using an injection volume of 450 µL methanol containing oxalic acid monohydrate (10 mg) in two injections and a linear gradient elution of 5-50% B in 30 min. The peak eluting at 16-22 min was collected and concentrated to give 10-deoxysancycline hydrochloride (JDB1-130.HCl) as a white powder (9.1 mg, 91%).

$^1$H NMR (500 MHz, CD$_3$OD, hydrochloride) δ 7.96 (d, 1H, J=7.3 Hz, ArH) 7.51 (dd, 1H, J=7.3, 7.3 Hz, ArH), 7.39 (dd, 1H, J=7.3, 7.3 Hz, ArH), 7.30 (d, 1H, J=7.3 Hz, ArH), 4.04 (s, 1H, CHN(CH$_3$)$_2$), 3.31-2.99 (m, 8H, CHCH$_2$CHCHN(CH$_3$)$_2$, CHCHN(CH$_3$)$_2$, N(CH$_3$)$_2$), 2.87 (dd, 1H, J=15.4, 4.3 Hz, CHH'CHCH$_2$CHCHN(CH$_3$)$_2$), 2.61 (dd, 1H, J=15.4, 15.4 Hz, CHH'CHCH$_2$CHCHN(CH$_3$)$_2$), 2.21 (ddd, J=12.8, 5.0, 2.5 Hz, CHH'CHCHN(CH$_3$)$_2$), 1.66 (ddd, 1H, J=12.8, 12.8, 12.8 Hz, CHH'CHCHN(CH$_3$)$_2$).

Example 7

A Convergent, Enantioselective Synthetic Route to Structurally Diverse 6-Deoxytetracycline Antibiotics Among tetracyclines, semi-synthetic approaches have led to the discovery of the 6-deoxytetracyclines doxycycline (2 in FIG. 15A) and minocycline (3 in FIG. 15A), clinically the most important agents in the class. 6-Deoxytetracyclines exhibit considerably improved chemical stability as compared to their 6-hydroxy counterparts and show equal or greater potencies in antibacterial assays (Stephens et al., J. Am. Chem. Soc. 85, 2643 (1963); M. Nelson, W. Hillen, R. A. Greenwald, Eds., Tetracyclines in Biology, Chemistry and Medicine (Birkhauser Verlag, Boston, 2001); each of which is incorporated herein by reference). It is evident that at present neither semi-synthesis nor modified biosynthesis is capable of addressing the great majority of novel structures that a chemist might wish to explore in pursuit of a lead structure like tetracycline; structures such as the D-ring heterocyclic analogs 4 and 5 in FIG. 15A, or new ring systems such as the pentacycline 6 (FIG. 15A) are exemplary. Absent a viable laboratory synthetic pathway, these structures and the regions of complex chemical space they represent must be ceded in the search for new antibiotics. Here, we report a short and efficient route for the synthesis of enantiomerically pure members of the 6-deoxytetracyclines from benzoic acid. The route we describe allows for the synthesis of 6-deoxytetracyclines (both with or without an hydroxyl group at C5) by a notably late-stage coupling reaction of the AB precursors 7 or 8 (FIG. 15B) with a variety of different D-ring precursors, and has provided compounds such as doxycycline (2 in FIG. 15A), the heterocyclic analogs 4 and 5 (FIG. 15A), the pentacycline 6 (FIG. 15A), as well as other 6-deoxytetracycline analogs.

The strategic advantage of a synthetic approach involving a late-stage C-ring construction (AB+D→ABCD, FIG. 15B) is that much of the polar functionality known to play a role in the binding of tetracyclines to the bacterial ribosome lies within the AB fragment (D. E. Brodersen et al., *Cell* 103, 1143 (2000); M. Pioletti et al., *EMBO J.* 20, 1829 (2001); each of which is incorporated herein by reference), while enormous structural variation on or near the D-ring is not only permissible, but has been cited as a means to overcome bacterial resistance. The advanced clinical candidate tigecycline (P.-E. Sum, P. Petersen, *Bioorg. Med. Chem. Lett.* 9, 1459 (1999); incorporated herein by reference), a minocycline derivative with a D-ring substituent, is exemplary, and is reported to be one of the most promising new antibiotics under evaluation by the FDA (K. Bush, M. Macielag, M. Weidner-Wells, *Curr. Opin. Microbiol.* 7, 466 (2004); incorporated herein by reference). Classically, approaches to the synthesis of the tetracycline antibiotics have proceeded by stepwise assembly of the ABCD ring system and begin with D or CD precursors, as exemplified by the Woodward synthesis of (±)-6-deoxy-6-demethyltetracycline (sancycline, 25 steps, ~0.002% yield) (J. J. Korst et al., *J. Am. Chem. Soc.* 90, 439 (1968); incorporated herein by reference), the Shemyakin synthesis of (±)-12a-deoxy-5a,6-anhydrotetracycline (A. I. Gurevich et al., *Tetrahedron Lett.* 8, 131 (1967); incorporated herein by reference), and the Muxfeldt synthesis of (±)-5-oxytetracycline (terramycin, 22 steps, 0.06% yield) (H. Muxfeldt et al., *J. Am. Chem. Soc.* 101, 689 (1979); incorporated herein by reference). Only one published synthesis of (−)-tetracycline itself has appeared, this from D-glucosamine (an A-ring precursor, 34 steps, 0.002% yield) (K. Tatsuta et al., *Chem. Lett.* 646 (2000); incorporated herein by reference), while the most efficient construction of the tetracycline ring system thus far is undoubtedly the synthesis of (±)-12a-deoxytetracycline by the Stork laboratory (16 steps, 18-25% yield) (G. Stork et al., *J. Am. Chem. Soc.* 118, 5304 (1996); incorporated herein by reference). The latter research served to identify $C_{12}$a oxygenation as perhaps the greatest challenge in tetracycline synthesis (it could not be achieved with 12a-deoxytetracycline as substrate), a conclusion supported by the results of prior synthetic efforts (J. J. Korst et al., *J. Am. Chem. Soc.* 90, 439 (1968); A. I. Gurevich et al., *Tetrahedron Lett.* 8, 131 (1967); H. Muxfeldt et al., *J. Am. Chem. Soc.* 101, 689 (1979); each of which is incorporated herein by reference). The problem is significant, for C12a oxygenation appears to greatly enhance antimicrobial activity (W. Rogalski, in *Handbook of Experimental Pharmacology*, J. J. Hlavka, J. H. Boothe, Eds. (Springer-Verlag, New York, 1985), vol. 78, chap. 5; incorporated herein by reference). A key feature of the synthetic approach to 6-deoxytetracyclines that we have developed is that it introduces the C12a hydroxyl group in the first step of the sequence (FIG. 16) and uses the stereogenic center produced in that step to elaborate all others in the target molecule. To protect the vinylogous carbamic acid function of the A-ring we used the 5-benzyloxyisoxazole group developed by Stork and Haggedorn for that purpose (G. Stork, A. A. Hagedorn, III, *J. Am. Chem. Soc.* 100, 3609 (1978); incorporated herein by reference), an innovation that proved critically enabling in the present work, while the dimethylamino group of the A-ring was incorporated without modification.

Figure 16:
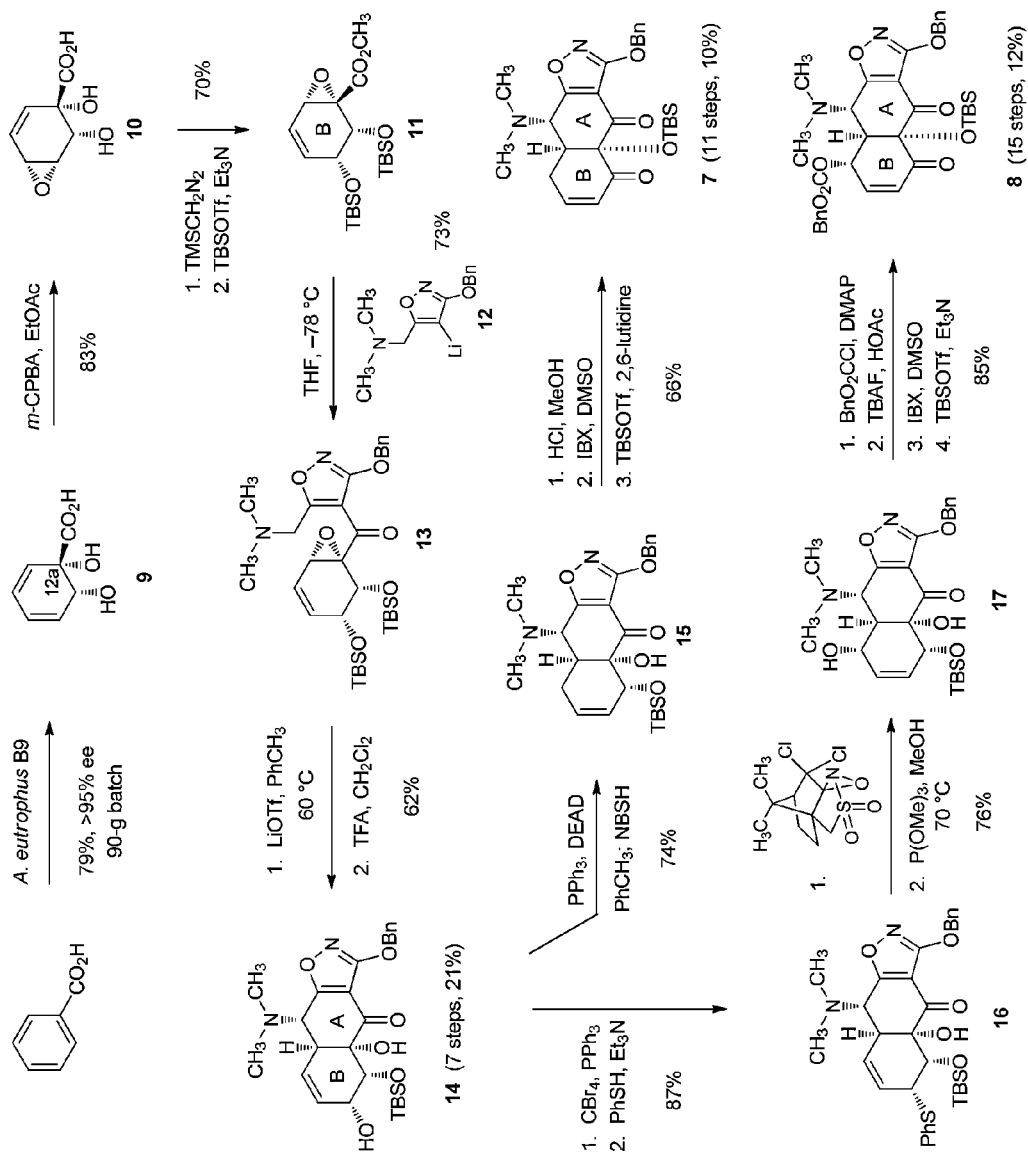
FIG. 16 shows the transformation of benzoic acid in 7 steps to the key bicyclic intermediate 14. This product is then used to prepare the AB precursor enone 7 by the 4-step sequence shown, or to enone 8, AB precursor to 6-deoxy-5-hydroxytetracycline derivatives, by the 8-step sequence shown.

Our synthesis of 6-deoxytetracyclines was initiated by whole-cell, microbial dihydroxylation of benzoic acid with a mutant strain of *Alcaligenes eutrophus* (A. M. Reiner, G. D. Hegeman, *Biochemistry* 10, 2530 (1971); A. G. Myers et al., *Org. Lett.* 3, 2923 (2001); each of which is incorporated herein by reference), producing the diol 9 (FIG. 16) with >95% ee in 79% yield (90-g batch, ~13 g/L, FIG. 16). Hydroxyl-directed epoxidation of the microcrystalline product (9, m-CPBA, EtOAc) provided the α-oriented epoxide 10 (FIG. 16) in 83% yield; esterification of this product (trimethylsilyldiazomethane) followed by bis-silylation and concomitant epoxide isomerization in the presence of tert-butyldimethylsilyl triflate (3 equiv.), afforded the epoxy ester 11 (FIG. 16) in 70% yield (A. G. Myers et al., *Org. Lett.* 3, 2923 (2001); incorporated herein by reference). Separately, 3-benzyloxy-5-dimethylaminomethylisoxazole, prepared on the mole-scale by a simple four-step sequence from glyoxylic acid (D. M. Vyas, Y. Chiang, T. W. Doyle, *Tetrahedron Lett.* 25, 487 (1984); P. Pevarello, M. Varasi, *Synth. Commun.* 22, 1939 (1992); each of which is incorporated herein by reference), was deprotonated at C4 with n-butyllithium, and the resulting organolithium reagent (12 in FIG. 16) was then added to the epoxy ester 11 (FIG. 16), forming the ketone 13 (73%) (FIG. 16). In a noteworthy transformation, and a key step of the synthesis, exposure of the ketone 13 (FIG. 16) to lithium triflate (5 mol %) at 60° C., followed by selective removal of the allylic silyl ether of the rearranged product (TFA), afforded the tricyclic AB precursor 14 (FIG. 16) in 62% yield after purification by flash column chromatography. The transformation of 13 to 14 (FIG. 16) is believed to involve initial $S_N$-prime opening of the allylic epoxide by the N,N-dimethylamino group followed by ylide formation and [2,3]-sigmatropic rearrangement, a process that is reminiscent of the Sommelet-Hauser rearrangement (S. H. Pine, *Organic Reactions*, 18, 403 (1970); incorporated herein by reference). Compound 14 (FIG. 16) possesses the requisite cis stereochemistry of the AB fusion as well as an α-oriented N,N-dimethylamino substituent (confirmed by X-ray crystallographic analysis of a derivative), and serves as a common intermediate for the synthesis of both the AB precursor enone 7 (4 steps, 49% yield, FIG. 16) and the AB precursor to 5-α-hydroxy-6-deoxytetracyclines, enone 8 (8 steps, 56% yield, FIG. 16), as detailed in sequence below.

To synthesize the AB precursor enone 7 (FIG. 15), intermediate 14 was subjected to reductive transposition (A. G. Myers, B. Zheng, *Tetrahedron Lett.* 37, 4841 (1996); incorporated herein by reference) in the presence of triphenylphosphine, diethyl azodicarboxylate, and o-nitrobenzenesulfonyl hydrazide (added last, a procedural variant), affording the transposed cycloalkene 15 in 74% yield. Hydrolysis of the silyl ether group within 15 (HCl, methanol), oxidation of the resulting allylic alcohol (IBX, DMSO) (M. Frigerio, M. Santagostino, *Tetrahedron Lett.* 35, 8019 (1994); incorporated herein by reference), and protection of the remaining (tertiary) carbinol (TBSOTf, 2,6-lutidine) (E. J. Corey et al., *Tetrahedron Lett.* 22, 3455 (1981); incorporated herein by reference) then provided the enone 7 (FIG. 15) in 66% yield (3 steps) after flash column chromatography. By a somewhat longer but slightly more efficient sequence the intermediate 14 (FIG. 15) could also be transformed into the enone 8 (FIG. 15), the AB precursor to 5-α-hydroxy-6-deoxytetracyclines. This sequence involved the transformation of 14 (FIG. 15) into the phenylthio ether 16 (with net retention), diastereoselective sulfoxidation using a chiral oxidant (F. A. Davis et al., *J. Org. Chem.* 57, 7274 (1992); incorporated herein by reference) (99:1 selectivity), and Mislow-Evans rearrangement (E. N. Prilezhaeva, *Russ. Chem. Rev.* 70, 897 (2001); incorporated herein by reference), producing the allylic alcohol 17 in 66% yield (4 steps). High diastereoselectivity in the sulfoxidation step was essential, for only one diastereomer (the major isomer under the conditions specified) underwent efficient thermal rearrangement. After protection of the allylic alcohol 17 (FIG. 15) using benzyl chloroformate, a sequence nearly identical to the final three steps of the synthesis of 7 (FIG. 15) was employed to transform the resulting benzyl carbonate into the enone 8 (FIG. 15) in 85% yield (56% yield and 8 steps from 14).

Figure 15:
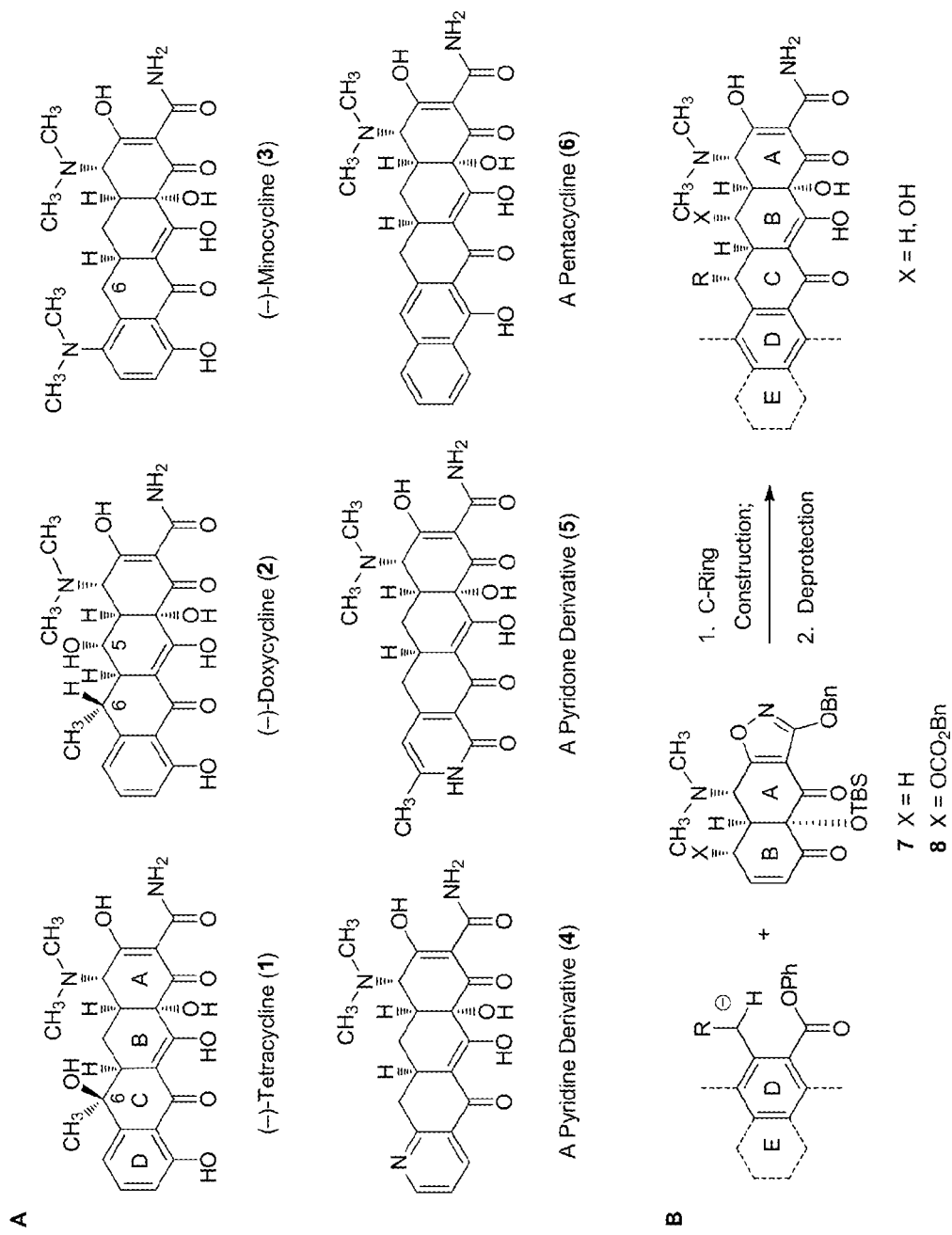
FIG. 15 shows the chemical structures of various tetracycline antibiotics. (−)-Tetracycline (1) was first produced semi-synthetically, by hydrogenolysis of the fermentation product aureomycin (7-chlorotetracycline), but later was discovered to be a natural product and is now produced by fermentation (M. Nelson, W. Hillen, R. A. Greenwald, Eds., *Tetracyclines in Biology, Chemistry and Medicine* (Birkhauser Verlag, Boston, 2001); incorporated herein by reference). (−)-Doxycycline (2) and minocycline (3) are clinically important non-natural antibiotics and are both manufactured by multi-step chemical transformations of fermentation products (semi-synthesis) (M. Nelson, W. Hillen, R. A. Greenwald, Eds., *Tetracyclines in Biology, Chemistry and Medicine* (Birkhauser Verlag, Boston, 2001); incorporated herein by reference). Structures 4-6 are representative of tetracycline-like molecules that cannot be prepared by any known semi-synthetic pathway, but which are now accessible by the convergent assembly depicted in FIG. 15B.
Figure 17:
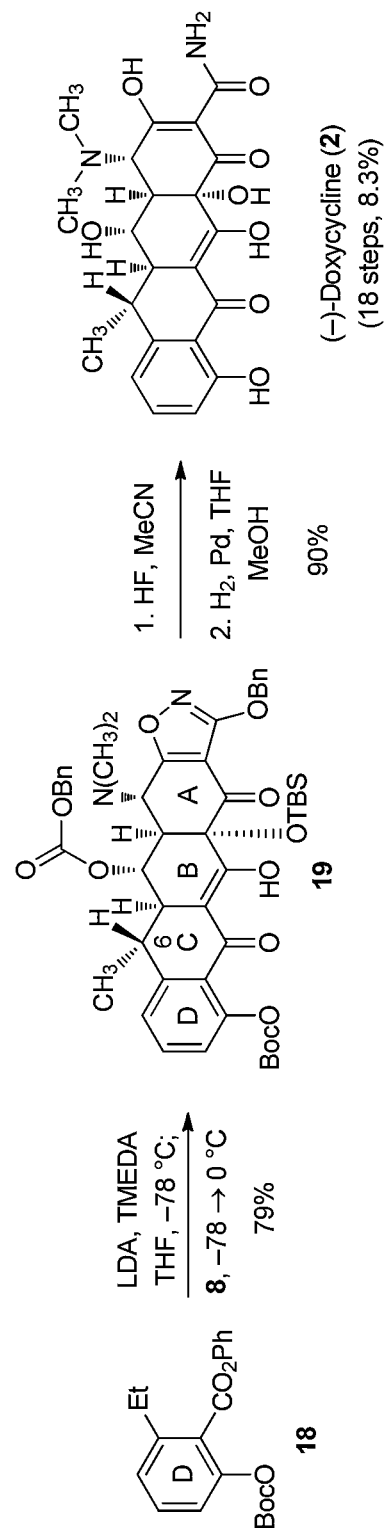
FIG. 17 shows the synthesis of the clinically important antibiotic (−)-doxycycline (2) by the convergent coupling of the o-toluate anion derived from 18 and the AB precursor enone 8.
Figures 1, 18:
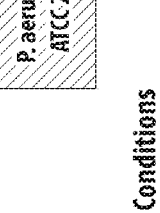
FIG. 1 shows the modular synthesis of tetracycline and tetracycline analogs starting from benzoic acid.
FIG. 18 shows the synthesis of structurally diverse 6-deoxytetracyclines by coupling of structurally diverse D-ring precursors and AB precursors 7 or 8. The number of steps and overall yields from benzoic acid are shown in parentheses below each structure synthesized. MIC values (μg/mL) are also shown for whole-cell antibacterial testing of each analog against 5 Gram-positive and 5-Gram-negative microorganisms. Corresponding MICs for tetracycline (1), a testing control, appear at bottom.
Figures 2, 18:
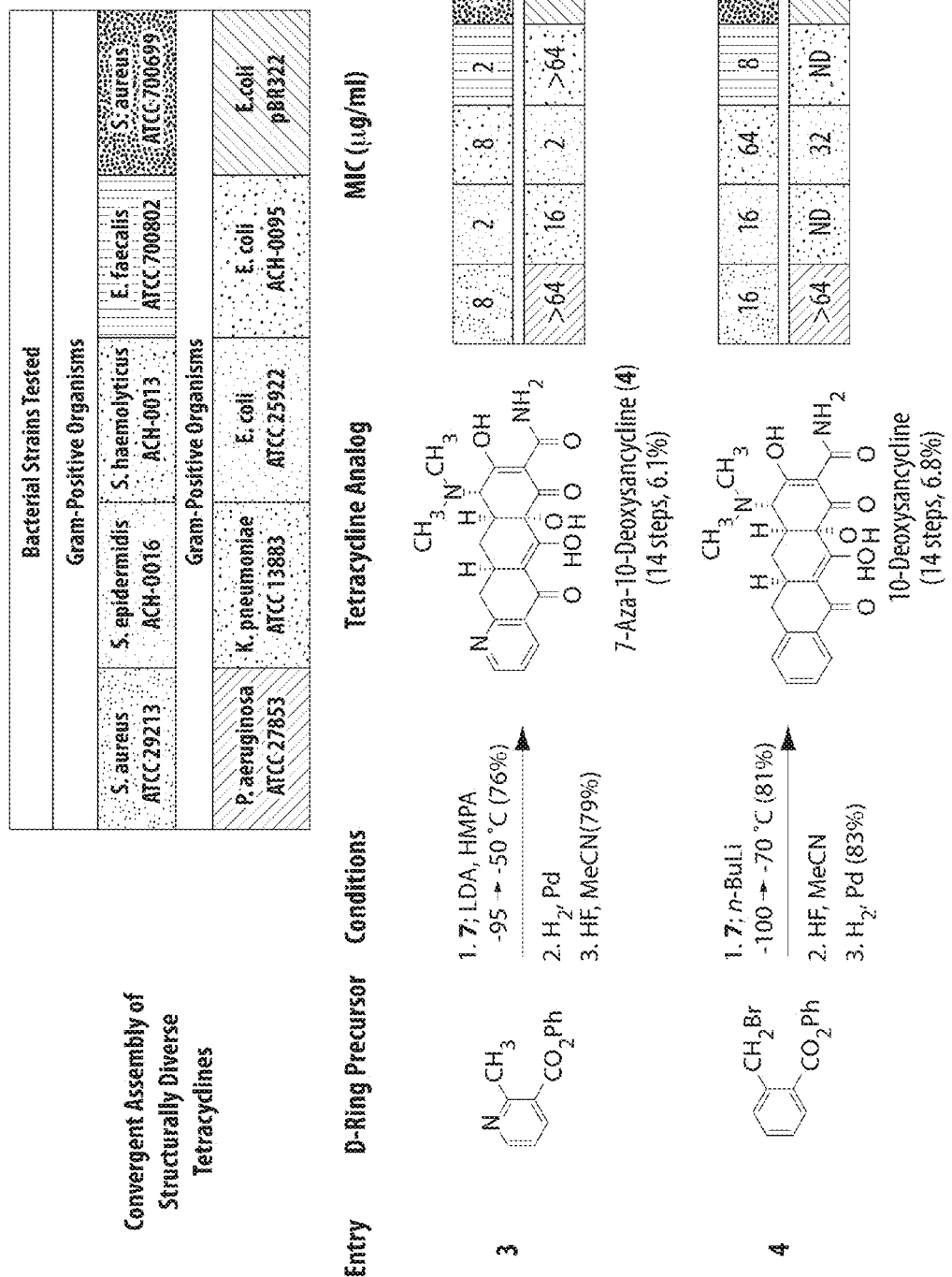
Figures 3, 18:
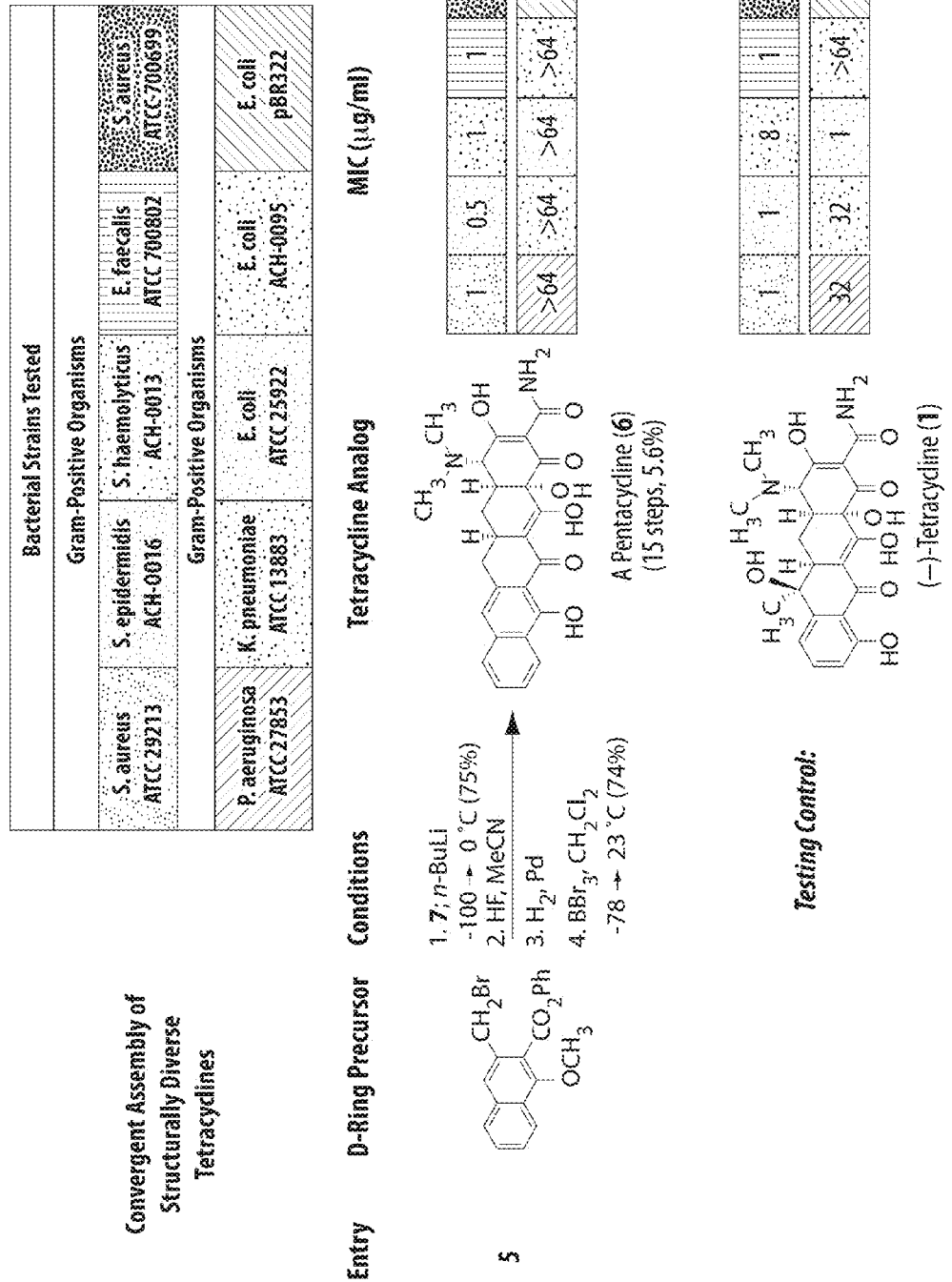
Figure 19:
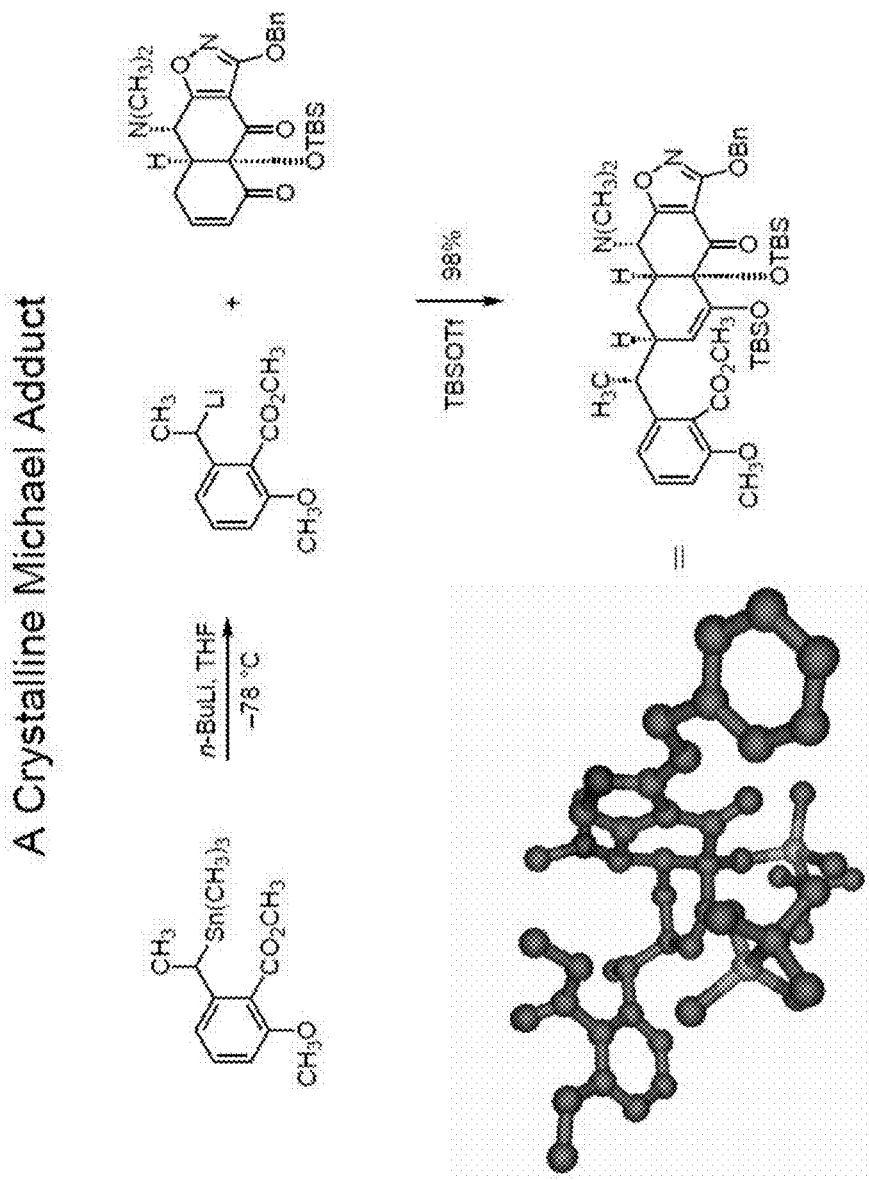
FIG. 19 shows a crystalline Michael adduct as the product of a lithium anion and a chiral enone.
Figure 20:
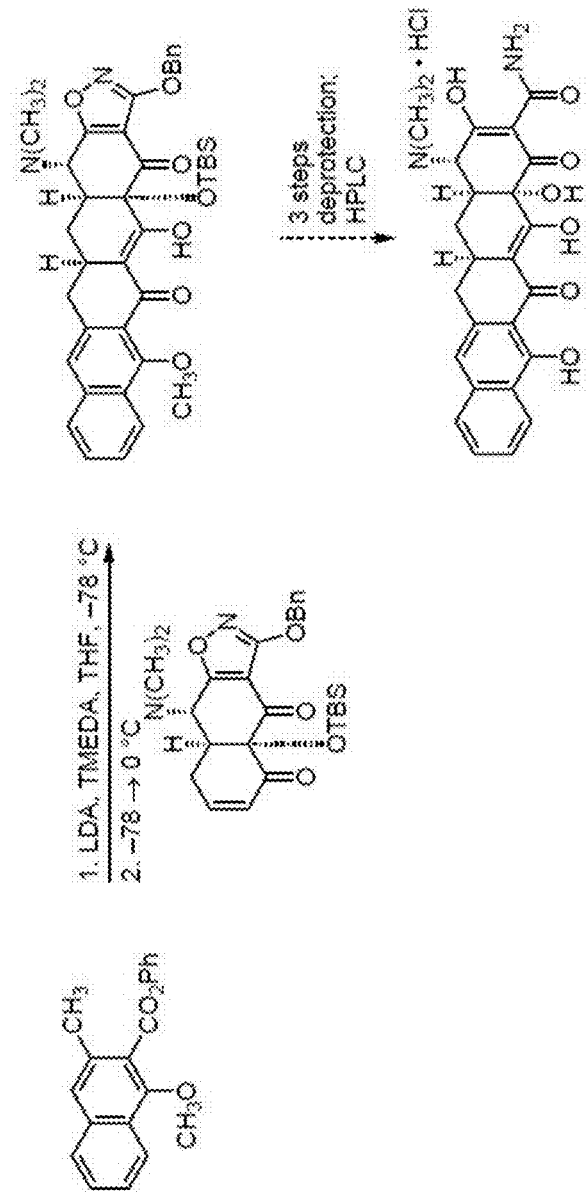
FIG. 20 shows the synthesis of a pentacycline via a Michael-Dieckman reaction sequence.

6-Deoxytetracyclines were assembled with all requisite functionality and stereochemistry in a single operation. In this process the AB precursors 7 or 8 (FIG. 15) are coupled with a range of different carbanionic D-ring precursors in a Michael-Dieckmann reaction sequence (T.-L. Ho, Tandem Organic Reactions (Wiley, New York, 1992); incorporated herein by reference) that forms two carbon-carbon bonds and the C-ring of the 6-deoxytetracyclines (FIGS. 15B, 17, and 18). The process is perhaps best illustrated in detail by the 3-step synthesis of (−)-doxycycline from the AB precursor 8 (FIG. 17). Deprotonation of the D-ring precursor 18 (4.5 equiv, LDA, TMEDA, THF, −78° C.), synthesized in 5 steps (42% yield) from anisic acid, followed by addition of the enone 8 (1 equiv, −78→0° C.), provided the tetracyclic coupling product 19 (FIG. 17) in diastereomerically pure form in 79% yield after purification by rp-HPLC. Removal of the protective groups (2 steps, 90% yield) and purification (rp-HPLC) afforded (−)-doxycycline hydrochloride (18 steps, 8.3% yield from benzoic acid). A remarkable feature of the convergent coupling reaction that produces the tetracyclic product 19 (FIG. 17) is its stereoselectivity. Although in theory four diastereomeric products can be formed, largely one was produced, corresponding in configuration (5aR,6R) to that of known biologically active 6-deoxytetracyclines. A minor diastereomeric impurity, believed to be 6-epi-19 (FIG. 17), was also isolated in separate rp-HPLC fractions (<7% yield). Michael-Dieckmann cyclization sequences (T.-L. Ho, *Tandem Organic Reactions* (Wiley, New York, 1992); incorporated herein reference) and condensations of o-toluate anions in particular (F. J. Leeper, J. Staunton, *J. C. S. Chem. Comm.*, 406 (1978); F. M. Hauser, R. P. Rhee, *J. Org. Chem.* 43, 178, (1978); J. H. Dodd, S. M. Weinreb, *Tetrahedron Lett.* 20, 3593 (1979); each of which is incorporated herein by reference) are extensively precedented in synthesis, but we are unaware of any example exhibiting the high degree of diastereoselectivity of the present case. Phenyl ester activation in toluate condensations is also precedented, though in a system that forms a fully aromatized cyclization product (White et al., *J. Org. Chem.* 51, 1150 (1986); incorporated herein by reference). We observed that the presence of the phenyl ester group of the D-ring precursor 18 (FIG. 17) was essential for successful cyclization to occur; anions derived from simple alkyl esters and phthalide-derived anions underwent Michael addition, but the resulting adducts did not cyclize. Perhaps even more remarkable than the condensation that produces 19 (FIG. 17) is the parallel transformation of 18 with the enone 7 (FIG. 18, entry 1), which forms (−)-6-deoxytetracycline in protected form with >20:1 diastereoselectivity, in 81% yield after purification by rp-HPLC (diastereomerically pure; a minor diastereomer, epimeric at C6, was also isolated separately). It appears that additions to 7 and 8 proceed almost exclusively by addition to the "top" face of each enone (as drawn), producing C5a-sterochemistry corresponding to natural tetracyclines, though why this should be the case is not obvious.

As the examples of entries 2-5 (FIG. 18) show, efficient and stereoselective condensations are not restricted to the o-toluate anion derived from the D-ring substrate 18 (FIG. 17); the novel D-ring heterocyclic analogs 4 and 5 (FIG. 18) were synthesized by a related sequence from o-toluate anions of very different structures, as was the pentacyline derivative 6 (FIG. 18). In each case it was necessary to optimize the specific conditions for o-toluate anion generation and trapping. For entries 3-5 (FIG. 18) anion generation was best conducted in situ, in the presence of the enone 7, either by selective deprotonation (entry 3) or by lithium-halogen exchange (entries 4 and 5). A number of potentially competing non-productive reaction sequences (e.g., enolization of 7) might have occurred during in situ anion generation; the observed efficiencies of the transformations are surprising in light of this. It is also noteworthy that in situ anion generation permits the use of o-toluates lacking an o-alkoxy substituent (entries 3 and 4), substrates known to be problematic from prior studies (F. M. Hauser et al., *Synthesis* 72 (1980); incorporated herein by reference). Finally, o-toluate anion formation by in situ or stepwise halogen-metal exchange (entries 4 and 5) is unprecedented.

The efficiencies of the synthetic sequences have allowed for the preparation of sufficient quantities of each tetracycline analog for antibacterial testing using standard serial-dilution techniques (5-20 mg amounts). Minimum inhibitory concentrations (MICs) are reported for each analog in whole-cell antimicrobial assays using five Gram-positive and five Gram-negative organisms (FIG. 18). Thus far, the pentacycline derivative 6 (FIG. 18) has shown the most promising antibacterial properties, with activity equal to or greater than tetracycline in each of the Gram-positive strains examined, including strains with resistance to tetracycline, methicillin, and vancomycin.

Experimentals

General Procedures.

All reactions were performed in flame-dried round bottomed or modified Schlenk (Kjeldahl shape) flasks fitted with rubber septa under a positive pressure of argon, unless otherwise noted. Air- and moisture-sensitive liquids and solutions were transferred via syringe or stainless steel cannula. Organic solutions were concentrated by rotary evaporation at −25 Ton (house vacuum). Flash column chromatography was performed on silica gel (60 Å, standard grade) as described by Still et al. (Still, W. C.; Kahn, M.; Mitra, A. *J. Org. Chem.* 1978, 43, 2923-2925; incorporated herein by reference). Analytical thin-layer chromatography was performed using glass plates pre-coated with 0.25 mm 230-400 mesh silica gel impregnated with a fluorescent indicator (254 nm). Thin-layer chromatography plates were visualized by exposure to ultraviolet light and/or exposure to ceric ammonium molybdate or an acidic solution of p-anisaldehyde followed by heating on a hot plate.

Materials.

Commercial reagents and solvents were used as received with the following exceptions. Triethylamine, diisopropylamine, N,N,N',N'-tetramethylethylene-diamine, DMPU, HMPA, and N,N-diisopropylethylamine were distilled from calcium hydride under an atmosphere of dinitrogen. Dichloromethane, methanol, tetrahydrofuran, acetonitrile, and toluene were purified by the method of Pangborn et al. (Pangborn, A. B.; Giardello, M. A.; Grubbs, R. H.; Rosen, R. K.; Timmers, F. J. *Organometallics* 1996, 15, 1518-1520; incorporated herein by reference).

Instrumentation.

Proton nuclear magnetic resonance ($^1$H NMR) spectra and carbon nuclear magnetic resonance ($^{13}$C NMR) spectra were recorded with Varian Unity/Inova 600 (600 MHz), Varian Unity/Inova 500 (500 MHz/125 MHz), or Varian Mercury 400 (400 MHz/100 MHz) NMR spectrometers. Chemical shifts for protons are reported in parts per million (δ scale) and are referenced to residual protium in the NMR solvents (CHCl$_3$: δ 7.26, C$_6$D$_5$H: δ 7.15, D$_2$HCOD: δ 3.31, CDHCl$_2$: δ 5.32, (CD$_2$H)CD$_3$SO: δ 2.49). Chemical shifts for carbon are reported in parts per million (δ scale) and are referenced to the carbon resonances of the solvent (CDCl$_3$: δ 77.0, C$_6$D$_6$: δ 128.0, CD$_3$OD: δ 44.9, CD$_2$Cl$_2$: δ 53.8, (CD$_3$)$_2$SO: δ 39.5). Data are represented as follows: chemical shift, multiplicity (s=singlet, d=doublet, t=triplet, q=quartet, m=multiplet, br=broad), integration, coupling constant in Hz, and assignment. Infrared (IR) absorbance spectra were obtained using a Perkin-Elmer 1600 FT-IR spectrophotometer referenced to a polystyrene standard. Data are represented as follows: frequency of the absorption (cm$^{-1}$), intensity of the absorption (s=strong, m=medium, w=weak, br=broad), and assignment (where appropriate). Optical rotations were determined using a JASCO DIP-370 digital polarimeter equipped with a sodium lamp source. High-resolution mass spectra were obtained at the Harvard University Mass Spectrometry Facilities.

Synthesis of (−)-Doxycycline

Cyclization Step:

A solution of n-butyllithium in hexanes (1.55 M, 155 μL, 0.240 mmol, 5.1 equiv) was added to a solution of N,N,N',N'-tetramethylethylenediamine (39 μL, 0.26 mmol, 5.5 equiv) and diisopropylamine (34 μL, 0.25 mmol, 5.1 equiv) in tetrahydrofuran (1 mL) at −78° C. The resulting mixture was stirred vigorously at −78° C. for 30 min whereupon a solution of 2-(phenoxycarbonyl)-3-ethylphenyl t-butyl carbonate (73.0 mg, 0.213 mmol, 4.5 equiv) in tetrahydrofuran (1 mL) was added dropwise via cannula. The resulting deep-red mixture was stirred vigorously at −78° C. for 75 min, then a solution of enone 8 (30.0 mg, 0.0474 mmol, 1 equiv) in tetrahydrofuran (1 mL) was added dropwise via cannula. The resulting light-red mixture was allowed to warm slowly to 0° C. over 2 h. The ice-cold product solution was then partitioned between aqueous potassium phosphate buffer solution (pH 7.0, 0.2 M, 10 mL) and dichloromethane (10 mL). The organic phase was separated and the aqueous phase was further extracted with two 10-mL portions of dichloromethane. The organic phases were combined and dried over anhydrous sodium sulfate. The dried solution was filtered and the filtrate was concentrated, providing a yellow oil. The product was purified by preparatory HPLC on a Coulter Ultrasphere ODS column [10 μm, 250×10 mm, UV detection at 350 nm, injection volume: 400 μL (methanol), isochratic elution with methanol-water (9:1), flow rate: 3.5 mL/min]. Fractions eluting at 36-42 min were collected and concentrated, affording the pentacyclic addition product depicted in diastereomerically pure form (33.0 mg, 79%, a light-yellow solid).

R$_f$ 0.35 (1:4 ethyl acetate-hexanes); $^1$H NMR (500 MHz, C$_6$D$_6$) δ 16.55 (br s, 1H, enol), 7.26 (d, 2H, J=7.0 Hz, o-ArH), 7.14 (d, 2H, J=7.5 Hz, ArH), 6.85-7.05 (m, 6H, ArH), 6.66-6.74 (m, 2H, ArH), 6.51 (dd, 1H, J=9.0, 1.5 Hz, ArH), 5.73 (br d, 1H, J=4.0 Hz, BnOCO$_2$CH), 5.17 (d, 1H, J=12.5 Hz, OCHH'Ph), 5.03 (d, 1H, J=12.5 Hz, OCHH'Ph), 4.99 (d, 1H, J=12.5 Hz, OCHH'Ph'), 4.93 (d, 1H, J=12.5 Hz, OCHH'Ph'), 3.58 (d, 1H, J=11.5 Hz, CHCHN(CH$_3$)$_2$), 3.35 (dd, 1H, J=12.5, 4.0 Hz, CH$_3$CHCH), 2.99 (d, 1H, J=11.5 Hz, CHCHN(CH$_3$)$_2$), 2.56 (dq, 1H, J=12.5, 7.0 Hz, CH$_3$CH), 2.18 (s, 6H, N(CH$_3$)$_2$), 1.33 (s, 9H, C(CH$_3$)$_3$), 1.16 (d, 3H, J=7.0 Hz, CH$_3$CH), 1.11 (s, 9H, C(CH$_3$)$_3$), 0.61 (s, 3H, CH$_3$), 0.36 (s, 3H, CH$_3$); $^{13}$C NMR (100 MHz, CDCl$_3$) δ 189.7, 186.3, 180.9, 178.4, 167.9, 154.7, 152.1, 150.8, 145.9, 136.1, 135.5, 133.9, 128.7, 128.6, 128.5, 127.3, 123.8, 122.7, 122.6, 108.9, 105.5, 83.0, 82.9, 74.8, 72.4, 69.2, 60.8, 52.7, 43.2, 38.4, 27.5, 26.6, 19.5, 16.3, −1.8, −2.7; FTIR (neat film), cm$^{-1}$ 2974 (w), 2933 (w), 2851 (w), 1760 (s, C=O), 1748 (s, C=O), 1723 (s, C=O), 1606 (m), 1513 (m), 1471 (m), 1370 (m), 1260 (s), 1232 (s), 1148 (s); HRMS (ES) m/z calcd for (C$_{48}$H$_{56}$N$_2$O$_{12}$Si)$^+$ 881.3681. found 881.3684.

Deprotection Step 1:

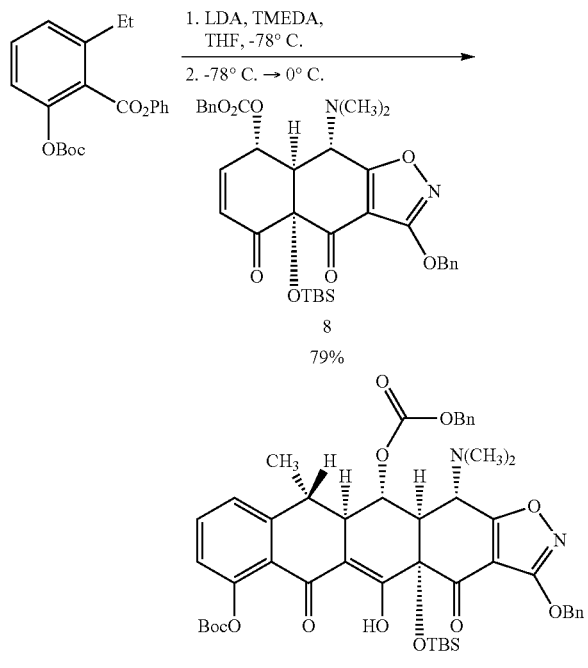

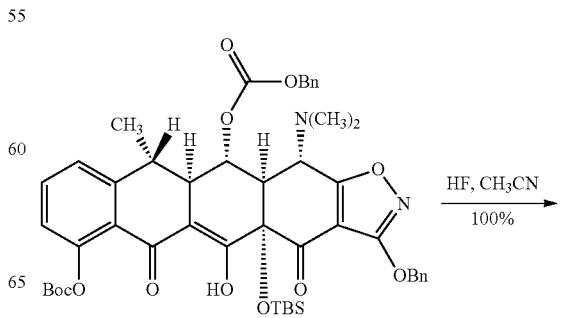

113
-continued

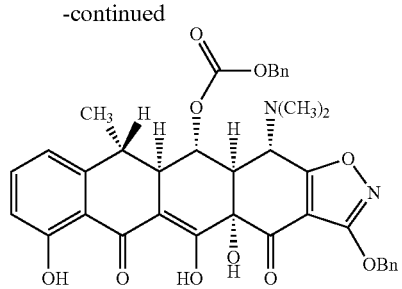

Concentrated aqueous hydrofluoric acid (48 wt %, 1.2 mL) was added to a polypropylene reaction vessel containing a solution of the purified pentacyclic addition product from the experiment above (33.0 mg, 0.0375 mmol, 1 equiv) in acetonitrile (7.0 mL) at 23° C. The resulting mixture was stirred vigorously at 23° C. for 60 h, then was poured into water (50 mL) containing dipotassium hydrogenphosphate (7.0 g). The resulting mixture was extracted with ethyl acetate (3×20 mL). The organic phases were combined and dried over anhydrous sodium sulfate. The dried solution was filtered and the filtrate was concentrated, affording the product depicted as a yellow oil (25.0 mg, 100%). This product was used in the next step without further purification.

$R_f$ 0.05 (1:4 ethyl acetate-hexanes); $^1$H NMR (600 MHz, $C_6D_6$, crude) δ 14.86 (br s, 1H, enol), 11.95 (s, 1H, phenol), 7.23 (d, 2H, J=7.8 Hz, o-ArH), 7.14 (d, 2H, J=7.2 Hz, o-ArH), 6.94-7.02 (m, 6H, ArH), 6.86 (t, 1H, J=8.4 Hz, ArH), 6.76 (d, 1H, J=8.4 Hz, ArH), 6.28 (d, 1H, J=7.8 Hz, ArH), 5.46 (dd, 1H, J=3.6, 3.0 Hz, BnOCO$_2$CH), 5.12 (d, 1H, J=12.0 Hz, OCHH'Ph), 5.04 (d, 1H, J=12.0 Hz, OCHH'Ph), 4.92 (s, 2H, OCH$_2$Ph), 3.41 (d, 1H, J=9.6 Hz, CHCHN(CH$_3$)$_2$), 2.82 (dd, 1H, J=9.6, 3.0 Hz, CHCHN(CH$_3$)$_2$), 2.65 (dd, 1H, J=13.2, 3.6 Hz, CH$_3$CHCH), 2.78 (dq, 1H, J=13.2, 7.2 Hz, CH$_3$CH), 2.05 (s, 6H, N(CH$_3$)$_2$), 1.04 (d, 3H, J=7.2 Hz, CH$_3$CH); $^{13}$C NMR (100 MHz, $C_6D_6$, crude) δ 193.4, 186.2, 181.3, 172.3, 167.9, 163.3, 154.6, 145.8, 136.6, 135.8, 128.6, 128.4, 127.2, 116.8, 116.0, 115.6, 107.6, 104.7, 76.8, 73.9, 72.5, 69.5, 60.3, 48.7, 43.0, 41.8, 37.5, 15.3; FTIR (neat film), cm$^{-1}$ 3424 (m, OH), 3059, 3030, 2925, 2857, 1744 (s, C=O), 1713 (s, C=O), 1614 (s), 1582 (s), 1455 (s), 1252 (s); HRMS (ES) m/z calcd for $(C_{37}H_{34}N_2O_{10}+H)^+$667.2292. found 667.2300.

Deprotection Step 2:

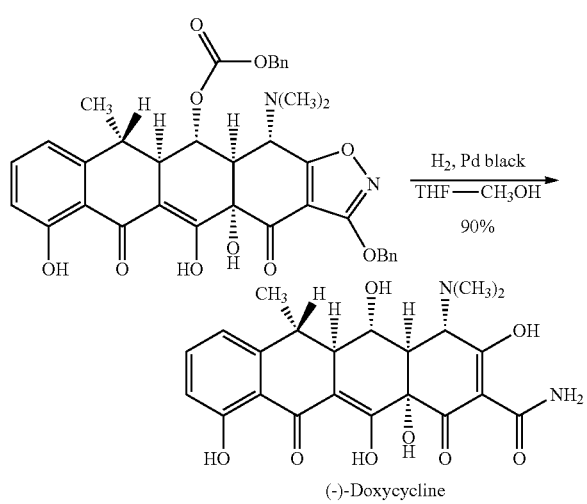

(-)-Doxycycline

114

Palladium black (7.00 mg, 0.0657 mmol, 1.75 equiv) was added in one portion to a solution of the product from the procedure above (25.0 mg, 0.0375 mmol, 1 equiv) in tetrahydrofuran-methanol (1:1, 2.0 mL) at 23° C. An atmosphere of hydrogen was introduced by briefly evacuating the flask, then flushing with pure hydrogen (1 atm). The palladium catalyst was initially observed to be a fine dispersion, but aggregated into clumps within 5 min. The yellow heterogeneous mixture was stirred at 23° C. for 2 h, then was filtered through a plug of cotton. The filtrate was concentrated, affording a yellow oil. The product was purified by preparatory HPLC on a Phenomenex Polymerx DVB column (10 250×10 mm, UV detection at 350 nm, Solvent A: methanol-0.005 N aq. HCl (1:4), Solvent B: acetonitrile, injection volume: 400 μL (solvent A containing 10 mg oxalic acid), isochratic elution with 5% B for 2 min, then gradient elution with 5→50% B for 20 min, flow rate: 4.0 mL/min]. Fractions eluting at 12-17 min were collected and concentrated, affording (-)-doxycycline hydrochloride as a yellow powder (16.2 mg, 90%), which was identical with natural (-)-doxycycline hydrochloride [reverse-phase HPLC (co-injection), $^1$H NMR (including measurement of an admixture of synthetic and natural doxycycline), $^{13}$C NMR, $[α]_D$, UV).

$^1$H NMR (600 MHz, CD$_3$OD, hydrochloride) δ 7.47 (t, 1H, J=8.4 Hz, ArH), 6.93 (d, 1H, J=8.4 Hz, ArH), 6.83 (d, 1H, J=8.4 Hz, ArH), 4.40 (s, 1H, (CH$_3$)$_2$NCH), 3.53 (dd, 1H, J=12.0, 8.4 Hz, CHOH), 2.95 (s, 3H, N(CH$_3$)CH$_3$'), 2.88 (s, 3H, N(CH$_3$)CH$_3$'), 2.80 (d, 1H, J=12.0 Hz, CHCHN(CH$_3$)$_2$), 2.74 (dq, 1H, J=12.6, 6.6 Hz, CH$_3$CH), 2.58 (dd, 1H, J=12.6, 8.4 Hz, CH$_3$CHCH), 1.55 (d, 3H, J=6.6 Hz, CH$_3$CHCH); $^{13}$C NMR (100 MHz, CD$_3$OD) δ 195.3, 188.2, 173.8, 172.1, 163.2, 149.0, 137.7, 117.1, 116.9, 116.6, 108.4, 96.0, 74.5, 69.8, 66.9, 47.5, 43.4, 43.0, 41.9, 40.0, 16.3; UV max (0.01 M methanolic HCl), nm 218, 267, 350; $[α]_D$=-109° (c=0.16 in 0.01 M methanolic HCl); HRMS (ES) m/z calcd for $(C_{22}H_{24}N_2O_8+H)^+$445.1611. found 445.1603.

Literature values (*The Merck Index: An Encyclopedia of Chemicals, Drugs, and Biologicals*, 12$^{th}$ ed. Budavari, S.; O'Neal, M. J.; Smith, A.; Heckelman, P. E.; Kinneary, J. F., Eds.; Merck & Co.: Whitehouse Station, N.J., 1996; entry 3496.): UV max (0.01 M methanolic HCl), nm 267, 351; $[α]_D$=-110° (c=1 in 0.01 M methanolic HCl).

Synthesis of (-)-6-Deoxytetracycline

Cyclization Step:

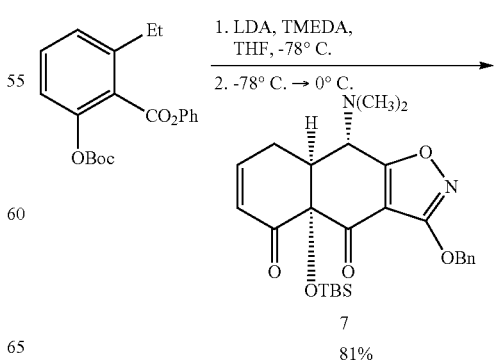

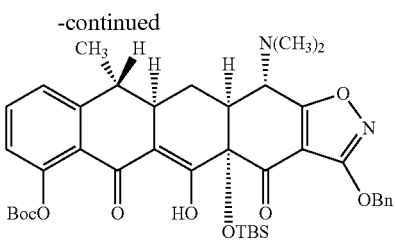

A solution of n-butyllithium in hexanes (1.65 M, 75 µL, 0.12 mmol, 3.9 equiv) was added to a solution of diisopropylamine (17 µL, 0.12 mmol, 3.9 equiv) and N,N,N',N'-tetramethylethylenediamine (19 µL, 0.13 mmol, 4.1 equiv) in tetrahydrofuran (1 mL) at −78° C. The resulting solution was stirred at −78° C. for 30 min whereupon a solution of 2-(phenoxycarbonyl)-3-ethylphenyl t-butyl carbonate (31.8 mg, 0.093 mmol, 3.0 equiv) in tetrahydrofuran (250 µL) was added dropwise via syringe. The resulting deep-red mixture was stirred at −78° C. for 90 min, then a solution of enone 7 (15.0 mg, 0.031 mmol, 1 equiv) in tetrahydrofuran (250 µL) was added dropwise via syringe. The resulting deep-red mixture was allowed to warm slowly to 0° C. over 3 h. The ice-cold product solution was then partitioned between aqueous potassium phosphate buffer solution (pH 7.0, 0.2 M, 15 mL) and dichloromethane (15 mL). The organic phase was separated and the aqueous phase was further extracted with two 15-mL portions of dichloromethane. The organic phases were combined and dried over anhydrous sodium sulfate. The dried solution was filtered and the filtrate was concentrated, providing a yellow oil. The product was purified by preparatory HPLC on a Coulter Ultrasphere ODS column [5 µm, 250×10 mm, UV detection at 350 nm, injection volume: 500 µL (methanol), isochratic elution with methanol-water (89:11), flow rate: 3.5 mL/min]. Fractions eluting at 39-60 min were collected and concentrated, affording the pentacyclic addition product depicted in diastereomerically pure form (18.5 mg, 81%, a light-yellow foam).

$R_f$ 0.37 (2:8 tetrahydrofuran-hexanes); $^1$H NMR (500 MHz, CDCl$_3$) 8 (s, 1H, 16.24, enol-OH), 7.55-7.50 (m, 3H, ArH), 7.40-7.35 (m, 4H, ArH), 7.10 (d, 1H, J=7.8 Hz, ArH), 5.39-5.34 (m, 2H, OCH$_2$Ph), 3.92 (d, 1H, J=10.7 Hz, CHN(CH$_3$)$_2$), 2.81-2.71 (m, 2H, CH$_3$CH, CH$_3$CHCH), 2.55 (dd, 1H, J=10.7, 5.7 Hz, CHCHN(CH$_3$)$_2$), 2.48 (s, 6H, N(CH$_3$)$_2$), 2.40 (d, 1H, J=14.7 Hz, CHH'CHCHN(CH$_3$)$_2$), 2.31 (ddd, 1H, J=14.7, 9.3, 5.7, CHH'CHCHN(CH$_3$)$_2$), 1.56 (s, 3H, CH$_3$), 1.55 (s, 9H, Boc), 0.84 (s, 9H, TBS), 0.27 (s, 3H, TBS), 0.13 (s, 3H, TBS); $^{13}$C NMR (125 MHz, CDCl$_3$) δ 187.4, 183.1, 182.8, 181.6, 167.6, 151.7, 150.2, 147.1, 135.0, 134.0, 128.5, 128.5, 123.4, 123.0, 122.4, 108.3, 107.4, 94.8, 83.9, 81.5, 72.5, 61.5, 46.4, 41.9, 39.5, 34.9, 27.7, 26.0, 20.7, 19.0, 16.0, −2.6, −3.7; FTIR (neat film), cm$^{-1}$ 2923 (m), 2841 (m), 1759 (s, C=O), 1718 (s, C=O), 1605 (s), 1508 (s), 1467 (m), 1456 (m), 1369 (m), 1277 (s), 1262 (m), 1231 (s), 1144 (s), 1005 (w); HRMS (ES) m/z calcd for (C$_{40}$H$_{50}$N$_2$O$_9$Si+H)$^+$ 731.3364. found 731.3370.

Deprotection:

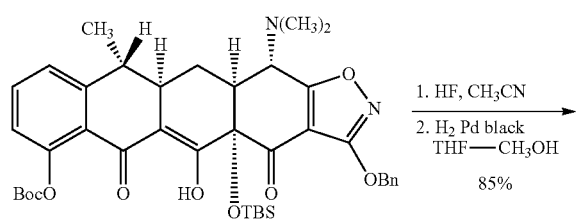

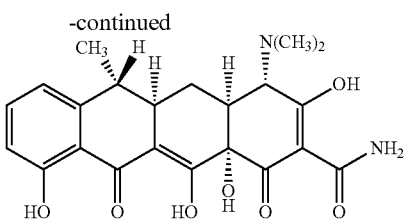

Concentrated aqueous hydrofluoric acid solution (48 wt %, 0.6 mL) was added to a polypropylene reaction vessel containing a solution of the purified pentacyclic addition product from the experiment above (15.0 mg, 0.0205 mmol, 1 equiv) in acetonitrile (3.5 mL) at 23° C. The reaction mixture was stirred at 23° C. for 55 h, then was poured into water (20 mL) containing dipotassium hydrogenphosphate (4.0 g). The resulting mixture was extracted with ethyl acetate (4×20 mL). The organic phases were combined and dried over anhydrous sodium sulfate. The dried solution was filtered and the filtrate was concentrated, affording a light-yellow oil. The residue was dissolved in methanol-tetrahydrofuran (1:1, 2 mL) and to the resulting solution was added palladium black (7.6 mg, 0.071 mmol, 3.5 equiv) in one portion. An atmosphere of hydrogen gas was introduced by briefly evacuating the flask, then flushing with pure hydrogen (1 atm). The yellow mixture was stirred at 23° C. for 2 h, then was filtered through a plug of cotton. The filtrate was concentrated, affording a yellow oil (10 mg). The product was purified by preparatory HPLC on a Phenomenex Polymerx DVB column [10 µm, 250×10 mm, UV detection at 365 nm, Solvent A: methanol-0.02 N HCl (1:4), Solvent B: acetonitrile, injection volume: 400 µL (methanol containing 10 mg oxalic acid), isochratic elution with 18% B for 15 min, then gradient elution with 18→60% B over 15 min, flow rate: 5 mL/min]. Fractions eluting at 17.5-22.5 min were collected and concentrated, affording 6-deoxytetracycline hydrochloride as a yellow powder (8.1 mg, 85%).

$^1$H NMR (500 MHz, CD$_3$OD, hydrochloride) δ 7.49 (t, 1H, J=7.8 Hz, ArH), 6.95 (d, 1H, J=7.8 Hz, ArH), 6.84 (d, 1H, J=7.8 Hz, ArH), 4.09 (s, 1H, CHN(CH$_3$)$_2$), 3.03 (br s, 3H, N(CH$_3$)), 2.97 (br s, 3H, N(CH$_3$)), 2.90 (br d, 1H, J=12.7 Hz, CHCHN(CH$_3$)$_2$), 2.67 (ddd, 1H, J=12.7, 12.7, 5.2 Hz, CH$_3$CHCH), 2.61-2.56 (m, 1H, CH$_3$CH), 2.30 (ddd, 1H, J=13.7, 5.2, 2.9 Hz, CHH'CHCHN(CH$_3$)$_2$), 1.54 (ddd, 1H, J=13.7, 12.7, 12.7 Hz, CHH'CHCHN(CH$_3$)$_2$), 1.38 (d, 3H, J=6.8 Hz, CH$_3$CH); UV max (0.01 M methanolic HCl), nm 269, 353; $[\alpha]_D$=−142° (c=0.20 in 0.01 M methanolic HCl); HRMS (ES) m/z calcd for (C$_{22}$H$_{24}$N$_2$O$_7$+H)$^+$ 429.1662. found 429.1660.

Synthesis of a (−)-D-ring Pyridone Analog of Tetracycline

Cyclization Step:

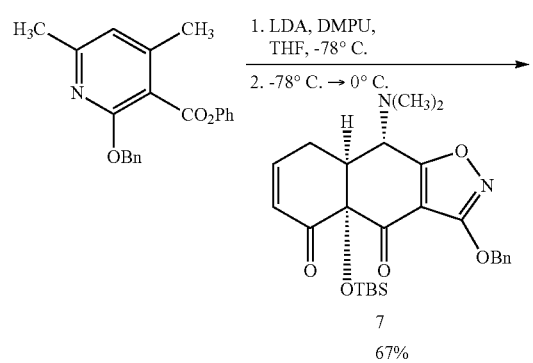

-continued

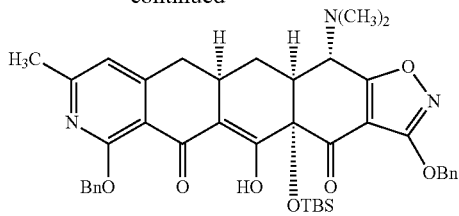

A solution of n-butyllithium in hexanes (1.67 M, 80 µL, 0.13 mmol, 4.3 equiv) was added to a solution of diisopropylamine (20 µL, 0.14 mmol, 4.6 equiv) in tetrahydrofuran (2.5 mL) at −78° C. The resulting solution was allowed to warm to 0° C. over 15 min. N,N′-dimethylpropyleneurea (17 µL, 0.14 mmol, 4.5 equiv) was added and the resulting solution was cooled to −78° C. A solution of phenyl 2-(benzyloxy)-4,6-dimethylpyridine-3-carboxylate (31.0 mg, 0.0930 mmol, 2.99 equiv) in tetrahydrofuran (250 µL) was then added via syringe to the cooled reaction solution. The resulting yellow solution was stirred for 5 min at −78° C., then a solution of enone 7 (15.0 mg, 0.0311 mmol, 1 equiv) in tetrahydrofuran (250 µL) was added via syringe. The resulting deep-red mixture was allowed to warm to 0° C. over 4 h. Acetic acid (40 µL) was added to the deep-red mixture at 0° C. The ice-cold product solution was then partitioned between aqueous potassium phosphate buffer solution (pH 7.0, 0.2 M, 15 mL) and dichloromethane (15 mL). The organic phase was separated and the aqueous phase was further extracted with two 15-mL portions of dichloromethane. The organic extracts were combined and then dried over anhydrous sodium sulfate. The dried solution was filtered and the filtrate was concentrated, providing a yellow oil. The product was purified by preparatory HPLC on a Coulter Ultrasphere ODS column [5 µm, 250×10 mm, UV detection at 350 nm, Solvent A: water, Solvent B: methanol, injection volume: 500 µL DMSO, gradient elution with 92→100% B over 30 min, flow rate: 3.5 mL/min]. Fractions eluting at 21-29 min were collected and concentrated, affording the pentacyclic addition product depicted in diasteromerically pure form (15.0 mg, 67%, a light-yellow solid).

$R_f$ 0.55 (3:7 ethyl acetate-hexanes); $^1$H NMR (600 MHz, CD$_2$Cl$_2$) δ 16.05 (s, 1H, enol-OH), 7.52-7.26 (m, 10H, ArH), 6.66 (s, 1H, pyr-H), 5.57 (d, 1H, J=12.7 Hz, OCHH'Ph), 5.43 (d, J=12.7 Hz, 1H, OCHH'Ph), 5.33-5.28 (m, 2H, OCH$_2$Ph), 3.99 (d, 2H, J=10.5 Hz, CHN(CH$_3$)$_2$), 3.04-3.00 (m, 1H, CHCH$_2$CHCHN(CH$_3$)$_2$), 2.84 (dd, 1H, J=16.1, 4.9 Hz, CHH'CHCH$_2$CHCHN(CH$_3$)$_2$), 2.74 (dd, 1H, J=16.1, 16.1 Hz, CHH'CHCH$_2$CHCHN(CH$_3$)$_2$), 2.53 (dd, 1H, J=10.5, 3.9 Hz, CHCHN(CH$_3$)$_2$), 2.51-2.43 (m, 10H, N(CH$_3$)$_2$, Ar—CH$_3$, CHH'CHCHN(CH$_3$)$_2$), 2.07 (d, 1H, J=14.2 Hz, CHH'CHCHN(CH$_3$)$_2$), 0.82 (s, 9H, TBS), 0.22 (s, 3H, TBS), 0.10 (s, 3H, TBS); $^{13}$C NMR (100 MHz, CD$_2$Cl$_2$) δ 187.9, 185.2, 182.5, 178.8, 167.9, 161.9, 161.8, 154.8, 137.9, 135.6, 129.1, 129.0, 129.0, 128.7, 127.9, 127.9, 116.4, 111.6, 108.6, 107.5, 82.0, 73.0, 68.1, 61.7, 46.9, 42.0, 39.2, 28.6, 26.1, 24.6, 23.0, 19.3, −2.4, −3.5; FTIR (neat film), cm$^{−1}$ 2939 (m), 2857 (w), 1720 (s, C=O), 1593 (s), 1510 (s), 1469 (m), 1449 (m), 1326 (s), 1254 (m), 1187 (w), 1157 (m), 1090 (m), 1064 (m), 1007 (m); HRMS (ES) m/z calcd for (C$_{41}$H$_{47}$N$_3$O$_7$Si+H)$^+$ 722.3262. found 722.3261.

Deprotection:

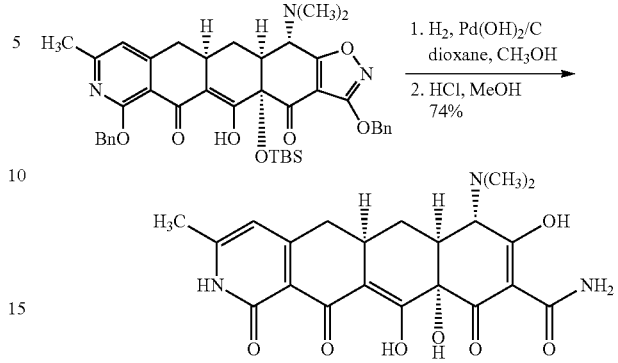

Pearlman's catalyst (10 mg, 0.0094 mmol, 0.68 equiv) was added to a solution of the purified pentacyclic addition product from the experiment above (10 mg, 0.014 mmol, 1 equiv) in dioxane-methanol (1:1, 10 mL) at 23° C. An atmosphere of hydrogen gas was introduced by briefly evacuating the flask, then flushing with pure hydrogen (1 atm). The reaction mixture was observed to form a green color within 10 min. After stiffing at 23° C. for 2 h, the reaction mixture was filtered through a plug of cotton and the filtrate was concentrated. The oily yellow residue was dissolved in methanol (10 mL) and to the resulting solution was added concentrated aqueous hydrochloric acid solution (37 wt %, 100 µL) at 23° C. The reaction mixture was stirred at 23° C. for 3 h, then was concentrated. The product was purified by preparatory HPLC on a Phenomenex Polymerx DVB column [10 µm, 250×10 mm, UV detection at 365 nm, Solvent A: 0.01 N aqueous hydrochloric acid, Solvent B: acetonitrile, injection volume: 500 µL (methanol containing 30 mg oxalic acid), linear gradient with 0→20% B over 40 min, flow rate: 4 ml/min]. Fractions eluting at 20-29 min were collected and concentrated, affording the D-ring pyridone hydrochloride as a yellow powder (4.8 mg, 74%).

$^1$H NMR (500 MHz, CD$_3$OD, hydrochloride) δ 6.37 (s, 1H, ArH), 4.06 (s, 1H, CHN(CH$_3$)$_2$), 3.05-2.95 (m, 8H, N(CH$_3$)$_2$, CHCHN(CH$_3$)$_2$, CHCH$_2$CHCHN(CH$_3$)$_2$), 2.79 (dd, 1H, J=16.1, 3.9 Hz, CHH'CHCH$_2$CHCHN(CH$_3$)$_2$), 2.55 (dd, 1H, J=16.1, 16.1 Hz, CHH'CHCH$_2$CHCHN(CH$_3$)$_2$)), 2.40 (s, 3H, Ar—CH$_3$), 2.18 (br. D, 1H, J=12.7 Hz, CHH'CHCHN (CH$_3$)$_2$), 1.59 (ddd, 1H, J=12.7, 12.7, 12.7 Hz, CHH'CHCHN (CH$_3$)$_2$); $^{13}$C NMR (100 MHz, (CD$_3$)$_2$SO) δ 187.3, 183.5, 177.8, 172.1, 160.6, 159.8, 153.3, 115.3, 107.2, 106.9, 95.6, 74.2, 68.4, 41.5, 35.7, 34.5, 33.9, 31.0, 19.2; UV max (0.01 M methanolic HCl), nm 267, 370; [α]$_D$=−146° (c=0.43 in 0.01 M methanolic HCl); HRMS (ES) m/z calcd for (C$_{21}$H$_{23}$N$_3$O$_7$+H)$^+$ 430.1614. found 430.1607.

Synthesis of a (−)-Pentacycline

Cyclization Step:

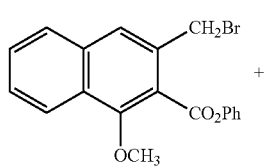

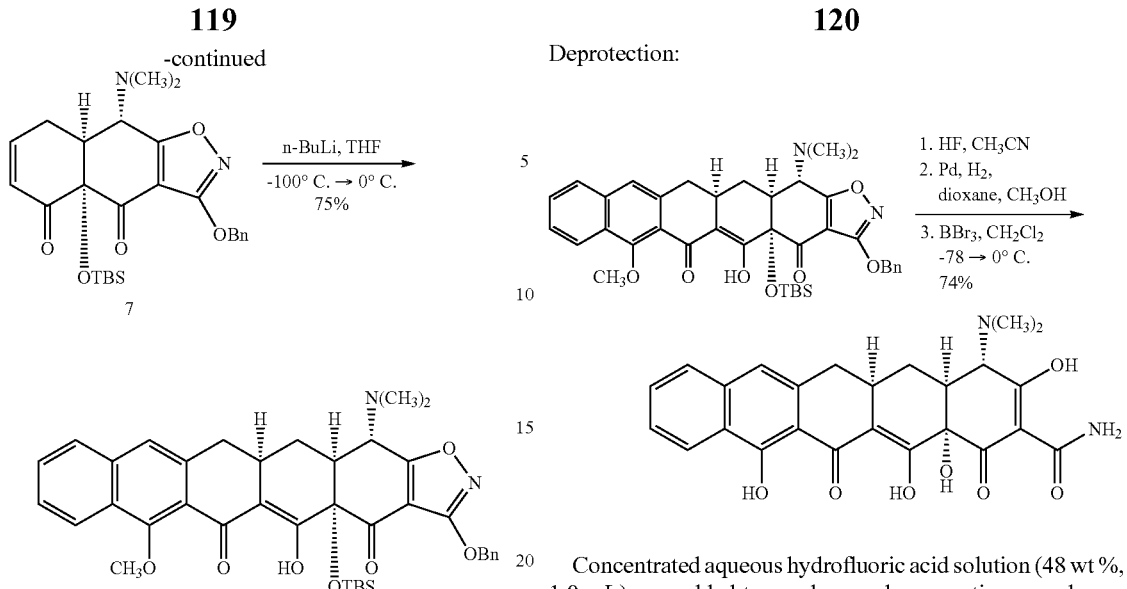

Deprotection:

A solution of n-butyllithium in hexanes (2.65 M, 107 µL, 0.284 mmol, 4.03 equiv) was added to a solution of phenyl 3-(bromomethyl)-1-methoxynaphthalene-2-carboxylate (105 mg, 0.283 mmol, 4.02 equiv) and enone 7 (34.0 mg, 0.0705 mmol, 1 equiv) in tetrahydrofuran (2.80 mL) at −100° C. The resulting light-red reaction mixture was allowed to warm to 0° C. over 70 min. The ice-cold product solution was then partitioned between aqueous potassium phosphate buffer solution (pH 7.0, 0.2 M, 15 mL) and dichloromethane (15 mL). The organic phase was separated and the aqueous phase was further extracted with two 15-mL portions of dichloromethane. The organic phases were combined and dried over anhydrous sodium sulfate. The dried solution was filtered, and the filtrate was concentrated, affording a yellow solid. The product was purified by preparatory HPLC on a Coulter Ultrasphere ODS column [10 µm, 250×10 mm, UV detection at 350 nm, Solvent A: water, Solvent B: methanol, two separate injections (750 µL each, acetonitrile), isochratic elution with 94% B for 20 min followed by a linear gradient elution with 94→100% B over 20 min, flow rate: 3.5 mL/min]. Fractions eluting at 24-38 min were collected and concentrated, affording the hexacyclic addition product in diastereomerically pure form (36.1 mg, 75%, a white solid).

$R_f$ 0.37 (3:7 ethyl acetate-hexanes); $^1$H NMR (500 MHz, CDCl$_3$) δ 16.25 (s, 1H, enol-OH), 8.30 (d, 1H, J=8.3 Hz, ArH), 7.75 (d, 1H, J=7.8 Hz, ArH), 7.59-7.34 (m, 7H, ArH), 7.26 (s, 1H, ArH), 5.38 (s, 2H, OCH$_2$Ph), 4.02 (s, 3H, OCH$_3$), 3.99 (d, 1H, J=10.7 Hz, CHN(CH$_3$)$_2$), 3.08-3.05 (m, 2H, CHCH$_2$CHCHN(CH$_3$)$_2$, CHH'CHCH$_2$CHCHN(CH$_3$)$_2$), 2.95-2.90 (m, 1H, CHH'CHCH$_2$CHCHN(CH$_3$)$_2$), 2.58 (dd, 1H, J=10.7, 5.9 Hz, CHCHN(CH$_3$)$_2$), 2.51 (s, 6H, N(CH$_3$)$_2$), 2.50-2.48 (m, 1H, CHH'CHCHN(CH$_3$)$_2$), 2.20-2.14 (m, 1H, CHH'CHCHN(CH$_3$)$_2$), 0.82 (s, 9H, TBS), 0.29 (s, 3H, TBS), 0.13 (s, 3H, TBS); $^{13}$C NMR (125 MHz, CDCl$_3$) δ 187.9, 184.1, 183.0, 182.0, 167.8, 159.2, 137.5, 136.7, 135.3, 129.5, 128.8, 128.7, 128.5, 127.5, 126.4, 124.2, 121.8, 119.5, 108.7, 108.7, 82.4, 72.8, 63.8, 61.6, 46.6, 42.1, 40.7, 29.3, 26.2, 23.1, 19.3, −2.2, −3.5; FTIR (neat film), cm$^{-1}$ 2934 (m), 2852 (m), 1718 (s, C=O), 1610 (s), 1513 (s), 1472 (m), 1452 (m), 1369 (m), 1339 (w), 1293 (m), 1252 (m), 1190 (w), 1159 (m), 1067 (m), 1026 (w), 1011 (w); HRMS (ES) m/z calcd for (C$_{39}$H$_{44}$N$_2$O$_7$Si+H)$^+$ 681.2996. found 681.2985.

Concentrated aqueous hydrofluoric acid solution (48 wt %, 1.0 mL) was added to a polypropylene reaction vessel containing a solution of the purified hexacyclic addition product from the experiment above (24.0 mg, 0.035, 1 equiv) in acetonitrile (9.0 mL) at 23° C. The reaction mixture was stirred at 23° C. for 22 h, then was poured into water (50 mL) containing dipotassium hydrogenphosphate (12.0 g). The resulting mixture was extracted with ethyl acetate (3×50 mL). The organic phases were combined and dried over anhydrous sodium sulfate. The dried solution was filtered and the filtrate was concentrated, affording a yellow oil. The residue was dissolved in methanol-dioxane (1:1, 5 mL) and to the resulting solution was added palladium black (10.0 mg, 0.0940 mmol, 2.67 equiv) in one portion. An atmosphere of hydrogen gas was introduced by briefly evacuating the flask, then flushing with pure hydrogen (1 atm). The yellow mixture was stirred at 23° C. for 4 h, then was filtered through a plug of cotton. The filtrate was concentrated, affording a yellow oil. The residue was dissolved in dichloromethane (4.5 mL) and to the resulting solution was added a solution of boron tribromide (1.0 M in dichloromethane, 0.5 mL, 14 equiv) at −78° C. The dark-red mixture was stirred at −78° C. for 15 min, then at 23° C. for 3.5 h. Methanol (20 mL) was added and the resulting yellow solution was stirred at 23° C. for 1 h. The solution was concentrated, affording a yellow oil. The product was purified by preparatory HPLC on a Phenomenex Polymerx DVB column [7 µm, 150×21.2 mm, UV detection at 350 nm, Solvent A: 0.01 N HCl, Solvent B: acetonitrile, injection volume: 500 µL (methanol containing 10 mg oxalic acid), gradient elution with 25→50% B over 60 min, flow rate: 6 mL/min]. Fractions eluting at 30-35 min were collected and concentrated, affording the pentacycline hydrochloride as a yellow powder (13.1 mg, 74%).

$^1$H NMR (600 MHz, CD$_3$OD, hydrochloride) δ 8.36 (d, 1H, J=7.7 Hz, ArH), 7.74 (d, 1H, J=7.7 Hz, ArH), 7.64 (dd, 1H, J=7.7, 7.7 Hz, ArH), 7.50 (dd, 1H, J=7.7, 7.7 Hz, ArH), 7.1 (s, 1H, ArH), 4.10 (s, 1H, CHN(CH$_3$)$_2$), 3.13-2.97 (m, 9H, N(CH$_3$)$_2$, CHCHN(CH$_3$)$_2$, CHCH$_2$CHCHN(CH$_3$)$_2$, CHH'CHCH$_2$CHCHN(CH$_3$)$_2$), 2.67 (dd, 1H, J=14.3, 14.3 Hz, CHH'CHCH$_2$CHCHN(CH$_3$)$_2$), 2.22 (ddd, 1H, J=13.6, 4.9, 2.9 Hz, CHH'CHCH(CH$_3$)$_2$), 1.64 (ddd, 1H, J=13.6, 13.6, 13.6 Hz, CHH'CHCHN(CH$_3$)$_2$); UV max (0.01 M methanolic HCl), nm 268, 345, 402; [α]$_D$=−113° (c=0.18 in 0.01 M methanolic HCl); HRMS (ES) m/z calcd for (C$_{25}$H$_{24}$N$_2$O$_7$+H)$^+$ 465.1662. found 465.1656.

Synthesis of (−)-7-Aza-10-Deoxysancycline

Cyclization Step:

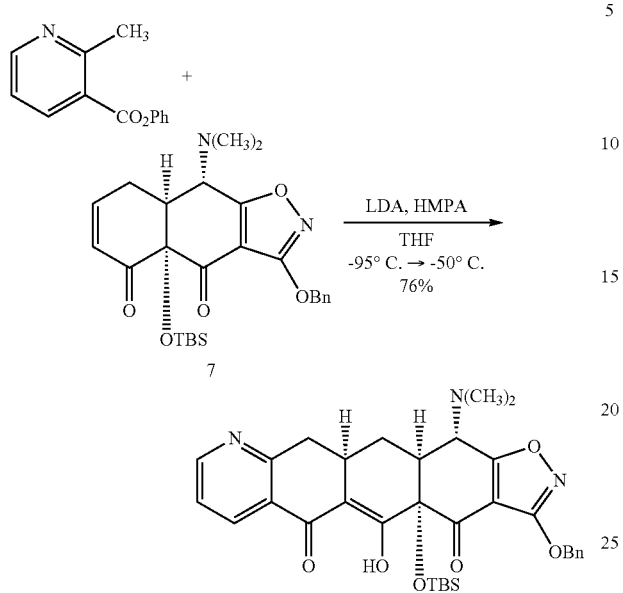

A solution of n-butyllithium in hexanes (2.65 M, 33.0 μL, 0.0945 mmol, 5.00 equiv) was added to a solution of diisopropylamine (13.2 μL, 0.0945 mmol, 5.00 equiv) in tetrahydrofuran (0.750 mL) at −78° C. The resulting solution was briefly warmed in an ice bath (10 min), then was cooled to −78° C. Hexamethylphosphoramide (33.0 μL, 0.189 mmol, 10.0 equiv) was added, producing a colorless solution, and this solution was then transferred (cold) dropwise via cannula to a solution containing phenyl 2-methylpyridine-3-carboxylate (16.0 mg, 0.0755 mmol, 4.00 equiv) and enone 7 (9.1 mg, 0.019 mmol, 1 equiv) in tetrahydrofuran (0.750 mL) at −95° C., forming a light-red mixture. The reaction solution was allowed to warm to −50° C. over 50 min. The product solution was then partitioned between aqueous potassium phosphate buffer solution (pH 7.0, 0.2 M, 10 mL) and dichloromethane (25 mL). The organic phase was separated and the aqueous phase was further extracted with three 15-mL portions of dichloromethane. The organic phases were combined and dried over anhydrous sodium sulfate. The dried solution was filtered and the filtrate was concentrated, affording a yellow solid. The product was purified by preparatory HPLC on a Coulter Ultrasphere ODS column [10 μm, 250×10 mm, UV detection at 350 nm, Solvent A: water, Solvent B: methanol, injection volume: 500 μL (methanol), gradient elution of 85→100% B over 30 min, flow rate: 3.5 mL/min]. Fractions eluting at 21-27 min were collected and concentrated, affording the pentacyclic addition product in diastereomerically pure form (8.6 mg, 76%, a white solid).

$R_f$ 0.07 (3:7 ethyl acetate-hexanes); $^1$H NMR (500 MHz, CD$_2$Cl$_2$) δ 15.21 (s, 1H, enol), 8.63 (d, 1H, J=4.5 Hz, pyr-H), 8.19 (d, 1H, J=7.5 Hz, pyr-H), 7.54-7.43 (m, 5H, ArH), 7.34 (d, 1H, J=4.5, 7.5 Hz, pyr-H), 5.36 (d, 1H, J=12.0 Hz, OCHH'Ph), 5.33 (d, 1H, J=12.0 Hz, OCHH'Ph), 4.03 (d, 1H, J=10.7 Hz, CHN(CH$_3$)$_2$), 3.36-3.31 (m, 1H, CHCH$_2$CHCHN (CH$_3$)$_2$), 3.23 (dd, 1H, J=16.3, 5.6 Hz, CHH'CH$_2$CHCHN (CH$_3$)$_2$), 2.99 (dd, 1H, J=16.3, 16.3 Hz, CHH'CHCH$_2$CHCHN(CH$_3$)$_2$), 2.63 (ddd, 1H, J=1.6, 4.4, 10.7 Hz, CHCHN(CH$_3$)$_2$), 2.54-2.48 (m, 7H, N(CH$_3$)$_2$, CHH'CHCHN(CH$_3$)$_2$), 2.19 (dd, 1H, J=1.6, 14.5 Hz, CHH'CHCHN(CH$_3$)$_2$), 0.87 (s, 9H, TBS), 0.26 (s, 3H, TBS), 0.13 (s, 3H, TBS); $^{13}$C NMR (100 MHz, CD$_2$Cl$_2$) δ 187.7, 183.5, 182.6, 182.2, 167.9, 161.2, 153.4, 137.6, 134.1, 129.2, 129.1, 129.1, 126.8, 123.0, 108.7, 106.9, 82.2, 73.0, 61.8, 47.0, 42.1, 41.4, 30.1, 28.4, 26.1, 23.2, 19.3, −2.4, −3.5; HRMS (ES) m/z calcd for (C$_{33}$H$_{39}$N$_3$O$_6$Si+H)$^+$ 602.2686. found 602.2686.

Deprotection:

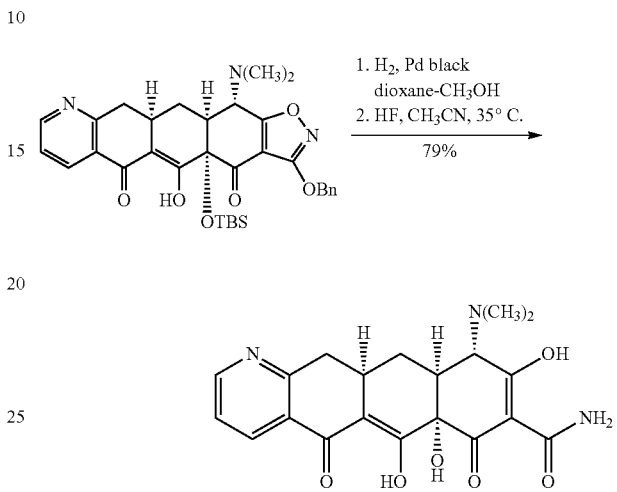

Palladium black (3.0 mg, 0.028 mmol, 2.6 equiv) was added in one portion to a solution of the purified pentacyclic addition product from the experiment above (6.5 mg, 0.011 mmol, 1 equiv) in dioxane-methanol (7:2, 9.0 mL) at 23° C. An atmosphere of hydrogen was introduced by briefly evacuating the flask, then flushing with pure hydrogen (1 atm). The resulting green mixture was stirred at 23° C. for 7 hr, then was filtered through a plug of cotton. The filtrate was concentrated, affording a yellow oil (7.0 mg). The residue was dissolved in acetonitrile (4.5 mL), transferred to a polypropylene reaction vessel, and concentrated aqueous hydrofluoric acid solution (48 wt %, 0.5 mL) was added to the resulting solution at 23° C. The reaction mixture was heated to 35° C. for 27 hr. Excess hydrofluoric acid was quenched by the addition of methoxytrimethylsilane (3.5 mL, 25 mmol). The reaction mixture was concentrated, affording a yellow solid. The product was purified by preparatory HPLC on a Phenomenex Polymerx DVB column [10 μm, 250×10 mm, UV detection at 350 nm, Solvent A: 0.5% trifluoroacetic acid in water, Solvent B: 0.5% trifluoroacetic acid in methanol-acetonitrile (1:1), injection volume: 500 μL (methanol), gradient elution with 0→20% B over 40 min, flow rate: 4 mL/min]. Fractions eluting at 35-45 min were collected and concentrated to give a yellow oil. The oil was dissolved in methanolic HCl (1.0 mL, 0.10 M) and concentrated, affording 7-aza-10-deoxysancycline hydrochloride as a yellow powder (3.7 mg, 79%). $^1$H NMR (500 MHz, CD$_3$OD, hydrochloride) δ 8.79-8.77 (m, 2H, pyr-H) 7.91 (dd, 1H, J=6.8, 6.8 Hz, pyr-H), 4.12 (s, 1H, CHN(CH$_3$)$_2$), 3.41-3.22 (m, 2H, CHH'CHCH$_2$CHCHN (CH$_3$)$_2$, CHCH$_2$CHCHN(CH$_3$)$_2$), 3.11-3.00 (m, 8H, CHH'CHCH$_2$CHCHN(CH$_3$)$_2$, CHCHN(CH$_3$)$_2$, N(CH$_3$)$_2$), 2.34 (ddd, 1H, J=12.9, 4.4, 2.4 Hz, CHH'CHCHN(CH$_3$)$_2$), 1.77 (ddd, 1H, J=12.9, 12.9, 12.9 Hz, CHH'CHCHN(CH$_3$)$_2$); UV max (0.01 M methanolic HCl), nm 264, 345; [α]$_D$=−154° (c=0.15 in 0.01 M methanolic HCl); HRMS (ES) m/z calcd for (C$_{20}$H$_{21}$N$_3$O$_6$+H)$^+$ 400.1508. found 400.1504.

Synthesis of (−)-10-Deoxysancycline

Cyclization Step:

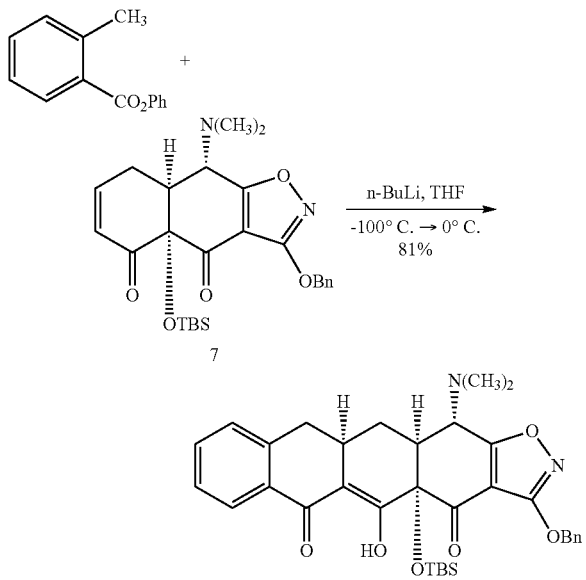

A solution of n-butyllithium in hexanes (2.65 M, 59 µL, 0.16 mmol, 4.0 equiv) was added to a solution of phenyl 2-(bromomethyl)benzoate (45.6 mg, 0.157 mmol, 3.97 equiv) and enone 7 (19.0 mg, 0.0394 mmol, 1 equiv) in tetrahydrofuran (1.57 mL) at −100° C. The resulting light-red solution was allowed to warm to 0° C. over 30 min. The ice-cold product solution was then partitioned between aqueous potassium phosphate buffer solution (pH 7.0, 0.2 M, 5 mL) and dichloromethane (25 mL). The organic phase was separated and the aqueous phase was further extracted with an additional 15-mL portion of dichloromethane. The organic phases were combined and dried over anhydrous sodium sulfate. The dried solution was filtered and the filtrate was concentrated, affording a yellow solid. The product was purified by preparatory HPLC on a Coulter Ultrasphere ODS column [10 µm, 250×10 mm, Solvent A: water, Solvent B: methanol, injection volume: 1.0 mL (methanol), gradient elution with 85→100% B over 30 min, UV detection at 350 nm, flow rate: 3.5 mL/min]. Fractions eluting at 25-30 min were collected and concentrated, affording the pentacyclic addition product in diastereomerically pure form (19.2 mg, 81%, a white solid).

$R_f$ 0.46 (3:7 ethyl acetate-hexanes); $^1$H NMR (500 MHz, $CD_2Cl_2$) δ 15.53 (s, 1H, enol), 7.94 (d, 1H, J=7.9 Hz, ArH), 7.54-7.28 (m, 8H, ArH, $OCH_2$ArH), 5.37-5.34 (m, 2H, $OCH_2$Ph), 4.05 (d, 1H, J=10.7 Hz, $CHN(CH_3)_2$), 3.24-3.18 (m, 1H, $CHCH_2CHCHN(CH_3)_2$), 2.99 (dd, 1H, J=15.5, 5.6 Hz, $CHH'CHCH_2CHCHN(CH_3)_2$), 2.88 (dd, 1H, J=15.5, 15.5 Hz, $CHH'CHCH_2CHCHN(CH_3)_2$), 2.61 (dd, 1H, J=4.4, 10.7 Hz, $CHCHN(CH_3)_2$), 2.54-2.44 (m, 7H, $N(CH_3)_2$, $CHH'CHCHN(CH_3)_2$), 2.14 (d, 1H, J=14.3 Hz, $CHH'CHCHN(CH_3)_2$), 0.86 (s, 9H, TBS), 0.25 (s, 3H, TBS), 0.12 (s, 3H, TBS); $^{13}$C NMR (100 MHz, $CD_2Cl_2$) δ 187.8, 183.0, 182.8, 182.4, 167.7, 141.7, 135.4, 133.4, 130.9, 129.0, 128.9, 128.9, 128.1, 127.5, 126.5, 108.5, 106.8, 82.1, 72.8, 61.5, 58.5, 46.9, 41.9, 38.6, 29.0, 25.9, 23.1, 19.1, −2.6, −3.7; HRMS (ES) m/z calcd for $(C_{34}H_{40}N_3O_6Si+H)^+$601.2734. found 601.2730.

Deprotection:

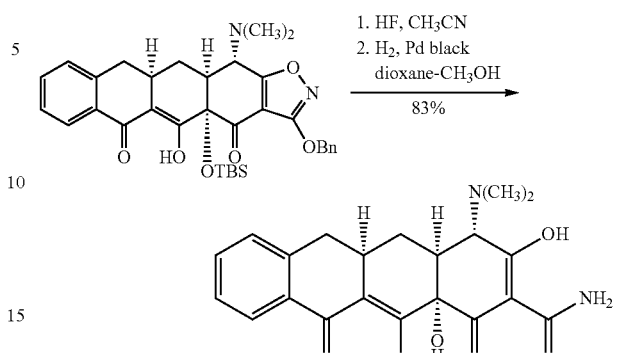

Concentrated aqueous hydrofluoric acid solution (48 wt %, 1.1 mL) was added to a polypropylene reaction vessel containing a solution of the pentacyclic addition product from the experiment above (15.1 mg, 0.0251 mmol, 1 equiv) in acetonitrile (10 mL) at 23° C. The resulting solution was stirred vigorously at 23° C. for 12 h, then was poured into water (50 mL) containing dipotassium hydrogenphosphate (4.7 g) and the product was extracted with ethyl acetate (3×25 mL). The organic phases were combined and dried over anhydrous sodium sulfate. The dried solution was filtered and the filtrate was concentrated, affording a yellow solid (12.2 mg, 99%). The residue was dissolved in methanol-dioxane (1:1, 3.0 mL) and palladium black (6.5 mg, 0.061 mmol, 2.4 equiv) was added to the resulting solution in one portion. An atmosphere of hydrogen was introduced by briefly evacuating the flask, then flushing with pure hydrogen (1 atm). The resulting light-yellow mixture was stirred at 23° C. for 20 min, then was filtered through a plug of cotton. The filtrate was concentrated, affording a yellow solid. The product was purified by preparatory HPLC on a Phenomenex Polymerx DVB column [10 µm, 250×10 mm, UV detection at 350 nm, Solvent A: 0.01 N HCl, Solvent B: acetonitrile, injection volume: 1.0 mL (methanol containing 10 mg oxalic acid), gradient elution with 5→50% B over 30 min, flow rate: 5 mL/min]. Fractions eluting at 16-22 min were collected and concentrated, affording 10-deoxysancycline hydrochloride as a white powder (9.1 mg, 83%).

$^1$H NMR (500 MHz, $CD_3OD$, hydrochloride) δ 7.96 (d, 1H, J=7.3 Hz, ArH) 7.51 (dd, 1H, J=7.3, 7.3 Hz, ArH), 7.39 (dd, 1H, J=7.3, 7.3 Hz, ArH), 7.30 (d, 1H, J=7.3 Hz, ArH), 4.04 (s, 1H, $CHN(CH_3)_2$), 3.31-2.99 (m, 8H, $CHCH_2CHCHN(CH_3)_2$, $CHCHN(CH_3)_2$, $N(CH_3)_2$), 2.87 (dd, 1H, J=15.4, 4.3 Hz, $CHH'CHCH_2CHCHN(CH_3)_2$), 2.61 (dd, 1H, J=15.4, 15.4 Hz, $CHH'CHCH_2CHCHN(CH_3)_2$), 2.21 (ddd, J=12.8, 5.0, 2.5 Hz, $CHH'CHCHN(CH_3)_2$), 1.66 (ddd, 1H, J=12.8, 12.8, 12.8 Hz, $CHH'CHCHN(CH_3)_2$); UV max (0.01 M methanolic HCl), nm 264, 348; $[α]_D$=−147° (c=0.15 in 0.01 M methanolic HCl); HRMS (ES) m/z calcd for $(C_{21}H_{22}N_2O_6+H)^+$399.1556. found 399.1554.

Biological Testing.

Whole-cell antibacterial activity was determined according to methods recommended by the NCCLS (National Committee for Clinical Laboratory Standards. 2002. *Methods for dilution antimicrobial susceptibility tests for bacteria that grow aerobically: approved standard-fifth edition*. NCCLS document M100-S12. National Committee for Clinical Laboratory Standards. Wayne, Pa.; incorporated herein by reference). Test compounds were dissolved in dimethyl sulfoxide (DMSO) and the resulting solutions were diluted in water (1:10) to produce stock solutions with a final concentration of 256 μg tetracycline analog per mL. In a 96-well microtiter plate, 50-μL aliquots of stock solutions were diluted serially into cation-adjusted Mueller-Hinton broth (MHB; Becton-Dickinson, Cockeysville, Md.). Test organisms (50 μL aliquots of solutions ~5×10$^5$ CFU/mL) were then added to the appropriate wells of the microtiter plate. Inoculated plates were incubated aerobically at 35° C. for 18-24 h. The MIC was the lowest concentration of compound determined to inhibit visible growth. Five Gram-positive and five Gram-negative bacterial strains were examined in minimum inhibitory concentration (MIC) assays. The Gram-positive strains were Staphylococcus aureus ATCC 29213, Staphylococcus epidermidis ACH-0016, Staphylococcus haemolyticus ACH-0013, Enterococcus faecalis ATCC 700802 (a VRE or vancomycin-resistant enterococcus strain), and Staphylococcus aureus ATCC 700699 (carrying the tetM resistance gene). The Gram-negative strains were Pseudomonas aeruginosa ATCC 27853, Klebsiella pneumoniae ATCC 13883, E. coli ATCC 25922, E. coli ACH-0095 (multiply antibiotic-resistant), and E. coli ATCC 53868:pBR322 (containing a plasmid encoding tetracycline-resistance). These strains are listed again below, along with certain other details of their origins and known resistance to antibiotics.

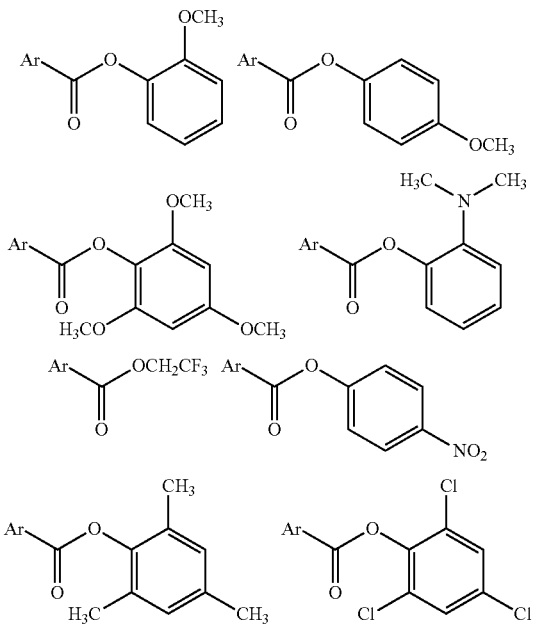

Bacterial Strains

| Gram-Positive Organisms: | |
|---|---|
| Staphylococcus aureus ATCC 29213 | QC strain for MIC testing |
| Staphylococcus aureus ATCC 700699 | Methicillin- and tetracycline-resistant clinical isolate with intermediate resistance to vancomycin |
| Staphylococcus epidermidis ACH-0018 | Clinical isolate (Achillion strain collection) |
| Staphylococcus haemolyticus ACH-0013 | Clinical isolate (Achillion strain collection) |
| Enterococcus faecalis ATCC 700802 | Vancomycin-resistant clinical isolate |
| Gram-Negative Organisms: | |
| E. coli ATCC 25922 | QC strain for MIC testing |
| E. coli ATCC 53868::pBR322 | Laboratory strain carrying a plasmid with a tetracycline-resistance marker |
| E. coli ACH-0095 | Multiply-resistant clinical isolate (Achillion strain collection) |
| Klebsiella pneumoniae ATCC 13883 | QC strain for MIC testing |
| Pseudomonas aeruginosa ATCC 27853 | QC strain for MIC testing |

ATCC = American Type Culture Collection, Manassas, VA

Example 8

Alternative Routes to Tetracycline Analogs

Many of the studies described above show the generation of the carbanionic D-ring precursor by metalization of phenyl esters of o-toluate derivatives. These self-condensation reactions at times required to use of up to 4-5 equivalents of a given D-ring precursor. The presence of an electron-withdrawing substituent on the α-carbon greatly improves the efficiency of metalation and coupling as described in Example 7 and elsewhere herein. Lithium-halogen exchange of benzylic bromides conducted in situ in the presence of the AB electrophile has been found to provide coupling products where benzylic metalation fails (see Example 7). These benzylic bromides can be prepared with surprising efficiencies (near quantitative yields) and are surprisingly stable. The developments may lead to a coupling reaction that could be conductable on a multi-kilo scale. Many different phenyl ester substituents (see below) may be used to optimize a coupling reaction.

-continued

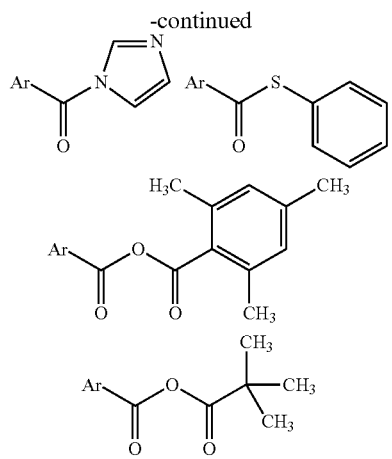

The optimal group for benzylic metalation, however, may not be the same as the optimal group for lithium-halogen exchange. In addition, for the lithium-halogen exchange process, besides ester modification, other metal reagents may be used including, but not limited to, other alkyllithium reagents (e.g., phenyllithium, mesityllithium), Grignard reagents (e.g., iso-propylmagesium chloride) and zinc-based systems. Barbier-type couplings will be explored using a variety of zero-valent metals for coupling.

The AB-ring precursors may also be prepared by alternative routes. The step-count for the synthesis of most 6-deoxytetracycline analogs is 14 from benzoic acid. Eleven of these 14 steps are dedicated to the synthesis of the AB-ring precursor. Any improvements in the length or efficiency of the route to these AB-ring precursors will have a substantial impact on the synthesis overall. Alternative syntheses of the AB-ring precursor are shown in FIGS. 22 and 23. Among the strategies for alternative A-ring closure sequences are intramolecular Michael additions, palladium-mediated processes, and iminium ion induce closures. Hypervalent iodine reagents may also be used instead of microbial dihydroxylation in the synthesis of the AB-ring precursors as shown in FIG. 23.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of Formula:

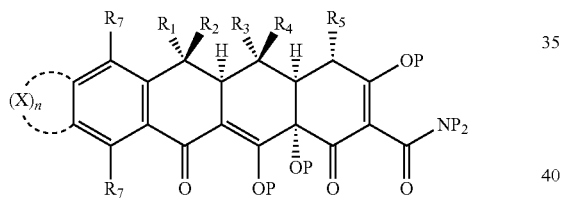

or a salt, isomer, or tautomer thereof;
wherein:
R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —OR$_A$; —C(=O)R$_A$; —CO$_2$R$_A$; —CN; —SCN; —SR$_A$; —SOR$_A$; —SO$_2$R$_A$; —NO$_2$; —N(R$_A$)$_2$; —NHC(O)R$_A$; or —C(R$_A$)$_3$; wherein each occurrence of R$_A$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —OR$_B$; —C(=O)R$_B$; —CO$_2$R$_B$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

R$_3$ is hydrogen; halogen; cyclic or acyclic, substituted or unsubstituted aliphatic; cyclic or acyclic, substituted or unsubstituted heteroaliphatic; substituted or unsubstituted acyl; substituted or unsubstituted aryl; substituted or unsubstituted heteroaryl; —OR$_C$; —C(=O)R$_C$; —CO$_2$R$_C$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —OR$_D$; —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —OR$_E$; —CN; —SCN; —SR$_E$; or —N(R$_E$)$_2$; wherein each occurrence of R$_E$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

each occurrence of R$_7$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —OR$_G$; —C(=O)R$_G$; —CO$_2$R$_G$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio;

each occurrence of P is independently hydrogen, substituted or unsubstituted aliphatic, substituted or unsubstituted heteroaliphatic, a protecting group, substituted or unsubstituted acyl, substituted or unsubstituted aryl, or substituted or unsubstituted heteroaryl;

represents a substituted or unsubstituted aryl, substituted or unsubstituted heteroaryl, substituted or unsubstituted carbocyclic, or substituted or unsubstituted heterocyclic moiety, wherein each occurrence of X is independently selected from the group consisting of O, S, $NR_8$, $C(R_8)_2$, $C(R_8)$, and N, n is an integer in the range of 1 to 5, inclusive, and the bonds between adjacent X moieties are either single or double bonds; and each occurrence of $R_8$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —$OR_H$; =O; —C(=O)$R_H$; —$CO_2R_H$; —CN; —SCN; —$SR_H$; —$SOR_H$; —$SO_2R_H$; —$NO_2$; —$N(R_H)_2$; —$NHC(O)R_H$; or —$C(R_H)_3$; wherein each occurrence of $R_H$ is independently hydrogen, a protecting group, aliphatic, heteroaliphatic, acyl, aryl, heteroaryl, alkoxy, aryloxy, alkylthio, arylthio, amino, alkylamino, dialkylamino, heteroaryloxy, or heteroarylthio.

2. The compound of claim 1, wherein each occurrence of P is hydrogen.

3. The compound of claim 1, wherein $R_1$ is hydrogen.

4. The compound of claim 1, wherein $R_2$ is hydrogen.

5. The compound of claim 1, wherein $R_3$ is hydrogen.

6. The compound of claim 1, wherein $R_4$ is hydrogen.

7. The compound of claim 1, wherein each occurrence of $R_1$, $R_2$, $R_3$, and $R_4$ is hydrogen.

8. The compound of claim 1, wherein $R_5$ is —$N(R_E)_2$.

9. The compound of claim 1, wherein $R_5$ is —$N(CH_3)_2$.

10. The compound of claim 1, wherein each occurrence of $R_7$ is independently hydrogen, halogen, —$OR_G$, —$SR_G$, or —$N(R_G)_2$.

11. The compound of claim 1, wherein

represents a substituted or unsubstituted phenyl moiety.

12. The compound of claim 1, wherein

represents a substituted or unsubstituted heteroaryl moiety.

13. The compound of claim 12, wherein

represents a substituted or unsubstituted heteroaryl moiety selected from the group consisting of pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl.

14. The compound of claim 1, wherein

represents a substituted or unsubstituted heterocyclic moiety.

15. The compound of claim 14, wherein

represents a substituted or unsubstituted heterocyclic moiety selected from the group consisting of pyrrolidinyl, pyrazolidinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

16. The compound of claim 1, wherein

is selected from the group consisting of:

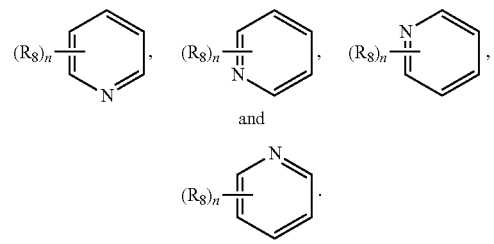

17. The compound of claim 1, wherein

is selected from the group consisting of:

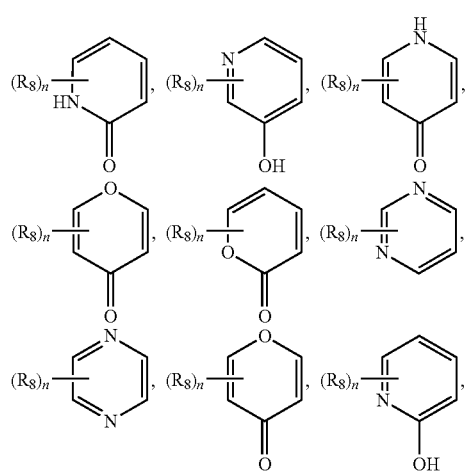

-continued
and
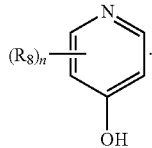
18. The compound of claim 1, wherein
is selected from the group consisting of:
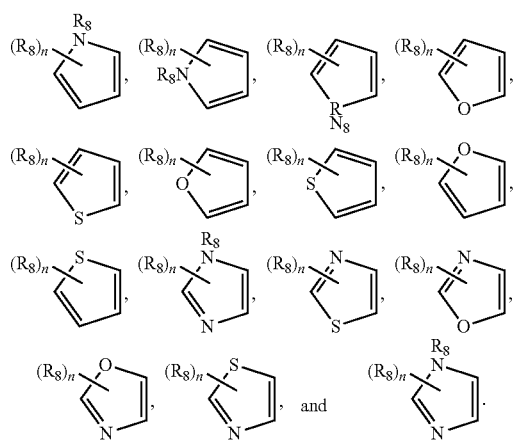
19. The compound of claim 1 of formula:
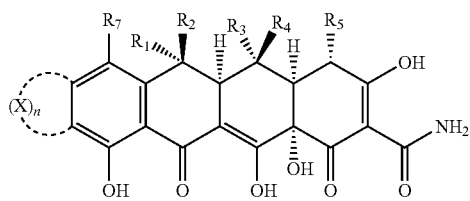
or a salt, isomer, or tautomer thereof.
20. The compound of claim 1 of formula:
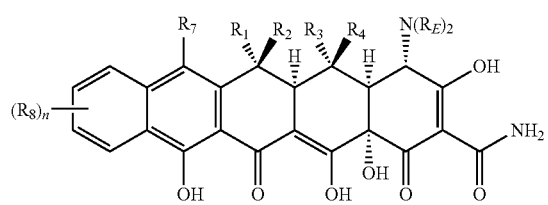
or a salt, isomer, or tautomer thereof.
21. The compound of claim 1 selected from the group consisting of:
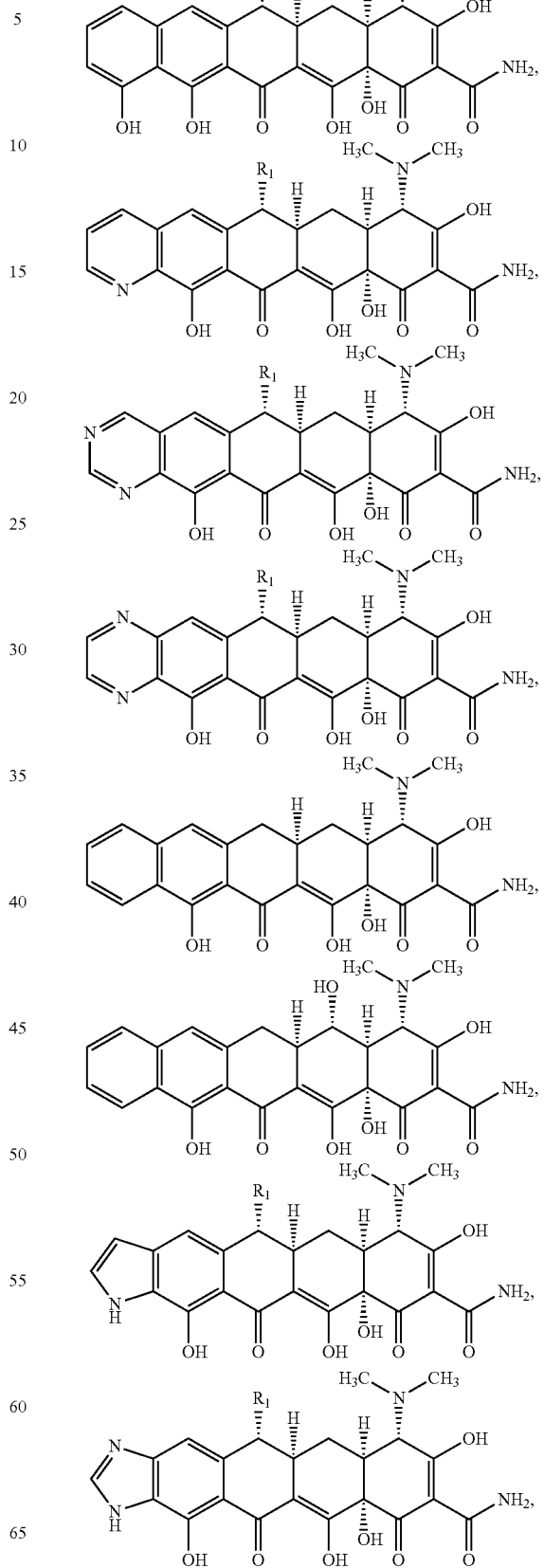

-continued

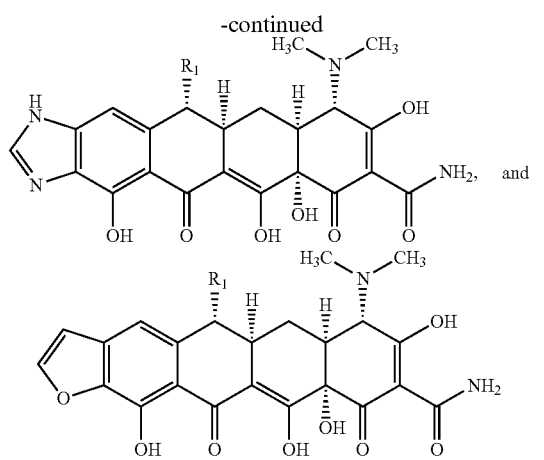

and salts, isomers, and tautomers thereof.

22. A pharmaceutical composition comprising a compound of claim 1, or a salt, isomer, or tautomer thereof, and a pharmaceutically acceptable excipient.

23. A method of treating a bacterial infection, the method comprising administering an amount of the compound of claim 1 effective to kill or inhibit the growth of the bacteria.

24. The method of claim 23, wherein the infection is caused by a Gram-positive organism.

25. The method of claim 23, wherein the infection is caused by a Gram-negative organism.

* * * * *

UNITED STATES PATENT AND TRADEMARK OFFICE
CERTIFICATE OF CORRECTION

PATENT NO. : 8,598,148 B2
APPLICATION NO. : 12/778797
DATED : December 3, 2013
INVENTOR(S) : Andrew G. Myers et al.

Page 1 of 1

It is certified that error appears in the above-identified patent and that said Letters Patent is hereby corrected as shown below:

*In the Specification*

At column 35, line 28-32, the formula: 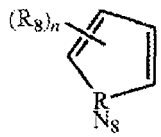 should be changed to the formula: 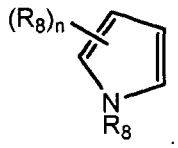

*In the Claims*

In claim 18, at column 131, lines 20-25, formula: 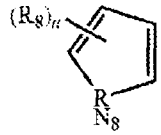 should be changed to the formula: 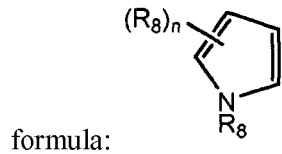

Signed and Sealed this
Twenty-seventh Day of May, 2014

Michelle K. Lee
*Deputy Director of the United States Patent and Trademark Office*